United States Patent
Fischer et al.

(10) Patent No.: US 12,240,898 B2
(45) Date of Patent: Mar. 4, 2025

(54) MONOCLONAL ANTI-IL-1RAcP ANTIBODIES

(71) Applicant: SANOFI BIOTECHNOLOGY SAS, Paris (FR)

(72) Inventors: Stephan Fischer, Weilheim (DE); Michael Brandt, Munich (DE)

(73) Assignee: SANOFI BIOTECHNOLOGY, Paris (FR)

( * ) Notice: Subject to any disclaimer, the term of this patent is extended or adjusted under 35 U.S.C. 154(b) by 517 days.

(21) Appl. No.: 17/522,600

(22) Filed: Nov. 9, 2021

(65) Prior Publication Data

US 2022/0169718 A1    Jun. 2, 2022

Related U.S. Application Data

(63) Continuation of application No. 16/898,074, filed on Jun. 10, 2020, now Pat. No. 11,198,728, which is a continuation of application No. 15/739,410, filed as application No. PCT/EP2016/064588 on Jun. 23, 2016, now Pat. No. 10,906,971.

(30) Foreign Application Priority Data

Jun. 26, 2015 (EP) .................................... 15174184
Dec. 17, 2015 (EP) .................................... 15200772

(51) Int. Cl.
  *C07K 16/24* (2006.01)
  *A61K 39/00* (2006.01)
  *C07K 16/28* (2006.01)
  *C12N 5/12* (2006.01)

(52) U.S. Cl.
  CPC ........ *C07K 16/245* (2013.01); *C07K 16/2866* (2013.01); *C12N 5/12* (2013.01); *A61K 2039/505* (2013.01); *C07K 2317/20* (2013.01); *C07K 2317/33* (2013.01); *C07K 2317/565* (2013.01); *C07K 2317/732* (2013.01); *C07K 2317/76* (2013.01)

(58) Field of Classification Search
  None
  See application file for complete search history.

(56) References Cited

U.S. PATENT DOCUMENTS

| | | | |
|---|---|---|---|
| 5,202,238 A | 4/1993 | Fell, Jr. et al. | |
| 5,204,244 A | 4/1993 | Fell et al. | |
| 5,283,179 A | 2/1994 | Wood | |
| 5,641,641 A | 6/1997 | Wood | |
| 5,650,289 A | 7/1997 | Wood | |
| 6,280,955 B1 | 8/2001 | Cao | |
| 6,586,207 B2 | 7/2003 | Tirrell et al. | |
| 6,602,684 B1 | 8/2003 | Umana et al. | |
| 7,390,880 B2 | 6/2008 | Bednarik et al. | |
| 10,906,971 B2 | 2/2021 | Fischer et al. | |
| 11,198,728 B2 | 12/2021 | Fischer et al. | |
| 11,203,642 B2 | 12/2021 | Fischer et al. | |
| 11,639,392 B2 | 5/2023 | Fischer et al. | |
| 12,024,564 B2 | 7/2024 | Fischer et al. | |
| 12,054,552 B2 | 8/2024 | Lange et al. | |
| 2003/0026806 A1 | 2/2003 | Witte et al. | |
| 2004/0214988 A1 | 10/2004 | Tirrell et al. | |
| 2012/0251531 A1 | 10/2012 | Baehner et al. | |
| 2014/0017167 A1 | 1/2014 | Fioretos et al. | |
| 2015/0315179 A1 | 11/2015 | Jiang et al. | |
| 2015/0315279 A1* | 11/2015 | Jiang .................. | C07K 16/2866 424/1.49 |
| 2019/0106487 A1 | 4/2019 | Fischer et al. | |
| 2019/0194336 A1 | 6/2019 | Fischer et al. | |

(Continued)

FOREIGN PATENT DOCUMENTS

| | | |
|---|---|---|
| CN | 1934072 A | 3/2007 |
| CN | 102939304 A | 2/2013 |

(Continued)

OTHER PUBLICATIONS

Paul, Fundamental Immunology, 3rd Edition, Raven Press, New York, 1993, Chapter 9, pp. 292-295.

(Continued)

*Primary Examiner* — Ruixiang Li
(74) *Attorney, Agent, or Firm* — LATHROP GPM LLP; James H. Velema, Esq.; Michael J. Spellberg, Esq.

(57) ABSTRACT

Monoclonal antibody that specifically binds IL-1RAcP, or an antigen binding fragment thereof, comprising:
  a) a heavy chain variable region (VH) comprising CDR1H, CDR2H and/or CDR3H, wherein the CDR1H region comprises an amino acid sequence selected from the group of SEQ ID NO: 155-231,
  wherein the CDR2H region comprises an amino acid sequence selected from the group of SEQ ID NO: 232-308,
  and wherein the CDR3H region comprises an amino acid sequence selected from the group of SEQ ID NO: 309-385; and
  b) a light chain variable region (VL) comprising CDR1L, CDR2L and/or CDR3L, wherein the CDR1L region comprises an amino acid sequence selected from the group of SEQ ID NO: 386-462,
  wherein the CDRL2 region comprises an amino acid sequence selected from the group of SEQ ID NO: 463-539,
  and wherein the CDR3L region comprises an amino acid sequence selected from the group of SEQ ID NO: 540-616

Figure 4:
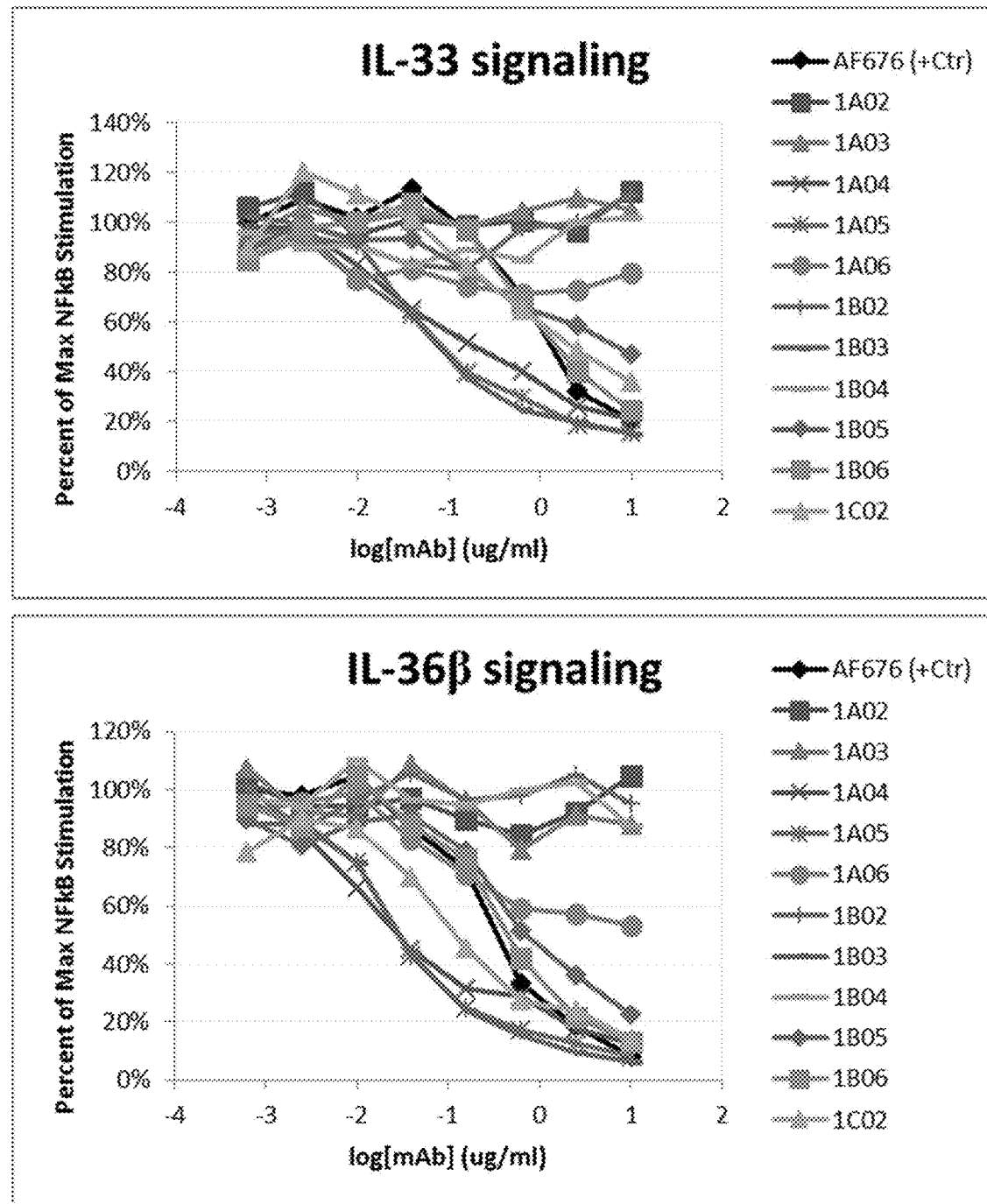

The monoclonal antibody is characterized in that it inhibits IL-1RAcP induced NFkB activity, useful in treatment of IL-1RAcP related diseases.

14 Claims, 37 Drawing Sheets

Specification includes a Sequence Listing.

(56) References Cited

U.S. PATENT DOCUMENTS

| | | | |
|---|---|---|---|
| 2020/0140559 A1 | 5/2020 | Fischer et al. |
| 2020/0407438 A1 | 12/2020 | Fischer et al. |
| 2022/0089751 A1 | 3/2022 | Fischer et al. |
| 2023/0383000 A1 | 11/2023 | Fischer et al. |
| 2024/0101691 A1 | 3/2024 | Coolbaugh et al. |

FOREIGN PATENT DOCUMENTS

| | | | |
|---|---|---|---|
| EP | | 0120694 A2 | 10/1984 |
| EP | | 0125023 A1 | 11/1984 |
| EP | | 0239400 A2 | 9/1987 |
| EP | | 0488470 A1 | 6/1992 |
| EP | | 0519596 A1 | 12/1992 |
| EP | | 0194276 B2 | 1/2002 |
| EP | | 1255780 A1 | 11/2002 |
| EP | | 1633787 A1 | 3/2006 |
| WO | WO 1986/001533 A1 | | 3/1986 |
| WO | WO 1988/007089 A1 | | 9/1988 |
| WO | WO 1996/014339 A1 | | 5/1996 |
| WO | WO 1996/023067 A1 | | 8/1996 |
| WO | WO 1997/037016 A1 | | 10/1997 |
| WO | WO 1998/005787 A1 | | 2/1998 |
| WO | WO 1998/023289 A1 | | 6/1998 |
| WO | WO 1998/048032 A2 | | 10/1998 |
| WO | WO 1999/051642 A1 | | 10/1999 |
| WO | WO 1999/058572 A1 | | 11/1999 |
| WO | WO 2000/009560 A2 | | 2/2000 |
| WO | WO 2000/032767 A1 | | 6/2000 |
| WO | WO 2000/042072 A2 | | 7/2000 |
| WO | WO 2001/055216 A1 | | 8/2001 |
| WO | WO 2002/044215 A2 | | 6/2002 |
| WO | WO 2002/060919 A2 | | 8/2002 |
| WO | WO 2002/064630 A2 | | 8/2002 |
| WO | WO 2003/014309 A2 | | 2/2003 |
| WO | WO 2002/064630 A3 | | 8/2003 |
| WO | WO 2003/073238 A2 | | 9/2003 |
| WO | WO 2003/074569 A2 | | 9/2003 |
| WO | WO 2004/009823 A1 | | 1/2004 |
| WO | WO 2004/016750 A2 | | 2/2004 |
| WO | WO 2004/022718 A2 | | 3/2004 |
| WO | WO 2004/029207 A2 | | 4/2004 |
| WO | WO 2004/035752 A2 | | 4/2004 |
| WO | WO 2004/063351 A2 | | 7/2004 |
| WO | WO 2004/065540 A2 | | 8/2004 |
| WO | WO 2004/074455 A2 | | 9/2004 |
| WO | WO 2004/099249 A2 | | 11/2004 |
| WO | WO 2004/100987 A1 | | 11/2004 |
| WO | WO 2004/106377 A1 | | 12/2004 |
| WO | WO 2005/035727 A2 | | 4/2005 |
| WO | WO 2005/040217 A2 | | 5/2005 |
| WO | WO 2005/044859 A2 | | 5/2005 |
| WO | WO 2005/070963 A1 | | 8/2005 |
| WO | WO 2005/073164 A1 | | 8/2005 |
| WO | WO 2005/074524 A2 | | 8/2005 |
| WO | WO 2005/077981 A2 | | 8/2005 |
| WO | WO 2005/092925 A2 | | 10/2005 |
| WO | WO 2005/123780 A2 | | 12/2005 |
| WO | WO 2006/019447 A1 | | 2/2006 |
| WO | WO 2006/047350 A2 | | 5/2006 |
| WO | WO 2006/085967 A2 | | 8/2006 |
| WO | WO 2007/003041 A1 | | 1/2007 |
| WO | WO 2007/031875 A2 | | 3/2007 |
| WO | WO 2008/045140 A1 | | 4/2008 |
| WO | WO 2009/120903 A2 | | 10/2009 |
| WO | WO 2010/108127 A1 | | 9/2010 |
| WO | WO 2011/021014 A2 | | 2/2011 |
| WO | WO 2011/124718 A1 | | 10/2011 |
| WO | WO 2011/147903 A1 | | 12/2011 |
| WO | WO 2012/098407 A1 | | 7/2012 |
| WO | WO 2012/142391 A1 | | 10/2012 |
| WO | WO 2012/177595 A1 | | 12/2012 |
| WO | WO 2013/023015 A2 | | 2/2013 |
| WO | WO 2013/165894 A2 | | 11/2013 |
| WO | WO 2013/165894 A3 | | 11/2013 |
| WO | WO 2014/100772 A1 | | 6/2014 |
| WO | WO 2014/113433 A1 | | 7/2014 |
| WO | WO 2015/132602 A1 | | 9/2015 |
| WO | WO 2016/020502 A1 | | 2/2016 |
| WO | WO 2016/207304 A2 | | 12/2016 |

OTHER PUBLICATIONS

Zhao et al., Construction of hydridoma calls with ILIRAP as a new marker for leukemia stem cells and detection of its monoclonal antibody, Journal of Exp Hematology, 2013, 21(6): 1390-1393.

Zubler, Polyclonal B Cell Responses in the Presence of Defined Filler Cells: Complementary Effects of Lipopolysaccharide and Anti-Immunoglobulin Antibodies, Eur J Immunol., 1984, 14(4):,357-363.

Rudikoff et al., Single amino acid substitution altering antigen-binding specificity, PNAS USA, Mar. 1982, 79: 1979-1983.

Vajdos et al., Comprehensive Functional Maps of the Antigen-Binding Site of an Anti-ErbB2 Antibody Obtained with Shotgun Scanning Mutagenesis, Journal of Molecular Biology, 2002, 320: 415-428.

Alam, J. and Cook, J.L., Reporter Genes: Application to the Study of Mammalian Gene Transcription. Anal Biochem. 1990; 188(2):245-54.

Ali, S. et al., IL-1 receptor Accessory Protein is Essential for IL-33-induced Activation of T Lymphocytes and Mast Cells. Proc Natl Acad Sci USA, 2007; 104(47):18660-5.

Ausubel, F. et al., ed. Current Protocols in Molecular Biology, Green Publishing and Wiley Interscience, New York (1987).

Balagurunathan, Y. et al., Gene Expression Profiling-Based Identification of Cell-Surface Targets for Developing Multimeric Ligands in Pancreatic Cancer. Mol Cancer Ther. 2008: 7(9):3071-80.

Barbas, C.F., III et al., In vitro Evolution of a Neutralizing Human Antibody to Human Immunodeficiency Virus Type 1 to Enhance Affinity and Broaden Strain Cross-Reactivity. Proc Natl Acad Sci USA. 1994; 91(9):3809-13.

Bardin, "Canakinumab for the Patient With Difficult-to-Treat Gouty Arthritis: Review of the Clinical Evidence", Joint Bone Spine, 2015, 82: eS9-eS16.

Barnes, L.M. et al., Advances in Animal Cell Recombinant Protein Production: GS-NSO Expression System. Cytotechnology. 2000; 32(2):109-23.

Barnes, L.M. et al., Characterization of the Stability of Recombinant Protein Production in the GS-NSO Expression System. Biotech Bioeng. 2001; 73(4):261-70.

Brueggemann, M. et al., Comparison of the Effector Functions of Human Immunoglobulins Using a Matched Set of Chimeric Antibodies. J Exp Med. 1987; 166(5):1351-61.

Capel, P.J.A. et al., Heterogeneity of Human IgG Fc Receptors. Immunomethods. 1994; 4(1):2534.

Carter, P. et al., Humanization of an Anti-p185$^{HER2}$ Antibody for Human Cancer Therapy. Proc Natl Acad Sci USA. 1992; 89(10):4285-9.

Chin, J.W. and Schultz, P.G., In Vivo Photocrosslinking with Unnatural Amino Acid Mutagenesis. ChemBioChem. 2002; 3(11):1135-7.

Chin, J.W. et al., Addition of a Photocrosslinking Amino Acid to the Genetic Code of *Escherichia co/i*. Proc Natl Acad Sci U.S.A. 2002; 99(17):11020-4.

Chin, J.W et al., Addition of p-Azido-L-phenylalanine to the Genetic Code of *Escherichia coli*. J Amer Chem Soc. 2002; 124:9026-7.

Cullinan et al., The IL-1 Receptor Accessory Protein Is an Essential Component of the IL-1 Receptor, J. Immunology, Nov. 15, 1998, 161(10): 5614-5620.

Daeron, M., Fc Receptor Biology. Annu Rev Immunol. 1997; 15:203-34.

Davis, R.S. et al., Fc Receptor Homologs: Newest Members of a Remarkably Diverse Fc Receptor Gene Family. Immunol Rev. 2002; 190:123-36.

De Haas et al., Fcy Receptors of Phagocytes. J Lab Clin Med. 1995; 126(4):330-41.

De Wet, J.R. et al., Firefly Luciferase Gene: Structure and Expression in Mammalian Cells. Mol Cell Biol. 1987; 7:725-37.

(56) References Cited

OTHER PUBLICATIONS

De Wildt, R.M. and Hoet, R.M., The Recovery of Immunoglobulin Sequences from Single Human B Cells by Clonal Expansion. Methods Mol Biol. 2002; 178:121-31.
Dinarello, C.A., Interleukin-1 in the Pathogenesis and Treatment of Inflammatory Diseases. Blood. 2011; 117(14):3720-32.
Dinarello, C.A., Immunological and Inflammatory Functions of the Interleukin-1 Family, Annual Review of Immunology, 2009, 27: 519-550.
Diu, A. et al., Activation of Resting Human B Cells by Helper T-cell Clone Supernatant: Characterization of a Human B-cell-activating Factor. Proc Natl Acad Sci USA. 1987; 84(24):91404.
Durocher, Y. et al., High-level and High-throughput Recombinant Protein Production by Transient Transfection of Suspension-growing Human 293-EBNA1 Cells. Nucleic Acids Res. 2002; 30(2):E9 (9 pages).
Edelman, et al., "The Covalent Structure of an Entire γG Immunoglobulin Molecule", PNAS USA, May 1, 1969, 63(1): 78-85.
Extended European Search Report for European Patent Application No. 21191122.7, mailed Nov. 24, 2021.
Geisse, S. et al., Eukaryotic Expression Systems: A Comparison. Protein Expr Purif. 1996; 8(3):271-82.
Guyer, R.L. et al., Immunoglobulin Binding by Mouse Intestinal Epithelial Cell Receptors. J Immunol. 1976; 117(2):587-93.
Hawkins, R.E. et al., Selection of Phage Antibodies by Binding Affinity: Mimicking Affinity Maturation. J Mol Biol. 1992; 226(3):889-96.
Hoffmann, P. et al., Murine Bone Marrow-derived Macrophages Constitute Feeder Cells for Human B Cell Hybridomas. J Immunol Methods. 1996; 196(1):85-91.
Huang, J. et al., Recruitment of IRAK to the Interleukin 1 Receptor Complex Requires Interleukin 1 Receptor Accessory Protein. Proc Natl Acad Sci USA. 1997; 94(24):12829-32.
Huston, J.S., Protein Engineering of Single-Chain Fv Analogs and Fusion Proteins. Methods Enzymol. 1991; 203:46-88.
International Preliminary Report on Patentability mailed on Dec. 26, 2017 by the International Searching Authority for Patent Application No. PCT/EP2016/064588, which was filed on Jun. 23, 2016 and published as WO 2016/207304 on Dec. 29, 2016 (Inventor—Fischer et al.; Applicant—MAB Discovery GMBH) (9 pages).
International Search Report and Written Opinion for PCT International Patent Application No. PCT/EP2018/061846, mailed Jul. 6, 2018, 12 pages.
International Search Report and Written Opinion for PCT International Patent Application No. PCT/EP2017/060925, mailed Jul. 7, 2017, 13 pages.
International Search Report and Written Opinion mailed on Jan. 11, 2017 by the International Searching Authority for Patent Application No. PCT/EP2016/064588, which was filed on Jun. 23, 2016 and published as WO 2016/207304 on Dec. 29, 2016 (Inventor—Fischer et al.; Applicant—MAB Discovery GMBH) (15 pages).
Jackson, J.R. et al., In vitro Antibody Maturation. Improvement of a High Affinity, Neutralizing Antibody Against IL-1 R. J Immunol. 1995; 154(7):3310-9.
Jaras, M. et al., Isolation and Killing of Candidate Chronic Myeloid Leukemia Stem Cells by Antibody Targeting of IL-1 Receptor Accessory Protein. Proc Natl Acad Sci USA. 2010; 107(37):16280-5.
Jefferis, R. et al., Interaction Sites on Human IgG-Fc for FOR: Current Models. Immunol Lett. 2002; 82(1-2):57-65.
Johnson, G. and Wu, T.T., Kabat Database and Its Applications: 30 Years After the First Variability Plot. Nucleic Acids Res. 2000; 28(1):214-8.
Kabat, E.A. et al., Sequences of Proteins of Immunological Interest, 5th ed., Public Health Service, National Institutes of Health, Bethesda, MD (1991).
Kaufman, R.J., Overview of Vector Design for Mammalian Gene Expression. Mol Biotechnol. 2000; 16(2):151-60.

Kim, J.-K et al., Localization of the Site of Murine IgG1 Molecule that is Involved in Binding to the Murine Intestinal Fc Receptor. Eur J Immunol. 1994; 24(10):2429-34.
Kodituwakko, A.P. et al., Isolation of Antigen-Specific B Cells. Immunol Cell Biol. 2003; 81(3):163-70.
Krupke, D.M. et al., The Mouse Tumor Biology Database. Nat Rev Cancer. 2008; 8(6):459-65.
Lefranc, M.-P., Nomenclature of the Human Immunoglobulin Genes. Curr Protoc Immunol. 2000; Appendix 1P (37 pages).
Li, X. et al., Mutant Cells That Do Not Respond to Interleukin-1 (IL-1) Reveal a Novel Role for IL-1 Receptor-Associated Kinase. Mol Cel Biol. 1999; 19(7):4643-52.
Love, T.W. et al., Recombinant Antibodies Possessing Novel Effector Functions. Methods Enzymol. 1989; 178:515-27.
Makrides, S.C., Components of Vectors for Gene Transfer and Expression in Mammalian Cells. Protein Expr Purif. 1999; 17(2):183-202.
Mansur et al., Engagement of IL-1 receptor accessory protein (IL-1RAcP) with the monoclonal antibody AY19 provides co-activating signals and prolongs the CD2-induced proliferation of peripheral blood lymphocytes, Immunol Lett., 2011, 139(1): 52-57.
Marks, J.D. et al., Bypassing Immunization: Building High Affinity Human Antibodies by Chain Shuffling. BioTechnology. 1992; 10(7):779-83.
Morrison, S.L. et al., Chimeric Human Antibody Molecules: Mouse Antigen-Binding Domains with Human Constant Region Domains. Proc Natl Acad Sci USA. 1984; 81(21):6851-5.
Neuberger, M.C. et al., A Hapten-Specific Chimaeric IgE with Human Physiological Effector Function. Nature. 1985; 314(6008):268-70.
Norderhaug, L. et al., Versatile Vectors for Transient and Stable Expression of Recombinant Antibody Molecules in Mammalian Cells. J Immunol Methods. 1997; 204(1):77-87.
Orencole, S.F. and Dinarello, C.A., Characterization of a Subclone (D10S) of the D10.G4.1 Helper T-cell Line which Proliferates to Attomolar Concentrations of Interleukin-1 in the Absence of Mitogens. Cytokine. 1989; 1(1):14-22.
Orlandi, R. et al., Cloning Immunoglobulin Variable Domains for Expression by the Polymerase Chain Reaction. Proc Natl Acad Sci USA. 1989; 86(10):3833-7.
Ow, D.W. et al., Transient and Stable Expression of the Firefly Luciferase Gene in Plant Cells and Transgenic Plants. Science. 1986; 234(4778):856-9.
Raju, T.S., Glycosylation Variations with Expression Systems and Their Impact on Biological Activity of Therapeutic Immunoglobulins. BioProcess Intl. 2003; 1(4):44-53.
Ravetch, J.V. and Kinet, J.P., Fc Receptors. Annu Rev Immunol. 1991; 9:457-92.
Riechmann, L. et al., Reshaping Human Antibodies for Therapy. Nature. 1988; 332:323-7.
Routier, F.H., The Glycosylation Pattern of a Humanized IgGI Antibody (D1.3) Expressed in CHO Cells. Glycoconj J. 1997; 14(2):201-7.
Roy, A. et al., Increased Efficiency of 7-Irradiated versus Mitomycin C-Treated Feeder Cells for the Expansion of Normal Human Cells in Long-Term Cultures. J Hematother Stem Cell Res. 2001; 10(6):873-80.
Schier, R. et al., Identification of Functional and Structural Amino-Acid Residues by Parsimonious Mutagenesis. Gene. 1995; 169(2):147-55.
Schlaeger, E.-J and Christensen, K., Transient Gene Expression in Mammalian Cells Grown in Serum-Free Suspension Culture. Cytotechnology. 1999; 30(1-3):71-83.
Schlaeger, E.-J., The Protein Hydrolysate, Primatone RL, is a Cost-Effective Multiple Growth Promoter of Mammalian Cell Culture in Serum-Containing and Serum-Free Media and Displays Anti-Apoptosis Properties. J Immunol Methods. 1996; 194(2):191-9.
Sonderman, P. et al., The 3.2-A Crystal Structure of the Human IgG1 Fc Fragment-FcγRIII Complex. Nature. 2000; 406(6793):267-73.

(56) References Cited

OTHER PUBLICATIONS

Towne, J.E. et al., Interleukin (IL)-1 F6, IL-1F8, and IL-F9 Signal Through IL-1 Rrp2 and IL-1RAcP to Activate the Pathway Leading to NF-KB and MAPKs. J Biol Chem. 2004; 279(14):13677-13688.
Umaria, P. et al., Engineered Glycoforms of an Antineuro-Blastoma IgG1 with Optimized Antibody-Dependent Cellular Cytotoxic Activity. Nature Biotechnol. 1999; 17(2):176-80.
Wang, L. and Schultz, P.G., Expanding the Genetic Code. Chem Commun. 2002; 0(1):1-11.
Wedemayer, G.J. et al., Structural Insights into the Evolution of an Antibody Combining Site. Science. 1997; 276(5319):1665-9.
Wen, L. et al., Limiting Dilution Assay for Human B Cells Based on Their Activation by Mutant EL4 Thymoma Cells: Total and Anti-Malaria Responder B Cell Frequencies. Eur J Immunol. 1987; 17(6):887-92.
Werner, R.G., Appropriate Mammalian Expression Systems for Biopharmaceuticals. Arzneimittelforschung. 1998; 48(8):870-80.
Windheim, M. et al., Interleukin-1 (IL-1) Induces the Lys63-linked Polyubiquitination of IL-1 Receptor-Associated Kinase 1 to Facilitate NEMO Binding and the Activation of 1-K13a Kinase. Mol Cell Biol. 2008; 28(5):1783-91.
Wood, K.V., Bioluminescence and Chemiluminescence: Current Status, Stanley, P. and Kricka, L. eds., John Wiley and Sons, Chichester, NY, 11 and 543.
Wood, K.V., Firefly Luciferase: A New Tool for Molecular Biologists. Promega Notes. 1990; 28:1-3.
Yamane-Ohnuki, N. and Satoh, M., Production of Therapeutic Antibodies with Controlled Fucosylation. MAbs. 2009; 1(3):230-6.
Yelton, D.E. et al., Affinity Maturation of the BR96 Anti-Carcinoma Antibody by Codon-Based Mutagenesis. J Immunol. 1995; 155(4):1994-2004.
Yoon, D.-Y. and Dinarello, C.A., Antibodies to Domains II and III of the IL-1 Receptor Accessory Protein Inhibit IL-1R Activity But Not Binding: Regulation of IL-1 Responses Is via Type I Receptor, Not the Accessory Protein. J Immunol. 1998; 160:3170-9.
Yoon, D.-Y. and Dinarello, C.A., Differential Effects of Anti-IL-1 R Accessory Protein Antibodies on IL-1a or IL-1 R-induced Production of PGE(2) and IL-6 from 3T3-L1 Cells. J Biochem Mol Biol. 2007; 40(4): 562-70.
Zhao et al., Construction of hybridoma cells with IL1RAP as a new marker for leukemia stem cells and detection of its monoclonal antibody, J Experimental Hematology, Dec. 2013, 12(6): 1390-1393.
Zubler, R.H. et al., Polyclonal B Cell Responses in the Presence of Defined Filler Cells: Complementary Effects of Lipopolysaccharide and Anti-Immunoglobulin Antibodies. Eur J Immunol. 1984; 14(4):357-63.
U.S. Appl. No. 15/739,410 2019/0106487 U.S. Pat. No. 10,906,971, filed Dec. 22, 2017 Apr. 11, 2019 Feb. 2, 2021, Stephan Fischer, Monoclonal Anti-IL-1RACP Antibodies.
U.S. Appl. No. 16/898,074 2020/0407438 U.S. Pat. No. 11,198,728, filed Jun. 10, 2020 Dec. 31, 2020 Dec. 14, 2021, Stephan Fischer, Monoclonal Anti-IL-1RACP Antibodies.
U.S. Appl. No. 17/522,600 2022/0169718, filed Nov. 9, 2021 Jun. 2, 2022, Stephan Fischer, Monoclonal Anti-IL-1RACP Antibodies.
U.S. Appl. No. 16/099,059 2019/0194336 U.S. Pat. No. 11,203,642, filed Nov. 5, 2018 Jun. 27, 2019 Dec. 21, 2021, Stephan Fischer, Humanized Anti-IL-1R3 Antibodies.
U.S. Appl. No. 17/410,153 2022/0089751, filed Aug. 24, 2021 Mar. 24, 2022, Stephan Fischer, Humanized Anti-IL-1R3 Antibodies.
U.S. Appl. No. 16/612,052 2020/0140559 U.S. Pat. No. 11,639,392, filed Nov. 8, 2019 May 7, 2020 May 2, 2023, Stephan Fischer, Anti-IL-1R3 Antibodies for Use in Inflammatory Conditions.
U.S. Appl. No. 18/184,759, filed Mar. 16, 2023, Stephan Fischer, Anti-IL-1R3 Antibodies for Use in Inflammatory Conditions.
U.S. Appl. No. 18/471,388, filed Sep. 21, 1023, Christian Lange, Humanized Anti-IL-1R3 Antibody and Methods of Use.

\* cited by examiner

Fig. 1: Results of experiments described in examples 3-6

| | Primary supernatant | | | Recombinant purified material | | | | | |
|---|---|---|---|---|---|---|---|---|---|
| | hu-IL1RaP ELISA (OD) | mu-IL1RaP ELISA (OD) | funct. assay (%inhibition) | ELISA EC50 (ng/ml) | | functional reporter gene assay (% inhibition) | | | |
| Antibody ID | | | | hu-IL1RaP | mu-IL1RaP | 5µg/mL mAb | 1µg/mL mAb | 0.2µg/mL mAb | 0.04µg/mL mAb |
| P013.S.01.B.A02 | 3,5 | 1,2 | 92 | 42 | 25 | 98 | 95 | 94 | 46 |
| P013.S.01.B.A03 | 3,3 | 0,0 | 95 | 225 | 0 | 99 | 98 | 94 | 77 |
| P013.S.01.B.A04 | 3,4 | 0,0 | 74 | 27 | 0 | 98 | 97 | 89 | 47 |
| P013.S.01.B.A06 | 3,5 | 0,0 | 96 | 27 | 0 | 100 | 99 | 85 | 14 |
| P013.S.01.B.B02 | 3,6 | 0,0 | 97 | 175 | no fit | 98 | 94 | 84 | 75 |
| P013.S.01.B.B04 | 3,5 | 0,5 | 97 | 42 | 0 | 99 | 93 | 83 | 42 |
| P013.S.01.B.B05 | 3,3 | 0,1 | 85 | no fit | 0 | 96 | 93 | 81 | 52 |

Fig. 1 (cont.)

| | | | | | | | | | |
|---|---|---|---|---|---|---|---|---|---|
| P013.S.01.B.C02 | 3,4 | -0,1 | 82 | 105 | 0 | 98 | 99 | 78 | 18 |
| P013.S.01.B.C03 | 3,2 | 2,3 | 83 | 32 | 332 | 90 | 84 | 77 | 54 |
| P013.S.01.B.C05 | 2,5 | 0,9 | 27 | 38 | no fit | 95 | 87 | 74 | 67 |
| P013.S.01.B.C06 | 3,4 | -0,1 | 72 | 70 | 0 | 93 | 92 | 70 | 15 |
| P013.S.01.B.D02 | 4,0 | 0,1 | 99 | no fit | 0 | 92 | 88 | 68 | 44 |
| P013.S.01.B.D04 | 3,9 | 0,0 | 95 | 247 | 0 | 89 | 87 | 67 | 27 |
| P013.S.01.B.D05 | 3,4 | 1,0 | 93 | no fit | no fit | 62 | 77 | 66 | 26 |
| P013.S.01.B.D06 | 3,7 | 0,0 | 80 | 53 | no fit | 97 | 96 | 66 | 24 |
| P013.S.01.B.E03 | 3,4 | 0,1 | 73 | 50 | 0 | 68 | 60 | 63 | 54 |
| P013.S.01.B.E04 | 3,3 | -0,1 | 88 | 72 | 0 | 98 | 88 | 62 | 39 |
| P013.S.01.B.E05 | 3,6 | -0,1 | 98 | 966 | 0 | 93 | 81 | 61 | 26 |
| P013.S.01.B.E06 | 3,4 | -0,1 | 72 | 447 | 0 | 91 | 93 | 60 | 44 |
| P013.S.01.B.F02 | 3,4 | -0,1 | 76 | no fit | 0 | 93 | 80 | 59 | 45 |

Fig. 1 (cont.)

| | | | | | | | | | |
|---|---|---|---|---|---|---|---|---|---|
| P013.S.01.B.F03 | 3,4 | -0,1 | 102 | 440 | 0 | 94 | 87 | 59 | 26 |
| P013.S.01.B.F04 | 3,6 | 0,3 | 97 | 46 | no fit | 96 | 95 | 58 | 38 |
| P013.S.01.B.F05 | 3,6 | 1,2 | 89 | 52 | no fit | 80 | 70 | 54 | 44 |
| P013.S.01.B.F06 | 2,8 | 3,4 | 75 | 39 | 28 | 70 | 68 | 52 | 41 |
| P013.S.01.B.G02 | 3,7 | 0,4 | 71 | 49 | no fit | 72 | 41 | 52 | 43 |
| P013.S.01.B.G03 | 3,2 | 0,0 | 89 | 144 | 0 | 92 | 82 | 51 | 38 |
| P013.S.01.B.G04 | 3,4 | 0,0 | 99 | 255 | 0 | 95 | 84 | 51 | 15 |
| P013.S.01.B.G05 | 3,3 | -0,1 | 81 | 817 | no fit | 93 | 82 | 50 | 21 |
| P013.S.01.B.G06 | 3,8 | -0,1 | 89 | 115 | 0 | 96 | 94 | 49 | 69 |
| P013.S.01.B.H03 | 3,5 | 0,5 | 43 | 104 | no fit | 60 | 59 | 49 | 28 |
| P013.S.01.B.H04 | 3,7 | 3,2 | 35 | 62 | 0 | 54 | 49 | 49 | 10 |
| P013.S.01.B.H05 | 3,3 | 0,4 | 95 | 485 | 0 | 90 | 88 | 47 | 20 |
| P013.S.01.B.H06 | 3,6 | 0,0 | 91 | 64 | 0 | 96 | 88 | 47 | 18 |
| P013.S.02.B.A01 | 3,8 | 0,7 | 67 | 73 | no fit | 87 | 67 | 45 | 7 |

Fig. 1 (cont.)

| | | | | | | | | | |
|---|---|---|---|---|---|---|---|---|---|
| P013.S.02.B.A05 | 3,6 | 0,0 | 80 | 362 | 0 | 48 | 47 | 42 | -16 |
| P013.S.02.B.B01 | 3,6 | 0,0 | 95 | no fit | no fit | 94 | 75 | 39 | 24 |
| P013.S.02.B.B02 | 3,4 | -0,1 | 95 | 359 | 0 | 87 | 33 | 37 | 26 |
| P013.S.02.B.B03 | 3,8 | -0,1 | 94 | 287 | 0 | 89 | 78 | 31 | 17 |
| P013.S.02.B.C01 | 3,5 | -0,1 | 88 | 256 | 0 | 96 | 73 | 28 | 19 |
| P013.S.02.B.C03 | 3,6 | 0,7 | 29 | 847 | 0 | 30 | 31 | 27 | 21 |
| P013.S.02.B.C04 | 2,7 | -0,1 | 65 | 758 | 0 | 91 | 40 | 26 | 29 |
| P013.S.02.B.C05 | 3,2 | 0,7 | 66 | no fit | 0 | 52 | 35 | 26 | 7 |
| P013.S.02.B.D01 | 3,4 | -0,1 | 85 | 555 | 0 | 79 | 54 | 22 | 9 |
| P013.S.02.B.D02 | 3,3 | 0,0 | 85 | 541 | 0 | 79 | 58 | 22 | 1 |
| P013.S.02.B.D04 | 3,6 | 0,0 | 88 | no fit | 206 | 87 | 47 | 19 | 4 |
| P013.S.02.B.D05 | 3,2 | 3,3 | 42 | no fit | 0 | 13 | 20 | 19 | 1 |
| P013.S.02.B.E01 | 3,7 | -0,1 | 79 | 137 | 0 | 86 | 56 | 14 | -6 |
| P013.S.02.B.E02 | 3,3 | 0,0 | 85 | 590 | 0 | 68 | 21 | 14 | 0 |

Fig. 1 (cont.)

| | | | | | | | | |
|---|---|---|---|---|---|---|---|---|
| P013.S.02.B.E03 | 3,3 | 0,8 | 37 | 363 | no fit | 25 | 16 | 12 | 6 |
| P013.S.02.B.E04 | 3,6 | 3,5 | -37 | no fit | no fit | -6 | 8 | 9 | 11 |
| P013.S.02.B.F03 | 3,4 | 3,3 | 57 | 451 | 385 | 0 | 11 | 7 | 11 |
| P013.S.02.B.F04 | 3,5 | 0,0 | 93 | 497 | 156 | 96 | 81 | 6 | 21 |
| P013.S.02.B.F05 | 0,1 | 0,4 | 40 | no fit | 0 | -2 | 11 | 5 | 15 |
| P013.S.02.B.G01 | 2,2 | 0,4 | -36 | no fit | 44 | -5 | 10 | 1 | 1 |
| P013.S.02.B.G02 | 3,6 | 3,4 | -39 | 493 | 0 | 0 | 5 | 0 | -2 |
| P013.S.02.B.G03 | 1,4 | 1,1 | -39 | no fit | 82 | 17 | 5 | 0 | 6 |
| P013.S.02.B.G04 | 2,9 | 3,4 | 27 | no fit | no fit | -18 | 4 | 0 | -1 |
| P013.S.02.B.H02 | 3,0 | 0,8 | 36 | no fit | no fit | 28 | 28 | -2 | 25 |
| P013.S.02.B.H04 | 3,2 | 1,7 | 52 | no fit | 644 | 4 | 15 | -6 | 7 |

Fig. 2: Sequences

| Clone ID | Antibody ID | No. | VH (SEQ ID NO: 1 - 77) | VL (SEQ ID NO: 78 - 154) | CDR_H1 (SEQ ID NO: 155 - 231) | CDR_H2 (SEQ ID NO: 232 - 308) | CDR_H3 (SEQ ID NO: 309 - 385) | CDR_K1 (SEQ ID NO: | CDR_K2 (SEQ ID NO: 463 - 539) | CDR_K3 (SEQ ID NO: 540 to 616) |
|---|---|---|---|---|---|---|---|---|---|---|
| P013.A.0 0003.H11 | P013.S.01. B.A02 | 1 | QSVEESGGRLVTPGTPL TLTCTVSGIDLSSYAMG WVRQAPGKGLEYIGVIT SSATTYYASWAKGRFTI SKTSSTTVDLRVTSLTT EDTATYFCARGGPGYST | AFEMTQTPSSVSEPVGG TVTIKCQASQSIYIYLS WYQQKPGQRPKLLIYDA SKLASGVPSRFSGSGSG TEFTLTISGVQSDDAAT | SYAM G | VITSS ATTYY ASWAK G | GGPGY STNTH YAFDP | QASQS IYIYL S | DASK LAS | QQGA TTYN VDNV |

Fig. 2 (cont.)

| | | | | | | | | |
|---|---|---|---|---|---|---|---|---|
| P013.A.0 0088.A07 | P013.S.01. B.A03 | 2 | NTHYAFDPWGPGTLVTV SS | QEQLEESGGDLVQPEGGS LTVTCTASGFSFGYY MCWVRQAPGKGLEWIAC IYGDSSDTLYANWAKGR FTVSKTSSTTVTLQMTS LTAADTATYFCARYPGG SYYNLWGPGTRVTVSS | YYCQQGATTYNVDNVFG GGTEVVVK | FGYY MC | CIYGD SSDTL YANWA KG | YPGGS YYNL | QASQT ISINL A | YAST LAS | QQGY TEDN IDNT |
| P013.A.0 0085.C03 | P013.S.01. B.A04 | 3 | | QEQLEESGGGLVKPGGT LTLTCKASGIDFSSYYY MCWVRQAPGKGLEWIAC IFIGYGDVTWYASWAKG RFTISKASSTTVTLQMT SLTAADTATYFCARALG SSGYRVNLWGPGTLVTV SS | ALVMTQTPSSVSAAVGG TVTINCQASENIYSSLA WYQQKPGQPPKLLIYDA SDLASGVPSRFKGSGSG KEFTLTISDLESDDAAT YYCQQGYYSGGTDNDVF GGTEVVVK | SYYY MC | CIFIG YGDVT WYASW AKG | ALGSS GYRVN L | QASEN IYSSL A | DASD LAS | QQGY YSGG TDND V |
| P013.A.0 0133.B12 | P013.S.01. B.A06 | 4 | | QSLEESGGRLVTPGTPL TLSCKVSGFSLSSYDMS WVRQTPGKGLEWIGTIY IGGTTAYASWPKGRFTI SKTSTTVDLKITSPTKE | DVVMTQTPASVSEPVGG TVTIKCQASQSIYSFLS WYQQKPGQPPKLLIYAA SDLESGVPSRFSGSGSYG TEFTLTISDLESADAAT | SYDM S | TIYIG GTTAY ASWPK G | LQGAN YYNSL AL | QASQS IYSFL S | AASD LES | QCNY IIDY GA |

Fig. 2 (cont.)

| ID 1 | ID 2 | # | Sequence 1 | Sequence 2 | CDR-H1 | CDR-H2 | CDR-H3 | CDR-L1 | CDR-L2 | CDR-L3 |
|---|---|---|---|---|---|---|---|---|---|---|
| P013.A.0 0014.B03 | P013.S.01. B.B02 | 5 | QQLEQSGGAEGGLVKP GGSLELCCKASGFSLSS SYWICWVRQAPGKGLEW IGCIYTGSSGITYYASW VNGRFTLSRDIDQSTGC LQLNSLTAADTAMYYCA KDGPSTLFNFWGQGTLV TVSS | DTATYFCARLQGANYN SLALWGQGTLVTVSS (heavy) / ALVMTQTPSPVSAAVGG TVTINCQASEDIYSNLA WFQQKPGQPPKLLIYRA STLASGVPSRFKGSGSG TEFTLTISGLQSDDAAT YYCLGVYTYPSADNAFG GGTEVVVR | SSYW IC | CIYTG SSGIT YYASW VNG | DGPST LFNF | QASED IYSNL A | RAST LAS | LGVY TYPS ADNA |
| P013.A.0 0086.E02 | P013.S.01. B.B04 | 6 | QSVEESGGRLVTPGTPL TLTCTVSGIDLDNYAMG WVRQAPGKGLEYIGVIS SDGFFYDASWAKGRFTI SKASSTTVDLKMTGLTP EDTATYFCARDRGTSTG SLDLWGQGTLVTVSS | ALVMTQTPASVSEPVGG TVTIKCQASENIGNGLA WYQQKPGQPNLLIYGA STLASGVPSRFSGSGYG TEFTLTVSDLESGDAAT YYCQCTYWNPDYIGGAF GGGTEVVVT | NYAM G | VISSD GFFYD ASWAK G | DRGTS TGSLD L | QASEN IGNGL A | GAST LAS | QCTY WNPD YIGG A |
| P013.A.0 0030.D07 | P013.S.01. B.B05 | 7 | QSLEESGGRLVTPGTPL TLTCTASGFSLSSYYMS WVRQAPGKGLEWVGIIS GSASTYYATWAKGRFTI SKTSTTTVDLKIASPTTE | AIEMTQSPPSLSASVGE TVRIRCLASEDIYSGIS WYQQKEGKPPTLLIYAA SNLESGVPPRFSGSGSG TDYTLTIGGVQAEDAAT | SYYM S | IISGS ASTYY ATWAK G | THYAA VAGYG YASRL DL | LASED IYSGI S | AASN LES | LGGY SYSN TGPT |

Fig. 2 (cont.)

| | | | | | | | | | | |
|---|---|---|---|---|---|---|---|---|---|---|
| P013.A.0 0014.C10 | P013.S.01. B.C02 | 8 | DTATYFCARTHYAAVAG YGYASRLDLWGQGTLVT VSS QSLEESGGDLVKPGASL TLTCTASGFSESSSSHYM CWVRQAPGKGLEWIACI YAGSSGNTYYANWAKGR FTISKTSSTTVTLQMTS LTAADTATYFCARVDAS SSGSWDLWGPGTLVTVS S | YCLGGYSYSNTGPTFG AGTKVEIK AIEMTQTPFSVSAAVGG TVTINCQASESIYSNLA WYQQILGQPPKLLIYAA SLLASGVPSRFKGSGSG TEYTLTISGVQSADAAT YYCQSASYSTGPDWTFG GGTEVVVE | SSHY MC | CIYAG SSGNT YYANW AKG | VDASS SGSWD L | QASES IYSNL A | AASL LAS | QSAS YSTG PDWT |
| P013.A.0 0133.D11 | P013.S.01. B.C03 | 9 | QSVEESGGRLVTPGTPL TLTCTVSGIDLSNYAMS WVRQAPGKGLEWIGSVI SGGSTYYATWARGRFTI SKSSTTVDLKMTSLTTE DTATYFCARGCPGYNGD KYTFDLWGPGTLVTVSS | AFEMTQTPSSVSEPVGG TVTIKCQASQSIYNYLS WYQQKPGQPRPKLLIYRA STLASGVPSRFKGSGSG TEFTLTISGVESADAAT YYCQQGATSYDIENPFG GGTEVVVK | NYAM S | SVISG GSTYY ATWAR G | GCPGY NGDKY TFDL | QASQS IYNYL S | RAST LAS | QQGA TSYD IENP |
| P013.A.0 0045.E06 | P013.S.01. B.C05 | 10 | QSVEESGGRLVTPGTPL TLTCTVSGFSLSNYAMS WVRQAPGKGLEYIGIID SGGSAYYATWARGRFTI | AFEMTQTPSSVSEPVGG TVTIKCQASQSIYNYLS WYQQKPGQPPKLLIYDA SELASGVPSRFKGSGSG | NYAM S | IIDSG GSAYY G | GGPAY STNTH YTLDL | QASQS IYNYL S | DASE LAS | QQGA TTYN IENV |

Fig. 2 (cont.)

| | | | VH | VL | H1 | H2 | H3 | L1 | L2 | L3 |
|---|---|---|---|---|---|---|---|---|---|---|
| P013.A.0 0014.D06 | P013.S.01. B.C06 | 11 | SRTSTTVDLKMTSPTTE DTATYFCARGGPAYSTN THYTLDLWGPGTLVTVS S | TEFTLTLTISGVQSDDAAT YYCQQGATTYNIENVFG GGTEVVVK | | ATWAR G | | | | |
| | | | QSVEESGGRLVTPGGSL TLTCTVSGFSLSIYAMG WFRQAPGKGLEWIGDIY AGSGSTWYASWAKGRFT ISKTSTTVDLKITSPTT EDTATYFCAREIDAGYV GYGFNLWGQGTLVTVSS | AQALTQTPSSVSAAVGG TVTINCQSSQSVYSDYL AWYQQKPGQPPKLLIYQ ASKLATGVPSRFKGSGS GTQFTLTISGVQSDDAA TYYCQATYYGSGWYRAF GGGTELVVK | IYAM G | DIYAG SGSTW YASWA KG | EIDAG YVGYG FNL | QSSQS VYSDY LA | QASK LAT | QATY YGSG WYRA |
| P013.A.0 0022.E06 | P013.S.01. B.D02 | 12 | QQLEQSGGAEGGLVKP GGSLELCCKASGFSLTT NYWICWVRQAPGKGLEW IGCIYANSVGSTYYASW VNGRFTLSRDIDQSTGC LQLNSLTAADTAMYYCA RVDPGYSFDAFDPWGPG TLVTVSS | ALVMTQTPSPVSAAVGG TVTINCQASEDIYSNLA WFQQKPGQPPKLLIYRA STLASGVPSRFSGSGSG TEFTLTISALQSDDAAT YYCLGVRTYFNTLNNSF GGGTEVVVK | TNYW IC | CIYAN SVGST YYASW VNG | VDPGY SFDAF DP | QASED IYSNL A | RAST LAS | LGVR TYFN TLNN S |

Fig. 2 (cont.)

| | | | VH | CDRH1 | CDRH2 | CDRH3 | VL | CDRL1 | CDRL2 | CDRL3 |
|---|---|---|---|---|---|---|---|---|---|---|
| P013.A.0 0088.B09 | P013.S.01. B.D04 | 13 | QEQLKESGGRLVTPGGS LTLTCTVSGFSLSIYAM GWFRQAPGKGLEWIGDI YPGSDSTWYASWAKGRF TISKTSTTVDLKITSPT TEDTATYFCAREIDAGY VGYGFDLWGQGTLVTVS S | IYAM G | DIYPG SDSTW YASWA KG | EIDAG YVGYG FDL | AQALTQTPSSVSAAVGG TVTINCQSSQSVYSDYL AWYQQKPGQSPKLLIYK ASKLASGVPSRFKGSGS GTEFTLTISGVQSDDAA TYYCQATYSVGWYRAF GGGTEVVVK | QSSQS VYSDY LA | KASK LAS | QATY YSVG WYRA |
| P013.A.0 0085.G03 | P013.S.01. B.D05 | 14 | QQLEQSGGGAEGGLVKP GGSLELYCKASGFSLSS DAWICWVRQAPGKGLEW IGCIYAGSASNTYYATW VNGRFTLSRDIAQSTGC LQLNSLTAADTAMYYCA RDRGYDDYGDITRLDLW GQGTLVTVSS | SDAW IC | CIYAG SASNT YYATW VNG | DRGYD DYGDI TRLDL | ALVLTQTPSPVSAAVGG TVTINCQASEDIYSNLA WFQQKPGQPPKLLIYRA STLASGVPSRFSGSGSG TEFTLTISGLQSDDAAT YYCLGVYTYLSDLFFVE GGGTEVVVK | QASED IYSNL A | RAST LAS | LGVY TYLS DLFF V |
| P013.A.0 0029.D02 | P013.S.01. B.D06 | 15 | QSLEESGGDLVKPGASL TLTCTASGFSSSYYM CWVRQAPGKGLEWIACI YAGSSVTYYASWAKGR FTISDTSSTTVTLQMTS | SSYY MC | CIYAG SSGVT YYASW AKG | ETDGN YFNL | ALVMTQTPSPVSAAVGG TVTINCQASEDIYSNLA WFQQKPGQPPKLLIYRA STLASGVPSRFSGSGSG TEFTLTISGLQSDDAAT | QASED IYSNL A | RAST LAS | LGVY TYST DIHA |

Fig. 2 (cont.)

| | | | | | | | | | |
|---|---|---|---|---|---|---|---|---|---|
| P013.A.0 0015.E03 | P013.S.01. B.E03 | 16 | LTAADTATYFCASETDG NYFNLWGPSTLVTVSS YCLGVYTYSTDIHAFG GGTEVVVK | NYHIS | YIYAG RDFTY YANWA EG | DGGSP NWTLD L | QASES ISDYL S | RAST LES | QSNY YDSR GNA |
| | | | DVVMTQTPASVSEPVGG TVTINCQASESISDYLS WYQQKPGQPPKLLIYRA STLESGVSSRFKGSGSG TQFTLTISDLRSADAAT YYCQSNYYDSRGNAFGG GTEVVVK | | | | | | |
| P013.A.0 0109.D07 | P013.S.01. B.E04 | 17 | QSVEESGGRLVTPGTPL TLTCTVSGIDLNSNGIN WVRQAPGKGLEWIGYIG AGDITYCASWAKGRFTI SKTSSTTVDLKITSLTT EDTATYFCARWGPGALD LWGQGTLVTVSS | SNGI N | YIGAG DITYC ASWAK G | WGPGA LDL | QSSQS VYNNN YLS | KAST LAS | AGFY ETTD VG |
| | | | AQVLTQTASSVSATVGG TVTISCQSSQSVYNNNY LSWYQQKPGQPPKLLIY KASTLASGVPLRFSGSG SGTQFTLTISGVQSDDA ATYYCAGFYETTDVGFG GGTEVVVK | | | | | | |
| P013.A.0 0086.F02 | P013.S.01. B.E05 | 18 | QSLEESGGDLVKPGASL TLTCTASGISFSSSDFM CWVRQAPGKGLEWIACI YAGSSVSIYYATWAKGR FTISKASSTTVTLQMAS LTVADTATYFCARSTGS | SSDF MC | CIYAG SSVSI YYATW AKG | STGSV GRGFN L | QASQS VYNSN BLS | SAST LAS | QGEF SCVS ADCI A |
| | | | AQVLTQTPSPVSAAVGG TVTISCQASQSVYNSNH LSWYQQKPGQPPRLLIY SASTLASGVPSRFKGSG SGTQFTLTISGVQSDDA | | | | | | |

Fig. 2 (cont.)

| | | | | | | | | | |
|---|---|---|---|---|---|---|---|---|---|
| P013.A.0030.F07 | P013.S.01.B.E06 | 19 | VGRGFNLWGQGTLVTVS S QSLEESGGDLVKPGASL TLTCTASGFSFSSTYYM CWVRQAPGKGLEWIACI YAGSSGSTYYASWAKGR FTISKTSSTTVTLQMTS LTAADTATYFCARVDGS SSGSWDLWGPGTLVTVS S | ATYYCQGEFSCVSADCI AFGGGTEVVVK AIEMTQTPSSVSAAVGG TVTINCQASQNIYSNLA WYQQKPGQRPKLLIYAA SLLASGVPSRFKGNGSG TEYTLTISDLRSADAAT YYCQGAVYSGNTEWAFG GGTEVVVK | STYY MC | CIYAG SSGST YYASW AKG | VDGSS SGSWD L | QASQN IYSNL A | AASL LAS | QGAV YSGN TEWA |
| P013.A.0043.D08 | P013.S.01.B.F02 | 20 | QEQLVESGGGLVQPEGGS LTLTCTASGFSSSNYW MCWVRQAPGKGLEWIAC IYTGGSGVTYYASWAKG RFTLSKTSSTTVTLQVT SLTAADTATYFCARDLV VVTSFNLWGQGTLVTVS S | ALMMTQTPSPVSAAVGG TVTINCQASEDIYSNLA WYQQKPGQPPKLLIYSA STLASGVPSRFSGSGSG TEFTLTISGVQSDDAAT YYCLGVCTDISVDDVYN SFGGGTEVVVK | SNYW MC | CIYTG GSGVT YYASW AKG | DLVVV TSFNL | QASED IYSNL A | SAST LAS | LGVC TDIS VDDV YNS |
| P013.A.0025.F02 | P013.S.01.B.F03 | 21 | QQLEQSGGGAEGGLVKP GGSLELCCKASGFSLGS SYWICWVRQAPGKGLEW IGCIYAGSSGITYYASW | ALVMTQTPSPVSAAVGG TVTINCQASEDIYSNLA WFQQKPGQPPKLLIYQA STLASGVPSRFSGSGSG | SSYW IC | CIYAG SSGIT | DIYAS TSGYD L | QASED IYSNL A | QAST LAS | LGVC TYIG |

Fig. 2 (cont.)

| | | | | | | | | | |
|---|---|---|---|---|---|---|---|---|---|
| P013.A.0 0133.A12 | P013.S.01. B.F04 | | VSGRFTLSRDIDQSTGC LQLNSLTAADTAMYYCA RDIYASTSGYDLWGQGT LVTVSS | TEFTLTISGLQSDDAAA YYCLGVCTYIGADNTLY NTFGGGTEVVVK | | YYASW VSG | | | ADNT LYNT |
| | | 22 | QQLEQSGGGAEGGLVKP GGSLELCCKASGFSLST SYWRCWVRQAPGKGLEW IGCIYAGSSDATYYANW VNGRFTLSRDIDQSTGC LQLNSLTAADTAMYYCA SGVGFGYFNLWGQGTLV TVSS | ALVMTQTPSPVSAAVGG TVTINCQASEDIYSNLA WFQQKPGQPPKLLIYDA STLASGVPSRFSGSGSG TEFTLTISGLQSDDAAT YYCLGVYTHISADNAFG GGTEVVVK | TSYW RC | CIYAG SSDAT YYANW VNG | GVGFG YFNL | QASED IYSNL A | DAST LAS | LGVY THIS ADNA |
| P013.A.0 0087.C06 | P013.S.01. B.F05 | 23 | QSLEESGGRLVTPGGSL TLTCTVSGIDLSNYAMS WVRQAPGKGLEWIGSVI SGGSTYYATWAKGRFTI SKTSTTVDLKMTSLTTE DTATYFCARGCPGYNGD KYALDLWGPGTVVTVSS | AFEMTQTPSSVSEPVGG TVTIKCQASQSIHNYLS WYQQKPGQRPKLLIYRA STLASGVPSRFKGSGSG TEFTLTISGVESADAAT YYCQQGATSYDIDNAFG GGTEVVVK | NYAM S | SVISG GSTYY ATWAK G | GCPGY NGDKY ALDL | QASQS IHNYL S | RAST LAS | QQGA TSYD IDNA |

Fig. 2 (cont.)

| P013.A.0 | P013.S.01 | # | Sequence | | | | | | |
|---|---|---|---|---|---|---|---|---|---|
| 0045.E09 | B.F06 | 24 | QSVEESGGRLVTPGTPL TLTCTVSGIDLSSDAVG WVRQAPGKGLEYIGIIV SSGETFYASWARGRCTI SKTSSTTVDLRITRLTT EDTATYFCARGGPGYSF DTEYAFDPWGPGTLVTV SS | AFEMTQTPASVEVAVGG TVTINCQASQSIGSWLS WYQQKVGQRPKLLISRA STLASGVPSRFKGSGSG TEYTLTISGVQSDDAAT FYCQQGATTYDVDNVEG GGTEVVVR | SDAV G | IIVSS GETFY ASWAR G | GGPGY SFDTE YAFDP | QASQS IGSWL S | RAST LAS | QQGA TTYD VDNV |
| 0085.B11 | B.G02 | 25 | QSVEESGGRLVTPGTPL TLTCTVSGFSLSSYYMS WVRQAPGKGLEWIGYIY AAGPITYYATWAKGRFT ISKTSTTVDLKITSPTT EDTATYFCVRDGSGSGT YGYNGMDLWGPGTLVTV SS | AYDMTQTPASVEAAVGG TVNIKCQASQSISNWLA WYQQKPGQRPKLLIYRA STLASGVSSRFKGSGSG TQFTLTISGVESADAAT YYCQQGASTTDVDNVFG GGTEVVVK | SYYM S | YIYAA GPITY YATWA KG | DGSGS GTYGY NGMDL | QASQS ISNWL A | RAST LAS | QQGA STTD VDNV |
| 0030.C03 | B.G03 | 26 | QEQLVESGGGLVQPEGS LTLTCKASGFDFSSNYY MCWVRQAPGKGLELIAC IYTNSGNTWSASWAKGR FTISKTSSTTVTLQMTS | DIVMTQTPASVEAAVGG TVTIKCQASQSIGYYLA WYQQKPGQPPKLLISRA STLASGVPSRFKGSGSG TQFTLTISDLESADVAT | SNYY MC | CIYTN SGNTW SASWA KG | DLNYP DTSNL | QASQS IGYYL A | RAST LAS | QSYY NSDS DA |

Fig. 2 (cont.)

| ID1 | ID2 | SEQ ID NO | VH | VL | CDRH1 | CDRH2 | CDRH3 | CDRL1 | CDRL2 | CDRL3 |
|---|---|---|---|---|---|---|---|---|---|---|
| | | | LTAADTATYFCARDLNYPDTSNLWGQGTLVTVSS | YYCQSYNSDSDAFGGGTEVVVK | | | | | | |
| P013.A.0 0013.G06 | P013.S.01. B.G04 | 27 | QSVEESGGRLVTPGTPLTLTCTVSGFSLSVYAMGWFRQAPGKGLEWIGDIYIASDGTWYANWAKGRFTISKTSTTVDLKITSPTTEDTATYFCAREIDAGYVGYGFNLWGQGTLVTVSS | AQALTQTPSPVSAAVGGTVTINCQSSQSVYSDYLGWYQQKPGQPPKLLIYWASKLETGVPSRFKGSGSGTQFTLTISGVQSDDAATYYCQATYYGSGWYRAFGGGTEVVVK | VYAM G | DIYIA SDGTW YANWA KG | EIDAG YVGYG FNL | QSSQS VYSDY LG | WASK LET | QATY YGSG WYRA |
| P013.A.0 0088.C10 | P013.S.01. B.G05 | 28 | QQLEQSGGGAEGGLVKPGGSLELCCKASGFSLSSAYWICWVRQAPGKGLEWVGCIYADSSSITYYASWVNGRFTLSRDIDQSTGCLQLNSLTAADTAMYYCAYYCLGVCTYINANGWDNAFGGGTEVVVK | ALVMTQTPSPVSAAVGGTVTISCQASEDIYSNLAWYQQKRGQPPKLLIYYASTLASGVPSRFSGSGSGTEFTLTISGLQSDDAATRDYGGSGYNFNLWGQGTLVTVSS | SAYW IC | CIYAD SSSIT YYASW VNG | DYGGS GYNFN L | QASED IYSNL A | YAST LAS | LGVC TYIN ANGW DNA |
| P013.A.0 0085.H05 | P013.S.01. B.G06 | 29 | QSLEESGGRLVTPGTPLTLFCTASGFTISSYYMSWVRQAPGKGLEWIGGIATDGNTYYANWAKGRFTVTDGNTYYANWAKGRFTVSRTSTTVDLKVTSPTAE | AYDMTQTPASVEVAVGGTVTIIKCQASQSIYIYLAWYQQKFGQRPKQLIYDASKLASGVPSRFSGSGSGTEFTLTISGVESADAAT | SYYM S | GIATD GNTYY ANWAK G | GGPAY SRGTH YAMDL | QASQS IYTYL A | DASK LAS | QQGA TIWN VDNP |

Fig. 2 (cont.)

| | | | | | | | | | |
|---|---|---|---|---|---|---|---|---|---|
| P013.A.0 0045.A02 | P013.S.01. B.H03 | 30 | QSVEESGGRLVTPGTPL TLTCTVSGFSLSSYYMS WVRQAPGKGLEWIGYIY AAGPITYYATWAKGRFT ISKTSTTVDLKITSPTT EDTATYFCVRDGSGSGT YGYNGMDLWGPGTLVTV SS | DTATYFCARGGPAYSRG THYAMDLWGPGTLVTVS S | YYCQQGATIWNVDNPFG GGTEVVVK | SYYM S | YIYAA GPITY YATWA KG | DGSGS GTYGY NGMDL | QASQS ISNWL A | RAST LAS | QQGA STTD VDNV |
| P013.A.0 0014.G05 | P013.S.01. B.H04 | 31 | QSVEESGGRLVTPGTPL TLTCTVSGFSLDSYAMG WVRQAPGKGLEWIGIIN SYGSIYYASWAKGRFTI SKTSTTVDLKMTSLTTE DTATYFCARSAYSNNGD RLHLWGQGTLVTVSS | DIVMTQTPSPVSGAVGG TVTIKCQASEDIYSNLA WYQQKPGQPPKLLIYYV STLESGVPSRFKGSRSG TDYTLTISDLESADAAT YYCQCTEGGSGSDYTFG GGTEVVVK | | SYAM G | IINSY GSIYY ASWAK G | SAYSN NGDRL HL | QASED IYSNL A | YVST LES | QCTE GGSG SDYT |
| P013.A.0 0109.F08 | P013.S.01. B.H05 | 32 | QQLEQSGGAEGGLVKP GGSLELCCKASGFSLSN SYWICWVRQAPGKGLEW IGCIYVGSSGSTYYASW | ALVMTQTPSPVSAAVGG TVTINCQASEDIYSNLA WFQQKPGQPPKLLIYRA STLASGVPSRFSGSGSG | | NSYW IC | CIYVG SSGST | DGATS TSGHL FEL | QASED IYSNL A | RAST LAS | LGIY TYIS SDYT |

Fig. 2 (cont.)

| | | | | | | | | | | |
|---|---|---|---|---|---|---|---|---|---|---|
| P013.A.0086.B03 | P013.S.01.B.H06 | 33 | QQLEQSGGGGEGGLVKP GGSLELCCKASGFSLSS SYWICWVRQAPGKGLEW IGCIYVGSSGSTYYASW VSGRFTLSRDIDQSTGC LQLNSLHAADTAMYYCA RDIYGSTNGYDLWGQGT LVTVSS | VNGRFTLSRDIDQSTGC LQLNSLTAADTAIYYCA RDGATSGHLFELWGQ GTLVTVSS | TEFLTLSGVQSDDAAT YYCIGIYTYISADGSLY NAFGGGTEVVVK | SSYW IC | CIYVG SSGST YYASW VSG | | DIYGS TNGYD L | QASED IYSNL A | QASK LAS | LGVG TYTS GDGS LDNA |
| P013.A.0087.A07 | P013.S.02.B.A01 | 34 | QSVEESGGGRLVTPGTPL TLFCTVSGFSLSSYYMS WVRQAPGKGLEWIGYIY AAGPITYYATWAKGRFT ISKTSTTVDLKITSPTT EDTATYFCVRDGSGSGT YGYNGMDLWGPGTLVTV SS | AYDMTQTPASVEAAVGG TVTIKCQASQSISNWLA WYQQKPGQRPKLLIYRA STLASGVSSRFKGSGSG TQFTLTISGVESADAAT YYCQQGASTTDVDNVFG GGTEVVVK | SYYM S | YIYAA GPITY YATWA KG | | DGSGS GTYGY NGMDL | QASQS ISNWL A | RAST LAS | QQGA STTD VDNV |
| | | | | | ADGS LYNA | YYASW VNG | | | | |

Fig. 2 (cont.)

| | | | | | | | | | |
|---|---|---|---|---|---|---|---|---|---|
| P013.A.0031.D11 | P013.S.02.B.A05 | 35 | QEQLVESGGGLVQPEGS LTLTCQASGFTFSSYYV ICWVRQAPGKGLEWIAC IGTGDGLTYYASWAKGR FTISKTSTTVTLQMTS LTAADTATYFCARDRYA TVSGILNLWGPGTLVTV SS | DVVMTQTPASVEAAVGG TVTIKCQASQNIYSNCA WYQQKLGQRPKLLIYYV STLESGVPSRFEGSGYG TEFTLTISDLQSADAAT YCQYTYDSSSTSWAF GGGTEVVVK | SYYV IC | CIGTG DGLTY YASWA KG | DRYAT VSGIL NL | QASQN IYSNC A | YVST LES | QYTY DSSS STSW A |
| P013.A.0088.A11 | P013.S.02.B.B01 | 36 | QSLEESGGRLVTPGTPL TLTCTVSGFSLSGYAMS WVRQAPGKGLEWIGIIY AGSGGTYYASWVKGRFT ISKTSTTVDLKITSLTT EDTATYFCARAVPDDSA GKKLMGQGTLVTVSS | DIVMTQTPASVEAAVGG TITINCQASENIYSSLA WYQQKPGQPPKLLIYDA STLASGVSSRFKGSGSG TQFTLTISGVQSDDAAT YCQSYYCSVSSSCGYG FGGGTEVVVK | GYAM S | IIYAG SGGTY YASWV KG | AVPDD SAGKK L | QASEN IYSSL A | DAST LAS | QSYY CSVS SSCG YG |
| P013.A.0045.H10 | P013.S.02.B.B02 | 37 | QQLAQSGGGAEGGLVKP GGSLELCCEASGFSLSS SYWICWVRQAPGKGLEW IGCIYTGSSGNTYYASW VNGRFTLSRDIDRSTGC LQLNSLTAADTAMYYCA | ALVMTQTPSPVSAAVGG TVTINCQASEDIYSNLA WFQQKPGQPPKLLIYDA STLASGVPSRFSGSGSG TEFTLTISGLQSDDAAT YCLGVYTYISADGTLV YNAFGGGTEVVVR | SSYW IC | CIYTG SSGNT YYASW VNG | DANSH YMMNL | QASED IYSNL A | DAST LAS | LGVY TYIS ADGT LVYN A |

Fig. 2 (cont.)

| | | | | | | | | | |
|---|---|---|---|---|---|---|---|---|---|
| | | | RDANSHYMNLWGQGTL VTVSS | | | | | | |
| P013.A.0 0045.F11 | P013.S.02. B.B03 | 38 | QEQLEESGGDLVKPEGS LTLTCTASGFSFSSNYW ICWVRQAPGKGLELIAC IYTSTGNTWYASWAKGR FTISKTSTTVTLQMTS LTVADTATYFCARDLIV VTSFNLWGQGTLVTVSS | SNYW IC | CIYTS TGNTW YASWA KG | DLLVV TSFNL A | QASED IYSNL A | GAST LAS | LGVC TDIS TDDL YNA |
| P013.A.0 0109.C12 | P013.S.02. B.C01 | 39 | QSVEESGGRLVTPGGSL TLTCTVSGFSLSVYAMG WFRQAPGKGLEWIGDIY TGSGSTWYASWAKGRFT ISKTSTTVDLKITSPTT EDTATYFCAREIDAGYV GYGFNLWGQGTLVTVSS | VYAM G | DIYTG SGSTW YASWA KG | EIDAG YVGYG FNL | QSSQS VYSDY LV | QASK LAS | QATY SSTG WYRA |
| P013.A.0 0085.G07 | P013.S.02. B.C03 | 40 | DIVMTQTPASVSAPVGG TVTINCQASESIYSDLA WYQQKPGQPPKLLISFV ATLESGGVPSRFKGSGS GTEFTLTISDLESADAAT TEFTLTISDLESADAAT | SYAM G | IISNS GTTYY ASWAK G | DRYAN THGIF SL | QASES IYSDL A | FVAT LES | QCTY GGSG SGNG AA |

Fig. 2 (cont.)

| | | | | | | | | |
|---|---|---|---|---|---|---|---|---|
| P013.A.0 0085.H07 | P013.S.02. B.C04 | 41 | EDTATYFCARDRYANTH GIFSLWGQSTLVTVSS | YYCQCTYGGSGSGNGAA FGGGTEVVVK | | | | |
| | | | QQLEQSGGGLVKPGGSL ELCCKASGFSLSSSYWI CWVRQAPGKGLEWIGCI YAGSSGSTYYANWVNGR FTLSRDIDQSTGCLQLS SLTAADTAMYYCARSIV DFSSGWGDLWGQGTLVT VSS | ALVMTQTPSPVSAAVGG TVTINCQASEDIYSNLA WYQQKPGQPPKLLMYGV STLASGVPSRFSDSGSG TEFTLTISGLQSDDAAT YYCLGVYTYISDVYYTF GGGTEVVVK | SSYW IC | CIYAG SSGST YYANW VNG | STVDF SSGWG DL | QASED IYSNL A | GVST LAS | LGVY TYIS DVYY T |
| P013.A.0 0085.F10 | P013.S.02. B.C05 | 42 | QSLEESGGRLVTPGTPL TLSCTASGFSLSTYYMS WVRQAPGKGLEWIGYMH VGGFPVYYASWAKGRFTI SKTSTTVDLKITSPTIE DTATYFCARDFGPPNWT LDLWGQGTLVTVSS | DVVMTQTPASVEAAVGG TVTIKCQASQSISSYCS WYQQKPGQPPKLLIYRA STLESGVPSRFKGSGSG TEFTLTISDLESADAAT YYCQSSYYDLLGNGFGG GTEVVVK | TYYM S | YMHVG GFPVY ASWAK G | DFGPP NWTLD L | QASQS ISSYC S | RAST LES | QSSY YDLL GNG |
| P013.A.0 0141.G02 | P013.S.02. B.D01 | 43 | QQLEQSGGGAEGGLVKP GGSLELCCKASGFSLSS NYWMCWVRQAPGKGLEW IGCIYAGSSDSTYYASW VNGRFTLSRDIDQSTGC | ALVMTQTPSPVSAAVGG TVTINCQASEDIYSNLA WFQQKPGQPPKLLIYDA STLASGVPSRFSGSGSG TEFTLTISGLQSDDAAT | SNYW MC | CIYAG SSDST YYASW VNG | PGYGG YGYYG L | QASED IYSNL A | DAST LAS | LGVY TYIS PDGT DNA |

Fig. 2 (cont.)

| | | | | | | | | | |
|---|---|---|---|---|---|---|---|---|---|
| P013.A.0 0086.F05 | P013.S.02. B.D02 | | LQLNSLTAADTAMYYCA SPGYGGYGYIGLWGQGT LVTVSS | YYCLGVYTYISPDGTDN AFGGGTEVVVK | | | | | |
| | | 44 | QSLEESGGDLVKPGASL KLSCTASGVSESSAYWM CWVRQAPGKGLEWIACI YAGSGSTYYASWAKGR FTISKTSSTTVTLQMTS LTAADTATYFCARHAAW FELDLWGPGTLVTVSS | ALVMTQTPSPVSAAVGG TVTINCQASQNIASAYL SWYQQKPGQPPKLLIYA ASTLTDGVPSRFKGSGS VTEFTLTISGVQSDDAA TYYCAGYKSYTDDEFAF GGGTEVVVK | SAYW MC | CIYAG SSGST YYASW AKG | HAAWF ELDL | QASQN IASAY LS | AAST LTD | AGYK SYTD DEFA |
| P013.A.0 0086.A06 | P013.S.02. B.D04 | 45 | QSLEESGGDLVQPGGSL TLTCKASGFSFSASYWI CWVRQAPGKGLEWIGCI YIGGGRYYASWAKGRF TISKTSSTTVTLQMTSL TAADTATYFCARDPVTS GSDYVYDLWGPGTLVTV AS | AYDMTQTPASVEVAVGG TVTIKCQASESISTWLA WYQQKPGQPPNLLIYRA STLASGVPSRFYGSGYG TEFTLTISGVESADAAT YYCQQGYTVNNIDNVFG GGTEVVVK | ASYW IC | CIYIG GGGRY YASWA KG | DPVTS GSDYV YDL | QASES ISTWL A | RAST LAS | QQGY TVNN IDNV |
| P013.A.0 0086.B09 | P013.S.02. B.D05 | 46 | QQQLVESGGGLVKPGAS LTLTCKASGFSSSGYY MCWVRQAPGKGLEWIAC IGMGSGKTYYASWAKGR STLASGVSSRFKGSGS | DIVMTQTPASVEAAVGG TVTIRCQASQSISSYLA WYQRKPGQPPKVLIYKA STLASGVSSRFKGSGSG | SGYY MC | CIGMG SGKTY | KDGSG NEHYN L | QASQS ISSYL A | KAST LAS | QQGY ASSG VDNV |

Fig. 2 (cont.)

| | | | | | | | | | | |
|---|---|---|---|---|---|---|---|---|---|---|
| P013.A.0 0013.G07 | P013.S.02. B.E01 | 47 | FTISKTSSTTVTLQMTS LTAADTATYFCARKDGS GNEHYNLWGPGTLVTVS S | TEYLTLTISDLESADAAT YYCQQGYASSGVDNVFG GGTEVVK | | YASWA KG | | | | |
| | | | QSLEESGGRLVTPGTPL TLTCTVSGFSLSIYGMG WVRQAPGEGLEWIGSIS SGGSTYYATWAKGRFTI SKTSSTTLDLKITSPTT EDTATYFCVRSDGYTNG DYDTYFNLWGQGTLVTV SS | DIVMTQTPASVSEPVGG TVTIRCQASQSISSWLS WYQQKPGQPPKLLIYQA SALASGVSSRFIGSGYG TEFTLTISGVQSEDAAT YYCQCTYGIGSNSDYGV AFGGGTEVVVK | IYGM G | SISSG GSTYY ATWAK G | SDGYT NGDYD TYFNL | QASQS ISSWL S | QASA LAS | QCTY GIGS NSDY GVA |
| P013.A.0 0087.E09 | P013.S.02. B.E02 | 48 | QSVEESGGRLVTPGTPL TLTCTVSGFSLNVYNMG WVRQAPGKGLEYIGIIS SSGTTYYASWAKGRFTI SKTSSTTVDLKITSLTT EDTATYFCARADGYTEG DYATYFNLWGQGTLVTV SS | DIVMTQTPASVSEPVGG TVTIRCQASQSITTWLA WYQQKPGQPPKLLIYQA SALASGVSSRFIGSGYG TEFTLTISGVQSEDAAT YYCQCTYGIGSGSSYGV AFGGGTEVVVK | VYNM G | IISSS GTTYY ASWAK G | ADGYT EGDYA TYFNL | QASQS ITTWL A | QASA LAS | QCTY GIGS GSSY GVA |

Fig. 2 (cont.)

| | | | VH | VL | CDR-H1 | CDR-H2 | CDR-H3 | CDR-L1 | CDR-L2 | CDR-L3 |
|---|---|---|---|---|---|---|---|---|---|---|
| P013.A.0 0091.A10 | P013.S.02. B.E03 | 49 | QSVEESGGRLVTPGTPL TLTCTVSGFSLSDYYMG WVRQAPGKGLEWIGTID GGGSTYYASWAKGRFTV SKTSTTVDLTITSPTTE DTAIYFCARNYYAGLSD VFFGWWGQGTLVTVSS | DVVMTQTPASVEAAVGG TVTIMCQASETIYSGLA WYQQKPGQPPKLLIYYT SSLASGVPSRFKGSGSG TEFTLTISDLESADAAT YYCQTYDSEGRSYGYN SFGGGTEVVVK | DYYM G | TIDGG GSTYY ASWAK G | NYYAG LSDVF FGW | QASET IYSGL A | YTSS LAS | QTYY DSEG RSYG YNS |
| P013.A.0 0088.A02 | P013.S.02. B.E04 | 50 | QSLEESGGDLVKPGASL TLTCTASGFSLSSGGMS WVRQAPGKGLGWIGYIN TGSGSTYYASWVNGRFT ISKTSSTTVSLQMTSLT AADTATYFCAGGLPSDL WGPGTLVTVSS | DIVMTQTPSSVEAAVGG TVTIIKCQASQS INSRLA STLASGVSSRFKGSGSG TEFTLTISDLESADGAT YYCLSHYLTSSSSYGDA FGGGTEVVVK | SGGM S | YINTG SGSTY YASWV NG | GLPSD L | QASQS INSRL A | SAST LAS | LSHY LTSS SSYG DA |
| P013.A.0 0013.D12 | P013.S.02. B.F03 | 51 | AQVLTQTPSSVSAAVGG TLTCTASGFSLIYTYVM CGVRQAPGKGLEWIACI YTGRSGGLYYANWAKGR FTISKTSSTTVTLQMTS LTAADTATYFCARYIGA WGPWSLWGPGTLVTVSS | AQVLTQTPSSVSAAVGG TVTINCQSSPSVYNNYL SWYQQKPGQPPKLLIYG ASSLASGVPSRFKGSGS GTQFTLTISDLESDDAA TYYCQGGYNSYSDTFAF GGGTEVLVK | YTYV MC | CIYTG RSGGL YYANW AKG | YIGAW GPWSL | QSSPS VYNNY LS | GASS LAS | QGGY NSYS DTFA |

Fig. 2 (cont.)

| | | | | | | | | | | |
|---|---|---|---|---|---|---|---|---|---|---|
| P013.A.0 0109.B02 | P013.S.02. B.F04 | 52 | QEQLVESGGDLVKPEGS LTLTCTASGFSFSSNYW ICWVRQAPGKGLEWIAC IYTSTDTTYYPNWAKGR FTISKTSTTVTLQMTS LTAADTATYFCARDLLV VTSFNLWGQGTLVTVSS | ALVMTQTPSPVSAAVGG TVTINCQASEDIYSNLA WFQQKPGQPPKLLIYGA STLASGVPSRFSGSGSG TEFTLTISGVQSDDAAT YYCLGVCTDISADDLYN TFGGGTEVVVK | SNYW IC | CIYTS TDTTY YPNWA KG | DLLVV TSFNL | QASED IYSNL A | GAST LAS | LGVC TDIS ADDL YNT |
| P013.A.0 0109.B04 | P013.S.02. B.F05 | 53 | RSLEESGGDLVKPGTSL TLTCTASGFSFSGNYYM CWVRQAPGKGLEWIACI VVGSGGNTYYAGWAKRR SKLASGVPSRFKGSGSG FTISKTSSTTVTLQMTS LTAADTATYFCASGSYD DYGDYWFTLWGQGTLV TVSS | AIDMTQTPSPASAGVGD TVTINCQASENIYNFLA WYQQKPGHSPKLLIYVA SKLASGVPSRFKGSGSG TQFTLTISDVQSDDAAT YYCQQTYRYNDGDTAFG GGTEVVVK | GNYY MC | CIVVG SGGNT YYAGW AKR | GSYDD YGDYW YFTL | QASEN IYNFL A | VASK LAS | QQTY RYND GDTA |
| P013.A.0 0015.G07 | P013.S.02. B.G01 | 54 | QSVEESGGRLVTPGGSL TLTCKVSGFSLSDYDIY WVRQAPGKGLEWIGVID IENSVYYPTWAKGRFTI SKTSTTVDLKITSPTTE DTATYFCARGDYIMTLD LWGQGTLVTVSS | AAVLTQTPSPVSAAVGG TVTISCQASQSVYKNNR LAWYQQKPGQPPKLLIY LASTLASGVPSRFKGSG SGTQFTLTISDLESDDA ATYYCAGGYSTISENAF GGGTEVVVK | DYDI Y | VIDIE NSVYY PTWAK G | GDYIM TLDL | QASQS VYKNN RLA | LAST LAS | AGGY STIS ENA |

Fig. 2 (cont.)

| | | | | | SGGM | YINTG | GLPSD | QASQS | DAST | LSHY |
|---|---|---|---|---|---|---|---|---|---|---|
| P013.A.0 0014.C07 | P013.S.02. B.G02 | 55 | QSLEESGGDLVKPGASL TLTCTASGFSLSSGGMT WVRQAPGKGLEWIGYIN TGSGRTYYASWAKGRFI ISKTSSTTVSLQMTSLT AADTATYFCAGGLPSDL WGPGTLVTVSS | DIVMTQTPSSVEAAVGG TVTIKCQASQSINSRLA WYQQKPGQPPKLLIYDA STLASGVSSRFSGSGTE FTLTISDLESADGATYY CLSHYLTSSSSYGNAFG GGTEVVVK | T | SGRTY YASWA KG | L | INSRL A | LAS | LTSS SSYG NA |
| P013.A.0 0014.D07 | P013.S.02. B.G03 | 56 | QSVEESGGRLVTPGTPL TLTCTVSGFSLSSYGMI WVRQAPGEGLEWIGFIG RGGATWYASWVKGRFTI SKTSTTVDLKITSPTAS DTATYFCARDGDSSDYY AFNLWGQGTLVTVSS | DVVMTQTPASVSEPVGG TVTIKCQASQNIGSNLA WYQQRSGQPPKLLIYGA STLASGVPSRFSGSGSG TEFTLTISGVQSADAAT YFCQCSGYDITGVFPFG GGSEVVVK | I | FIGRG GATWY ASWVK G | DGDSS DYYAF NL | QASQN IGSNL A | GAST LAS | QCSG YDIT GVFP |
| P013.A.0 0015.A11 | P013.S.02. B.G04 | 57 | QSLEESGGRLVTPGTPL TLTCTVSGFSLSRCAMI WVRQAPGKGLEWIGFIG RGGSTWYASWVNGRFTI SKTSTTVDLKITSPTTE DTATYFCARDGDYSDYY TFDLWGQGTLVTVSS | DVVMTQTPASVSERVGG TVTIKCQASQSIGSNLA WYQQKPGQPPKLLIYGA SNLESGVPSRFSGSGSG TEFTLSISGVQSADAAT YYCQCSGYDTTGVFPFG GGSEVVVK | I | FIGRG GSTWY ASWVN G | DGDYS DYYTF DL | QASQS IGSNL A | GASN LES | QCSG YDTT GVFP |

Fig. 2 (cont.)

| | | | | | | | | | | |
|---|---|---|---|---|---|---|---|---|---|---|
| P013.A.0 0015.B10 | P013.S.02. B.H02 | 58 | QSLEESGGRLVTPGTPL TLTCTVSGFSLSSCAMI WVRQAPGKGLEWIGFIG RGGSTWYASWVNGRFTI SKTSTTVDLKITSPTTE DTATYFCARDGDFSDYY TFNLWGQGTLVTVSS | DVVMTQTPASVSEPVGG TVTIKCQASQNIGSNLA WYQQKPGQPPKLLIYGA STLASGVPSRFSGSGSG TEFTLTISGVQSADATT YYCQCSGYDTTGVFPFG GGSEVVVR | SCAM I | FIGRG GSTWY ASWVN G | DGDFS DYYTF NL | QASQN IGSNL A | GAST LAS | QCSG YDTT GVFP |
| P013.A.0 0029.F11 | P013.S.02. B.H04 | 59 | QSVEESGGRLVKPDETL TLTCTVSGIDLSSYAMG WVRQAPGKGLEYIGIIS SSGRTYYANWAKGRFTI SKASSTTVDLKITSPTT EDTATYFCARLITVDYY IYDYFNLWGQGTLVTVS S | AYDMTQTPASVEAAVGG TVTIKCQASQSISSYLS WYQQKPGQPPKLLIYGA STLASGVPSRFKGSGSG TEYTLTISGVQSESDDAAT YYCQQGYSYNNVDNTFG GGTEVVVK | SYAM G | IISSS GRTYY ANWAK G | LITVD YYIYD YFNL | QASQS ISSYL S | GAST LAS | QQGY SYNN VDNT |
| P013.A.0 0109.C07 | P013.S.01. B.B03 | 60 | QSLEESGGRLVTPGTPL TLTCKASGFSLSSYWMS WVRQARGKGLEWIGMIY GSGYTYYASWAKGRFTI STTSTTVDLSVTSPTAE DTATYFCARDPQYFILW GQGTQVTVSS | QAVVTQTPSPVSAAVGG TVIISCQSSQSVDGNNL LSWYQQKPGQPPKLLIY DASNLASGVPSRFSGSG SGTQFTLTISGVQSDDA ATYYCGGSYYSSSWYNV FGGGTEVVVK | SYWM S | MIYGS GYTYY ASWAK G | DPQYF IL | QSSQS VDGNN LLS | DASN LAS | QGSY YSSS WYNV |

Fig. 2 (cont.)

| | | | | | | | | | | |
|---|---|---|---|---|---|---|---|---|---|---|
| P013.A.0 0029.F08 | P013.S.02. B.A04 | 61 | QSVEESGGRLVTPGGSL TLTCTVSGFSLSIYAMG WFRQAPGKGLEWIGDIY AGSGSTWYASWVKGRFT ISSTSTTVDLKITSPTT EDTATYFCAREIDAGIV GYGFNLWGQGTLVTVSS | AQALTQTPSSVSAAVGG TVTINCQSSQSVYSDYL AWYQQKPGQPPKLLIYW ASKLASGVPSRFKGSGS GTQFTLTISGVQSDDAA TYYCQATYNGRGWYRAF GEGTEVVVK | IYAM G | DIYAG SGSTW YASWV KG | EIDAG YVGYG FNL | QSSQS VYSDY LA | WASK LAS | QATY NGRG WYRA |
| P013.A.0 0015.E05 | P013.S.01. B.A05 | 62 | QQLEQSGGAEGGLVKP GGSLELCCKASGFSLST SYWRCWVRQAPGKGLEW IGCIYAGSGDVTYYANW VNGRFTLSRDIDQSTGC LQLNSLTAADTAMYYCA SGVGFGYFNLWGQGTLV TVSS | ALVMTQTPSPVSAAVGG TVTINCQASEDIYSNLA WFQQKPGQPPKLLIYDA STLASGVPSRFSGSGSG TEFTLTISGLQSDDAAT YYCLGVYTHISADNAFG GGTEVVVK | TSYW RC | CIYAG SGDVT YYANW VNG | GVGEG YFNL | QASED IYSNL A | DAST LAS | LGVY THIS ADNA |
| P013.A.0 0030.G09 | P013.S.02. B.A02 | 63 | QSVEESGGRLVTPGTPL TLTCTVSGIDLSSYDMS WVRQAPGEGLEWIGTIY VSGRVYYATWAKGRFTI SKTSSTTVDLEITSPTT EDTATYFCARGSIDYDP WGPGTLVTVSS | AYDMTQTPASVEAAVGG TVTIKCQASQSISSWLS WYQQKPGQPPKQLIYRA STLASGVSSRFKGSGSG TDYTLTISGVQSDDAAT YYCQQGYITSSNIKNVF GGGTEVVVK | SYDM S | TIYVS GRVYY ATWAK G | GSIDY DP | QASQS ISSWL S | RAST LAS | QQGY ITSS NIKN V |

Fig. 2 (cont.)

| | | | | | | | | | | | |
|---|---|---|---|---|---|---|---|---|---|---|---|
| | | | | | SSYW IC | CIYTG SGGTY YASWE KG | DPGYS SWL | QASES ISNYL S | LAST LAS | QNWW VIEH NGAA | |
| P013.A.0 0086.H05 | P013.S.02. B.D03 | 64 | QSLEESGGGLVQPEGSL TLTCTASGFSFSSSYWI CWVRQAPGKGLEWIGCI YTGSGGTYYASWEKGRF TISKSTSTTVTLQMTSL TAADTATYFCARDPGYS SWLWGQGTLVTVSS | DVVMTQTPASVSGPVGG TVTINCQASESISNYLS WYQQKSGQPPKLLIYLA STLASGVPSRFKGSGSG TEFTLTISDLESADAAT YYCQNWWVIEHNGAAFG GGTEVVVK | | | | | | | |
| P013.A.0 0087.F04 | P013.S.01. B.C04 | 65 | QSVEESGGRLVTPGTPL TLTCTVSGIDLSTYTMS WVRQAPGKGLEYIGIIL SSGSTYYATWAKGRFTI SKTSSTTVDLKMTSLTT EDTAMYFCARGGPGYSI DTKYAFDPWGPGTLVTV SS | AFEMTQTPSSVSEPVGG TVTIKCQASQNIYIYLS WYQQKPGQPPKLLIYDA STLASGVSSRFSGSGSG TEFTLTISGVQSEDAAI YYCQQGATTYDVDNVFG GGTEVVVK | TYTM S | IILSS GSTYY ATWAK G | GGPGY SIDTK YAFDP | QASON IYIYL S | DAST LAS | QQGA TTYD VDNV | |
| P013.A.0 0087.B02 | P013.S.01. B.H02 | 66 | QEQLEESGGGLVQPEGS LTLTCTASGFSFSSGYD MCWVRQAPGKGLEWIGC IYTGSGSTYYANWAKGR FTISKTSSTTVTLQMTS LTAADTATYFCARNSND WMYFNLWGPGTLVTVSS | DIVMTQTPASVEAAVGG TVTIKCQASESISANYW SWYQQKPGQPPKLLIYG ASTLASGVPSRFKGSGS GPQFTLTISDLESADAA TYFCQSWYSGSGSYHS WAFGGGTEVVLK | SGYD MC | CIYTG SGSTY YANWA KG | NSNDW MYFNL | QASES ISANY WS | GAST LAS | QSWY YSGS GSYH SWA | |

Fig. 2 (cont.)

| | | | Heavy Chain | CDR-H1 | CDR-H2 | CDR-H3 | Light Chain | CDR-L1 | CDR-L2 | CDR-L3 |
|---|---|---|---|---|---|---|---|---|---|---|
| P013.A.0 0013.B07 | P013.S.01. B.B06 | 67 | QSLEESGGRLVTPGTPL TLFCTASGFTISSYHMS WVRQAPGKGLEWIGGIA TDGNTYYANWAKGRFTV SRTSTTVDLKVTSPTAE DTATYFCARGGPAYSRG THYAMDLWGPGTLVTVS S | SYHMS | GIATD GNTYY ANWAK G | GGPAY SRGTH YAMDL | AYDMTQTPASVEVAVGG TVTIKCQASQSIYIYLA WYQQKPGQRPKQLIYDA SKLASGVPSRFSGSGSG TEFTLTISGVESADAAT YYCQQGATIWNVDNPFG GGTEVVVK | QASQS IYIYL A | DASK LAS | QQGA TIWN VDNP |
| P013.A.0 0029.G05 | P013.S.02. B.H01 | 68 | QSLEESGGRLVTPGTPL TLTCTVSGIDLSSYAMS WVRQAPGKGLEYIGVIG SSGNLYYASWAKGRFTI SKTSTTVDLKMTSLTTE DTATYFCARYTIDSGIY TYDLWGQGTLVTVSA | SYAMS | VIGSS GNLYY ASWAK G | YTIDS GIYTY DL | AAVLTQTPSPVSAAVGG TVSISCQSSQSVYGNNE LSWFQQKPGQPPKLLIY GASILASGVPSRFSGSG SGTEFTLTISDVQSDDA ATYYCAGGYSSTSDNAF GGGTEVVVK | QSSQS VYGNN ELS | GASI LAS | AGGY SSTS DNA |
| P013.A.0 0014.B07 | P013.S.02. B.F01 | 69 | QSVEESGGRLVTPGTPL TLTCTVSGFDSSVYAMS WVRQAPGKGLEWIGISV SNIRTWYATWAKGRFTI SKTSTMVDLKMTSLTTE DTATYFCARHVSRSGNY GLDLWGQGTLVTVSS | VYAMS | ISVSN IRTWY ATWAK G | HVSRS GNYGL DL | DVVMTQTPASVSEPVGG TVTIKCQASEDISSYLA WYQQKPGQPPKLLIYDA SDLASGVPSRFSGGGYG TEFSLTISDLESADAAT YYCQCADYATTYGLGAF GGGTEVVVK | QASED ISSYL A | DASD LAS | QCAD YATT YGLG A |

Fig. 2 (cont.)

| | | | | | | | | | | |
|---|---|---|---|---|---|---|---|---|---|---|
| P013.A.0 0031.D05 | P013.S.02. B.B04 | 70 | QSVEESGGRLVTPGGSL TLTCTVSGFSLSVYAMG WFRQAPGKGLEWIGDIY AGSVNTWYATWAKGRFT ISKTSTTVDLKITSPTT EDTATYFCAREIDAGYV GYGFNLWGQGTLVTVSS | AQALTQTPSSVSAAVGG TVTINCQSSQSVYSDYL AWYQQKPGQPPKLLISQ ASKLASGVPSRFKGSGS GTQFTLTISDLESDDAA TYYCQATYSSSGWYRAF GGGTEVVVK | VYAM G | DIYAG SVNTW YATWA KG | EIDAG YVGYG FNL | QSSQS VYSDY LA | QASK LAS | QATY SSSG WYRA |
| P013.A.0 0085.D06 | P013.S.02. B.C02 | 71 | QSLEESGGRLITPGGSL TLTCTVSGFSLSSYHMQ WVRQAPGKGLEYIGYIN SLGGSYYASWAKGRFTI SKTSTTVDLKITSPTTA DTATYFCARDFAGSDLW GQGTLVTVAS | AYDMTQTPASVEVAVGG TVTIKCQASQSIDYYLA WYQQKPGQPPKLLIYRA STLASGVSSRFKGSGSG TDYTLTISGVESADAAT YYCQQGYSGNNVDNTFG GGTEVVVK | SYHM Q | YINSL GGSYY ASWAK G | DFAGS DL | QASQS IDYYL A | RAST LAS | QQGY SGNN VDNT |
| P013.A.0 0055.F08 | P013.S.02. B.B05 | 72 | QSVEESGGRLVTPGTPL TLTCTVSGFSLNDYAMI WVRQAPGEGLEYIGFIE PGGRAYCASWAKGRFTI SRTSTTVDLKMTSLTTE DTATYFCARSYVFYSTY PYASDLWGQGTLVTVSS | AQVLTQTASPVSAAVGG TVTINCQSSQSVNGNNY LAWYQQKPGQPPKLLIW LASSLASGVPSRFKGSG SGTQFALTISDLESDDA ATYYCAGAYSTSGEENA FGGGTEVVVK | DYAM I | FIEPG GRAYC ASWAK G | SYVFY STYPY ASDL | QSSVFY VNGNN YLA | LASS LAS | AGAY STSG EENA |

Fig. 2 (cont.)

| | | | | | | | | | |
|---|---|---|---|---|---|---|---|---|---|
| P013.A.0 0013.A04 | P013.S.01. B.D03 | 73 | QEQLVESGGGLVQPEGS LTLTCTASGFSFSSIYY MCWVRQAPGKGLEWIGC IYTGNSDFTYANWAKG RLSISRSTSLSTVTLQM TSLTAADTATYFCARFR DDYASLKLWGPGTLVTV SS | DVVMTQTPASVSEPVGG TVTIKCQASQSISSYLS WYQQKPGQPPKLLIYGA SNLASGVPSRFKGSSG TEFTLTISDLESADAAT YYCQCTYYDNNYGGAFG GGTEVVVK | SIYY MC | CIYTG NSDFT YYANW AKG | FRDDY ASLKL | QASQS ISSYL S | GASN LAS | QCTY YDNN YGGA |
| P013.A.0 0029.G11 | P013.S.01. B.E02 | 74 | QEHLMESGGGLVQPEGS LTLSCTASGFSFSSTYW ICWVRQAPGKGLEWIGC INTGSGSTYYANWVKG RFTISKTSSTTVTLQMT SLTAADTATYFCARGDD SYYELMGQGTLVTVSS | DTVLTQTPSSVSAAVGD TVTIKCQASQNIYSGLA WYQQKPGQPPKLLIYYA STLASGVPSRFKGSSG TEFTLTISDLESADAAT YYCQTYYGVYYGIIFG GGTEVVVK | STYW IC | CINTG SGGST YYANW VKG | GDDSY YEL | QASQN IYSGL A | YAST LAS | QTYY GVVV YGII |
| P013.A.0 0029.F07 | P013.S.02. B.A03 | 75 | QQLEQSGGGAEGGLVKP GGSLELCCKASGFSQSN NYWMHWVRQAPGKGLEW IGCIYAGSSDSTYYASW VNGRFTLSRDIDQSIGC LQLNSLTAADTAIYYCA | ALVMTQTPSPVSAAVGG TVTINCQASEDIYSNLA WFQQKPGQPPKLLIYGA STLASGVPSRFSGSGSG TEFTLTISGLQSDDAAT YCYLGVCTDISAVYNVF GGGTEVVVK | NNVW MH | CIYAG SSDST YYASW VNG | AIADF SSGWG DL | QASED IYSNL A | GAST LAS | LGVC TDIS AVYN V |

Fig. 2 (cont.)

| | | | | | | | | | | |
|---|---|---|---|---|---|---|---|---|---|---|
| | | | RAIADFSSGWGDLWGQG TLVTVSS | | | | | | | |
| P013.A.0 0015.H10 | P013.S.02. B.H03 | 76 | QSLEESGGGLVTPGASL TLTCTASGFTLSSDYWI CWRQAPGKGLEWIACI YAGSSVTYYARWAKGRF TISKTSSTTVTLQMTSL TAADTATYFCARGGLWG PGTLVTVSS | AQVLTQTPSSMSAAVGG TVTINCQASQSVYKNNY LSWYQQKPGQPPKRLMY SASTLDSGVPLRFSGSG SGTQFTLTISDVQSEDA ATYYCQGNYDCSSADCI AFGGGTEVVVK | SDYW IC | CIYAG SSVTY YARWA KG | GGL | QASQS VYKNN YLS | SAST LDS | QGNY DCSS ADCI A |
| P013.A.0 0133.G05 | P013.S.02. B.G05 | 77 | QSLEESGGRLVTPGTPL TLTCTVSGFSLSRCAMI WVRQAPGKGLEWIGFIG RGGSTWYASWVNGRFTI SKTSSTTVDLKITSPTT EDTATYFCARDGDYSDY YTFDLWGQGTLVTVSS | DVVMTQTPASVSEPVGG TVTIKCQASQNIGSNLA WYQQKPGQPPKLLIYGA STLASGVPSRFSGSGSG TEFTLTISGVQSADAAT YYCQCSGYDTTGVFPFG GGSEVVVK | RCAM I | FIGRG GSTWY ASWVN G | DGDYS DYYTF DL | QASQN IGSNL A | GAST LAS | QCSG YDTT GVFP |

Fig. 3: Inhibition of ligand induced signaling

| Antibody ID | IL1α | IL-1β | IL-33 | IL-36 |
|---|---|---|---|---|
| P013.S.01.B.B03 | Yes | Yes | Yes | Yes |
| P013.S.02.B.A04 | Yes | Yes | Yes | Yes |
| P013.S.01.B.A05 | Yes | Yes | Yes | Yes |
| P013.S.02.B.A02 | Yes | Yes | Yes | Yes |
| P013.S.02.B.D03 | Yes | Yes | Yes | Yes |
| P013.S.01.B.C04 | Yes | Yes | Yes | Yes |
| P013.S.01.B.H02 | Yes | Yes | Yes | Yes |
| P013.S.01.B.B06 | Yes | Yes | Yes | Yes |
| P013.S.02.B.H01 | Yes | Yes | Yes | Yes |
| P013.S.02.B.F01 | Yes | Yes | Yes | Yes |
| P013.S.02.B.B04 | Yes | Yes | Yes | Yes |
| P013.S.02.B.C02 | Yes | Yes | Yes | Yes |
| P03.S.02.B.B05 | Yes | Yes | Yes | Yes |
| P013.S.01.B.D03 | Yes | Yes | Yes | Yes |
| P013.S.01.B.E02 | Yes | Yes | Yes | Yes |
| P013.S.02.B.A03 | NO | Yes | Yes | Yes |
| P013.S.02.B.H03 | Yes | Yes | Yes | Yes |
| P013.S.02.B.G05 | Yes | Yes | Yes | Yes |

Fig. 4: Inhibition of ligand induced signaling by selected antibodies
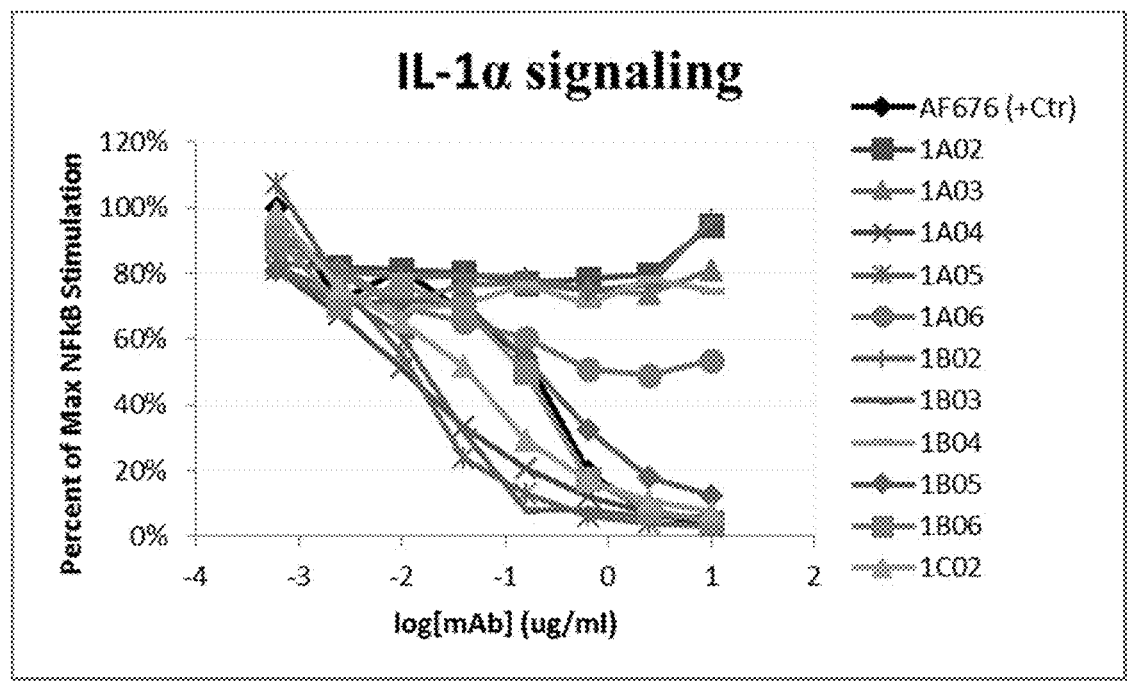
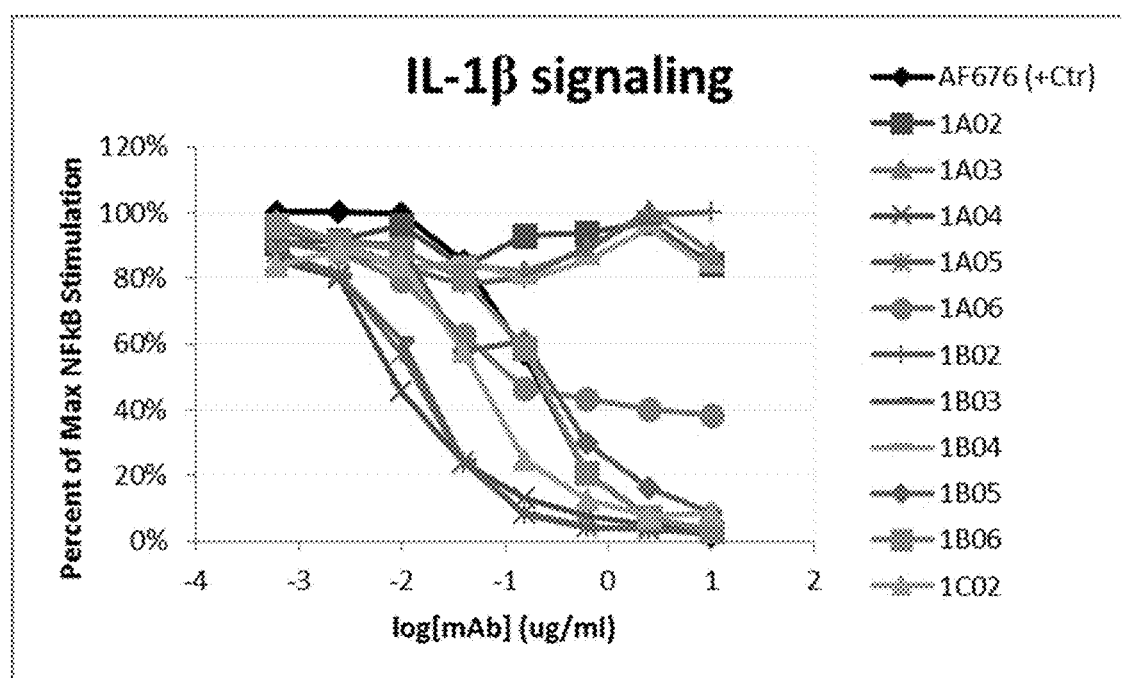

Fig. 5: NF-κB neutralizing activity of selected antibodies against IL-1RAcP

| Antibody ID | % inhibition | | | |
|---|---|---|---|---|
| | 5 ug/ml mAb | 1 ug/ml mAb | 0,2 ug/ml mAb | 0,04 ug/ml mAb |
| P013.S.01.B.B03 | 99 | 98 | 94 | 77 |
| P013.S.02.B.A04 | 98 | 94 | 84 | 75 |
| P013.S.01.B.A05 | 96 | 94 | 49 | 69 |
| P013.S.02.B.A02 | 97 | 94 | 83 | 69 |
| P013.S.02.B.D03 | 85 | 80 | 76 | 69 |
| P013.S.01.B.C04 | 95 | 87 | 74 | 67 |
| P013.S.01.B.H02 | 90 | 84 | 77 | 54 |
| P013.S.01.B.B06 | 96 | 92 | 80 | 53 |
| P013.S.02.B.H01 | 96 | 93 | 81 | 52 |
| P013.S.02.B.F01 | 97 | 92 | 85 | 51 |
| P013.S.02.B.B04 | 98 | 97 | 89 | 47 |
| P013.S.02.B.C02 | 98 | 95 | 94 | 46 |
| P03.S.02.B.B05 | 93 | 80 | 59 | 45 |
| P013.S.01.B.D03 | 92 | 88 | 68 | 44 |
| P013.S.01.B.E02 | 91 | 93 | 60 | 44 |
| P013.S.02.B.A03 | 75 | 72 | 49 | 44 |
| P013.S.02.B.H03 | 80 | 70 | 54 | 44 |
| P013.S.02.B.G05 | 96 | 83 | 66 | 43 |

Fig. 6: Inhibition of ligand induced signaling of antibodies with preferred sequences

| VH (SEQ ID NO.) | VL (SEQ ID NO.) | IL-1α | IL-1β | IL-33 | IL-36 |
|---|---|---|---|---|---|
| 60 | 137 | + | + | + | + |
| 62 | 139 | + | + | + | + |
| 65 | 142 | + | + | + | + |
| 66 | 143 | + | + | + | + |
| 67 | 144 | + | + | + | + |
| 74 | 151 | + | + | + | + |
| 2 | 79 | + | + | + | + |
| 5 | 82 | + | + | + | + |
| 29 | 106 | + | + | + | + |
| 10 | 87 | + | + | + | + |
| 9 | 86 | + | + | + | + |
| 7 | 84 | + | + | + | + |
| 3 | 80 | + | + | + | + |
| 1 | 78 | + | + | + | + |
| 20 | 97 | + | + | + | + |
| 12 | 89 | + | + | + | + |
| 19 | 96 | + | + | + | + |
| 23 | 100 | + | + | + | + |
| 4 | 81 | + | + | + | + |

MONOCLONAL ANTI-IL-1RAcP ANTIBODIES

RELATED APPLICATIONS

This application is a continuation of U.S. patent application Ser. No. 16/898,074, filed Jun. 10, 2020, which is a continuation of U.S. patent application Ser. No. 15/739,410, filed Dec. 22, 2017, now U.S. Pat. No. 10,906,971, which is a 35 U.S.C. § 371 filing of International Patent Application No. PCT/EP2016/064588, filed Jun. 23, 2016, which claims priority to European Patent Application Nos. 15200772.0, filed Dec. 17, 2015, and 15174184.0, filed Jun. 26, 2015, the entire disclosures of which are hereby incorporated herein by reference.

FIELD OF THE INVENTION

The present invention relates to monoclonal anti-IL-1RAcP antibodies, methods for the production and uses thereof.

BACKGROUND

Human IL-1RAcP (Q9NPH3 (IL1AP_HUMAN, UniProtKB/Swiss-Prot) is an accessory protein that is required to transmit signals through receptors of the IL-1 family. The interleukin-1 receptor complex is a heterodimer of IL-1R1 and IL-1RAcP. Upon binding of IL-1, IL-1R1 associates with IL-1RAcP forming a functional signaling receptor complex, which stimulates NFkB activity.

IL-33, its receptor ST2, and IL-1RAcP form also a complex (IL-33/ST2/IL-1RAcP) with a similar activity in regard to NFkB activation as the IL-1β/IL-1R1/IL-1RAcP complex. IL-36 (IL-36α (IL-1F6), IL-36β (IL-1F8), and IL-36γ (IL-1F9)), their receptor IL-36R, and IL-1RAcP form also a complex (IL-36/IL-36R/IL-1RAcP) with a similar activity in regard to NFkB activation as the IL-1β/IL-1R1/IL-1RAcP complex.

WO199623067 relates to an IL-1RAcP antibody, which binds specifically to murine IL-1 receptor accessory protein. Examples 15 and 16 describe the attempt to generate anti-human IL1RAcP antibodies, which neutralize IL-1 biological activity. However, no such antibody is provided by WO199623067 and example 16, describing an IL-1 induced IL-6 assay is only hypothetical. Do-Young Yoon D-Y and Charles A. Dinarello C A describe in J. Immunol. 1998; 160:3170-3179 polyclonal antibodies to domains II and III of the murine IL-1RAcP which inhibit IL-1beta activity but not binding. However, at higher concentrations of IL-1beta (1000 pg/ml), this polyclonal antiserum did not block the proliferation of D10S cells. (D10S is a subclone of the murine D10.G4.1 helper T-cell which proliferates to sub-femtomolar (attomolar) concentrations of IL-1 beta or alpha in the absence of mitogens, cf. Orencole S F and Dinarello C A; Cytokine 1 (1989) 14-22). Jaras M. et al., PNAS 107 (2010) 16280-16285 describe the use of rabbit polyclonal anti-IL1RAcP antibody KMT-1 for killing CML stems cell. This antibody induces ADCC in an IL1RAcP-independent manner caused by its rabbit Fc part. Jaras et al. expect that "potential future therapeutic IL1RAP-targeting antibodies are expected to show low toxicity on normal hematopoietic cells". Polyclonal rabbit antibodies against murine IL-1RAcP were also mentioned in Do-Young Yoon and Charles A. Dinarello, Journal of Biochemistry and Molecular Biology, Vol. 40, No. 4, July 2007, pp. 562-570.

A rabbit polyclonal antibody binding to mouse, rat, and human IL1RAcP (ab8110) is commercially available from Abcam, Cambridge, Massachusetts, USA. Abcam's ab8109 binds only to human IL1RAcP. BALAGURUNATHAN Y. et al., Mol. Cancer Ther. 7 (2008) 3071-3080 mentions the use of Abcam's polyclonal rabbit anti-IL1 RAP antibody for identifying pancreatic tumor cells.

WO2002064630 relates also to IL-1RAcP and its use, but no antibodies against IL-1RAcP are described. WO2004022718 and WO2009120903 mention theoretically that antibodies against CSF1R, IL13RA1, IL1RAP, IFNAR1, IL5R, INSR, IL1RL1, LTK, and TACSTD1 could be generated according to the state of the art. However, here also no antibody against IL-1RAcP is described. WO2011021014 and WO 2012098407 (US20140017167) relate to the polyclonal rabbit anti-human IL-1RAcP antiserum KMT-1 (see Jaras et al. 2010) and its use. WO2014100772 relates to an anti-IL-1RAcP antibody binding to IL-1RAcP. However, no activity in regard to inhibition of any functional signaling receptor complex (like IL-1β(IL-1R1/IL-1RAcP) which stimulates NFkB activity is described. U.S. Pat. No. 6,280,955 relates to IL-1RAcP and its use, but again no antibodies against IL-1RAcP are described. U.S. Pat. No. 7,390,880 mentions a N-terminal fragment of IL1RAcP, but describe also no antibodies against IL-1RAcP.

WO2004100987 relates to the use of an interleukin-I (IL-1) antagonist in the preparation of a medicament for the treatment of neointimal hyperplasia and to the use of an IL-1 antagonist for the treatment of neointimal hyperplasia. As such an antagonist an anti-IL-1RAcP antibody is suggested but not further described. US2003026806 relates to antibodies binding to IL-1. WO2002064630 relates also to an IL-1 antagonist ant to IL-1RAcP protein. Though to the use of IL-1RAcP for screening for IL-1RAcP antagonists are mentioned, no such method or antagonist is disclosed.

WO2003014309 relates to the use of IL-1RAcP protein to treat chronic myelogenous leukemia. WO2013023015 relates to a method for determining the prognosis of AML and to a method for treating AML by administering an agent inhibiting expression or activity of IL-1RAcP in early stem cells. As such an agent shRNA of IL-1RAcP is mentioned.

Human NF-kB is an important regulator of expression of several genes involved in inflammation, immune response and apoptosis and therefore dysfunction of NFkB is involved in the in the pathology of various diseases, including autoimmune diseases, neurodegenerative diseases, inflammation, and cancers. For example, NF-kB pathway is an important target in the treatment of OA and inhibition of human IL1beta stimulated human NFkB activity may be for example important in the treatment of osteoarthritis. Therefore, a monoclonal antibody which regulates the human NFkB pathway via inhibiting the signaling activity of the human IL-1R1/IL-1RAcP complex would be a valuable therapeutic agent in treating various diseases of human beings.

However, attempts since about more than 15 years to generate functional monoclonal antibodies against human IL1RAcP failed and such need exists therefore still today.

SUMMARY OF THE INVENTION

The invention provides a monoclonal antibody against human IL-1RAcP. Preferably the antibody according to the invention binds in addition to murine IL-1RAcP.

The invention provides a monoclonal antibody against human IL-1RAcP characterized in inhibiting IL-1RAcP induced NFkB activity.

The invention provides a monoclonal antibody specifically binding to human IL-1RAcP. Preferably the antibody according to the invention binds in addition to murine IL-1RAcP.

The invention provides a monoclonal antibody specifically binding to human IL-1RAcP characterized in inhibiting IL-1RAcP induced NFkB activity. Preferably, the antibody according to the invention inhibits in addition murine IL-1RAcP induced murine NFkB activity.

The invention provides a monoclonal antibody against human IL-1RAcP characterized in inhibiting NFkB activity stimulated by IL-1alpha, IL-1beta, IL-33 and/or IL-36. The invention provides a monoclonal antibody against human IL-1RAcP characterized in inhibiting IL1alpha stimulated NFkB activity. The invention provides a monoclonal antibody against human IL-1RAcP characterized in inhibiting IL1beta stimulated NFkB activity.

The invention provides a monoclonal antibody against human IL-1RAcP characterized in inhibiting IL33 stimulated NFkB activity. The invention provides a monoclonal antibody against human IL-1RAcP characterized in inhibiting IL36 stimulated NFkB activity.

The invention provides a monoclonal antibody against human IL-1RAcP characterized in inhibiting NFkB activity stimulated by a complex selected from the group consisting of IL-1β/IL-1R1/IL-1RAcP, IL-1α/IL-1R1/IL-1RAcP IL-33/ST2/IL-1RAcP, and IL-36/IL-36R/IL-1RAcP.

Preferably, the antibody according to the invention is characterized in binding to murine IL-1RAcP and inhibiting murine IL-1RAcP induced murine NFkB activity.

Preferably, the antibody according to the invention is characterized in inhibiting in a concentration of 5 µg/ml (rabbit IgG isotype has a molecular weight of 150 KD) NFkB activity in 293T/17 cell lysates (293T/17 [HEK 293T/17] (ATCC® CRL-11268™)) stimulated with 0.5 µg/ml human IL-1alpha, IL-1beta, IL-33 and/or IL-36 (molecular weight see UniProtKB/Swiss-Prot), for 70% or more, preferably for 80% or more, preferably for 90% and more, and more preferably for 95% or more, related to the same assay without said antibody according to the invention.

Preferably the antibody according to the invention is characterized in inhibiting in a concentration of 5 µg/ml NFkB activity in respective mouse cell line lysates stimulated with 0.5 µg/ml murine IL-1alpha, IL-1beta, IL-33 and/or IL-36 (molecular weight see UniProtKB/Swiss-Prot), for 70% or more, preferably for 80% or more, preferably for 90% and more, and more preferably for 95% or more, related to the same assay without said antibody according to the invention.

Preferably the antibody according to the invention is characterized in exhibiting an ADCC reduced to at least 20% or lower, preferably to at least 10% or lower, of the ADCC induced by the antibody according to the invention comprising a wild-type human IgG Fc region.

Preferably the antibody according to the invention is characterized in exhibiting a reduced affinity to the human FcγRIIIA and/or FcγRIIA and/or FcγRI compared to an antibody according to the invention comprising the wildtype IgG Fc region, and wherein the ADCC induced by said antibody according to the invention is reduced to at least 20% of the ADCC induced by the antibody according to the invention comprising a wild-type human IgG Fc region.

Preferably the antibody according to the invention has a decreased effector function, like decreased ADCC and/or C1q binding. In particular the invention provides an antibody according to the invention comprising an Fc variant of a wild-type human IgG Fc region, said Fc variant comprising an amino acid substitution at position Pro329 and at least one further amino acid substitution, wherein the residues are numbered according to the EU index of Kabat, and wherein said antibody according to the invention exhibits a reduced affinity to the human FcγRIIIA and/or FcγRIIA and/or FcγRI compared to an antibody according to the invention comprising the wildtype IgG Fc region, and wherein the ADCC induced by said antibody according to the invention is reduced to at least 20% of the ADCC induced by the antibody according to the invention comprising a wild-type human IgG Fc region.

In a specific embodiment Pro329 of a wild-type human Fc region in the polypeptide described above is substituted with glycine or arginine or an amino acid residue large enough to destroy the proline sandwich within the Fcγ receptor interface, that is formed between the proline329 of the Fc and tryptophane residues Trp 87 and Trp 110 of FcγRIII (Sondermann et al.: Nature 406, 267-273 (20 Jul. 2000)). In a further aspect of the invention the at least one further amino acid substitution in the Fc variant is selected from the group consisting of S228P, E233P, L234A, L235A, L235E, N297A, N297D, or P331S and still in another embodiment said at least one further amino acid substitution is L234A and L235A of the human IgG1 Fc region or S228P and L235E of the human IgG4 Fc region.

In another aspect of the invention the antibody according to the invention provided exhibits a reduced affinity to at least one further receptor of the group comprising the human receptors FcγI, FcγIIA and C1q compared to the antibody according to the invention comprising a wild-type human IgG Fc region. In still another aspect of the invention the antibody according to the invention comprises a human IgG1 or IgG4 Fc region.

A further aspect of the invention is a use of an antibody according to the invention comprising an Fc variant of a wild-type human IgG Fc region, said antibody according to the invention having Pro329 of the human IgG Fc region substituted with glycine, wherein the residues are numbered according to the EU index of Kabat, wherein said antibody according to the invention exhibits a reduced affinity to the human FcγRIIIA and FcγRIIA for down-modulation of ADCC to at least 20% of the ADCC induced by the antibody according to the invention comprising the wildtype human IgG Fc region, and/or for down-modulation of ADCC.

Another aspect of the invention is use of an antibody according to the invention comprising an Fc variant of a wild-type human IgG Fc region, said antibody according to the invention having Pro329 of the human IgG Fc region substituted with glycine and wherein the Fc variant comprises at least two further amino acid substitutions at L234A and L235A of the human IgG1 Fc region or S228P and L235E of the human IgG4 Fc region, wherein the residues are numbered according to the EU index of Kabat, wherein said antibody according to the invention exhibits a reduced affinity to the human FcγRIIIA and FcγRIIA, for down-modulation of ADCC to at least 20% of the ADCC induced by the antibody according to the invention comprising the wildtype human IgG Fc region, and/or for down-modulation of ADCC.

In another aspect of the invention a method of treating an individual having a disease is provided, wherein said individual is treated with an antibody according to the invention, said antibody according to the invention having Pro329 of the human IgG Fc region substituted with glycine, wherein the residues are numbered according to the EU index of Kabat, wherein said antibody according to the invention is characterized by a strongly reduced binding FcγRIIIA and/or FcγRIIA compared to an antibody according to the invention comprising a wildtype human IgG Fc region, comprising administering to the individual an effective amount of said antibody according to the invention.

In still another aspect of the invention the antibody according to the invention used in said method comprises at least two further amino acid substitutions at L234A and L235A of the human IgG1 Fc region or S228P and L235E of the human IgG4 Fc region.

The invention provides preferably an antibody against human IL-1RAcP, characterized in that the heavy chain variable (VH) region is at least 90% identical to a VH region selected from the group consisting of VH regions of SEQ ID NO: 1 to 77.

The invention provides preferably an antibody against human IL-1RAcP, characterized in that the light chain variable (VL) region is at least 90% identical to a VL region selected from the group consisting of VL regions of SEQ ID NO: 78 to 154.

The invention provides preferably an antibody according to the invention, characterized in that its VH region is at least 90% identical to a VH region of SEQ ID NO: 1+n and its VL region is at least 90% identical to a VL region of SEQ ID NO: 78+n, wherein n is a number selected from the group consisting of 0 to 76.

The invention provides preferably an antibody according to the invention, characterized in that its VH region is selected from the group consisting of VH regions of SEQ ID NO: 1+n and its VL region is selected from the group consisting of VL regions of SEQ ID NO: 78+n, wherein n is a number selected from the group consisting of 0 to 76.

The invention provides preferably an antibody according to the invention, characterized in that the antibody comprises a VH region selected from the group of VH regions comprising a CDR1H region of SEQ ID NO: 155+n, a CDR2H region of SEQ ID NO: 232+n and aCDR3H region of SEQ ID NO: 309+n, wherein n is a number selected from the group consisting of 0 to 76.

The invention provides preferably an antibody according to the invention, characterized in that the antibody comprises a VL region selected from the group of VL regions comprising a CDR1L region of SEQ ID NO: 386+n, a CDR2L region of SEQ ID NO: 463+n and a CDR3L region of SEQ ID NO: 540+n, wherein n is a number selected from the group consisting of 0 to 76.

The invention provides preferably an antibody according to the invention, characterized in that the antibody comprises a VH region selected from the group of VH regions comprising a CDR1H region of SEQ ID NO:155+n, a CDR2H region of SEQ ID NO:232+n and aCDR3H region of SEQ ID NO:309+n and in that the antibody comprises a VL region selected from the group of VL regions comprising a CDR1L region of SEQ ID NO:386+n, a CDR2L region of SEQ ID NO: 463+n and aCDR3L region of SEQ ID NO:540+n, wherein n is a number selected from the group consisting of 0 to 76.

The invention provides preferably an antibody according to the invention, characterized in comprising a VH region and a VL region comprising the respective CDR1, CDR2 and CDR3 regions of an antibody selected from the group consisting of antibodies P013.S.01.B.B03, P013.S.01.B.A05, P013.S.01.B.004, P013.S.01.B.H01, P013.S.01.B.D03, P013.S.01.B.E02, P013.S.02.B.A04, P013.S.02.B.A05, P013.S.02.B.A02, P013.S.02.B.D03, P013.S.02.B.H01, P013.S.02.B.F01, P013.S.02.B.B04, P013.S.02.B.C02, P013.S.02.B.B05, P013.S.02.B.A03, P013.S.02.B.H03, and P013.S.02.B.G05.

The invention provides preferably an antibody according to the invention, characterized in comprising a VH region and a VL region comprising the respective CDR1, CDR2 and CDR3 regions of an antibody selected from the group consisting of antibodies P013.S.01.B.B03, P013.S.01.B.A05, P013.S.01.B.004, P013.S.01.B.H01, P013.S.01.B.D03, P013.S.01.B.E02, P013.S.02.B.A04, P013.S.02.B.A05, P013.S.02.B.A02, P013.S.02.B.D03, P013.S.02.B.H01, P013.S.02.B.F01, P013.S.02.B.B04, P013.S.02.B.C02, P013.S.02.B.B05, P013.S.02.B.A03, P013.S.02.B.H03, and P013.S.02.B.G05.

The invention preferably provides an antibody specifically binding to human IL-1RAcP characterized in inhibiting IL-1RAcP induced NFkB activity, binding to the same epitope as an antibody selected from the group of antibodies P013.S.01.B.B03, P013.S.01.B.A05, P013.S.01.B.004, P013.S.01.B.H01, P013.S.01.B.D03, P013.S.01.B.E02, P013.S.02.B.A04, P013.S.02.B.A05, P013.S.02.B.A02, P013.S.02.B.D03, P013.S.02.B.H01, P013.S.02.B.F01, P013.S.02.B.B04, P013.S.02.B.C02, P013.S.02.B.B05, P013.S.02.B.A03, P013.S.02.B.H03, and P013.S.02.B.G05, The invention provides preferably an antibody according to the invention, characterized in being a monoclonal rabbit, rabbit/human chimeric or humanized rabbit antibody.

The invention provides a method for the production of a monoclonal rabbit antibody against human IL-1RAcP characterized in inhibiting IL1beta stimulated NFkB activity according to the invention, characterized in
  i) that after immunizing said rabbit with IL-1RAcP, a number of antibody producing single cells derived from said rabbit are isolated,
  ii) binding to IL-1RAcP is measured separately for the supernatants of said single cells,
  iii) a single cell is selected if its supernatant shows binding to human IL-1RAcP and murine, and inhibits NFkB activity stimulated by IL-1alpha, IL-1beta, IL-33 and/or IL-36,
  iv) an antibody with the properties of iii) is isolated from said selected cell.

Preferably the rabbit antibody producing single cell is a single B rabbit hybridoma cell.

The invention provides a method for the production of a monoclonal rabbit antibody binding to human IL-1RAcP, and inhibits NFkB activity stimulated by IL-1alpha, IL-1beta, IL-33 and/or IL-36

The invention provides a method for the production of a monoclonal rabbit antibody according to the invention, characterized in that after immunizing said rabbit with said antigen, a single antibody producing cell, preferably from a B cell is isolated from said animal or a rabbit hybridoma cell derived from said rabbit, is isolated, for which binding to human IL-1RAcP, and inhibition of NFkB activity stimulated by IL-1alpha, IL-1beta, IL-33 and/or IL-36, is found according to the invention.

The invention preferably provides the use of an antibody according to the invention for the manufacture of a pharmaceutical composition.

The invention provides a supernatant of a rabbit antibody producing single cell, preferably a single B cell or a rabbit hybridoma cell, characterized in binding to human IL-1RAcP, and inhibition NFkB activity stimulated by IL-1alpha, IL-1beta, IL-33 and/or IL-36, according to the invention.

The invention preferably provides a supernatant of a rabbit antibody producing single cell, preferably a single B cell or a rabbit hybridoma cell according to the invention, characterized in binding to human IL-1RAcP, and inhibition NFkB activity stimulated by IL-1alpha, IL-1beta, IL-33 and/or IL-36 according to the invention, binding to human IL-1RAcP, and inhibition NFkB activity stimulated by IL-1alpha, IL-1beta, IL-33 and/or IL-36 is measured for the supernatant of said cell and said antibody is isolated from said cell if it shows the properties according to the invention.

The invention provides a method for the production of a monoclonal rabbit antibody according to the invention, characterized in
  i) that after immunizing said rabbit with said target antigen, a number of antibody producing single cells derived from said rabbit are isolated,
  ii) binding to IL-1RAcP is measured separately for the supernatants of said single cells,
  iii) a single cell is selected if its supernatant shows binding to human IL-1RAcP and murine, and inhibits NFkB activity stimulated by IL-1alpha, IL-1beta, IL-33 and/or IL-36 according to the invention,
  iv) and an antibody is isolated from said selected cell if the antibody shows the properties according to iii).

Preferably the antigen used for immunization (IL-1RAcP) is a fusion polypeptide consisting of said antigen and a human Fc polypeptide. Preferably in step i) CFA is used as adjuvant. Preferably in step i) CFA and IFA are used together as adjuvants.

Preferably in step ii) B cells are isolated from the blood of the rabbit. B cells are isolated preferably as PBMCs and depleted from macrophages. The antigens used for isolating B cells in step iv) is the target proteins IL-1RAcP or a functional fragment thereof, preferably the extracellular domain or parts thereof, cells presenting the antigens on their surface or the like.

Preferably in step iii) single B cells, secreting immunoglobulin, preferably IgG, are separated, preferably by FACS. Preferably the single B cell is then treated with a feeder cell before performing step vi).

Preferably in step iii) single B cells are separated, characterized in secreting an antibody specifically binding to human IL-1RAcP and inhibiting IL-1RAcP induced NFkB activity. Preferably in step iii) single B cells are separated, characterized in secreting an antibody specifically binding to human and murine IL-1RAcP and inhibiting in addition murine IL-1RAcP induced murine NFkB activity.

Preferably in step iii) single B cells are separated, characterized in secreting an antibody against human IL-1RAcP characterized in inhibiting NFkB activity stimulated by IL-1alpha, IL-1beta, IL-33 and/or IL-36. Preferably in step iii) single B cells are separated, characterized in secreting an antibody against human IL-1RAcP inhibiting IL1alpha stimulated NFkB activity. Preferably in step iii) single B cells are separated, characterized in secreting an antibody against human IL-1RAcP and inhibiting IL1beta stimulated NFkB activity.

Preferably in step iii) single B cells are separated, characterized in secreting an antibody against human IL-1RAcP and inhibiting IL33 stimulated NFkB activity. Preferably in step iii) single B cells are separated, characterized in secreting an antibody against human IL-1RAcP and inhibiting IL36 stimulated NFkB activity.

Preferably in step iii) single B cells are separated, characterized in secreting an antibody against human IL-1RAcP and inhibiting NFkB activity stimulated by a complex selected from the group consisting of IL-1β/IL-1R1/IL-1RAcP, IL-1α/IL-1R1/IL-1RAcP IL-33/ST2/IL-1RAcP, and IL-36/IL-36R/IL-1RAcP.

Preferably in step iii) single B cells are separated, characterized in secreting an antibody binding to murine IL-1RAcP and inhibiting murine IL-1RAcP induced murine NFkB activity.

Preferably in step iii) single B cells are separated, characterized in secreting an antibody inhibiting in a concentration of 5 μg/ml (rabbit IgG isotype has a molecular weight of 150 KD) NFkB activity in 293T/17 cell lysates (293T/17 [HEK 293T/17] (ATCC® CRL-11268™)) stimulated with 0.5 μg/ml human IL-1alpha, IL-1beta, IL-33 and/or IL-36 (molecular weight see UniProtKB/Swiss-Prot), for 70% or more, preferably for 80% or more, preferably for 90% and more, and more preferably for 95% or more, related to the same assay without said antibody according to the invention.

Preferably in step iii) single B cells are separated, characterized in secreting an antibody inhibiting in a concentration of 5 μg/ml NFkB activity in respective mouse cell line lysates stimulated with 0.5 μg/ml murine IL-1alpha, IL-1beta, IL-33 and/or IL-36 (molecular weight see UniProtKB/Swiss-Prot), for 70% or more, preferably for 80% or more, preferably for 90% and more, and more preferably for 95% or more, related to the same assay without said antibody according to the invention.

Preferably in step iii) single B cells are separated, characterized in secreting an antibody stimulated with mol/l IL-1alpha, IL-1beta, IL-33 and/or IL-36, like antibody XX, or more in 293T/17 cells transfected with luciferase under control of NF-kB reporter gene).

Preferably the method according to the invention is characterized in selecting in step iii) a single B cell which comprises mRNA encoding a VH region of an antibody which binds specifically to human IL-1RAcP.

Preferably the antibody is a rabbit monoclonal antibody.

Preferably the antibody produced by the single B cell is tested, preferably by ELISA, whether it binds specifically to the respective antigens.

Preferably the antibody is tested whether it binds specifically to IL-1RAcP and selected if it binds. Preferably the antibody is produced recombinantly based on its nucleic acid and/or polypeptide sequence.

Preferably in step iii) a single B cell is selected which comprises mRNA encoding a VH region of a IL-1RAcP specific antibody as specified in FIG. 2, which is at least 90% identical to a VH region of SEQ ID NO: 1+n and mRNA encoding a VL region of an antibody specifically binding to IL-1RAcP, which is at least 90% identical to a VL region of SEQ ID NO:78+n, wherein n is a number selected from the group of 0 to 76.

"n is a number selected from the group of 0 to 76" according to the invention means a number selected from the group of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 51, 52, 53, 54, 55, 56, 57, 58, 59, 60, 61, 62, 63, 64, 65, 66, 67, 68, 69, 70, 71, 72, 73, 74, 75, and 76. The number "n" according to the invention is meant to be identical for the same antibody, its heavy and light chains, its variable regions and CDR regions.

The invention comprises a monoclonal antibody, characterized in specifically binding to comprising amino acid sequences as described herein.

The heavy chain variable (VH) region of a IL-1RAcP specific antibody is preferably characterized in that said VH region is at least 90% identical to a VH region selected from the group consisting of VH regions of SEQ ID NO: 1 to 77. The light chain variable (VL) region of a HER specific antibody is preferably characterized in that said VL region is at least 90% identical to a VL region selected from the group consisting of VL regions of SEQ ID NO: 78 to 154. The antibody according to the invention is preferably characterized in that its VH region is at least 90% identical to a VH region of SEQ ID NO: 1+n and its VL region is at least 90% identical to a VL region of SEQ ID NO: 78+n, wherein n is a number selected from the group consisting of 0 to 76. The antibody according to the invention is preferably characterized in that its VH region is selected from the group consisting of VH regions of SEQ ID NO: 1+n and its VL region is selected from the group consisting of VL regions of SEQ ID NO: 78+n, wherein n is a number selected from the group consisting of 0 to 76. The antibody according to the invention is preferably characterized in comprising a VH region and a VL region comprising the respective CDR1, CDR2 and CDR3 regions of an antibody selected from the group consisting of antibodies listed in FIG. 2. The antibody according to the invention is preferably characterized in that the antibody comprises a VH region selected from the group of VH regions comprising a CDR1H region of SEQ ID NO: 155+n, a CDR2H region of SEQ ID NO: 232+n and aCDR3H region of SEQ ID NO: 309+n, wherein n is a number selected from the group consisting of 0 to 76.

The antibody according to the invention is preferably characterized in that the antibody comprises a VL region selected from the group of VL regions comprising a CDR1L region of SEQ ID NO: 386+n, a CDR2L region of SEQ ID NO: 463+n and aCDR3L region of SEQ ID NO: 540+n, wherein n is a number selected from the group consisting of 0 to 76.

The antibody according to the invention is preferably characterized in that the antibody comprises a VH region selected from the group of VH regions comprising a CDR1H region of SEQ ID NO: 155+n, a CDR2H region of SEQ ID NO: 232+n and aCDR3H region of SEQ ID NO:309+n, and in that the antibody comprises a VL region selected from the group of VL regions comprising a CDR1L region of SEQ ID NO: 386+n, a CDR2L region of SEQ ID NO: 463+n and a CDR3L region of SEQ ID NO: 540+n, wherein n is a number selected from the group consisting of 0 to 76.

The invention provides also compositions, B cells, methods of use, and methods of production of the antibodies according to the invention.

The antibody according to the invention is preferably characterized in being a humanized or chimeric version of said antibody. Preferably, the antibody according to the invention is an antibody comprising antigen binding sequences from a rabbit donor grafted to a heterologous non-human, human, or humanized sequence (e.g., framework and/or constant domain sequences). Preferably, an antibody of the invention has rabbit V regions or rabbit CDR regions and a human C region and/or framework. Preferably, the rabbit VL region or a human framework region comprising rabbit light chain CDRs is fused to a human kappa light chain constant region. Preferably, the rabbit VH region or a human framework region comprising rabbit heavy chain CDRs is fused to a human constant region, preferably IgG1. Preferably the invention relates to a chimeric or humanized rabbit antibody, characterized in comprising serine instead of the cysteine which is located at a position between amino acid 75 to 85 in the variable light chain VL.

The invention also provides a pharmaceutical composition characterized by comprising an antibody according to the invention. The invention also provides the use of an antibody according to the invention for the manufacture of a pharmaceutical composition. The invention also provides an antibody according to the invention for the treatment of a patient in the need of such treatment, preferably in the treatment of cancer. The invention also provides an antibody according to the invention for the treatment of breast, colon, lung, or pancreatic cancer. The invention also provides the use of an antibody according to the invention for manufacture of a medicament for the treatment of a patient in the need of such treatment, preferably in the treatment of cancer. The invention also provides the use of an antibody according to the invention for manufacture of a medicament for the treatment of breast, colon, lung, or pancreatic cancer. The invention also provides an antibody according to the invention for use in the treatment of a patient in the need of such treatment, preferably in the treatment of cancer, preferably in the treatment of breast, colon, lung, or pancreatic cancer.

The invention also provides a nucleic acid encoding an antibody according to the invention. The invention also provides an expression vector characterized in comprising a nucleic acid according to the invention for the expression of an antibody according to the invention in a prokaryotic or eukaryotic host cell. The invention also provides a prokaryotic or eukaryotic host cell comprising a nucleic acid according to the invention. The invention also provides a method of producing an antibody according to the invention characterized by expressing a nucleic acid according to the invention in a prokaryotic or eukaryotic host cell and recovering said antibody from said cell or the cell culture supernatant.

Preferably the antibodies of the present invention are antagonistic antibodies.

Sequences of said antibodies, antibodies comprising said VH and/or VL regions or said CDR regions are shown in FIG. 2.

DETAILED DESCRIPTION OF THE INVENTION

The term "rabbit" according to the invention means an animal of the members of the taxonomic order Lagomorpha, which includes the families (hares and rabbits) and Ochotonidae (pikas), preferably of genus *Oryctolagus*.

The term "antibody" encompasses the various forms of antibody structures including, but not being limited to, whole antibodies and antibody fragments as long as it shows the properties according to the invention. The antibody according to the invention is in its primary form produced by a B-cell of a rabbit and binds to IL-1RACP. Therefore, the antibody according to the invention binds specifically to IL-1RACP based on its antigen-binding portion, preferably its VH region comprising three VH CDRs and/or its VL region comprising three VL CDRs.

The term "rabbit monoclonal antibody" according to the invention means a monoclonal antibody produced by immunizing a rabbit and isolated from an antigen producing cell of said rabbit as well as such an antibody which is further modified, preferably a humanized antibody, a chimeric antibody, a fragment thereof, or a further genetically engineered and recombinant produced antibody as long as the characteristic properties according to the invention are retained. Preferably the antibody is from a B cell or a rabbit hybridoma cell of said rabbit.

The term "antibody producing cell" according to the invention means a rabbit B cell which produce antibodies, preferably a B cell or rabbit hybridoma cell.

"Native antibodies" are usually heterotetrameric glycoproteins composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light-chain variable domain is aligned with the variable domain of the heavy chain.

Particular amino acid residues are believed to form an interface between the light chain and heavy chain variable domains.

The term "VL (or VH) region" has the same meaning as VL (or VH) domain. The antibody according to the invention is in its primary form a mature antibody, which may be different from a simple germline antibody. Without being bound by theory, it is believed that binding of the antigen to a germline antibody might lead to significant structural rearrangements, whereas the unbound state of a matured antibody might be closer to its bond state. Therefore, the mature form of the antibody has probably a more rigid structure than the germline form. The germline antibody might be therefore more conformational flexible, resulting in a slower binding rate (see e.g. Wedemayer G J et al., Science. 1997 Jun. 13; 276(5319): 1665-9; Structural insights into the evolution of an antibody combining site). The presumably lower flexible structure of the mature antibody may improve the physicochemical properties of the antibody according to the invention, as being e.g. solubility or low aggregation, leading to improved therapeutic properties. The antibody according to the invention as identified from a rabbit B cell is an antibody having variable regions of natural origin. "Natural origin" means according to the invention, that such an antibody has variable regions which are identical in their amino acid sequences to the sequences of variable regions naturally occurring in rabbits. The antibody according to the invention can be further modified and is preferably a rabbit antibody, a humanized antibody, a chimeric antibody, a fragment thereof, or a further genetically engineered and recombinant produced antibody as long as the characteristic properties according to the invention are retained. The antibody can be bound to a further agent, e.g. as being an immunoconjugate. Preferably the antibody according to the invention is a rabbit antibody.

Preferably the antibody in its primary form binds specifically to human IL-1RAcP and murine IL-1RAcP.

The term "supernatant of a single cell" according to the invention means the supernatant of the culture of a rabbit antibody producing single cell, preferably a B cell or a rabbit hybridoma cell. Such supernatant comprises a monoclonal antibody according to the invention. The Fc part/constant part is therefore in a naturally occurring glycosylation condition.

The terms "Fc receptor" or "FcR" according to the invention refers to a human receptor that binds to the Fc region of an antibody. FcRs bind IgG antibodies and include receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daeron, Annu. Rev. Immunol. 15:203-234 (1997)). FcRIIIA (CD16a) mediaties ADCC. FcRs are reviewed in Ravetch and Kinet, Annu. Rev. Immunol 9:457-92 (1991); Capel et al, Immunomethods 4:25-34 (1994); and de Haas et al, J. Lab. CHn. Med. 126:330-41 (1995). These and all other FcRs are encompassed by the term "FcR" herein. The term also includes the neonatal receptor, FcRn, which is responsible for the transfer of maternal IgGs to the fetus (Guyer et al, J. Immunol. 117:587 (1976) and Kim et al, J. Immunol. 24:249 (1994)) and mediates slower catabolism, thus longer half-life.

The "constant domains (constant parts)" are not involved directly in binding of an antibody to an antigen, but exhibit e.g. also effector functions. The heavy chain constant region that corresponds to human IgG1 is called γ1 chain. The heavy chain constant region that correspond to human IgG3 is called γ3 chain. Human constant γ heavy chains are described in detail by Kabat, E. A. et al., Sequences of Proteins of Immunological Interest, 5th ed., Public Health Service, National Institutes of Health, Bethesda, MD (1991), and by Brueggemann, M., et al., J. Exp. Med. 166 (1987) 1351-1361; Love, T. W., et al., Methods Enzymol. 178 (1989) 515-527. Constant domains of IgG1 or IgG3 type are glycosylated at Asn297. "Asn 297" according to the invention means amino acid asparagine located at about position 297 in the Fc region; based on minor sequence variations of antibodies, Asn297 can also be located some amino acids (usually not more than +3 amino acids) upstream or downstream.

Glycosylation of human IgG1 or IgG3 occurs at Asn297 as core fucosylated bianntennary complex oligosaccharide glycosylation terminated with up to 2 Gal (galactose) residues. These structures are designated as G0, G1 (α1,6 or α1,3) or G2 glycan residues, depending from the amount of terminal Gal residues (Raju, T. S., BioProcess International 1 (2003) 44-53). CHO type glycosylation of antibody Fc parts is e.g. described by Routier, F. H., Glycoconjugate J. 14 (1997) 201-207. Cell-mediated effector functions like ADCC of antibodies according to the invention can be further enhanced by engineering the oligosaccharides attached at the Fc region of the antibody (defucosylation) as described in Umana, P., et al, Nature Biotechnol. 17 (1999) 176-180, Naoko Yamane-Ohnuki and Mitsuo Satoh, MAbs. 2009; 1 (3): 230-236 and U.S. Pat. No. 6,602,684, WO 2005/044859, WO 2004/065540, WO2007/031875. Such methods are e.g. use of the host cells with reduced intrinsic α-1,6 fucosylation ability, e.g., Lec13, a variant of CHO cells partially deficient in GMD function, or YB2/0, a rat-rat hybridoma cell line with intrinsically reduced FUT8 activity; introduction of small interfering RNA (siRNA) against the α-1,6 fucosylation relevant genes; co-introduction of β-1,4-N-acetylglucosaminyltransferase (GnTIII) and Golgi α-mannosidase II (ManII); 58,83,84 and disruption of the genomic locus responsible for α-1,6 fucosylation.

The term "antibody effector function(s)," or "effector function" as used herein refers to a function contributed by an Fc effector domain(s) of an IgG (e.g., the Fc region of an immunoglobulin). Such function can be effected by, for example, binding of an Fc effector domain(s) to an Fc receptor on an immune cell with phagocytic or lytic activity or by binding of an Fc effector domain(s) to components of the complement system. Typical effector functions are ADCC, ADCP and CDC. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

"Antibody-dependent cell-mediated cytotoxicity" and "ADCC" refer to a cell-mediated reaction in which nonspecific cytotoxic cells that express FcRs (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FCYRIII. FCR expression on hematopoietic cells is summarized in Table 3 on page 464 of Ravetch, and Kinet, Annu. Rev. Immunol 9 (1991) 457-492. The term "Antibody-dependent cellular phagocytosis" and "ADCP" refer to a process by which antibody-coated cells are internalized, either in whole or in part, by phagocytic immune cells (e.g., macrophages, neutrophils and dendritic cells) that bind to an immunoglobulin Fc region.

C1q" is a polypeptide that includes a binding site for the Fc region of an immunoglobulin. C1q together with two serine proteases, C1r and C1s, forms the complex C1, the first component of the complement dependent cytotoxicity (CDC) pathway. Human C1q can be purchased commercially from, e.g. Quidel, San Diego, Calif.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgGi, $IgG_2$, $IgG_3$, $IgG_4$, $IgA_i$, and $IgA_2$. The heavy chain constant domains that correspond to the different classes of immunoglobulins are called α, δ, ε, γ, and μ, respectively.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis (ADCP); down regulation of cell surface receptors (e.g. B cell receptor); and B cell activation. A "reduced effector function" as used herein refers to a reduction of a specific effector function, like for example ADCC or CDC, in comparison to a control (for example a polypeptide with a wildtype Fc region), by at least 20% and a "strongly reduced effector function" as used herein refers to a reduction of a specific effector function, like for example ADCC or CDC, in comparison to a control, by at least 50%.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat, et al., Sequences of Proteins of Immunological Interest, 5th Ed. Public Health Service, National Institutes of Health, Bethesda, MD (1991). A "variant Fc region" comprises an amino acid sequence which differs from that of a "native" or "wildtype" sequence Fc region by virtue of at least one "amino acid modification" as herein defined. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

The term "Fc-variant" as used herein refers to a polypeptide comprising a modification in an Fc domain. The Fc variants of the present invention are defined according to the amino acid modifications that compose them. Thus, for example, P329G is an Fc variant with the substitution of proline with glycine at position 329 relative to the parent Fc polypeptide, wherein the numbering is according to the EU index. The identity of the wildtype amino acid may be unspecified, in which case the aforementioned variant is referred to as P329G. For all positions discussed in the present invention, numbering is according to the EU index. The EU index or EU index as in Kabat or EU numbering scheme refers to the numbering of the EU antibody (Edelman, et al., Proc Natl Acad Sci USA 63 (1969) 78-85, hereby entirely incorporated by reference.) The modification can be an addition, deletion, or substitution. Substitutions can include naturally occurring amino acids and non-naturally occurring amino acids. Variants may comprise non-natural amino acids. Examples include U.S. Pat. No. 6,586,207; WO 98/48032; WO 03/073238; US 2004/0214988 A1; WO 05/35727 A2; WO 05/74524 A2; Chin, J. W., et al., Journal of the American Chemical Society 124 (2002) 9026-9027; Chin, J. W., and Schultz, P. G., ChemBioChem 11 (2002) 1135-1137; Chin, J. W., et al., PICAS United States of America 99 (2002) 11020-11024; and, Wang, L., and Schultz, P. G., Chem. (2002) 1-10, all entirely incorporated by reference.

The term "Fc region-containing polypeptide" refers to a polypeptide, such as an antibody or immunoadhesin (see definitions below), which comprises an Fc region.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain, (see review in Daeron, M., Annu. Rev. Immunol. 15 (1997) 203-234). FcRs are reviewed in Ravetch, and Kinet, Annu. Rev. Immunol 9 (1991) 457-492; Capel, et al., Immunomethods 4 (1994) 25-34; and de Haas, et al., J. Lab. Clin. Med. 126 (1995) 330-41. Other FcRs, including those to be identified in the future, are encompassed by the term "FcR" herein. The term also includes the neonatal receptor, FcRn, which is responsible for the transfer of maternal IgGs to the fetus (Guyer, et al., J. Immunol. 117 (1976) 587 and Kim, et al., J. Immunol. 24 (1994) 249).

By "IgG Fc ligand" as used herein is meant a molecule, preferably a polypeptide, from any organism that binds to the Fc region of an IgG antibody to form an Fc/Fc ligand complex. Fc ligands include but are not limited to FcγRs, FcγRs, FcγRs, FcRn, Clq, C3, mannan binding lectin, mannose receptor, staphylococcal protein A, streptococcal protein G, and viral FcγR. Fc ligands also include Fc receptor homologs (FcRH), which are a family of Fc receptors that are homologous to the FcγRs (Davis, et al., Immunological Reviews 190 (2002) 123-136, entirely incorporated by reference). Fc ligands may include undiscovered molecules that bind Fc. Particular IgG Fc ligands are FcRn and Fc gamma receptors. By "Fc ligand" as used herein is meant a molecule, preferably a polypeptide, from any organism that binds to the Fc region of an antibody to form an Fc/Fc ligand complex.

By "Fc gamma receptor", "FcγR" or "FcgammaR" as used herein is meant any member of the family of proteins that bind the IgG antibody Fc region and is encoded by an FcγR gene. In humans this family includes but is not limited to FcγRI (CD64), including isoforms FcγRIA, FcγRIB, and FcγRIC; FcγRII (CD32), including isoforms FcγRIIA (including allotypes H131 and R131), FcγRIIB (including FcγRIIB-I and FcγRIIB-2), and FcγRIIc; and FcγRIII (CD 16), including isoforms FcγRIIIA (including allotypes VI 58 and F158) and FcγRIIIb (including allotypes FcγRIIB-NAI and FcγRIIB-NA2) (Jefferis, et al., Immunol Lett 82 (2002) 57-65, entirely incorporated by reference), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD 16), and FCYRIII-2 (CD 16-2), as well as any undiscovered mouse FcγRs or FcγR isoforms or allotypes.

By "FcRn" or "neonatal Fc Receptor" as used herein is meant a protein that binds the IgG antibody Fc region and is encoded at least in part by an FcRn gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin and the heavy chain is encoded by the FcRn gene.

Unless otherwise noted herein, FcRn or an FcRn protein refers to the complex of FcRn heavy chain with beta-2-microglobulin.

The term "IL-1RAcP specific antibody", as used herein refers to an antibody specifically to human IL-1RAcP. "IL-1RAcP specific antibody" in conjunction with the VH, VL and CDR sequences specified in example 1 denotes an antibody with the specificity shown in FIG. 2. Therefore and for example a "IL-1RAcP specific antibody, characterized in that its VH region is selected from the group consisting of VH regions of SEQ ID NO:1+n and its VL region is selected from the group consisting of VL regions of SEQ ID NO:37+ n, wherein n is a number from 0 to 3" means "an antibody selected from the group consisting of the IL-1RACP specific antibodies, characterized by a VH region of SEQ ID NO:1 and a VL region of SEQ ID NO:37, by a VH region of SEQ ID NO:2 and a VL region of SEQ ID NO:38, by a VH region of SEQ ID NO:4 and a VL region of SEQ ID NO:40, and of the IL-1RACP specific antibody, characterized by a VH region of SEQ ID NO:3 and a VL region of SEQ ID NO:39.

An "immunoconjugate" means an antibody conjugated to one or more cytotoxic agents, such as a chemotherapeutic agent, a drug, a growth inhibitory agent, a toxin, another antibody or a radioactive isotope.

"Antibody fragments" comprise a portion of a full length antibody, preferably the variable regions thereof, or at least the antigen binding site thereof. Examples of antibody fragments include diabodies, Fab fragments, and single-chain antibody molecules. scFv antibodies are, e.g., described in Huston, J. S., Methods in Enzymol. 203 (1991) 46-88.

The terms "monoclonal antibody" or "monoclonal antibody composition" as used herein refer to a preparation of antibody molecules of a single amino acid composition. The term "chimeric antibody" refers to a monoclonal antibody comprising a variable region, i.e., binding region, from rabbit and at least a portion of a constant region derived from a different source or species, usually prepared by recombinant DNA techniques. According to the invention chimeric antibodies comprising a rabbit variable region and a human constant region and humanized rabbit antibodies are especially preferred. Other forms of "chimeric antibodies" encompassed by the present invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art (see, e.g., Morrison, S. L., et al, Proc. Natl. Acad. Sci. USA 81 (1984) 6851-6855; U.S. Pat. Nos. 5,202,238 and 5,204,244).

The term "humanized antibody" or "humanized version of an antibody" refers to antibodies in which a human variable region has been modified to comprise the CDRs of an antibody according to the invention. In a preferred embodiment, the CDRs of the VH and VL are grafted into the framework region of human antibody to prepare the "humanized antibody." See e.g. Riechmann, L., et al, Nature 332 (1988) 323-327; and Neuberger, M. S., et al, Nature 314 (1985) 268-270. The heavy and light chain variable framework regions can be derived from the same or different human antibody sequences. The human antibody sequences can be the sequences of naturally occurring human antibodies. Human heavy and light chain variable framework regions are listed e.g. in Lefranc, M.-P., Current Protocols in Immunology (2000)—Appendix IP A.1P.1-A.1P.37 and are accessible via IMGT, the international ImMunoGeneTics information system® (http://imgt.cines.fr) or via http://vbase.mrc-cpe.cam.ac.uk.

Preferably the invention relates to a chimeric or humanized rabbit antibody, characterized in comprising serine instead of the cysteine which is located at a position between amino acid 75 to 85 in the variable light chain VL.

The term "recombinant antibody", as used herein, is intended to include all antibodies according to the invention that are prepared by recombinant means, such as antibodies from a host cell such as a NS0 or CHO cell using a recombinant expression vector transfected into a host cell. Such recombinant human antibodies have variable and constant regions in a rearranged form.

The terms "specifically binding, against target, or antitarget antibody", as used herein, refer to binding of the antibody to the respective antigen (target), measured by ELISA, wherein said ELISA preferably comprises coating the respective antigen to a solid support, adding said antibody under conditions to allow the formation of an immune complex with the respective antigen or protein, detecting said immune complex by measuring the Optical Density values (OD) using a secondary antibody binding to an antibody according to the invention and using a peroxidase-mediated color development. The term "antigen" according to the invention refers to the antigen used for immunization or a protein comprising said antigen as part of its protein sequence. For example, for immunization a fragment of the extracellular domain of a protein (e.g. the first 20 amino acids) can be used and for detection/assay and the like the extracellular domain of the protein or the full length protein can be used.

The term "specifically binding" or "specifically recognized" herein means that an antibody exhibits appreciable affinity for an antigen and, preferably, does not exhibit significant crossreactivity. "Appreciable" binding affinity includes binding with an affinity of at least 10 exp7M$^{-1}$, specifically at least 10 exp8M$^{-1}$, more specifically at least 10 exp9M$^{-1}$, or even yet more specifically at least 10 exp10M$^{-1}$. An antibody that "does not exhibit significant crossreactivity" is one that will not appreciably bind to an undesirable other protein. An antibody specific for an epitope according to the invention will, for example, not significantly cross-react with other epitopes on IL-1RAcP. Specific binding can be determined according to any art-recognized means for determining such binding. In some embodiments, specific binding is determined by competitive binding assays (e.g. ELISA). The term "inhibiting IL-1RAcP induced NFkB activity" as used herein refers to inhibition of NFkB activity in a luciferase reporter experiment. 293T/17 [HEK 293T/17] (ATCC® CRL-11268™) cells, which express a NF-kB-RE firefly luciferase reporter, are seeded into Poly-D-Lysin-Cell culture plates. After stimulation of of IL-1RAcP the cell lysate is tested for activated NF-kB using the Steady-Glo® Luciferase Assay Kit (Promega Corp. Madison USA). Supernatants with functional antibodies bind to IL-1RAcP and inhibit the NF-kB activation, which is shown in low signal. The Steady-Glo® Luciferase Assay Kit is described in https://www.promega.de/resources/protocols/technical-manuals/0/steady-glo-luciferase-assay-system-protocol and Alam, J. and Cook, J. L. (1990) Anal. Biochem. 188, 245-54; Wood, K. V. (1991) In: Bioluminescence and Chemiluminescence: Current Status, Stanley, P., and Kricka, L., eds., John Wiley and Sons, Chichester, NY, 543; Ow, D. W. et al. (1986). Science 234, 856-9; De Wet, J. R. et al. (1987) Mol. Cell. Biol. 7, 725-37; Wood, K. V. (1990) Promegallotes 28, 1-3; Wood, K. V. (1991) In: Bioluminescence and Chemiluminescence: Current Status, Stanley, P. and Kricka, L., eds., John Wiley and Sons, Chichester, NY, 11; and U.S. Pat. Nos. 5,283,179, 5,641,641, 5,650,289.

The antibody according to the invention comprises a VH region and a VL region or parts thereof, which are both together sufficient for the specific binding to the respective antigen.

All protein terms as used herein refers to the human proteins. If a protein from another species is meant, this is explicitly mentioned.

The term "IL-1RAcP"", as used herein, refers to human IL-1RAcP (UniProtKB Q9NPH3), which is a Coreceptor for IL1RL2 in the IL-36 signaling system (By similarity). Coreceptor with IL1R1 in the IL-1 signaling system. Associates with IL1R1 bound to IL1B to form the high affinity interleukin-1 receptor complex which mediates interleukin-1-dependent activation of NF-kappa-B and other pathways (UniProtKB). The term "murine IL-1RAcP"", as used herein, refer to murine IL-1RAcP (UniProtKB Q61730).

The term "IL-1alpha"", as used herein, refers to human IL-1 (UniProtKB P01583). The term "IL-1beta"", as used herein, refer to human IL-1beta (UniProtKB P01584). IL-1 stimulates thymocyte proliferation by inducing IL-2 release, B-cell maturation and proliferation, and fibroblast growth factor activity. IL-1 proteins are involved in the inflammatory response, being identified as endogenous pyrogens (UniProtKB).

The term "IL-33"", as used herein, refers to human IL-33 (UniProtKB O95760), acytokine that binds to and signals through the IL1RL1/ST2 receptor which in turn activates NF-kappa-B and MAPK signaling pathways in target cells (UniProtKB).

The term "IL-36"", as used herein, refers to human IL-36alpha (UniProtKB Q9UHA7, IL-36beta (UniProtKB Q9NZH7) and or IL-36gamma (UniProtKB Q9NZH8). IL-36 are cytokines that bind to and signal through the IL1RL2/IL-36R receptor which in turn activates NF-kappa-B and MAPK signaling pathways in target cells linked to a pro-inflammatory response. Part of the IL-36 signaling system that is thought to be present in epithelial barriers and to take part in local inflammatory response; similar to the IL-1 system with which it shares the coreceptor IL1RAP. IL-36 seems to be involved in skin inflammatory response by acting on keratinocytes, dendritic cells and indirectly on T cells to drive tissue infiltration, cell maturation and cell proliferation (UniProtKB).

The term "NFkB" as used herein, refer to human nuclear factor NF-kappa-B, which consists of p105 subunit (P19838) and p100 subunit (Q00653). "Inhibition of NFkB" is measured according to the invention as inhibition of NFkB dependent luciferase gene expression in human cells. Such methods are e.g. described in Windheim M. et al., Mol. Cell. Biol. 28 (2008) 1783-1791; Huang J. et al. PNAS USA 94 (1997) 12829-12832; Xiaoxia L. et al., Mol. Cell, Biol. 19 (1999) 4643-4652. The method used according to the invention as inhibition of IL1beta induced NFkB expression in 293T/17 cells is described in the example section of this patent application. If murine NFkB is meant herein it is explicitly mentioned.

The "variable region (or domain) of an antibody according to the invention" (variable region of a light chain (VL), variable region of a heavy chain (VH)) as used herein denotes each of the pair of light and heavy chain regions which are involved directly in binding the antibody to the antigen. The variable light and heavy chain regions have the same general structure and each region comprises four framework (FR) regions whose sequences are widely conserved, connected by three complementary determining regions, CDRs. The term "antigen-binding portion of an antibody" when used herein refer to the amino acid residues of an antibody which are responsible for antigen-binding. The antigen-binding portion of an antibody comprises preferably amino acid residues from the "complementary determining regions" or "CDRs". The CDR sequences are defined according to Kabat et al, Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable region. For example, a heavy chain variable region may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence. The variable domain of the heavy chain of an antibody according to the invention is composed of a single immunoglobulin domain and is about 110 to 120 amino acids long. The variable domain of the light chain of an antibody according to the invention is composed of a single immunoglobulin domain and is about 110 to 120 amino acids long.

In one embodiment the antibody according to the invention comprises a Fc part or constant heavy and light parts derived from human origin and preferably comprising all parts of the human constant regions. As used herein the term "Fc part derived from human origin" denotes a Fc part which is either a Fc part of a human antibody of the subclass IgG1, IgG2, IgG3 or IgG4, e.g. a Fc part from human IgG1 subclass, a mutated Fc part from human IgG1 subclass (preferably with a mutation on L234A+L235A), a Fc part from human IgG4 subclass or a mutated Fc part from human IgG4 subclass (preferably with a mutation on S228P). In one embodiment the antibody according to the invention is of human IgG1 subclass. Human constant chains are well known in the state of the art and e.g. described by Kabat, E. A., (see e.g. Johnson, G. and Wu, T. T., Nucleic Acids Res. 28 (2000) 214-218).

In one embodiment the antibody according to the invention comprises a heavy chain variable region (VH) sequence having at least 90%, 91%, 92%>, 93%>, 94%, 95%, 96%, 97%, 98%, 99%, or 100% sequence identity to an amino acid sequence selected from the group of VH sequences according to the invention. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, whereby the antibody retains the ability to bind specifically according to the invention to the respective antigen. In certain embodiments, a total of 1 to 10 amino acids have been substituted, inserted and/or deleted in each of said VH sequences. In certain embodiments, substitutions, insertions, or deletions occur in regions outside the CDRs (i.e., in the FRs).

In one embodiment the antibody according to the invention comprises a light chain variable region (VL) having at least 90%, 91%, 92%, 93%, 94%, 95%, 96%, 97%, 98%, 99%, or 100% sequence identity to the amino acid sequence of the VL sequences according to the invention, wherein n is a number from 0 to 5. In certain embodiments, a VL sequence having at least 90%, 91%, 92%, 93%, 94%, 95%, 96%, 97%, 98%, or 99% o identity contains substitutions (e.g., conservative substitutions), insertions, or deletions relative to the reference sequence, whereby the antibody retains the ability to bind specifically to the respective antigen. In certain embodiments, a total of 1 to 10 amino acids have been substituted, inserted and/or deleted in said VL sequences. In certain embodiments, the substitutions, insertions, or deletions occur in regions outside the CDRs (i.e., in the FRs). The invention also comprises affinity matured antibodies which can be produced according to methods known in the art. Marks et al. Bio/Technology 10:779-783 (1992) describes affinity maturation by VH and VL domain shuffling. Random mutagenesis of CDR and/or framework residues is described by: Barbas et al., Proc Nat. Acad. Sci, USA 91: 3809-3813 (1994); Schier et al., Gene 169: 147-155 (1995); Yelton et al., J. Immunol. 1 55: 1994-2004 (1995); Jackson et al., J. Immunol. 1 54 (7): 3310-9 (1995); and Hawkins et al., J. Mol. Biol. 226:889-896 (1992) and WO2010108127. "Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNAS-TAR) software.

The antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression nucleic acids encoding light and heavy chains of an antibody according to the invention or fragments thereof are inserted into expression vectors by standard methods. Expression is performed in appropriate prokaryotic or eukaryotic host cells, such as CHO cells, NSO cells, SP2/0 cells, HEK293 cells, COS cells, yeast, or E. coli cells, and the antibody is recovered from the cells (from the supernatant or after cells lysis). Recombinant production of antibodies is well-known in the state of the art and described, for example, in the review articles of Makrides, S. C., Protein Expr. Purif. 17 (1999) 183-202; Geisse, S., et al, Protein Expr. Purif. 8 (1996) 271-282; Kaufman, R. J., Mol. Biotechnol. 16 (2000) 151-161; Werner, R. G., Drug Res. 48 (1998) 870-880. The antibodies may be present in whole cells, in a cell lysate, or in a partially purified, or pure form. Purification is performed in order to eliminate other cellular components or other contaminants, e.g., other cellular nucleic acids or proteins, by standard techniques, including, column chromatography and others well known in the art (see Ausubel, F., et al, ed. Current Protocols in Molecular Biology, Greene Publishing and Wiley Interscience, New York (1987)). Expression in NSO cells is described by, e.g., Barnes, L. M., et al, Cytotechnology 32 (2000) 109-123; Barnes, L. M., et al, Biotech. Bioeng. 73 (2001) 261-270. Transient expression is described by, e.g., Durocher, Y., et al, Nucl. Acids. Res. 30 (2002) E9. Cloning of variable domains is described by Orlandi, R., et al, Proc. Natl. Acad. Sci. USA 86 (1989) 3833-3837; Carter, P., et al, Proc. Natl. Acad. Sci. USA 89 (1992) 4285-4289; Norderhaug, L., et al, J. Immunol. Methods 204 (1997) 77-87. A preferred transient expression system (HEK 293) is described by Schlaeger, E.-J. and Christensen, K., in Cytotechnology 30 (1999) 71-83, and by Schlaeger, E.-J., in J. Immunol. Methods 194 (1996) 191-199. Monoclonal antibodies are suitably separated from the culture medium by conventional immunoglobulin purification procedures such as, for example, protein A-Sepharose, hydroxylapatite chromatography or affinity chromatography.

DNA and RNA encoding the monoclonal antibodies are sequenced using conventional procedures. RT PCR is preferably used.

Antibodies obtained from said cell lines are preferred embodiments of the invention. Amino acid sequence variants of an antibody are prepared by introducing nucleotide changes into the antibody encoding DNA, or by peptide synthesis. Any cysteine residue not involved in maintaining the proper conformation of the antibody may also be substituted, generally with serine, to improve the oxidative stability of the molecule and to prevent aberrant crosslinking. Conversely, cysteine bond(s) may be added to the antibody to improve its stability (particularly where the antibody is an antibody fragment such as an Fv fragment).

The heavy and light chain variable regions according to the invention are combined with sequences of promoter, translation initiation, constant region, 3' untranslated region, polyadenylation, and transcription termination to form expression vector constructs. The heavy and light chain expression constructs can be combined into a single vector, co-transfected, serially transfected, or separately transfected into host cells which are then fused to form a single host cell expressing both chains.

One aspect of the invention is a pharmaceutical composition comprising an antibody according to the invention. Another aspect of the invention is the use of an antibody according to the invention for the manufacture of a pharmaceutical composition. A further aspect of the invention is a method for the manufacture of a pharmaceutical composition comprising an antibody according to the invention. In another aspect, the present invention provides a composition, e.g. a pharmaceutical composition, containing an antibody according to the present invention, formulated together with a pharmaceutical carrier.

Furthermore, the antibodies according to the invention are especially useful for the treatment of diseases where the dysregulation of the target is the underlying reason. One aspect of the invention is a pharmaceutical composition for the treatment of cancer.

Another aspect of the invention is an antibody according to the invention for the treatment of cancer. For this the antibody according to the invention can be investigated in a respective mouse tumor model e.g. according to Krupke D M; Begley D A; Sundberg J P; Bult O; Eppig J T, The Mouse Tumor Biology database., Nat Rev Cancer 2008 June; 8 (6):459-65. Therefore, one aspect of the invention is a pharmaceutical composition for the treatment of cancer.

Another aspect of the invention is an antibody according to the invention for the treatment of cancer.

Another aspect of the invention is the use of an antibody according to the invention for the manufacture of a medicament for the treatment of cancer.

Another aspect of the invention is a method of treatment of a patient suffering from cancer by administering an antibody according to the invention to said patient in the need of such treatment.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

The term "cancer" as used herein may be, for example, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, lymphoma, lymphocytic leukemia, including refractory versions of any of the above cancers, or a combination of one or more of the above cancers. Preferably such cancer is a breast cancer, colon cancer, lung cancer, or pancreatic cancer.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin. Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art. Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The method according to the invention comprises in summary the steps of immunization, B cell isolation, enrichment of B cells, isolation of single B cells, preferably co-cultivation with feeder cells, selection of a single B cell which comprises respective mRNA, and production of the antibody according to the invention. Such methods are mentioned for the production of monospecific antibodies e.g. in WO2011147903, WO2007003041, WO2008045140, WO2004106377, EP1255780, and EP1633787.

Immunization

Immunization can be performed according to the methods known of the state of the art, e.g. by using DNA of the target antigens or fragments thereof, complete protein antigens or fragments thereof, antigen expressing cells. Preferably the IL-1RACP antigen is a fusion polypeptide consisting of said antigen and a human Fc polypeptide. Preferably immunization in step i) is repeated at least three times and appropriately up to six times during 90 days (if an antibody according to the invention is identified already after e.g. the fourth immunization, further immunizations are not necessary). Preferably complete Freund's adjuvant (CFA) or CFA and incomplete Freund's adjuvant (IFA) is (are) used as adjuvant.

B Cell Isolation

The B-cells are isolated from the rabbit, preferably from the blood of the rabbit. The B-cells are isolated up to 8 days, preferably 5 to 7 days, after 3rd to 6th immunization. Preferably PBMCs are isolated and depleted from macrophages (see e.g. EP0488470) and used as B cells. Isolation of B cells can be for example also performed by labeling non-B cells with non B cell markers, e.g. anti CD2, CD14, CD16, CD36, CD43, and CD235a antibodies and separating the labeled non B cells from non-labeled B cells.

Enrichment of B Cells

Antibody producing and antigen specific B cells are preferably isolated (enriched) by treating the B cells with IL-1RACP antigen used for immunization, or a cell expressing the respective antigen. Preferably the antigen and the cell expressing the antigen are used in immobilized manner, so that the antigen specific B cells can be separated easiily. Such methods are e.g. described in Kodituwakko A P et al., Immunol. Cell Biol. (2003) 81, 163-170 and EP0488470.

Isolation of Single B Cells

Isolation of single rabbit B cells is preferably performed by FACS. Preferably an anti-rabbit IgG, is used for FACS selection. Such selected single B cells are antibody producing B cells.

Co-Cultivation with Feeder Cells

Preferably the antigen producing B cells are co-cultivated with feeder cells before the selection step (see below) is performed. Such a feeder cell is preferably a thymoma cell line such as the murine EL4 thymoma cell line, which is preferably mutagenized; preferably the thymoma cell line is mutagenized to a bromo-deoxyuridine-resistant mutant (e.g. EL4-B5 cells, Wen L. et al., Eur. J. Immunol. 17 (1987) 887-92). This increases the amount of antibody in the cell supernant (see e.g. Zubler, R. H., et al., Eur. J. Immunol. 14 (1984) 357-63, Wen L. et al., Eur. J. Immunol. 17 (1987) 887-92, Hoffmann P et al., J Immunol. Methods 1996; 196 (1):85-91, Roy A. et al., J Hematother. Stem Cell Res. 2001; 10 (6):873-80, Dlu A. et al., Proc. Nati. Acad. Sci. USA Vol. 84, pp. 9140-9144, 1987, and EP0488470) and facilitates analysis and selection of secreted rabbit antibodies.

Selection of a Single B Cell Which Comprises mRNA

Selection of a single B cell which comprises mRNA encoding polypeptides comprising a heavy and light chain variable region of an antibody according to the invention can be performed, preferably after co-cultivated with feeder cells, by analyzing the cell supernatant for secreted rabbit antibodies specifically binding to the IL-1RACP antigen used for immunization. Analysis is preferably performed by ELISA. Immunoglobulin sequences can be then recovered from the selected single human B cell e.g. according to de Wildt R M, Hoet R M. Methods Mol. Biol. 2002; 178:121-31 and analyzed e.g. by RT PCR.

The production of an antibody according to the invention, expressed by a single B cell, can be performed by recombinant means.

Techniques and procedures described or referenced herein are for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

A Chinese hamster ovary tissue-derived CHO cell or cell line suitable in accordance with the present invention is any cell which is a cell line established from an ovary tissue of Chinese hamster (Cricetulus griseus). Examples include CHO cells described in documents such as Journal of Experimental Medicine, 108, 945 (1958); Proc. Nat Acad. Sci. USA, 60, 1275 (1968); Genetics, 55, 513 (1968); Chromosoma, 41, 129 (1973); Methods in Cell Science, 18, 115 (1996); Radiation Research, 148, 260 (1997); Proc. Nat Acad. Sci. USA, 77, 4216 (1980); Proc. Nat Acad. Sci., 60, 1275 (1968); Cell, 6, 121 (1975); Molecular Cell Genetics, Appendix I, II (pp. 883-900); and the like. In addition, CHO-K1 (ATCC CCL-61), DUXB1 1 (ATCC CCL-9096) and Pro-5 (ATCC CCL-1781) registered in ATCC (The American Type Culture Collection) as well as CHO-S (Life Technologies, Cat #1 1619) or sub-cell lines obtained by adapting the cell lines using various media can also be employed in the present invention.

In the following specific embodiments of the invention are listed:

The invention relates to a monoclonal antibody specifically binding to human IL-1RAcP.

It is preferably characterized in binding in addition to murine IL-1RAcP.

It is further preferably characterized in inhibiting IL-1RAcP induced NFkB activity.

It is further preferably characterized in inhibiting in addition murine IL-1RAcP induced murine NFkB activity.

It is further preferably characterized in inhibiting IL-1alpha, IL-1beta, IL-33, and/or IL-36 stimulated NFkB activity.

The antibody is characterized in inhibiting IL-1alpha stimulated NFkB activity.

The antibody is further characterized in inhibiting IL-1beta stimulated NFkB activity.

The antibody is also characterized in inhibiting IL-33 stimulated NFkB activity.

The antibody is further characterized in inhibiting IL-36 stimulated NFkB activity.

It is characterized in inhibiting NFkB activity stimulated by a complex selected from the group consisting of IL-1β/IL-1R1/IL-1RAcP, IL-1α/IL-1R1/IL-1RAcP IL-33/ST2/IL-1RAcP, and/or IL-36/II-36R/IL-1RAcP.

The antibody is characterized in inhibiting in a concentration of 5 µg/ml (rabbit IgG isotype has a molecular weight of 150 KD) NFkB activity in 293T/17 cell lysates (293T/17 [HEK 293T/17] (ATCC® CRL-11268™)) stimulated with 0.5 µg/ml human IL-1alpha, IL-1beta, IL-33 and/or IL-36 (molecular weight see UniProtKB/Swiss-Prot), for 70% or more, preferably for 80% or more, preferably for 90% and more, and more preferably for 95% or more, related to the same assay without said antibody according to the invention.

Preferably the antibody is characterized in inhibiting in a concentration of 5 µg/ml NFkB activity in respective mouse cell line lysates stimulated with 0.5 µg/m murine IL-1alpha, IL-1beta, IL-33 and/or IL-36 (molecular weight see UniProtKB/Swiss-Prot), for 70% or more, preferably for 80% or more, preferably for 90% and more, and more preferably for 95% or more, related to the same assay without said antibody according to the invention.

It inhibits IL-1alpha, IL-1beta, IL-33, and/or IL-36, respectively, stimulated luciferase activity in 293T/17 cells (293T/17-FR cells transfected with luciferase under control of NF-kB reporter gene).

It is also characterized in exhibiting an ADCC reduced to at least 20% of the ADCC induced by the antibody according to the invention comprising a wild-type human IgG Fc region.

Preferably, it is characterized in exhibiting a reduced affinity to the human FcγRIIIA and/or FcγRIIA and/or FcγRI compared to an antibody according to the invention comprising the wildtype IgG Fc region, and wherein the ADCC induced by said antibody according to the invention is reduced to at least 20% of the ADCC induced by the antibody according to the invention comprising a wild-type human IgG Fc region.

The antibody is characterized in comprising at least amino acid substitutions at L234A and L235A of the human IgG1 Fc region or S228P and L235E of the human IgG4 Fc region.

The antibody is further characterized in that the heavy chain variable (VH) region is at least 90% identical to a VH region selected from the group consisting of VH regions of SEQ ID NO:1 to 77.

The antibody is preferably characterized in that the light chain variable (VL) region is at least 90% identical to a VL region selected from the group consisting of VL regions of SEQ ID NO:78 to 154.

The antibody is also preferably characterized in that its VH region is at least 90% identical to a VH region of SEQ ID NO:1+n and its VL region is at least 90% identical to a VL region of SEQ ID NO:78+n, wherein n is a number selected from the group consisting of 0 to 76.

Preferred is an antibody according to the invention characterized in that the antibody comprises a VH region comprising a heavy chain CDRH1 sequence selected from SEQ ID NO: 214, 216, 219, 220, 221, 228, 156, 159, 183, 164, 163, 161, 157, 155, 174, 166, 173, 177, 158, a CDRH2 sequence selected from the group of SEQ ID NO: 291, 293, 296, 297, 298, 305, 233, 236, 260, 241, 240, 238, 234, 232, 251, 243, 250, 254, 235, and a CDRH3 sequence selected from the group of SEQ ID NO: 368, 370, 373, 374, 375, 382, 310, 313, 337, 318, 317, 315, 311, 309, 328, 320, 327, 331, 312, respectively.

Also preferred is an antibody characterized in that the antibody comprises a VL region comprising a light chain CDRL1 sequence selected from the group of SEQ ID NO: 445, 447, 450, 451, 452, 459, 387, 390, 414, 395, 394, 392, 388, 386, 405, 397, 404, 408, 389, a CDRL2 sequence selected from the group of SEQ ID NO: 522, 524, 527, 528, 529, 536, 464, 467, 491, 472, 471, 469, 465, 463, 482, 474, 481, 485, 466, and a CDRL3 sequence selected from the group of SEQ ID NO: 599, 601, 604, 605, 606, 613, 541, 544, 568, 549, 548, 546, 542, 540, 559, 551, 558, 562, 543, respectively.

In a further embodiment the antibody is characterized in that said VH region is selected from the group consisting of VH regions of SEQ ID NO:1 to 77.

It is also preferred that the antibody is characterized in that said VL region is selected from the group consisting of VL regions of SEQ ID NO: 78 to 154.

Further preferred is an antibody characterized in that its VH region is selected from the group consisting of VH regions of SEQ ID NO: 60, 62, 65, 66, 67, 74, 2, 5, 29, 10, 9, 7, 3, 1, 20, 12, 19, 23, 4.

Preferably, the heavy chain variable region (VH) sequence is SEQ ID NO: 60, alternatively SEQ ID NO:62, or SEQ ID NO:65, SEQ ID NO:66, SEQ ID NO:67, SEQ ID NO:74, SEQ ID NO:2, SEQ ID NO:5, SEQ ID NO:29, SEQ ID NO:10, SEQ ID NO:9, SEQ ID NO:7, SEQ ID NO:3, SEQ ID NO:1, SEQ ID NO:20, SEQ ID NO:12, SEQ ID NO:19, SEQ ID NO:23, or alternatively SEQ ID NO:4.

Further preferred is an antibody characterized in that its VL region is selected from the group consisting of VL regions of SEQ ID NO: 137, 139, 142, 143, 144, 151, 79, 82, 106, 87, 86, 84, 80, 78, 97, 89, 96, 100, 81.

Preferably, the light chain variable region (VL) sequence is SEQ ID NO: 137, alternatively SEQ ID NO: 139, or SEQ ID NO: 142, SEQ ID NO: 143, SEQ ID NO: 144, SEQ ID NO: 151, SEQ ID NO: 79, SEQ ID NO: 82, SEQ ID NO: 106, SEQ ID NO: 87, SEQ ID NO: 86, SEQ ID NO: 84, SEQ ID NO: 80, SEQ ID NO: 78, SEQ ID NO: 97, SEQ ID NO: 89, SEQ ID NO: 96, SEQ ID NO: 100, or alternatively SEQ ID NO: 81.

Most preferred is an antibody characterized in that its VH region is selected from the group consisting of VH regions of SEQ ID NO: 60, 62, 65, 66, 67, 74, 2, 5, 29, 10, 9, 7, 3, 1, 20, 12, 19, 23, 4, and its VL region is selected from the group consisting of VL regions of SEQ ID NO: 137, 139, 142, 143, 144, 151, 79, 82, 106, 87, 86, 84, 80, 78, 97, 89, 96, 100, 81.

In one embodiment, the antibody according to the invention comprises SEQ ID NO.: 137 and 60, or SEQ ID NO.: 139 and 62. An antibody according to the invention may also comprise SEQ ID NO.: 142 and 65, or SEQ ID NO.: 143 and 66, or SEQ ID NO.: 144 and 67, SEQ ID NO.: 151 and 74, or SEQ ID NO.: 79 and 2, or SEQ ID NO.: 82 and 5., or SEQ ID NO.: 106 and 29, or SEQ ID NO.: 87 and 10, or SEQ ID NO.: 86 and 9, or SEQ ID NO.: 84 and 7, or SEQ ID NO.: 80 and 3, or SEQ ID NO.: 78 and 1. Alternatively, an antibody according to the invention comprises SEQ ID NO.: 97 and 20, or SEQ ID NO.: 89 and 12, or SEQ ID NO.: 96 and 19, or SEQ ID NO.: 100 and 23, or SEQ ID NO.: 81 and 4.

Particularly preferred is an antibody according to the invention comprising SEQ ID NO.: 79 and 2, or SEQ ID NO.: 81 and 4, or SEQ ID NO.: 139 and 62, or SEQ ID NO.: 80 and 3, or SEQ ID NO.: 78 and 1.

The antibody is preferably characterized in that its VH region is selected from the group consisting of VH regions of SEQ ID NO: 1+n and its VL region is selected from the group consisting of VL regions of SEQ ID NO: 78+n, wherein n is a number selected from the group consisting of 0 to 76.

In a further embodiment the antibody is characterized in that the antibody comprises a VH region selected from the group of VH regions comprising a CDR1H region of SEQ ID NO: 155+n, a CDR2H region of SEQ ID NO: 232+n and aCDR3H region of SEQ ID NO: 309+n, wherein n is a number selected from the group consisting of 0 to 76.

The antibody is preferably characterized in that the antibody comprises a VL region selected from the group of VL regions comprising a CDR1L region of SEQ ID NO: 386+n, a CDR2L region of SEQ ID NO: 463+n and aCDR3L region of SEQ ID NO: 540+n, wherein n is a number selected from the group consisting of 0 to 76.

The antibody is preferably characterized in that the antibody comprises a VH region selected from the group of VH regions comprising a CDR1H region of SEQ ID NO: 155+n, a CDR2H region of SEQ ID NO: 232+n and aCDR3H region of SEQ ID NO: 309+n, and in that the antibody comprises a VL region selected from the group of VL regions comprising a a CDR1L region of SEQ ID NO: 386+n, a CDR2L region of SEQ ID NO: 463+n and aCDR3L region of SEQ ID NO: 540+n, wherein n is a number selected from the group consisting of 0 to 76.

The antibody may be characterized in comprising a VH region and a VL region comprising the respective CDR1, CDR2 and CDR3 regions of an antibody selected from the group consisting of antibodies listed in FIG. 2.

Preferably the antibody is characterized in inhibiting IL-1RAcP induced NFkB activity, binding to the same epitope as an antibody selected from the group of antibodies P013.S.01.B.B03, P013.S.01.B.A05, P013.S.01.B.004, P013.S.01.B.H01, P013.S.01.B.D03, P013.S.01.B.E02, P013.S.02.B.A04, P013.S.02.B.A05, P013.S.02.B.A02, P013.S.02.B.D03, P013.S.02.B.H01, P013.S.02.B.F01, P013.S.02.B.B04, P013.S.02.B.C02, P013.S.02.B.B05, P013.S.02.B.A03, P013.S.02.B.H03, and P013.S.02.B.G05.

In one embodiment the antibody is characterized in being a rabbit/human chimeric or humanized antibody.

The invention also relates to a method for the production of a monoclonal rabbit antibody against human IL-1RAcP characterized in inhibiting IL1beta stimulated NFkB activity according to the invention, characterized in
i) that after immunizing said rabbit with IL-1RAcP, a number of antibody producing single cells derived from said rabbit are isolated,
ii) binding to IL-1RAcP is measured separately for the supernatants of said single cells,
iii) a single cell is selected if its supernatant shows binding to human IL-1RAcP and murine, and inhibits NFkB activity stimulated by IL-1alpha, IL-1beta, IL-33 and/or IL-36,
iv) an antibody with the properties of iii) is isolated from said selected cell.

Preferably the method is characterized in that the rabbit antibody producing single cell is a single B rabbit hybridoma cell.

The method is also characterized in that after immunizing said rabbit with said antigen, a single antibody producing cell is isolated from said animal or a rabbit hybridoma cell derived from said rabbit is isolated, for which binding to human IL-1RAcP, and inhibition of NFkB activity stimulated by IL-1alpha, IL-1beta, IL-33 and/or IL-36 is found.

The invention relates to the use of the antibody for the manufacture of a pharmaceutical composition.

It relates to a supernatant of a rabbit antibody producing single cell, characterized in binding to human IL-1RAcP, and inhibition of NFkB activity stimulated by IL-1alpha, IL-1beta, IL-33 and/or IL-36.

The invention relates to a method of treating an IL-1 mediated disease in a patient, comprising administering to a patient a pharmaceutically effective amount of the antibody.

The invention relates to a pharmaceutical composition comprising a pharmaceutically acceptable carrier and a therapeutically effective amount of the antibody according to any one of embodiments.

It also relates to a method of treating an IL-1 mediated disease in a patient, comprising administering to a patient the present pharmaceutical composition.

EXAMPLES

Example 1: Compounds

| MAB ID | Host/ species | Substance | Company | Cat. No. |
| --- | --- | --- | --- | --- |
| P013_01 | | rhIL-1RAcP/Fc Chimera | R&D | 676-CP |
| P013_02 | rabbit | IL1RAcP purified MaxPab rabbit polyclonal Ab (D01P) against TARDBP (NP_031401.1) | Abnova | H00003556-D01P |
| P013_03 | human | rhIL-1RAcP/Fc Chimera | | |
| P013_04 | murine | mIL1RAcP-Fc | | |
| P013_05 | human | recombinant human IL-1ß | R&D | 201-LB-005 |
| P013_06 | goat | Human IL-1 RAcP/ IL-1 R3 affinity purified polyclonal antibody | R&D | AF676 |
| P013_07 | human | hIL1RAcP | | C477 |

Example 2: Immunization of Rabbits

Rabbits were immunized with hu-IL-1RAcP-Fc repeatedly. Blood of these animals was collected and B lymphocytes thereof were isolated. Single B-cells were sorted into wells of microtiter plates and propagated. Supernatants conditioned by these B-cells were analyzed in hu-IL-1RAcP ELISA. 409 monoclonal antibodies (=4.7% of all tested supernatants) were identified to bind to hu-IL-1RAcP. 23 monoclonal antibodies were found to bind also to murine IL-1RACP and inhibit IL1beta induced human or murine NF-κB activity.

a) Immunization of Rabbits (Scheme 1)

Recombinant human Fc-chimera proteins fused human IL-1RACP (IL-1RAcP-Fc) was used as immunogen. Two different immunization schemes, scheme 1 and scheme 2, were explored. For the immunization according to scheme 1, three New Zealand White (NZW) rabbits were immunized by injecting 1 ml of immunogen in each of the animals at day 0, 7, 14, 28, 42, and 56. Proteins were diluted in PBS, pooled in equimolar amounts and mixed 1:1 (v/v) with complete Freund's adjuvant (CFA) before use. A final concentration of 400 µg of immunogen was used per animal for the 1st immunization and for the 2nd, 3rd, 4th, 5th and 6th immunization 200 µg of immunogen and per animal was used. Blood samples were collected in tubes, coated with EDTA, five, six and seven days post-immunization after the 3rd, 4th, 5th and 6th immunization. Anti IL-1RACP antibodies according to the invention were isolated from the blood sample taken after the third immunization. Antibodies according to the invention were isolated from blood samples taken after the 3rd, 4th, 5th and 6th immunization.

b) Immunization of Rabbits (Scheme 2)

For the immunization according to scheme 2, each of the six NZW rabbits were immunized subcutaneously with 1 ml of immunogen at day 0, 7, 14, 28, 42, 56, 70 and 84. For the first injection, proteins were diluted in PBS, pooled in equimolar amounts and mixed 1:1 (v/v) with CFA before use. A final concentration of 200 µg of Immunogen per animal was used for the 1st immunization. For the 2nd, 3rd, 4th, 5th and 6th immunization, proteins were diluted in PBS, pooled in equimolar amounts and mixed 1:1 (v/v) with incomplete Freund's adjuvant (IFA) before use. 100 µg of Immunogen was used per animal. Blood samples were collected in tubes, coated with EDTA, five six and seven days post-immunization after the 3rd, 4th, 5th and 6th Immunization at intervals of 2 weeks.

Example 3

Immunogen Coating/Cell Preparation

The fusion-protein used for immunization was coated onto a surface of a cell-culture 6-well plate with a concentration of 8 µg in PBS/10 cm2 and incubated. Alternatively, plates were seeded with a cell line BT-474 (DSMZ ACC 64) on their cell surface. One day before use cells were seeded in DMEM+5% FCS at a density leading to about 90% confluence after 24 h.

Isolation of Peripheral Blood Mononuclear Cells from Rabbits

PBMCs were isolated from whole blood of immunized rabbits. The blood was diluted 1:1 with PBS and layered on Lympholyte® according to the manufacturer's instructions (Cedarlane, CL5120). Peripheral blood mononuclear cells (PBMC) were separated from erythrocytes by density gradient centrifugation (800×g, 20 min, RT). Cells were removed from the interface, washed twice with PBS (800×g, 10 min) and suspended in RPMI 1640 based cell culture medium.

Monocyte Depletion

PBMCs were incubated in cell culture medium on plastic. Unbound lymphocytes were collected after incubation time.

Enrichment of Antigen Specific Cells

Antigen specific lymphocytes were enriched on immunogen coated plates or directly on BT-474 cells. Lymphocytes were washed twice with PBS to remove unspecific cells and subsequently incubated with 750 µl Trypsin per 10 cm2 culture surface for 7-10 min. Detached cells were collected in cell culture medium for further steps.

Single-Cell Sorting of Immunoglobulin G-Secreting Lymphocytes

PBMCs/lymphocytes were stained with a FITC (Fluorescein Isothiocyanate Isomer 1) conjugated goat anti-rabbit IgG antibody, Abd Serotec, STAR121F). A flow cytometric analysis and single-cell sorting was performed with a FACS cytometer. Single positive lymphocytes were sorted directly to 200 µl cell culture medium covering 3.0×106 irradiated EL-4 B5 feeder cells. The cell culture medium described above was supplemented with 5% activated T-cell macrophage supernatant from rabbits (MicroCoat). Co-cultivation medium was supplemented with 2×10-06 g/ml SAC (*Staphylococcus Aureus* Cowan) solution. After co-cultivation of B-cells and feeder cells for 7 days supernatants were transferred for antibody detection and cells were harvested in 100 µl RNA isolation buffer (Qiagen, RLT).

Screening for Immunoglobulin's Via Enzyme-Linked Immunosorbent Assay

Secreted rabbit antibodies were detected by analyzing the supernatant via a biotinylated capturing antibody (anti-rabbit IgG antibody produced in goat) with a final concentration of 1 µg/ml PBS+0.5% BSA+0.05% Tween® 20, coated on streptavidin microtiter plates and a horse radish peroxidase coupled anti-rabbit IgG detection antibody with a final concentration of 1:7500. Washing steps were performed by using PBS+0.1% Tween® 20. 3,3',5,5'-Tetramethylbenzidine (TMB) was used as substrate and HCl to stop the enzymatic reaction.

Determination of IL-1RACP Specific Antibodies in B-Cell Supernatants

Microtiter plates were coated IL-1RACP and/or IL12Rβ1 protein (recombinant Fc chimeric conjugates of human IL-1RACP or IL12Rβ1). After a blocking process, specific antibodies from B-cell supernatants bind to the targets and are then detected by a POD-labeled anti-rabbit IgG antibody. The IL12Rβ1 binding was used as a counter screen. IL-1RACP protein was tagged with a linker, huFc and His like the IL12Rβ1 protein. Antibodies which bind to the tag were positive in both assays, whereas antigen specific antibodies just bound to IL-1RACP and not to IL12Rβ1.

12.5 µL 0.5 µg/mL IL-1RACP protein in PBS was transferred to a microtiter plate, incubated and washed 3× with Wash Buffer. 90 µL Block Buffer was added to each well, incubated and washed. 12.5 µl Standard Antibody (rabbit mAb against IL-1RAcP, anti IL12Rbeta1 antibody: IL-12Rbeta1 antibody; GeneTex; Cat. No. GTX103917) or sample diluted in ELISA buffer was added, incubated and washed. 12.5 µl 1:5000 POD-Antibody (Anti-rabbit IgG, peroxidase-linked species-specific Fab2 fragment (from donkey) (ECL); assay dilution: 1:5000) in Elisa Buffer was added, incubated and washed. 15 µl TMB was added and 15 µl HCl was added after sufficient development. Absorbance (Optical Density O.D.) was read at 450 nm/620 nm. Results are shown in FIG. 1.

ELISA Buffer: PBS, 0.5% BSA, 0.05% Tween® 20
Wash Buffer: PBS, 0.1% Tween® 20
Block Buffer: PBS, 2% BSA, 0.05% Tween® 20

Example 4: Antibody Binding to Human IL-1RAcP

Assay Principle:

NUNC Maxisorp® 384 well microtiter plates are coated with P013_03. After a blocking process, specific antibodies from B-cell supernatants bind to the antigen human (P013-03) or murine IL-1RACP (P013-04) and are then detected by a POD-labeled antibody. Samples are tested 1:2 diluted.

Materials:

Plates: 384 well NUNC Maxisorp® plates; Cat. No. 464718
Proteins: P013-03 (Conc. 1.5 mg/ml; Assay Conc. 0.5 m/ml) human
P013-04 (Conc. 1.3 mg/ml; Assay Conc. 0.5 m/ml) murine
Standard Ab: P013-02 (Conc. 1 mg/ml; Start Assay Conc. 2 µg/ml)
Detection Ab: Anti-rabbit IgG, peroxidase-linked species-specific whole antibody (from donkey) (ECL); GE; Cat. No. NA9340; assay dilution: 1:5000
PBS: Buffers in a Box, Premixed PBS Buffer, 10×; Roche Applied Sciences; Cat. No. 11666789001
BSA: Bovine Serum Albumin Fraction V from bovine serum; Roche Applied Sciences; Cat. No. 10735086001
Tween® 20: Tween® 20; Carl Roth; Cat. No. 9127.2
TMB: TMB Solution; Life Technologies; Cat. No. SB02

HCl: 1M Titripur® Hydrochloric Acid; Merck; Cat. No. 1090571000
ELISA Buffer: PBS, 0.5% BSA, 0.05% Tween®
Wash Buffer: PBS, 0.1% Tween®
Block Buffer: PBS, 2% BSA, 0.05% Tween®
Samples: 1:2 dilution in Elisa Buffer Procedure:
1. Add 12.5 µL P013-03 (0.5 µg/ml) in PBS to a 384 well NUNC Maxisorp® plate and incubate for 1 h at RT.
2. Wash 3× with 90 µl Wash Buffer.
3. Add 904 Blocking buffer to each well and incubate for 1 h at RT.
4. Wash 3× with Wash Buffer.
5. Add 12.54 Standard Antibody in 1:2 dilutions or sample 1:2 diluted in Elisa Buffer and incubate for 1 h at RT.
6. Wash 3× with Wash Buffer.
7. Add 12.5 µL 1:5000 POD-Antibody in Elisa Buffer and incubate for 1 h at RT.
8. Wash 6× with Wash Buffer.
9. Add 15 µL TMB.
10. Add 15 µL HCl after sufficient development.
11. Read absorbance at 450 nm/620 nm.

Example 5: Antibody Binding to Murine IL-1RAcP

Assay Principle:
NUNC Maxisorp® 384 well microtiter plates are coated with P013_04. After a blocking process, specific antibodies from B-cell supernatants bind to the antigen and are then detected by a POD-labeled antibody. Samples are tested 1:2 diluted.

Materials:
Plates: 384 well NUNC Maxisorp® plates; Cat. No. 464718
Proteins: P013-04 (Conc. 1.3 mg/ml; Assay Conc. 0. µg/ml)
Standard Ab: P013-02 (Conc. 1 mg/ml; Start Assay Conc. 2 µg/ml)
Detection Ab: Anti-rabbit IgG, peroxidase-linked species-specific whole antibody (from donkey) (ECL); GE; Cat. No. NA9340; assay dilution: 1:5000
PBS: Buffers in a Box, Premixed PBS Buffer, 10×; Roche Applied Sciences; Cat. No. 11666789001
BSA: Bovine Serum Albumin Fraction V from bovine serum; Roche Applied Sciences; Cat. No. 10735086001
Tween 20: Tween® 20; Carl Roth; Cat. No. 9127.2
TMB: TMB Solution; Life Technologies; Cat. No. SB02
HCl: 1M Titripur® Hydrochloric Acid; Merck; Cat. No. 1090571000
ELISA Buffer: PBS, 0.5% BSA, 0.05% Tween®
Wash Buffer: PBS, 0.1% Tween®
Block Buffer: PBS, 2% BSA, 0.05% Tween®
Samples: 1:2 dilution in Elisa Buffer Procedure:
1. Add 12.5 µL P013-04 (0.5 µg/ml) in PBS to a 384 well NUNC Maxisorp® plate and incubate for 1 h at RT.
2. Wash 3× with 90 µL Wash Buffer.
3. Add 90 µL Blocking buffer to each well and incubate for 1 h at RT.
4. Wash 3× with Wash Buffer.
5. Add 12. µL Standard Antibody in 1:2 dilutions or sample 1:2 diluted in Elisa Buffer and incubate for 1 h at RT.
6. Wash 3× with Wash Buffer.
7. Add 12.5 µL 1:5000 POD-Antibody in Elisa Buffer and incubate for 1 h at RT.
8. Wash 6× with Wash Buffer.
9. Add 15 µL TMB.
10. Add 15 µL HCl after sufficient development.
11. Read absorbance at 450 nm/620 nm.

Example 6: EC50 Determination in ELISA

The binding of an antibody according to the invention to human IL-1RAcP was analyzed in ELISA: EC50 values were calculated according to the state of the art.

Example 7: NF-κB Neutralizing Activity of Antibodies Against IL-1RAcP in a Luciferase-Based Genetic Reporter Assay Assay Principle:
293T/17-FR cells, which express a NF-kB-RE firefly luciferase reporter, are seeded into Poly-D-lysine-Cell culture plates. After stimulation of P013 the 293T/17-FR lysate is tested for activated NF-kB using the Steady-Glo Luciferase Assay Kit. Supernatants with functional antibodies bind to P013 and inhibit the NF-kB activation, which is shown in low signal. Samples are tested 1:2 diluted in P013 solution.

Materials:
Plates: Cell plate: 384 well PDL Costar Cell Culture plate; Cat. No. 3844
Assay plate: 384 well Lumitrac® white-plate; Corning; Cat. No. 3572
Cells: 293T/17-FR; assay conc. 250.000 cells/ml
Proteins: P013_05 (Conc. 0.03 mg/ml; Assay Conc. 115 pg/ml; Working Conc. 230 pg/ml) IL-1alpha, IL-33 and IL-36
Standard Ab: P013_06 (Conc. 0.2 mg/ml; Start Working Conc. 6 µg/ml)
Kit: Steady-Glo Luciferase Assay System; Promega; Cat. No. E2510
Cell-Medium: DMEM Medium; PAN Biotech; Cat. No. P04-04510
FCS: Fetal Bovine Serum, HyClone; Thermo; Cat. No. St30070.03
293T/17-FR Medium: DMEM Medium, 10% FCS, (+20 µg/ml Hygromycin-B, just for cultivation)
Conditioned B-cell Medium (MAB Discovery)
Samples: 1:2 dilution with P013_05 in DMEM-Medium+10% FCS Procedure:
1. Split confluent 293T/17-FR cells every Monday (seed out: 5×106 cells/T175 flask) and Friday (seed out: 3×106 cells/T175 flask) using trypsin/EDTA (incubate just for 30 sec at RT).
2. Seed cells (0.25×106 cells/ml) in 25 µl DMEM+10% FCS to a 384-well PDL-plate (Corning cat #3844) and incubate over night at 37° C. and 5% CO2.
3. Aspirate media and add 12.5 µl Sample or P013_06 in 1:3 dilution in Conditioned Medium or just Conditioned Medium and incubate for 30 min at 37° C. and 5% CO2 (program: 3 Aspiration and Sample transfer)
4. Add 12.5 µl P013_05 in DMEM+10% FCS and incubate for 5 hours at 37° C. and 5% CO2 (program: 4_Add P013_05).
5. Equilibrate cultured cells to RT for 10 min.
6. Add 25 µl Steady-Glo® Reagent and mix several times with pipette (program: 6_Steady Glo®)
7. Wait 5 minutes before transfer 45 µl supernatant to a 384-well Lumitrac® white plate (Corning Cat #3572) (program: 7_Transfer 45 µl)

8. Measure luminescence in Tecan Reader (Tecan Group Mannedorf, CH): Integration Time: 0.5 sec

Example 8: IL-1α Neutralization Assay

Materials:
Cells: HEK-293T cells stably expressing firefly luciferase NF-kB reporter and Renilla Luciferase (for normalization control). IL1RAcP and the IL1R1 are endogenously expressed.
Media: DMEM (ATCC Cat #30-2002)+10% heat inactivated FBS
Reagents IL-1α—R&D #200-LA; 10 ug/ml PBS+0.1% BSA
  Anti-IL1RAcP Positive Control Antibody—R&D #AF676; 200 ug/ml
  MAB Discovery Antibodies—Plate 1 antibodies at 750 ug/ml.
    Plate 2 antibodies at 250 ug/ml
  Luciferase Assay System—Promega #E1500
Procedure:
1. Plate cells at 50,000/well into 96 well plate in 100 ul DMEM+10% FBS. Incubate overnight 37° C., 5% $CO_2$
2. Prepare 4 fold dilution of antibodies at 2× final concentration in DMEM+10% FBS
3. Aspirate media off cells and add antibodies at 2× final concentration in 60 ul DMEM+10% FBS. Incubate cells 30 m at 37° C. 5% $CO_2$
4. Add IL-1α to 175 pg/ml final concentration in 60 ul complete media. (175 pg/ml is the $EC_{50}$.) Incubate 4 h at 37° C. 5% $CO_2$
5. Wash cells with 150 ul PBS
6. Lyse cells in 50 ul 1× cell culture lysis reagent (from Luciferase Assay System) for 15 m on shaker at ambient temperature.
7. Pipet up and down and transfer 20 ul lysate to lumitrac-200 plate. Add 100 ul luciferase assay reagent and read luminescence using Wallac Victor2 with liquid injector or other suitable luminometer.

Example 9: IL-1β Neutralization Assay

Materials:
Cells: HEK-293T cells stably expressing firefly luciferase NF-kB reporter and Renilla Luciferase (for normalization control). IL1RAcP and the IL1R1 are endogenously expressed.
Media: DMEM (ATCC Cat #30-2002)+10% heat inactivated FBS
Reagents: IL-1β—R&D #201-LB; 25 ug/ml PBS+0.1% BSA
  Anti-IL1RAcP Positive Control Antibody—R&D #AF676; 200 ug/ml
  Anti-IL1RAcP Rabbit pAb Positive Control Antibody—ONCO Lot AP14/200 ug/ml PBS
  Normal Rabbit IgG-JL #011-000-003; 200 ug/ml PBS
  MAB Discovery Antibodies—Plate 1 antibodies at 750 ug/ml.
    Plate 2 antibodies at 250 ug/ml
  Luciferase Assay System—Promega #E1500
Procedure:
1. Plate cells at 50,000/well into 96 well plate in 100 ul DMEM+10% FBS. Incubate overnight 37° 5% $CO_2$
2. Prepare 4 fold dilution of antibodies at 2× final concentration in DMEM+10% FBS
3. Aspirate media off cells and add antibodies at 2× final concentration in 60 ul DMEM+10% FBS. Incubate cells 30 m at 37° 5% $CO_2$
4. Add IL-1β to 175 pg/ml final concentration in 60 ul complete media. 175 pg/ml is the $EC_{50}$. Incubate 4 h at 37° 5% $CO_2$
5. Wash cells with 150 ul PBS
6. Lyse cells in 50 ul 1× cell culture lysis reagent (from Luciferase Assay System) for 15 m on shaker at ambient temperature.
7. Pipet up and down and transfer 20 ul lysate to lumitrac-200 plate. Add 100 ul luciferase assay reagent and read luminescence using Wallac Victor2 with liquid injector or other suitable luminometer.

Example 10: IL-33 Neutralization Assay

Materials:
Cells: HEK-293T cells transiently transfected with firefly luciferase NF-kB reporter, renilla luciferase (for normalization control), and IL-33R driven by the CMV promoter. IL1RAcP is endogenously expressed.
Media: DMEM (ATCC Cat #30-2002)+10% heat inactivated FBS
Reagents: IL-33—R&D #3625-IL; 10 ug/ml PBS+0.1% BSA
  Anti-IL1RAcP Positive Control Antibody—R&D #AF676; 200 ug/ml
  MAB Discovery Antibodies—Plate 1 antibodies at 750 ug/ml.
    Plate 2 antibodies at 250 ug/ml
  Luciferase Assay System—Promega #E1500
Procedure:
1. Transfect cells with luciferase reporters and IL-33R at 25,000 cells/well approximately 24 h before assay.
2. Prepare 4 fold dilution of antibodies at 2× final concentration in DMEM+10% FBS
3. Aspirate media off cells and add antibodies at 2× final concentration in 60 ul DMEM+10% FBS. Incubate cells 30 m at 37° 5% $CO_2$
4. Add IL-33 to 250 pg/ml final concentration in 60 ul complete media. Incubate 4 h at 37° 5% $CO_2$
5. Wash cells with 150 ul PBS
6. Lyse cells in 50 ul 1× cell culture lysis reagent (from Luciferase Assay System) for 15 m on shaker at ambient temperature.
7. Pipet up and down and transfer 20 ul lysate to lumitrac-200 plate. Add 100 ul luciferase assay reagent and read luminescence using Wallac Victor2 with liquid injector or other suitable luminometer.

Example 11: IL-36β (IL1F8) Neutralization Assay

Materials:
Cells: HEK-293T cells stably transfected with firefly luciferase NF-kB reporter, renilla luciferase (for normalization control), and IL-36R driven by the CMV promoter. IL1RAcP is endogenously expressed.
Media: DMEM (ATCC Cat #30-2002)+10% heat inactivated FBS
Reagents: IL-36β—R&D #6834-IL; 100 ug/ml PBS+0.1% BSA
  Anti-IL1RAcP Positive Control Antibody—R&D #AF676; 200 ug/ml
  MAB Discovery Antibodies—Plate 1 antibodies at 750 ug/ml.
    Plate 2 antibodies at 250 ug/ml
  Luciferase Assay System—Promega #E1500

Procedure:
1. Plate cells at 50,000/well into 96 well plate in 100 ul DMEM+10% FBS. Incubate overnight 37° 5% $CO_2$
2. Prepare 4-fold dilution of antibodies at 2× final concentration in DMEM+10% FBS
3. Aspirate media off cells and add antibodies at 2× final concentration in 60 ul DMEM+10% FBS. Incubate cells 30 m at 37° 5% $CO_2$
4. Add IL-36β to 15 ng/ml final concentration in 60 ul complete media. (15 ng/ml is the $EC_{50}$.) Incubate 4 h at 37° 5% $CO_2$
5. Wash cells with 150 ul PBS
6. Lyse cells in 50 ul 1× cell culture lysis reagent (from Luciferase Assay System) for 15 m on shaker at ambient temperature.
7. Pipet up and down and transfer 20 ul lysate to lumitrac-200 plate. Add 100 ul luciferase assay reagent and read luminescence using Wallac Victor2 with liquid injector or other suitable luminometer.

FIGURE LEGENDS

FIG. 1: Antibody binding to human and murine IL-1RAcP
Results of experiments described in examples 3-6.
FIG. 2: Sequences (amino acids in one letter code)
D, A, S, K, L, A, S means DASKLAS. The same holds true for all other sequences of FIG. 2.
CDRH1: SEQ ID NO: 155-231
CDRH2: SEQ ID NO: 232-308
CDRH3: SEQ ID NO: 309-385
CDRL1: SEQ ID NO: 386-462
CDRL2: SEQ ID NO: 463-539
CDRL3: SEQ ID NO: 540-616
FIG. 3: Inhibition of ligand induced signaling
Summary table of results of signaling inhibition for the most promising 18 antibodies is shown. Experimental procedures are detailed in examples 8-11.
FIG. 4: Inhibition of ligand induced signaling by selected antibodies
Exemplary graphs of results from experiments described in examples 8-11. Shown is the percentage of nFkB stimulation due to signaling of different ligands, as cited in the title of each figure. Different colors correspond to different antibodies. Only a selection of tested antibodies is shown.
FIG. 5: NF-κB neutralizing activity of selected antibodies against IL-1RAcP
Results of experiments described in Example 7. Shown is the NF-κB neutralizing activity of antibodies against IL-1RAcP in a luciferase-based genetic reporter assay.
FIG. 6: Inhibition of ligand induced signaling of antibodies with preferred sequences
Shown are the results of signaling inhibition experiments for 19 preferred antibodies. Experimental procedures are detailed in examples 8-11.

The invention claimed is:

1. A monoclonal antibody, or antigen binding fragment thereof, that specifically binds to human IL-1RAcP, wherein the monoclonal antibody or antigen binding fragment thereof comprises:
a heavy chain variable (VH) region comprising the CDR1H region of SEQ ID NO: 158, the CDR2H region of SEQ ID NO: 235 and the CDR3H region of SEQ ID NO: 312, and
a light chain variable (VL) region comprising the CDR1L region of SEQ ID NO: 389, the CDR2L region of SEQ ID NO: 466 and the CDR3L region of SEQ ID NO: 543.

2. The monoclonal antibody, or antigen binding fragment thereof, of claim 1, wherein ADCC activity of the antibody is reduced by at least 20% relative to an antibody comprising a wild-type human IgG1 Fc region.

3. The monoclonal antibody, or antigen binding fragment thereof, of claim 1, wherein the antibody has reduced affinity to the human FcγRIIIA, FcγRIIA, and/or FcγRI relative to an antibody comprising a wild-type human IgG1 Fc region.

4. The monoclonal antibody, or antigen binding fragment thereof, of claim 1, comprising amino acid substitutions at L234A and L235A of the human IgG1 Fc region, or S228P and L235E of the human IgG4 Fc region.

5. The monoclonal antibody, or antigen binding fragment thereof, of claim 1, comprising a heavy chain variable (VH) region that is at least 90% identical to the VH region of SEQ ID NO: 4.

6. The monoclonal antibody, or antigen binding fragment thereof, of claim 1, comprising a light chain variable (VL) region that is at least 90% identical to the VL region of SEQ ID NO: 81.

7. The monoclonal antibody, or antigen binding fragment thereof, of claim 1, comprising the VH region amino acid sequence of SEQ ID NO:4.

8. The monoclonal antibody, or antigen binding fragment thereof, of claim 1, comprising the VL region amino acid sequence of SEQ ID NO: 81.

9. The monoclonal antibody, or antigen binding fragment thereof, of claim 1, comprising the VH region of SEQ ID NO:4, and comprising the VL region of SEQ ID NO: 81.

10. The monoclonal antibody, or antigen binding fragment thereof, of claim 1, comprising a rabbit/human chimeric antibody, or antigen binding fragment thereof.

11. A pharmaceutical composition comprising a pharmaceutically acceptable carrier and a therapeutically effective amount of the monoclonal antibody, or antigen binding fragment thereof, of claim 1.

12. The monoclonal antibody, or antigen binding fragment thereof, of claim 1, comprising a humanized antibody, or antigen binding fragment thereof.

13. The monoclonal antibody, or antigen binding fragment thereof, of claim 1, comprising a human IgG1 Fc region.

14. The monoclonal antibody, or antigen binding fragment thereof, of claim 1, comprising a human IgG4 Fc region.

* * * * *

SEQUENCE LISTING

```
<160> NUMBER OF SEQ ID NOS: 616

<210> SEQ ID NO 1
<211> LENGTH: 121
<212> TYPE: PRT
<213> ORGANISM: Oryctolagus cuniculus

<400> SEQUENCE: 1

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Ala
            20                  25                  30

Met Gly Trp Val Arg Gln Ala Pro Gly Lys Gly Leu Glu Tyr Ile Gly
        35                  40                  45

Val Ile Thr Ser Ser Ala Thr Thr Tyr Tyr Ala Ser Trp Ala Lys Gly
    50                  55                  60

Arg Phe Thr Ile Ser Lys Thr Ser Ser Thr Thr Val Asp Leu Arg Val
65                  70                  75                  80

Thr Ser Leu Thr Thr Glu Asp Thr Ala Thr Tyr Phe Cys Ala Arg Gly
            85                  90                  95

Gly Pro Gly Tyr Ser Thr Asn Thr His Tyr Ala Phe Asp Pro Trp Gly
            100                 105                 110

Pro Gly Thr Leu Val Thr Val Ser Ser
        115                 120

<210> SEQ ID NO 2
<211> LENGTH: 118
<212> TYPE: PRT
<213> ORGANISM: Oryctolagus cuniculus

<400> SEQUENCE: 2

Gln Glu Gln Leu Glu Glu Ser Gly Gly Asp Leu Val Gln Pro Glu Gly
```

```
1               5                   10                  15
Ser Leu Thr Val Thr Cys Thr Ala Ser Gly Phe Ser Phe Ser Phe Gly
            20                  25                  30

Tyr Tyr Met Cys Trp Val Arg Gln Ala Pro Gly Lys Gly Leu Glu Trp
            35                  40                  45

Ile Ala Cys Ile Tyr Gly Asp Ser Ser Asp Thr Leu Tyr Ala Asn Trp
            50                  55                  60

Ala Lys Gly Arg Phe Thr Val Ser Lys Thr Ser Ser Thr Thr Val Thr
65                  70                  75                  80

Leu Gln Met Thr Ser Leu Thr Ala Ala Asp Thr Ala Thr Tyr Phe Cys
            85                  90                  95

Ala Arg Tyr Pro Gly Gly Ser Tyr Tyr Asn Leu Trp Gly Pro Gly Thr
            100                 105                 110

Arg Val Thr Val Ser Ser
            115

<210> SEQ ID NO 3
<211> LENGTH: 121
<212> TYPE: PRT
<213> ORGANISM: Oryctolagus cuniculus

<400> SEQUENCE: 3

Gln Glu Gln Leu Glu Glu Ser Gly Gly Gly Leu Val Lys Pro Gly Gly
1               5                   10                  15

Thr Leu Thr Leu Thr Cys Lys Ala Ser Gly Ile Asp Phe Ser Ser Tyr
            20                  25                  30

Tyr Tyr Met Cys Trp Val Arg Gln Ala Pro Gly Lys Gly Leu Glu Trp
            35                  40                  45

Ile Ala Cys Ile Phe Ile Gly Tyr Gly Asp Val Thr Trp Tyr Ala Ser
            50                  55                  60

Trp Ala Lys Gly Arg Phe Thr Ile Ser Lys Ala Ser Ser Thr Thr Val
65                  70                  75                  80

Thr Leu Gln Met Thr Ser Leu Thr Ala Ala Asp Thr Ala Thr Tyr Phe
            85                  90                  95

Cys Ala Arg Ala Leu Gly Ser Ser Gly Tyr Arg Val Asn Leu Trp Gly
            100                 105                 110

Pro Gly Thr Leu Val Thr Val Ser Ser
            115                 120

<210> SEQ ID NO 4
<211> LENGTH: 117
<212> TYPE: PRT
<213> ORGANISM: Oryctolagus cuniculus

<400> SEQUENCE: 4

Gln Ser Leu Glu Glu Ser Gly Gly Arg Leu Val Thr Pro Gly Thr Pro
1               5                   10                  15

Leu Thr Leu Ser Cys Lys Val Ser Gly Phe Ser Leu Ser Ser Tyr Asp
            20                  25                  30

Met Ser Trp Val Arg Gln Thr Pro Gly Lys Gly Leu Glu Trp Ile Gly
            35                  40                  45

Thr Ile Tyr Ile Gly Gly Thr Thr Ala Tyr Ala Ser Trp Pro Lys Gly
            50                  55                  60

Arg Phe Thr Ile Ser Lys Thr Ser Thr Thr Val Asp Leu Lys Ile Thr
65                  70                  75                  80

Ser Pro Thr Lys Glu Asp Thr Ala Thr Tyr Phe Cys Ala Arg Leu Gln
```

85                  90                  95

Gly Ala Asn Tyr Tyr Asn Ser Leu Ala Leu Trp Gly Gln Gly Thr Leu
                100                 105                 110

Val Thr Val Ser Ser
        115

<210> SEQ ID NO 5
<211> LENGTH: 123
<212> TYPE: PRT
<213> ORGANISM: Oryctolagus cuniculus

<400> SEQUENCE: 5

Gln Gln Leu Glu Gln Ser Gly Gly Gly Ala Glu Gly Gly Leu Val Lys
1               5                   10                  15

Pro Gly Gly Ser Leu Glu Leu Cys Cys Lys Ala Ser Gly Phe Ser Leu
            20                  25                  30

Ser Ser Ser Tyr Trp Ile Cys Trp Val Arg Gln Ala Pro Gly Lys Gly
        35                  40                  45

Leu Glu Trp Ile Gly Cys Ile Tyr Thr Gly Ser Ser Gly Ile Thr Tyr
    50                  55                  60

Tyr Ala Ser Trp Val Asn Gly Arg Phe Thr Leu Ser Arg Asp Ile Asp
65                  70                  75                  80

Gln Ser Thr Gly Cys Leu Gln Leu Asn Ser Leu Thr Ala Ala Asp Thr
                85                  90                  95

Ala Met Tyr Tyr Cys Ala Lys Asp Gly Pro Ser Thr Leu Phe Asn Phe
            100                 105                 110

Trp Gly Gln Gly Thr Leu Val Thr Val Ser Ser
        115                 120

<210> SEQ ID NO 6
<211> LENGTH: 117
<212> TYPE: PRT
<213> ORGANISM: Oryctolagus cuniculus

<400> SEQUENCE: 6

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Asp Asn Tyr Ala
            20                  25                  30

Met Gly Trp Val Arg Gln Ala Pro Gly Lys Gly Leu Glu Tyr Ile Gly
        35                  40                  45

Val Ile Ser Ser Asp Gly Phe Phe Tyr Asp Ala Ser Trp Ala Lys Gly
    50                  55                  60

Arg Phe Thr Ile Ser Lys Ala Ser Ser Thr Thr Val Asp Leu Lys Met
65                  70                  75                  80

Thr Gly Leu Thr Pro Glu Asp Thr Ala Thr Tyr Phe Cys Ala Arg Asp
                85                  90                  95

Arg Gly Thr Ser Thr Gly Ser Leu Asp Leu Trp Gly Gln Gly Thr Leu
            100                 105                 110

Val Thr Val Ser Ser
        115

<210> SEQ ID NO 7
<211> LENGTH: 122
<212> TYPE: PRT
<213> ORGANISM: Oryctolagus cuniculus

<400> SEQUENCE: 7

```
Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Tyr
            20                  25                  30

Met Ser Trp Val Arg Gln Ala Pro Gly Lys Gly Leu Glu Trp Val Gly
        35                  40                  45

Ile Ile Ser Gly Ser Ala Ser Thr Tyr Tyr Ala Thr Trp Ala Lys Gly
50                      55                  60

Arg Phe Thr Ile Ser Lys Thr Ser Thr Thr Val Asp Leu Lys Ile Ala
65                  70                  75                  80

Ser Pro Thr Thr Glu Asp Thr Ala Thr Tyr Phe Cys Ala Arg Thr His
                85                  90                  95

Tyr Ala Ala Val Ala Gly Tyr Gly Tyr Ala Ser Arg Leu Asp Leu Trp
                100                 105                 110

Gly Gln Gly Thr Leu Val Thr Val Ser Ser
            115                 120

<210> SEQ ID NO 8
<211> LENGTH: 120
<212> TYPE: PRT
<213> ORGANISM: Oryctolagus cuniculus

<400> SEQUENCE: 8

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Ser His
            20                  25                  30

Tyr Met Cys Trp Val Arg Gln Ala Pro Gly Lys Gly Leu Glu Trp Ile
        35                  40                  45

Ala Cys Ile Tyr Ala Gly Ser Ser Gly Asn Thr Tyr Tyr Ala Asn Trp
50                  55                      60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Val Asp Ala Ser Ser Gly Ser Trp Asp Leu Trp Gly Pro
                100                 105                 110

Gly Thr Leu Val Thr Val Ser Ser
            115                 120

<210> SEQ ID NO 9
<211> LENGTH: 119
<212> TYPE: PRT
<213> ORGANISM: Oryctolagus cuniculus

<400> SEQUENCE: 9

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Asn Tyr Ala
            20                  25                  30

Met Ser Trp Val Arg Gln Ala Pro Gly Lys Gly Leu Glu Trp Ile Gly
        35                  40                  45

Ser Val Ile Ser Gly Gly Ser Thr Tyr Tyr Ala Thr Trp Ala Arg Gly
50                  55                      60

Arg Phe Thr Ile Ser Lys Ser Ser Thr Thr Val Asp Leu Lys Met Thr
65                  70                  75                  80
```

Ser Leu Thr Thr Glu Asp Thr Ala Thr Tyr Phe Cys Ala Arg Gly Cys
                85                  90                  95

Pro Gly Tyr Asn Gly Asp Lys Tyr Thr Phe Asp Leu Trp Gly Pro Gly
            100                 105                 110

Thr Leu Val Thr Val Ser Ser
        115

<210> SEQ ID NO 10
<211> LENGTH: 120
<212> TYPE: PRT
<213> ORGANISM: Oryctolagus cuniculus

<400> SEQUENCE: 10

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Ala
            20                  25                  30

Met Ser Trp Val Arg Gln Ala Pro Gly Lys Gly Leu Glu Tyr Ile Gly
        35                  40                  45

Ile Ile Asp Ser Gly Gly Ser Ala Tyr Tyr Ala Thr Trp Ala Arg Gly
    50                  55                  60

Arg Phe Thr Ile Ser Arg Thr Ser Thr Thr Val Asp Leu Lys Met Thr
65                  70                  75                  80

Ser Pro Thr Thr Glu Asp Thr Ala Thr Tyr Phe Cys Ala Arg Gly Gly
                85                  90                  95

Pro Ala Tyr Ser Thr Asn Thr His Tyr Thr Leu Asp Leu Trp Gly Pro
            100                 105                 110

Gly Thr Leu Val Thr Val Ser Ser
        115                 120

<210> SEQ ID NO 11
<211> LENGTH: 119
<212> TYPE: PRT
<213> ORGANISM: Oryctolagus cuniculus

<400> SEQUENCE: 11

Gln Ser Val Glu Glu Ser Gly Gly Arg Leu Val Thr Pro Gly Gly Ser
1               5                   10                  15

Leu Thr Leu Thr Cys Thr Val Ser Gly Phe Ser Leu Ser Ile Tyr Ala
            20                  25                  30

Met Gly Trp Phe Arg Gln Ala Pro Gly Lys Gly Leu Glu Trp Ile Gly
        35                  40                  45

Asp Ile Tyr Ala Gly Ser Gly Ser Thr Trp Tyr Ala Ser Trp Ala Lys
    50                  55                  60

Gly Arg Phe Thr Ile Ser Lys Thr Ser Thr Thr Val Asp Leu Lys Ile
65                  70                  75                  80

Thr Ser Pro Thr Thr Glu Asp Thr Ala Thr Tyr Phe Cys Ala Arg Glu
                85                  90                  95

Ile Asp Ala Gly Tyr Val Gly Tyr Gly Phe Asn Leu Trp Gly Gln Gly
            100                 105                 110

Thr Leu Val Thr Val Ser Ser
        115

<210> SEQ ID NO 12
<211> LENGTH: 126
<212> TYPE: PRT
<213> ORGANISM: Oryctolagus cuniculus

```
<400> SEQUENCE: 12

Gln Gln Leu Glu Gln Ser Gly Gly Ala Glu Gly Gly Leu Val Lys
1               5                   10                  15

Pro Gly Gly Ser Leu Glu Leu Cys Cys Lys Ala Ser Gly Phe Ser Leu
            20                  25                  30

Thr Thr Asn Tyr Trp Ile Cys Trp Val Arg Gln Ala Pro Gly Lys Gly
        35                  40                  45

Leu Glu Trp Ile Gly Cys Ile Tyr Ala Asn Ser Val Gly Ser Thr Tyr
50                  55                  60

Tyr Ala Ser Trp Val Asn Gly Arg Phe Thr Leu Ser Arg Asp Ile Asp
65                  70                  75                  80

Gln Ser Thr Gly Cys Leu Gln Leu Asn Ser Leu Thr Ala Ala Asp Thr
                85                  90                  95

Ala Met Tyr Tyr Cys Ala Arg Val Asp Pro Gly Tyr Ser Phe Asp Ala
            100                 105                 110

Phe Asp Pro Trp Gly Pro Gly Thr Leu Val Thr Val Ser Ser
        115                 120                 125

<210> SEQ ID NO 13
<211> LENGTH: 120
<212> TYPE: PRT
<213> ORGANISM: Oryctolagus cuniculus

<400> SEQUENCE: 13

Gln Glu Gln Leu Lys Glu Ser Gly Gly Arg Leu Val Thr Pro Gly Gly
1               5                   10                  15

Ser Leu Thr Leu Thr Cys Thr Val Ser Gly Phe Ser Leu Ser Ile Tyr
            20                  25                  30

Ala Met Gly Trp Phe Arg Gln Ala Pro Gly Lys Gly Leu Glu Trp Ile
        35                  40                  45

Gly Asp Ile Tyr Pro Gly Ser Asp Ser Thr Trp Tyr Ala Ser Trp Ala
50                  55                  60

Lys Gly Arg Phe Thr Ile Ser Lys Thr Ser Thr Thr Val Asp Leu Lys
65                  70                  75                  80

Ile Thr Ser Pro Thr Thr Glu Asp Thr Ala Thr Tyr Phe Cys Ala Arg
                85                  90                  95

Glu Ile Asp Ala Gly Tyr Val Gly Tyr Gly Phe Asp Leu Trp Gly Gln
            100                 105                 110

Gly Thr Leu Val Thr Val Ser Ser
        115                 120

<210> SEQ ID NO 14
<211> LENGTH: 129
<212> TYPE: PRT
<213> ORGANISM: Oryctolagus cuniculus

<400> SEQUENCE: 14

Gln Gln Leu Glu Gln Ser Gly Gly Ala Glu Gly Gly Leu Val Lys
1               5                   10                  15

Pro Gly Gly Ser Leu Glu Leu Tyr Cys Lys Ala Ser Gly Phe Ser Leu
            20                  25                  30

Ser Ser Asp Ala Trp Ile Cys Trp Val Arg Gln Ala Pro Gly Lys Gly
        35                  40                  45

Leu Glu Trp Ile Gly Cys Ile Tyr Ala Gly Ser Ala Ser Asn Thr Tyr
50                  55                  60
```

-continued

```
Tyr Ala Thr Trp Val Asn Gly Arg Phe Thr Leu Ser Arg Asp Ile Ala
 65                  70                  75                  80

Gln Ser Thr Gly Cys Leu Gln Leu Asn Ser Leu Thr Ala Ala Asp Thr
                 85                  90                  95

Ala Met Tyr Tyr Cys Ala Arg Asp Arg Gly Tyr Asp Asp Tyr Gly Asp
            100                 105                 110

Ile Thr Arg Leu Asp Leu Trp Gly Gln Gly Thr Leu Val Thr Val Ser
        115                 120                 125

Ser

<210> SEQ ID NO 15
<211> LENGTH: 118
<212> TYPE: PRT
<213> ORGANISM: Oryctolagus cuniculus

<400> SEQUENCE: 15

Gln Ser Leu Glu Glu Ser Gly Gly Asp Leu Val Lys Pro Gly Ala Ser
 1               5                  10                  15

Leu Thr Leu Thr Cys Thr Ala Ser Gly Phe Ser Phe Ser Ser Ser Tyr
             20                  25                  30

Tyr Met Cys Trp Val Arg Gln Ala Pro Gly Lys Gly Leu Glu Trp Ile
         35                  40                  45

Ala Cys Ile Tyr Ala Gly Ser Ser Gly Val Thr Tyr Tyr Ala Ser Trp
 50                  55                  60

Ala Lys Gly Arg Phe Thr Ile Ser Asp Thr Ser Ser Thr Val Thr
 65                  70                  75                  80

Leu Gln Met Thr Ser Leu Thr Ala Ala Asp Thr Ala Thr Tyr Phe Cys
                 85                  90                  95

Ala Ser Glu Thr Asp Gly Asn Tyr Phe Asn Leu Trp Gly Pro Gly Thr
            100                 105                 110

Leu Val Thr Val Ser Ser
        115

<210> SEQ ID NO 16
<211> LENGTH: 117
<212> TYPE: PRT
<213> ORGANISM: Oryctolagus cuniculus

<400> SEQUENCE: 16

Gln Ser Leu Glu Glu Ser Gly Gly Arg Leu Val Thr Pro Gly Thr Pro
 1               5                  10                  15

Leu Thr Leu Thr Cys Thr Ala Ser Gly Phe Ser Ile Thr Asn Tyr His
             20                  25                  30

Ile Ser Trp Val Arg Gln Ala Pro Gly Lys Gly Leu Glu Trp Ile Gly
         35                  40                  45

Tyr Ile Tyr Ala Gly Arg Asp Phe Thr Tyr Tyr Ala Asn Trp Ala Glu
 50                  55                  60

Gly Arg Phe Thr Ile Ser Lys Thr Ser Thr Thr Val Asp Leu Gln Val
 65                  70                  75                  80

Thr Val Pro Thr Thr Glu Asp Thr Ala Thr Tyr Phe Cys Ala Arg Asp
                 85                  90                  95

Gly Gly Ser Pro Asn Trp Thr Leu Asp Leu Trp Gly Gln Gly Thr Leu
            100                 105                 110

Val Thr Val Ser Ser
        115
```

```
<210> SEQ ID NO 17
<211> LENGTH: 114
<212> TYPE: PRT
<213> ORGANISM: Oryctolagus cuniculus

<400> SEQUENCE: 17

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Asn Ser Asn Gly
                20                  25                  30

Ile Asn Trp Val Arg Gln Ala Pro Gly Lys Gly Leu Glu Trp Ile Gly
            35                  40                  45

Tyr Ile Gly Ala Gly Asp Ile Thr Tyr Cys Ala Ser Trp Ala Lys Gly
        50                  55                  60

Arg Phe Thr Ile Ser Lys Thr Ser Ser Thr Thr Val Asp Leu Lys Ile
65                  70                  75                  80

Thr Ser Leu Thr Thr Glu Asp Thr Ala Thr Tyr Phe Cys Ala Arg Trp
                85                  90                  95

Gly Pro Gly Ala Leu Asp Leu Trp Gly Gln Gly Thr Leu Val Thr Val
            100                 105                 110

Ser Ser

<210> SEQ ID NO 18
<211> LENGTH: 120
<212> TYPE: PRT
<213> ORGANISM: Oryctolagus cuniculus

<400> SEQUENCE: 18

Gln Ser Leu Glu Glu Ser Gly Gly Asp Leu Val Lys Pro Gly Ala Ser
1               5                   10                  15

Leu Thr Leu Thr Cys Thr Ala Ser Gly Ile Ser Phe Ser Ser Ser Asp
                20                  25                  30

Phe Met Cys Trp Val Arg Gln Ala Pro Gly Lys Gly Leu Glu Trp Ile
            35                  40                  45

Ala Cys Ile Tyr Ala Gly Ser Ser Val Ser Ile Tyr Tyr Ala Thr Trp
        50                  55                  60

Ala Lys Gly Arg Phe Thr Ile Ser Lys Ala Ser Ser Thr Thr Val Thr
65                  70                  75                  80

Leu Gln Met Ala Ser Leu Thr Val Ala Asp Thr Ala Thr Tyr Phe Cys
                85                  90                  95

Ala Arg Ser Thr Gly Ser Val Gly Arg Gly Phe Asn Leu Trp Gly Gln
            100                 105                 110

Gly Thr Leu Val Thr Val Ser Ser
            115                 120

<210> SEQ ID NO 19
<211> LENGTH: 120
<212> TYPE: PRT
<213> ORGANISM: Oryctolagus cuniculus

<400> SEQUENCE: 19

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Thr Tyr
                20                  25                  30

Tyr Met Cys Trp Val Arg Gln Ala Pro Gly Lys Gly Leu Glu Trp Ile
            35                  40                  45
```

```
Ala Cys Ile Tyr Ala Gly Ser Gly Ser Thr Tyr Ala Ser Trp
    50              55                  60

Ala Lys Gly Arg Phe Thr Ile Ser Lys Thr Ser Ser Thr Val Thr
65              70              75                  80

Leu Gln Met Thr Ser Leu Thr Ala Ala Asp Thr Ala Thr Tyr Phe Cys
                85              90                  95

Ala Arg Val Asp Gly Ser Ser Gly Ser Trp Asp Leu Trp Gly Pro
            100             105                 110

Gly Thr Leu Val Thr Val Ser Ser
        115             120
```

<210> SEQ ID NO 20
<211> LENGTH: 120
<212> TYPE: PRT
<213> ORGANISM: Oryctolagus cuniculus

<400> SEQUENCE: 20

```
Gln Glu Gln Leu Val Glu Ser Gly Gly Leu Val Gln Pro Glu Gly
1               5                   10                  15

Ser Leu Thr Leu Thr Cys Thr Ala Ser Gly Phe Ser Phe Ser Ser Asn
            20                  25                  30

Tyr Trp Met Cys Trp Val Arg Gln Ala Pro Gly Lys Gly Leu Glu Trp
        35                  40                  45

Ile Ala Cys Ile Tyr Thr Gly Gly Ser Gly Val Thr Tyr Tyr Ala Ser
    50                  55                  60

Trp Ala Lys Gly Arg Phe Thr Leu Ser Lys Thr Ser Ser Thr Val
65              70                  75                  80

Thr Leu Gln Val Thr Ser Leu Thr Ala Ala Asp Thr Ala Thr Tyr Phe
                85                  90                  95

Cys Ala Arg Asp Leu Val Val Thr Ser Phe Asn Leu Trp Gly Gln
            100                 105                 110

Gly Thr Leu Val Thr Val Ser Ser
        115             120
```

<210> SEQ ID NO 21
<211> LENGTH: 125
<212> TYPE: PRT
<213> ORGANISM: Oryctolagus cuniculus

<400> SEQUENCE: 21

```
Gln Gln Leu Glu Gln Ser Gly Gly Gly Ala Glu Gly Gly Leu Val Lys
1               5                   10                  15

Pro Gly Gly Ser Leu Glu Leu Cys Cys Lys Ala Ser Gly Phe Ser Leu
            20                  25                  30

Gly Ser Ser Tyr Trp Ile Cys Trp Val Arg Gln Ala Pro Gly Lys Gly
        35                  40                  45

Leu Glu Trp Ile Gly Cys Ile Tyr Ala Gly Ser Ser Gly Ile Thr Tyr
    50                  55                  60

Tyr Ala Ser Trp Val Ser Gly Arg Phe Thr Leu Ser Arg Asp Ile Asp
65              70                  75                  80

Gln Ser Thr Gly Cys Leu Gln Leu Asn Ser Leu Thr Ala Ala Asp Thr
                85                  90                  95

Ala Met Tyr Tyr Cys Ala Arg Asp Ile Tyr Ala Ser Thr Ser Gly Tyr
            100                 105                 110

Asp Leu Trp Gly Gln Gly Thr Leu Val Thr Val Ser Ser
        115                 120                 125
```

<210> SEQ ID NO 22
<211> LENGTH: 123
<212> TYPE: PRT
<213> ORGANISM: Oryctolagus cuniculus

<400> SEQUENCE: 22

```
Gln Gln Leu Glu Gln Ser Gly Gly Gly Ala Glu Gly Gly Leu Val Lys
1               5                   10                  15

Pro Gly Gly Ser Leu Glu Leu Cys Cys Lys Ala Ser Gly Phe Ser Leu
            20                  25                  30

Ser Thr Ser Tyr Trp Arg Cys Trp Val Arg Gln Ala Pro Gly Lys Gly
        35                  40                  45

Leu Glu Trp Ile Gly Cys Ile Tyr Ala Gly Ser Ser Asp Ala Thr Tyr
    50                  55                  60

Tyr Ala Asn Trp Val Asn Gly Arg Phe Thr Leu Ser Arg Asp Ile Asp
65                  70                  75                  80

Gln Ser Thr Gly Cys Leu Gln Leu Asn Ser Leu Thr Ala Ala Asp Thr
                85                  90                  95

Ala Met Tyr Tyr Cys Ala Ser Gly Val Gly Phe Gly Tyr Phe Asn Leu
            100                 105                 110

Trp Gly Gln Gly Thr Leu Val Thr Val Ser Ser
        115                 120
```

<210> SEQ ID NO 23
<211> LENGTH: 119
<212> TYPE: PRT
<213> ORGANISM: Oryctolagus cuniculus

<400> SEQUENCE: 23

```
Gln Ser Leu Glu Glu Ser Gly Gly Arg Leu Val Thr Pro Gly Gly Ser
1               5                   10                  15

Leu Thr Leu Thr Cys Thr Val Ser Gly Ile Asp Leu Ser Asn Tyr Ala
            20                  25                  30

Met Ser Trp Val Arg Gln Ala Pro Gly Lys Gly Leu Glu Trp Ile Gly
        35                  40                  45

Ser Val Ile Ser Gly Gly Ser Thr Tyr Tyr Ala Thr Trp Ala Lys Gly
    50                  55                  60

Arg Phe Thr Ile Ser Lys Thr Ser Thr Thr Val Asp Leu Lys Met Thr
65                  70                  75                  80

Ser Leu Thr Thr Glu Asp Thr Ala Thr Tyr Phe Cys Ala Arg Gly Cys
                85                  90                  95

Pro Gly Tyr Asn Gly Asp Lys Tyr Ala Leu Asp Leu Trp Gly Pro Gly
            100                 105                 110

Thr Val Val Thr Val Ser Ser
        115
```

<210> SEQ ID NO 24
<211> LENGTH: 121
<212> TYPE: PRT
<213> ORGANISM: Oryctolagus cuniculus

<400> SEQUENCE: 24

```
Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Asp Ala
            20                  25                  30

Val Gly Trp Val Arg Gln Ala Pro Gly Lys Gly Leu Glu Tyr Ile Gly
```

```
                    35                  40                  45
Ile Ile Val Ser Ser Gly Glu Thr Phe Tyr Ala Ser Trp Ala Arg Gly
        50                  55                  60

Arg Cys Thr Ile Ser Lys Thr Ser Ser Thr Thr Val Asp Leu Arg Ile
 65                  70                  75                  80

Thr Arg Leu Thr Thr Glu Asp Thr Ala Thr Tyr Phe Cys Ala Arg Gly
                85                  90                  95

Gly Pro Gly Tyr Ser Phe Asp Thr Glu Tyr Ala Phe Asp Pro Trp Gly
            100                 105                 110

Pro Gly Thr Leu Val Thr Val Ser Ser
            115                 120

<210> SEQ ID NO 25
<211> LENGTH: 121
<212> TYPE: PRT
<213> ORGANISM: Oryctolagus cuniculus

<400> SEQUENCE: 25

Gln Ser Val Glu Glu Ser Gly Gly Arg Leu Val Thr Pro Gly Thr Pro
  1               5                  10                  15

Leu Thr Leu Thr Cys Thr Val Ser Gly Phe Ser Leu Ser Ser Tyr Tyr
                20                  25                  30

Met Ser Trp Val Arg Gln Ala Pro Gly Lys Gly Leu Glu Trp Ile Gly
            35                  40                  45

Tyr Ile Tyr Ala Ala Gly Pro Ile Thr Tyr Tyr Ala Thr Trp Ala Lys
        50                  55                  60

Gly Arg Phe Thr Ile Ser Lys Thr Ser Thr Thr Val Asp Leu Lys Ile
 65                  70                  75                  80

Thr Ser Pro Thr Thr Glu Asp Thr Ala Thr Tyr Phe Cys Val Arg Asp
                85                  90                  95

Gly Ser Gly Ser Gly Thr Tyr Gly Tyr Asn Gly Met Asp Leu Trp Gly
            100                 105                 110

Pro Gly Thr Leu Val Thr Val Ser Ser
            115                 120

<210> SEQ ID NO 26
<211> LENGTH: 119
<212> TYPE: PRT
<213> ORGANISM: Oryctolagus cuniculus

<400> SEQUENCE: 26

Gln Glu Gln Leu Val Glu Ser Gly Gly Gly Leu Val Gln Pro Glu Gly
  1               5                  10                  15

Ser Leu Thr Leu Thr Cys Lys Ala Ser Gly Phe Asp Phe Ser Ser Asn
                20                  25                  30

Tyr Tyr Met Cys Trp Val Arg Gln Ala Pro Gly Lys Gly Leu Glu Leu
            35                  40                  45

Ile Ala Cys Ile Tyr Thr Asn Ser Gly Asn Thr Trp Ser Ala Ser Trp
        50                  55                  60

Ala Lys Gly Arg Phe Thr Ile Ser Lys Thr Ser Ser Thr Thr Val Thr
 65                  70                  75                  80

Leu Gln Met Thr Ser Leu Thr Ala Ala Asp Thr Ala Thr Tyr Phe Cys
                85                  90                  95

Ala Arg Asp Leu Asn Tyr Pro Asp Thr Ser Asn Leu Trp Gly Gln Gly
            100                 105                 110

Thr Leu Val Thr Val Ser Ser
```

-continued

```
                 115

<210> SEQ ID NO 27
<211> LENGTH: 119
<212> TYPE: PRT
<213> ORGANISM: Oryctolagus cuniculus

<400> SEQUENCE: 27

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Val Tyr Ala
            20                  25                  30

Met Gly Trp Phe Arg Gln Ala Pro Gly Lys Gly Leu Glu Trp Ile Gly
        35                  40                  45

Asp Ile Tyr Ile Ala Ser Asp Gly Thr Trp Tyr Ala Asn Trp Ala Lys
    50                  55                  60

Gly Arg Phe Thr Ile Ser Lys Thr Ser Thr Thr Val Asp Leu Lys Ile
65                  70                  75                  80

Thr Ser Pro Thr Thr Glu Asp Thr Ala Thr Tyr Phe Cys Ala Arg Glu
                85                  90                  95

Ile Asp Ala Gly Tyr Val Gly Tyr Gly Phe Asn Leu Trp Gly Gln Gly
            100                 105                 110

Thr Leu Val Thr Val Ser Ser
        115

<210> SEQ ID NO 28
<211> LENGTH: 125
<212> TYPE: PRT
<213> ORGANISM: Oryctolagus cuniculus

<400> SEQUENCE: 28

Gln Gln Leu Glu Gln Ser Gly Gly Ala Glu Gly Gly Leu Val Lys
1               5                   10                  15

Pro Gly Gly Ser Leu Glu Leu Cys Cys Lys Ala Ser Gly Phe Ser Leu
            20                  25                  30

Ser Ser Ala Tyr Trp Ile Cys Trp Val Arg Gln Ala Pro Gly Lys Gly
        35                  40                  45

Leu Glu Trp Val Gly Cys Ile Tyr Ala Asp Ser Ser Ile Thr Tyr
    50                  55                  60

Tyr Ala Ser Trp Val Asn Gly Arg Phe Thr Leu Ser Arg Asp Ile Asp
65                  70                  75                  80

Gln Ser Thr Gly Cys Leu Gln Leu Asn Ser Leu Thr Ala Ala Asp Thr
                85                  90                  95

Ala Met Tyr Tyr Cys Ala Arg Asp Tyr Gly Gly Ser Gly Tyr Asn Phe
            100                 105                 110

Asn Leu Trp Gly Gln Gly Thr Leu Val Thr Val Ser Ser
        115                 120                 125

<210> SEQ ID NO 29
<211> LENGTH: 120
<212> TYPE: PRT
<213> ORGANISM: Oryctolagus cuniculus

<400> SEQUENCE: 29

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Thr Ile Ser Ser Tyr Tyr
            20                  25                  30
```

```
Met Ser Trp Val Arg Gln Ala Pro Gly Lys Gly Leu Glu Trp Ile Gly
            35                  40                  45

Gly Ile Ala Thr Asp Gly Asn Thr Tyr Tyr Ala Asn Trp Ala Lys Gly
 50                  55                  60

Arg Phe Thr Val Ser Arg Thr Ser Thr Thr Val Asp Leu Lys Val Thr
65                  70                  75                  80

Ser Pro Thr Ala Glu Asp Thr Ala Thr Tyr Phe Cys Ala Arg Gly Gly
                85                  90                  95

Pro Ala Tyr Ser Arg Gly Thr His Tyr Ala Met Asp Leu Trp Gly Pro
            100                 105                 110

Gly Thr Leu Val Thr Val Ser Ser
            115                 120

<210> SEQ ID NO 30
<211> LENGTH: 121
<212> TYPE: PRT
<213> ORGANISM: Oryctolagus cuniculus

<400> SEQUENCE: 30

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Tyr
            20                  25                  30

Met Ser Trp Val Arg Gln Ala Pro Gly Lys Gly Leu Glu Trp Ile Gly
            35                  40                  45

Tyr Ile Tyr Ala Ala Gly Pro Ile Thr Tyr Tyr Ala Thr Trp Ala Lys
 50                  55                  60

Gly Arg Phe Thr Ile Ser Lys Thr Ser Thr Thr Val Asp Leu Lys Ile
65                  70                  75                  80

Thr Ser Pro Thr Thr Glu Asp Thr Ala Thr Tyr Phe Cys Val Arg Asp
                85                  90                  95

Gly Ser Gly Ser Gly Thr Tyr Gly Tyr Asn Gly Met Asp Leu Trp Gly
            100                 105                 110

Pro Gly Thr Leu Val Thr Val Ser Ser
            115                 120

<210> SEQ ID NO 31
<211> LENGTH: 117
<212> TYPE: PRT
<213> ORGANISM: Oryctolagus cuniculus

<400> SEQUENCE: 31

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asp Ser Tyr Ala
            20                  25                  30

Met Gly Trp Val Arg Gln Ala Pro Gly Lys Gly Leu Glu Trp Ile Gly
            35                  40                  45

Ile Ile Asn Ser Tyr Gly Ser Ile Tyr Tyr Ala Ser Trp Ala Lys Gly
 50                  55                  60

Arg Phe Thr Ile Ser Lys Thr Ser Thr Thr Val Asp Leu Lys Met Thr
65                  70                  75                  80

Ser Leu Thr Thr Glu Asp Thr Ala Thr Tyr Phe Cys Ala Arg Ser Ala
                85                  90                  95

Tyr Ser Asn Asn Gly Asp Arg Leu His Leu Trp Gly Gln Gly Thr Leu
            100                 105                 110
```

```
Val Thr Val Ser Ser
        115
```

<210> SEQ ID NO 32
<211> LENGTH: 127
<212> TYPE: PRT
<213> ORGANISM: Oryctolagus cuniculus

<400> SEQUENCE: 32

```
Gln Gln Leu Glu Gln Ser Gly Gly Gly Ala Glu Gly Gly Leu Val Lys
1               5                   10                  15

Pro Gly Gly Ser Leu Glu Leu Cys Cys Lys Ala Ser Gly Phe Ser Leu
            20                  25                  30

Ser Asn Ser Tyr Trp Ile Cys Trp Val Arg Gln Ala Pro Gly Lys Gly
        35                  40                  45

Leu Glu Trp Ile Gly Cys Ile Tyr Val Gly Ser Ser Gly Ser Thr Tyr
    50                  55                  60

Tyr Ala Ser Trp Val Asn Gly Arg Phe Thr Leu Ser Arg Asp Ile Asp
65                  70                  75                  80

Gln Ser Thr Gly Cys Leu Gln Leu Asn Ser Leu Thr Ala Ala Asp Thr
                85                  90                  95

Ala Ile Tyr Tyr Cys Ala Arg Asp Gly Ala Thr Ser Thr Ser Gly His
            100                 105                 110

Leu Phe Glu Leu Trp Gly Gln Gly Thr Leu Val Thr Val Ser Ser
        115                 120                 125
```

<210> SEQ ID NO 33
<211> LENGTH: 125
<212> TYPE: PRT
<213> ORGANISM: Oryctolagus cuniculus

<400> SEQUENCE: 33

```
Gln Gln Leu Glu Gln Ser Gly Gly Gly Glu Gly Gly Leu Val Lys
1               5                   10                  15

Pro Gly Gly Ser Leu Glu Leu Cys Cys Lys Ala Ser Gly Phe Ser Leu
            20                  25                  30

Ser Ser Ser Tyr Trp Ile Cys Trp Val Arg Gln Ala Pro Gly Lys Gly
        35                  40                  45

Leu Glu Trp Ile Gly Cys Ile Tyr Val Gly Ser Ser Gly Ser Thr Tyr
    50                  55                  60

Tyr Ala Ser Trp Val Ser Gly Arg Phe Thr Leu Ser Arg Asp Ile Asp
65                  70                  75                  80

Gln Ser Thr Gly Cys Leu Gln Leu Asn Ser Leu Thr Ala Ala Asp Thr
                85                  90                  95

Ala Met Tyr Tyr Cys Ala Arg Asp Ile Tyr Gly Ser Thr Asn Gly Tyr
            100                 105                 110

Asp Leu Trp Gly Gln Gly Thr Leu Val Thr Val Ser Ser
        115                 120                 125
```

<210> SEQ ID NO 34
<211> LENGTH: 121
<212> TYPE: PRT
<213> ORGANISM: Oryctolagus cuniculus

<400> SEQUENCE: 34

```
Gln Ser Val Glu Glu Ser Gly Gly Arg Leu Val Thr Pro Gly Thr Pro
1               5                   10                  15
```

Leu Thr Leu Thr Cys Thr Val Ser Gly Phe Ser Leu Ser Tyr Tyr
            20                  25                  30

Met Ser Trp Val Arg Gln Ala Pro Gly Lys Gly Leu Glu Trp Ile Gly
        35                  40                  45

Tyr Ile Tyr Ala Ala Gly Pro Ile Thr Tyr Tyr Ala Thr Trp Ala Lys
    50                  55                  60

Gly Arg Phe Thr Ile Ser Lys Thr Ser Thr Thr Val Asp Leu Lys Ile
65                  70                  75                  80

Thr Ser Pro Thr Thr Glu Asp Thr Ala Thr Tyr Phe Cys Val Arg Asp
                85                  90                  95

Gly Ser Gly Ser Gly Thr Tyr Gly Tyr Asn Gly Met Asp Leu Trp Gly
            100                 105                 110

Pro Gly Thr Leu Val Thr Val Ser Ser
        115                 120

<210> SEQ ID NO 35
<211> LENGTH: 121
<212> TYPE: PRT
<213> ORGANISM: Oryctolagus cuniculus

<400> SEQUENCE: 35

Gln Glu Gln Leu Val Glu Ser Gly Gly Gly Leu Val Gln Pro Glu Gly
1               5                   10                  15

Ser Leu Thr Leu Thr Cys Gln Ala Ser Gly Phe Thr Phe Ser Ser Tyr
            20                  25                  30

Tyr Val Ile Cys Trp Val Arg Gln Ala Pro Gly Lys Gly Leu Glu Trp
        35                  40                  45

Ile Ala Cys Ile Gly Thr Gly Asp Gly Leu Thr Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Asp Arg Tyr Ala Thr Val Ser Gly Ile Leu Asn Leu Trp Gly
            100                 105                 110

Pro Gly Thr Leu Val Thr Val Ser Ser
        115                 120

<210> SEQ ID NO 36
<211> LENGTH: 117
<212> TYPE: PRT
<213> ORGANISM: Oryctolagus cuniculus

<400> SEQUENCE: 36

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Gly Tyr Ala
            20                  25                  30

Met Ser Trp Val Arg Gln Ala Pro Gly Lys Gly Leu Glu Trp Ile Gly
        35                  40                  45

Ile Ile Tyr Ala Gly Ser Gly Thr Tyr Tyr Ala Ser Trp Val Lys
    50                  55                  60

Gly Arg Phe Thr Ile Ser Lys Thr Ser Thr Thr Val Asp Leu Lys Ile
65                  70                  75                  80

Thr Ser Leu Thr Thr Glu Asp Thr Ala Thr Tyr Phe Cys Ala Arg Ala
                85                  90                  95

```
Val Pro Asp Asp Ser Ala Gly Lys Lys Leu Trp Gly Gln Gly Thr Leu
            100                 105                 110
Val Thr Val Ser Ser
            115

<210> SEQ ID NO 37
<211> LENGTH: 124
<212> TYPE: PRT
<213> ORGANISM: Oryctolagus cuniculus

<400> SEQUENCE: 37

Gln Gln Leu Ala Gln Ser Gly Gly Gly Ala Glu Gly Gly Leu Val Lys
1               5                   10                  15
Pro Gly Gly Ser Leu Glu Leu Cys Cys Glu Ala Ser Gly Phe Ser Leu
            20                  25                  30
Ser Ser Ser Tyr Trp Ile Cys Trp Val Arg Gln Ala Pro Gly Lys Gly
        35                  40                  45
Leu Glu Trp Ile Gly Cys Ile Tyr Thr Gly Ser Ser Gly Asn Thr Tyr
    50                  55                  60
Tyr Ala Ser Trp Val Asn Gly Arg Phe Thr Leu Ser Arg Asp Ile Asp
65                  70                  75                  80
Arg Ser Thr Gly Cys Leu Gln Leu Asn Ser Leu Thr Ala Ala Asp Thr
                85                  90                  95
Ala Met Tyr Tyr Cys Ala Arg Asp Ala Asn Ser His Tyr Met Met Asn
            100                 105                 110
Leu Trp Gly Gln Gly Thr Leu Val Thr Val Ser Ser
        115                 120

<210> SEQ ID NO 38
<211> LENGTH: 119
<212> TYPE: PRT
<213> ORGANISM: Oryctolagus cuniculus

<400> SEQUENCE: 38

Gln Glu Gln Leu Glu Glu Ser Gly Gly Asp Leu Val Lys Pro Glu Gly
1               5                   10                  15
Ser Leu Thr Leu Thr Cys Thr Ala Ser Gly Phe Ser Phe Ser Ser Asn
            20                  25                  30
Tyr Trp Ile Cys Trp Val Arg Gln Ala Pro Gly Lys Gly Leu Glu Leu
        35                  40                  45
Ile Ala Cys Ile Tyr Thr Ser Thr Gly Asn Thr Trp Tyr Ala Ser Trp
    50                  55                  60
Ala Lys Gly Arg Phe Thr Ile Ser Lys Thr Ser Ser Thr Thr Val Thr
65                  70                  75                  80
Leu Gln Met Thr Ser Leu Thr Val Ala Asp Thr Ala Thr Tyr Phe Cys
                85                  90                  95
Ala Arg Asp Leu Leu Val Val Thr Ser Phe Asn Leu Trp Gly Gln Gly
            100                 105                 110
Thr Leu Val Thr Val Ser Ser
        115

<210> SEQ ID NO 39
<211> LENGTH: 119
<212> TYPE: PRT
<213> ORGANISM: Oryctolagus cuniculus

<400> SEQUENCE: 39

Gln Ser Val Glu Glu Ser Gly Gly Arg Leu Val Thr Pro Gly Gly Ser
```

```
                1               5                   10                  15
Leu Thr Leu Thr Cys Thr Val Ser Gly Phe Ser Leu Ser Val Tyr Ala
                    20                  25                  30

Met Gly Trp Phe Arg Gln Ala Pro Gly Lys Gly Leu Glu Trp Ile Gly
            35                  40                  45

Asp Ile Tyr Thr Gly Ser Gly Ser Thr Trp Tyr Ala Ser Trp Ala Lys
        50                  55                  60

Gly Arg Phe Thr Ile Ser Lys Thr Ser Thr Thr Val Asp Leu Lys Ile
65                  70                  75                  80

Thr Ser Pro Thr Thr Glu Asp Thr Ala Thr Tyr Phe Cys Ala Arg Glu
                85                  90                  95

Ile Asp Ala Gly Tyr Val Gly Tyr Gly Phe Asn Leu Trp Gly Gln Gly
            100                 105                 110

Thr Leu Val Thr Val Ser Ser
        115

<210> SEQ ID NO 40
<211> LENGTH: 118
<212> TYPE: PRT
<213> ORGANISM: Oryctolagus cuniculus

<400> SEQUENCE: 40

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Ala
                    20                  25                  30

Met Gly Trp Val Arg Gln Ala Pro Gly Lys Gly Leu Glu Tyr Ile Gly
            35                  40                  45

Ile Ile Ser Asn Ser Gly Thr Thr Tyr Tyr Ala Ser Trp Ala Lys Gly
        50                  55                  60

Arg Phe Thr Ile Ser Lys Thr Ser Ser Thr Val Asp Leu Lys Met
65                  70                  75                  80

Thr Ser Pro Thr Thr Glu Asp Thr Ala Thr Tyr Phe Cys Ala Arg Asp
                85                  90                  95

Arg Tyr Ala Asn Thr His Gly Ile Phe Ser Leu Trp Gly Gln Gly Thr
            100                 105                 110

Leu Val Thr Val Ser Ser
        115

<210> SEQ ID NO 41
<211> LENGTH: 122
<212> TYPE: PRT
<213> ORGANISM: Oryctolagus cuniculus

<400> SEQUENCE: 41

Gln Gln Leu Glu Gln Ser Gly Gly Gly Leu Val Lys Pro Gly Gly Ser
1               5                   10                  15

Leu Glu Leu Cys Cys Lys Ala Ser Gly Phe Ser Leu Ser Ser Ser Tyr
                    20                  25                  30

Trp Ile Cys Trp Val Arg Gln Ala Pro Gly Lys Gly Leu Glu Trp Ile
            35                  40                  45

Gly Cys Ile Tyr Ala Gly Ser Ser Gly Ser Thr Tyr Tyr Ala Asn Trp
        50                  55                  60

Val Asn Gly Arg Phe Thr Leu Ser Arg Asp Ile Asp Gln Ser Thr Gly
65                  70                  75                  80

Cys Leu Gln Leu Ser Ser Leu Thr Ala Ala Asp Thr Ala Met Tyr Tyr
```

```
                        85                  90                  95
Cys Ala Arg Ser Ile Val Asp Phe Ser Ser Gly Trp Gly Asp Leu Trp
               100                 105                 110
Gly Gln Gly Thr Leu Val Thr Val Ser Ser
               115                 120

<210> SEQ ID NO 42
<211> LENGTH: 116
<212> TYPE: PRT
<213> ORGANISM: Oryctolagus cuniculus

<400> SEQUENCE: 42

Gln Ser Leu Glu Glu Ser Gly Gly Arg Leu Val Thr Pro Gly Thr Pro
1               5                   10                  15
Leu Thr Leu Ser Cys Thr Ala Ser Gly Phe Ser Leu Ser Thr Tyr Tyr
                20                  25                  30
Met Ser Trp Val Arg Gln Ala Pro Gly Lys Gly Leu Glu Trp Ile Gly
                35                  40                  45
Tyr Met His Val Gly Gly Phe Pro Val Tyr Ala Ser Trp Ala Lys Gly
            50                  55                  60
Arg Phe Thr Ile Ser Lys Thr Ser Thr Thr Val Asp Leu Lys Ile Thr
65                  70                  75                  80
Ser Pro Thr Ile Glu Asp Thr Ala Thr Tyr Phe Cys Ala Arg Asp Phe
                85                  90                  95
Gly Pro Pro Asn Trp Thr Leu Asp Leu Trp Gly Gln Gly Thr Leu Val
                100                 105                 110
Thr Val Ser Ser
            115

<210> SEQ ID NO 43
<211> LENGTH: 125
<212> TYPE: PRT
<213> ORGANISM: Oryctolagus cuniculus

<400> SEQUENCE: 43

Gln Gln Leu Glu Gln Ser Gly Gly Gly Ala Glu Gly Gly Leu Val Lys
1               5                   10                  15
Pro Gly Gly Ser Leu Glu Leu Cys Cys Lys Ala Ser Gly Phe Ser Leu
                20                  25                  30
Ser Ser Asn Tyr Trp Met Cys Trp Val Arg Gln Ala Pro Gly Lys Gly
            35                  40                  45
Leu Glu Trp Ile Gly Cys Ile Tyr Ala Gly Ser Ser Asp Ser Thr Tyr
    50                  55                  60
Tyr Ala Ser Trp Val Asn Gly Arg Phe Thr Leu Ser Arg Asp Ile Asp
65                  70                  75                  80
Gln Ser Thr Gly Cys Leu Gln Leu Asn Ser Leu Thr Ala Ala Asp Thr
                85                  90                  95
Ala Met Tyr Tyr Cys Ala Ser Pro Gly Tyr Gly Tyr Gly Tyr Tyr
                100                 105                 110
Gly Leu Trp Gly Gln Gly Thr Leu Val Thr Val Ser Ser
            115                 120                 125

<210> SEQ ID NO 44
<211> LENGTH: 118
<212> TYPE: PRT
<213> ORGANISM: Oryctolagus cuniculus

<400> SEQUENCE: 44
```

-continued

Gln Ser Leu Glu Glu Ser Gly Gly Asp Leu Val Lys Pro Gly Ala Ser
1               5                   10                  15

Leu Lys Leu Ser Cys Thr Ala Ser Gly Val Ser Phe Ser Ser Ala Tyr
                20                  25                  30

Trp Met Cys Trp Val Arg Gln Ala Pro Gly Lys Gly Leu Glu Trp Ile
            35                  40                  45

Ala Cys Ile Tyr Ala Gly Ser Ser Gly Ser Thr Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg His Ala Ala Trp Phe Glu Leu Asp Leu Trp Gly Pro Gly Thr
            100                 105                 110

Leu Val Thr Val Ser Ser
            115

<210> SEQ ID NO 45
<211> LENGTH: 121
<212> TYPE: PRT
<213> ORGANISM: Oryctolagus cuniculus

<400> SEQUENCE: 45

Gln Ser Leu Glu Glu Ser Gly Gly Asp Leu Val Gln Pro Gly Gly Ser
1               5                   10                  15

Leu Thr Leu Thr Cys Lys Ala Ser Gly Phe Ser Phe Ser Ala Ser Tyr
                20                  25                  30

Trp Ile Cys Trp Val Arg Gln Ala Pro Gly Lys Gly Leu Glu Trp Ile
            35                  40                  45

Gly Cys Ile Tyr Ile Gly Gly Gly Arg Tyr Tyr Ala Ser Trp Ala
    50                  55                  60

Lys Gly Arg Phe Thr Ile Ser Lys Thr Ser Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Asp Pro Val Thr Gly Ser Asp Tyr Val Tyr Asp Leu Trp Gly
            100                 105                 110

Pro Gly Thr Leu Val Thr Val Ala Ser
            115                 120

<210> SEQ ID NO 46
<211> LENGTH: 120
<212> TYPE: PRT
<213> ORGANISM: Oryctolagus cuniculus

<400> SEQUENCE: 46

Gln Gln Gln Leu Val Glu Ser Gly Gly Leu Val Lys Pro Gly Ala
1               5                   10                  15

Ser Leu Thr Leu Thr Cys Lys Ala Ser Gly Phe Ser Phe Ser Ser Gly
                20                  25                  30

Tyr Tyr Met Cys Trp Val Arg Gln Ala Pro Gly Lys Gly Leu Glu Trp
            35                  40                  45

Ile Ala Cys Ile Gly Met Gly Ser Gly Lys Tyr Tyr Ala Ser Trp
    50                  55                  60

Ala Lys Gly Arg Phe Thr Ile Ser Lys Thr Ser Ser Thr Thr Val Thr
65                  70                  75                  80

-continued

Leu Gln Met Thr Ser Leu Thr Ala Ala Asp Thr Ala Thr Tyr Phe Cys
                    85                  90                  95

Ala Arg Lys Asp Gly Ser Gly Asn Glu His Tyr Asn Leu Trp Gly Pro
            100                 105                 110

Gly Thr Leu Val Thr Val Ser Ser
        115                 120

<210> SEQ ID NO 47
<211> LENGTH: 120
<212> TYPE: PRT
<213> ORGANISM: Oryctolagus cuniculus

<400> SEQUENCE: 47

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Ile Tyr Gly
            20                  25                  30

Met Gly Trp Val Arg Gln Ala Pro Gly Glu Gly Leu Glu Trp Ile Gly
        35                  40                  45

Ser Ile Ser Ser Gly Gly Ser Thr Tyr Tyr Ala Thr Trp Ala Lys Gly
    50                  55                  60

Arg Phe Thr Ile Ser Lys Thr Ser Ser Thr Thr Leu Asp Leu Lys Ile
65                  70                  75                  80

Thr Ser Pro Thr Thr Glu Asp Thr Ala Thr Tyr Phe Cys Val Arg Ser
                85                  90                  95

Asp Gly Tyr Thr Asn Gly Asp Tyr Asp Thr Tyr Phe Asn Leu Trp Gly
            100                 105                 110

Gln Gly Thr Leu Val Thr Val Ser
        115                 120

<210> SEQ ID NO 48
<211> LENGTH: 121
<212> TYPE: PRT
<213> ORGANISM: Oryctolagus cuniculus

<400> SEQUENCE: 48

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Val Tyr Asn
            20                  25                  30

Met Gly Trp Val Arg Gln Ala Pro Gly Lys Gly Leu Glu Tyr Ile Gly
        35                  40                  45

Ile Ile Ser Ser Ser Gly Thr Thr Tyr Tyr Ala Ser Trp Ala Lys Gly
    50                  55                  60

Arg Phe Thr Ile Ser Lys Thr Ser Ser Thr Thr Val Asp Leu Lys Ile
65                  70                  75                  80

Thr Ser Leu Thr Thr Glu Asp Thr Ala Thr Tyr Phe Cys Ala Arg Ala
                85                  90                  95

Asp Gly Tyr Thr Glu Gly Asp Tyr Ala Thr Tyr Phe Asn Leu Trp Gly
            100                 105                 110

Gln Gly Thr Leu Val Thr Val Ser Ser
        115                 120

<210> SEQ ID NO 49
<211> LENGTH: 118
<212> TYPE: PRT
<213> ORGANISM: Oryctolagus cuniculus -continued

```
<400> SEQUENCE: 49

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asp Tyr Tyr
            20                  25                  30

Met Gly Trp Val Arg Gln Ala Pro Gly Lys Gly Leu Glu Trp Ile Gly
        35                  40                  45

Thr Ile Asp Gly Gly Ser Thr Tyr Tyr Ala Ser Trp Ala Lys Gly
    50                  55                  60

Arg Phe Thr Val Ser Lys Thr Ser Thr Val Asp Leu Thr Ile Thr
65                  70                  75                  80

Ser Pro Thr Thr Glu Asp Thr Ala Ile Tyr Phe Cys Ala Arg Asn Tyr
                85                  90                  95

Tyr Ala Gly Leu Ser Asp Val Phe Phe Gly Trp Trp Gly Gln Gly Thr
            100                 105                 110

Leu Val Thr Val Ser Ser
        115

<210> SEQ ID NO 50
<211> LENGTH: 113
<212> TYPE: PRT
<213> ORGANISM: Oryctolagus cuniculus

<400> SEQUENCE: 50

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Leu Ser Ser Gly Gly
            20                  25                  30

Met Ser Trp Val Arg Gln Ala Pro Gly Lys Gly Leu Gly Trp Ile Gly
        35                  40                  45

Tyr Ile Asn Thr Gly Ser Gly Ser Thr Tyr Tyr Ala Ser Trp Val Asn
    50                  55                  60

Gly Arg Phe Thr Ile Ser Lys Thr Ser Ser Thr Thr Val Ser Leu Gln
65                  70                  75                  80

Met Thr Ser Leu Thr Ala Ala Asp Thr Ala Thr Tyr Phe Cys Ala Gly
                85                  90                  95

Gly Leu Pro Ser Asp Leu Trp Gly Pro Gly Thr Leu Val Thr Val Ser
            100                 105                 110

Ser

<210> SEQ ID NO 51
<211> LENGTH: 119
<212> TYPE: PRT
<213> ORGANISM: Oryctolagus cuniculus

<400> SEQUENCE: 51

Gln Ser Leu Glu Ala Ser Gly Gly Gly Leu Phe Gln Pro Gly Ala Ser
1               5                   10                  15

Leu Thr Leu Thr Cys Thr Ala Ser Gly Phe Ser Leu Ile Tyr Thr Tyr
            20                  25                  30

Val Met Cys Gly Val Arg Gln Ala Pro Gly Lys Gly Leu Glu Trp Ile
        35                  40                  45

Ala Cys Ile Tyr Thr Gly Arg Ser Gly Gly Leu Tyr Tyr Ala Asn Trp
    50                  55                  60

Ala Lys Gly Arg Phe Thr Ile Ser Lys Thr Ser Ser Thr Thr Val Thr
```

```
                65                  70                  75                  80
Leu Gln Met Thr Ser Leu Thr Ala Ala Asp Thr Ala Thr Tyr Phe Cys
                    85                  90                  95

Ala Arg Tyr Ile Gly Ala Trp Gly Pro Trp Ser Leu Trp Gly Pro Gly
                100                 105                 110

Thr Leu Val Thr Val Ser Ser
            115

<210> SEQ ID NO 52
<211> LENGTH: 119
<212> TYPE: PRT
<213> ORGANISM: Oryctolagus cuniculus

<400> SEQUENCE: 52

Gln Glu Gln Leu Val Glu Ser Gly Gly Asp Leu Val Lys Pro Glu Gly
1               5                   10                  15

Ser Leu Thr Leu Thr Cys Thr Ala Ser Gly Phe Ser Phe Ser Ser Asn
            20                  25                  30

Tyr Trp Ile Cys Trp Val Arg Gln Ala Pro Gly Lys Gly Leu Glu Trp
        35                  40                  45

Ile Ala Cys Ile Tyr Thr Ser Thr Asp Thr Thr Tyr Tyr Pro Asn Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                    85                  90                  95

Ala Arg Asp Leu Leu Val Val Thr Ser Phe Asn Leu Trp Gly Gln Gly
                100                 105                 110

Thr Leu Val Thr Val Ser Ser
            115

<210> SEQ ID NO 53
<211> LENGTH: 123
<212> TYPE: PRT
<213> ORGANISM: Oryctolagus cuniculus

<400> SEQUENCE: 53

Arg Ser Leu Glu Glu Ser Gly Gly Asp Leu Val Lys Pro Gly Thr Ser
1               5                   10                  15

Leu Thr Leu Thr Cys Thr Ala Ser Gly Phe Ser Phe Ser Gly Asn Tyr
            20                  25                  30

Tyr Met Cys Trp Val Arg Gln Ala Pro Gly Lys Gly Leu Glu Trp Ile
        35                  40                  45

Ala Cys Ile Val Val Gly Ser Gly Asn Thr Tyr Tyr Ala Gly Trp
    50                  55                  60

Ala Lys Arg Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                    85                  90                  95

Ala Ser Gly Ser Tyr Asp Asp Tyr Gly Asp Tyr Trp Tyr Phe Thr Leu
                100                 105                 110

Trp Gly Gln Gly Thr Leu Val Thr Val Ser Ser
            115                 120

<210> SEQ ID NO 54
<211> LENGTH: 114
<212> TYPE: PRT
```

<213> ORGANISM: Oryctolagus cuniculus

<400> SEQUENCE: 54

Gln Ser Val Glu Glu Ser Gly Gly Arg Leu Val Thr Pro Gly Gly Ser
1               5                   10                  15

Leu Thr Leu Thr Cys Lys Val Ser Gly Phe Ser Leu Ser Asp Tyr Asp
                20                  25                  30

Ile Tyr Trp Val Arg Gln Ala Pro Gly Lys Gly Leu Glu Trp Ile Gly
            35                  40                  45

Val Ile Asp Ile Glu Asn Ser Val Tyr Tyr Pro Thr Trp Ala Lys Gly
        50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Asp
                85                  90                  95

Tyr Ile Met Thr Leu Asp Leu Trp Gly Gln Gly Thr Leu Val Thr Val
                100                 105                 110

Ser Ser

<210> SEQ ID NO 55
<211> LENGTH: 113
<212> TYPE: PRT
<213> ORGANISM: Oryctolagus cuniculus

<400> SEQUENCE: 55

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Leu Ser Ser Gly Gly
                20                  25                  30

Met Thr Trp Val Arg Gln Ala Pro Gly Lys Gly Leu Glu Trp Ile Gly
            35                  40                  45

Tyr Ile Asn Thr Gly Ser Gly Arg Thr Tyr Tyr Ala Ser Trp Ala Lys
        50                  55                  60

Gly Arg Phe Ile Ile Ser Lys Thr Ser Ser Thr Thr Val Ser Leu Gln
65                  70                  75                  80

Met Thr Ser Leu Thr Ala Ala Asp Thr Ala Thr Tyr Phe Cys Ala Gly
                85                  90                  95

Gly Leu Pro Ser Asp Leu Trp Gly Pro Gly Thr Leu Val Thr Val Ser
                100                 105                 110

Ser

<210> SEQ ID NO 56
<211> LENGTH: 117
<212> TYPE: PRT
<213> ORGANISM: Oryctolagus cuniculus

<400> SEQUENCE: 56

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Gly
                20                  25                  30

Met Ile Trp Val Arg Gln Ala Pro Gly Glu Gly Leu Glu Trp Ile Gly
            35                  40                  45

Phe Ile Gly Arg Gly Gly Ala Thr Trp Tyr Ala Ser Trp Val Lys Gly
        50                  55                  60

Arg Phe Thr Ile Ser Lys Thr Ser Thr Thr Val Asp Leu Lys Ile Thr

```
                65                  70                  75                  80
Ser Pro Thr Ala Ser Asp Thr Ala Thr Tyr Phe Cys Ala Arg Asp Gly
                    85                  90                  95

Asp Ser Ser Asp Tyr Tyr Ala Phe Asn Leu Trp Gly Gln Gly Thr Leu
                100                 105                 110

Val Thr Val Ser Ser
        115

<210> SEQ ID NO 57
<211> LENGTH: 117
<212> TYPE: PRT
<213> ORGANISM: Oryctolagus cuniculus

<400> SEQUENCE: 57

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Arg Cys Ala
                20                  25                  30

Met Ile Trp Val Arg Gln Ala Pro Gly Lys Gly Leu Glu Trp Ile Gly
            35                  40                  45

Phe Ile Gly Arg Gly Gly Ser Thr Trp Tyr Ala Ser Trp Val Asn Gly
        50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Asp Gly
                    85                  90                  95

Asp Tyr Ser Asp Tyr Tyr Thr Phe Asp Leu Trp Gly Gln Gly Thr Leu
                100                 105                 110

Val Thr Val Ser Ser
        115

<210> SEQ ID NO 58
<211> LENGTH: 117
<212> TYPE: PRT
<213> ORGANISM: Oryctolagus cuniculus

<400> SEQUENCE: 58

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Cys Ala
                20                  25                  30

Met Ile Trp Val Arg Gln Ala Pro Gly Lys Gly Leu Glu Trp Ile Gly
            35                  40                  45

Phe Ile Gly Arg Gly Gly Ser Thr Trp Tyr Ala Ser Trp Val Asn Gly
        50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Asp Gly
                    85                  90                  95

Asp Phe Ser Asp Tyr Tyr Thr Phe Asn Leu Trp Gly Gln Gly Thr Leu
                100                 105                 110

Val Thr Val Ser Ser
        115

<210> SEQ ID NO 59
<211> LENGTH: 120
<212> TYPE: PRT
```

<213> ORGANISM: Oryctolagus cuniculus

<400> SEQUENCE: 59

Gln Ser Val Glu Glu Ser Gly Gly Arg Leu Val Lys Pro Asp Glu Thr
1               5                   10                  15

Leu Thr Leu Thr Cys Thr Val Ser Gly Ile Asp Leu Ser Ser Tyr Ala
            20                  25                  30

Met Gly Trp Val Arg Gln Ala Pro Gly Lys Gly Leu Glu Tyr Ile Gly
        35                  40                  45

Ile Ile Ser Ser Ser Gly Arg Thr Tyr Tyr Ala Asn Trp Ala Lys Gly
    50                  55                  60

Arg Phe Thr Ile Ser Lys Ala Ser Ser Thr Thr Val Asp Leu Lys Ile
65                  70                  75                  80

Thr Ser Pro Thr Thr Glu Asp Thr Ala Thr Tyr Phe Cys Ala Arg Leu
                85                  90                  95

Ile Thr Val Asp Tyr Tyr Ile Tyr Asp Tyr Phe Asn Leu Trp Gly Gln
            100                 105                 110

Gly Thr Leu Val Thr Val Ser Ser
            115                 120

<210> SEQ ID NO 60
<211> LENGTH: 112
<212> TYPE: PRT
<213> ORGANISM: Oryctolagus cuniculus

<400> SEQUENCE: 60

Gln Ser Leu Glu Glu Ser Gly Gly Arg Leu Val Thr Pro Gly Thr Pro
1               5                   10                  15

Leu Thr Leu Thr Cys Lys Ala Ser Gly Phe Ser Leu Ser Ser Tyr Trp
            20                  25                  30

Met Ser Trp Val Arg Gln Ala Arg Gly Lys Gly Leu Glu Trp Ile Gly
        35                  40                  45

Met Ile Tyr Gly Ser Gly Tyr Thr Tyr Tyr Ala Ser Trp Ala Lys Gly
    50                  55                  60

Arg Phe Thr Ile Ser Thr Thr Ser Thr Thr Val Asp Leu Ser Val Thr
65                  70                  75                  80

Ser Pro Thr Ala Glu Asp Thr Ala Thr Tyr Phe Cys Ala Arg Asp Pro
                85                  90                  95

Gln Tyr Phe Ile Leu Trp Gly Gln Gly Thr Gln Val Thr Val Ser Ser
            100                 105                 110

<210> SEQ ID NO 61
<211> LENGTH: 119
<212> TYPE: PRT
<213> ORGANISM: Oryctolagus cuniculus

<400> SEQUENCE: 61

Gln Ser Val Glu Glu Ser Gly Gly Arg Leu Val Thr Pro Gly Gly Ser
1               5                   10                  15

Leu Thr Leu Thr Cys Thr Val Ser Gly Phe Ser Leu Ser Ile Tyr Ala
            20                  25                  30

Met Gly Trp Phe Arg Gln Ala Pro Gly Lys Gly Leu Glu Trp Ile Gly
        35                  40                  45

Asp Ile Tyr Ala Gly Ser Gly Ser Thr Trp Tyr Ala Ser Trp Val Lys
    50                  55                  60

Gly Arg Phe Thr Ile Ser Ser Thr Ser Thr Thr Val Asp Leu Lys Ile
65                  70                  75                  80

```
Thr Ser Pro Thr Thr Glu Asp Thr Ala Thr Tyr Phe Cys Ala Arg Glu
                85                  90                  95

Ile Asp Ala Gly Tyr Val Gly Tyr Gly Phe Asn Leu Trp Gly Gln Gly
            100                 105                 110

Thr Leu Val Thr Val Ser Ser
        115

<210> SEQ ID NO 62
<211> LENGTH: 123
<212> TYPE: PRT
<213> ORGANISM: Oryctolagus cuniculus

<400> SEQUENCE: 62

Gln Gln Leu Glu Gln Ser Gly Gly Gly Ala Glu Gly Gly Leu Val Lys
1               5                   10                  15

Pro Gly Gly Ser Leu Glu Leu Cys Cys Lys Ala Ser Gly Phe Ser Leu
            20                  25                  30

Ser Thr Ser Tyr Trp Arg Cys Trp Val Arg Gln Ala Pro Gly Lys Gly
        35                  40                  45

Leu Glu Trp Ile Gly Cys Ile Tyr Ala Gly Ser Gly Asp Val Thr Tyr
    50                  55                  60

Tyr Ala Asn Trp Val Asn Gly Arg Phe Thr Leu Ser Arg Asp Ile Asp
65                  70                  75                  80

Gln Ser Thr Gly Cys Leu Gln Leu Asn Ser Leu Thr Ala Ala Asp Thr
                85                  90                  95

Ala Met Tyr Tyr Cys Ala Ser Gly Val Gly Phe Gly Tyr Phe Asn Leu
            100                 105                 110

Trp Gly Gln Gly Thr Leu Val Thr Val Ser Ser
        115                 120

<210> SEQ ID NO 63
<211> LENGTH: 113
<212> TYPE: PRT
<213> ORGANISM: Oryctolagus cuniculus

<400> SEQUENCE: 63

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Asp
            20                  25                  30

Met Ser Trp Val Arg Gln Ala Pro Gly Glu Gly Leu Glu Trp Ile Gly
        35                  40                  45

Thr Ile Tyr Val Ser Gly Arg Val Tyr Tyr Ala Thr Trp Ala Lys Gly
    50                  55                  60

Arg Phe Thr Ile Ser Lys Thr Ser Ser Thr Thr Val Asp Leu Glu Ile
65                  70                  75                  80

Thr Ser Pro Thr Thr Glu Asp Thr Ala Thr Tyr Phe Cys Ala Arg Gly
                85                  90                  95

Ser Ile Asp Tyr Asp Pro Trp Gly Pro Gly Thr Leu Val Thr Val Ser
            100                 105                 110

Ser

<210> SEQ ID NO 64
<211> LENGTH: 116
<212> TYPE: PRT
<213> ORGANISM: Oryctolagus cuniculus
```

<400> SEQUENCE: 64

Gln Ser Leu Glu Glu Ser Gly Gly Leu Val Gln Pro Glu Gly Ser
1               5                   10                  15

Leu Thr Leu Thr Cys Thr Ala Ser Gly Phe Ser Phe Ser Ser Tyr
                20                  25                  30

Trp Ile Cys Trp Val Arg Gln Ala Pro Gly Lys Gly Leu Glu Trp Ile
            35                  40                  45

Gly Cys Ile Tyr Thr Gly Ser Gly Gly Thr Tyr Tyr Ala Ser Trp Glu
        50                  55                  60

Lys Gly Arg Phe Thr Ile Ser Lys Thr Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Asp Pro Gly Tyr Ser Ser Trp Leu Trp Gly Gln Gly Thr Leu Val
            100                 105                 110

Thr Val Ser Ser
        115

<210> SEQ ID NO 65
<211> LENGTH: 121
<212> TYPE: PRT
<213> ORGANISM: Oryctolagus cuniculus

<400> SEQUENCE: 65

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Thr Tyr Thr
                20                  25                  30

Met Ser Trp Val Arg Gln Ala Pro Gly Lys Gly Leu Glu Tyr Ile Gly
            35                  40                  45

Ile Ile Leu Ser Ser Gly Ser Thr Tyr Tyr Ala Thr Trp Ala Lys Gly
        50                  55                  60

Arg Phe Thr Ile Ser Lys Thr Ser Ser Thr Thr Val Asp Leu Lys Met
65                  70                  75                  80

Thr Ser Leu Thr Thr Glu Asp Thr Ala Met Tyr Phe Cys Ala Arg Gly
                85                  90                  95

Gly Pro Gly Tyr Ser Ile Asp Thr Lys Tyr Ala Phe Asp Pro Trp Gly
            100                 105                 110

Pro Gly Thr Leu Val Thr Val Ser Ser
        115                 120

<210> SEQ ID NO 66
<211> LENGTH: 119
<212> TYPE: PRT
<213> ORGANISM: Oryctolagus cuniculus

<400> SEQUENCE: 66

Gln Glu Gln Leu Glu Glu Ser Gly Gly Gly Leu Val Gln Pro Glu Gly
1               5                   10                  15

Ser Leu Thr Leu Thr Cys Thr Ala Ser Gly Phe Ser Phe Ser Ser Gly
                20                  25                  30

Tyr Asp Met Cys Trp Val Arg Gln Ala Pro Gly Lys Gly Leu Glu Trp
            35                  40                  45

Ile Gly Cys Ile Tyr Thr Gly Ser Gly Ser Thr Tyr Tyr Ala Asn Trp
        50                  55                  60

Ala Lys Gly Arg Phe Thr Ile Ser Lys Thr Ser Ser Thr Thr Val Thr

```
            65                  70                  75                  80
Leu Gln Met Thr Ser Leu Thr Ala Ala Asp Thr Ala Thr Tyr Phe Cys
                    85                  90                  95

Ala Arg Asn Ser Asn Asp Trp Met Tyr Phe Asn Leu Trp Gly Pro Gly
                100                 105                 110

Thr Leu Val Thr Val Ser Ser
            115
```

<210> SEQ ID NO 67
<211> LENGTH: 120
<212> TYPE: PRT
<213> ORGANISM: Oryctolagus cuniculus

<400> SEQUENCE: 67

```
Gln Ser Leu Glu Glu Ser Gly Gly Arg Leu Val Thr Pro Gly Thr Pro
1               5                   10                  15

Leu Thr Leu Thr Cys Thr Ala Ser Gly Phe Thr Ile Ser Ser Tyr His
            20                  25                  30

Met Ser Trp Val Arg Gln Ala Pro Gly Lys Gly Leu Glu Trp Ile Gly
        35                  40                  45

Gly Ile Ala Thr Asp Gly Asn Thr Tyr Tyr Ala Asn Trp Ala Lys Gly
    50                  55                  60

Arg Phe Thr Val Ser Arg Thr Ser Thr Val Asp Leu Lys Val Thr
65                  70                  75                  80

Ser Pro Thr Ala Glu Asp Thr Ala Thr Tyr Phe Cys Ala Arg Gly Gly
                85                  90                  95

Pro Ala Tyr Ser Arg Gly Thr His Tyr Ala Met Asp Leu Trp Gly Pro
                100                 105                 110

Gly Thr Leu Val Thr Val Ser Ser
            115                 120
```

<210> SEQ ID NO 68
<211> LENGTH: 117
<212> TYPE: PRT
<213> ORGANISM: Oryctolagus cuniculus

<400> SEQUENCE: 68

```
Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Ala
            20                  25                  30

Met Ser Trp Val Arg Gln Ala Pro Gly Lys Gly Leu Glu Tyr Ile Gly
        35                  40                  45

Val Ile Gly Ser Gly Asn Leu Tyr Tyr Ala Ser Trp Ala Lys Gly
    50                  55                  60

Arg Phe Thr Ile Ser Lys Thr Ser Thr Val Asp Leu Lys Met Thr
65                  70                  75                  80

Ser Leu Thr Thr Glu Asp Thr Ala Thr Tyr Phe Cys Ala Arg Tyr Thr
                85                  90                  95

Ile Asp Ser Gly Ile Tyr Thr Tyr Asp Leu Trp Gly Gln Gly Thr Leu
                100                 105                 110

Val Thr Val Ser Ala
            115
```

<210> SEQ ID NO 69
<211> LENGTH: 117
<212> TYPE: PRT

<213> ORGANISM: Oryctolagus cuniculus

<400> SEQUENCE: 69

Gln Ser Val Glu Glu Ser Gly Gly Arg Leu Val Thr Pro Gly Thr Pro
1               5                   10                  15

Leu Thr Leu Thr Cys Thr Val Ser Gly Phe Asp Ser Ser Val Tyr Ala
            20                  25                  30

Met Ser Trp Val Arg Gln Ala Pro Gly Lys Gly Leu Glu Trp Ile Gly
        35                  40                  45

Ile Ser Val Ser Asn Ile Arg Thr Trp Tyr Ala Thr Trp Ala Lys Gly
    50                  55                  60

Arg Phe Thr Ile Ser Lys Thr Ser Thr Met Val Asp Leu Lys Met Thr
65                  70                  75                  80

Ser Leu Thr Thr Glu Asp Thr Ala Thr Tyr Phe Cys Ala Arg His Val
                85                  90                  95

Ser Arg Ser Gly Asn Tyr Gly Leu Asp Leu Trp Gly Gln Gly Thr Leu
            100                 105                 110

Val Thr Val Ser Ser
            115

<210> SEQ ID NO 70
<211> LENGTH: 119
<212> TYPE: PRT
<213> ORGANISM: Oryctolagus cuniculus

<400> SEQUENCE: 70

Gln Ser Val Glu Glu Ser Gly Gly Arg Leu Val Thr Pro Gly Gly Ser
1               5                   10                  15

Leu Thr Leu Thr Cys Thr Val Ser Gly Phe Ser Leu Ser Val Tyr Ala
            20                  25                  30

Met Gly Trp Phe Arg Gln Ala Pro Gly Lys Gly Leu Glu Trp Ile Gly
        35                  40                  45

Asp Ile Tyr Ala Gly Ser Val Asn Thr Trp Tyr Ala Thr Trp Ala Lys
    50                  55                  60

Gly Arg Phe Thr Ile Ser Lys Thr Ser Thr Thr Val Asp Leu Lys Ile
65                  70                  75                  80

Thr Ser Pro Thr Thr Glu Asp Thr Ala Thr Tyr Phe Cys Ala Arg Glu
                85                  90                  95

Ile Asp Ala Gly Tyr Val Gly Tyr Gly Phe Asn Leu Trp Gly Gln Gly
            100                 105                 110

Thr Leu Val Thr Val Ser Ser
            115

<210> SEQ ID NO 71
<211> LENGTH: 112
<212> TYPE: PRT
<213> ORGANISM: Oryctolagus cuniculus

<400> SEQUENCE: 71

Gln Ser Leu Glu Glu Ser Gly Gly Arg Leu Ile Thr Pro Gly Gly Ser
1               5                   10                  15

Leu Thr Leu Thr Cys Thr Val Ser Gly Phe Ser Leu Ser Ser Tyr His
            20                  25                  30

Met Gln Trp Val Arg Gln Ala Pro Gly Lys Gly Leu Glu Tyr Ile Gly
        35                  40                  45

Tyr Ile Asn Ser Leu Gly Gly Ser Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Ala Asp Thr Ala Thr Tyr Phe Cys Ala Arg Asp Phe
                85                  90                  95

Ala Gly Ser Asp Leu Trp Gly Gln Gly Thr Leu Val Thr Val Ala Ser
            100                 105                 110

<210> SEQ ID NO 72
<211> LENGTH: 119
<212> TYPE: PRT
<213> ORGANISM: Oryctolagus cuniculus

<400> SEQUENCE: 72

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asp Tyr Ala
            20                  25                  30

Met Ile Trp Val Arg Gln Ala Pro Gly Glu Gly Leu Glu Tyr Ile Gly
        35                  40                  45

Phe Ile Glu Pro Gly Gly Arg Ala Tyr Cys Ala Ser Trp Ala Lys Gly
    50                  55                  60

Arg Phe Thr Ile Ser Arg Thr Ser Thr Thr Val Asp Leu Lys Met Thr
65                  70                  75                  80

Ser Leu Thr Thr Glu Asp Thr Ala Thr Tyr Phe Cys Ala Arg Ser Tyr
                85                  90                  95

Val Phe Tyr Ser Thr Tyr Pro Tyr Ala Ser Asp Leu Trp Gly Gln Gly
            100                 105                 110

Thr Leu Val Thr Val Ser Ser
        115

<210> SEQ ID NO 73
<211> LENGTH: 121
<212> TYPE: PRT
<213> ORGANISM: Oryctolagus cuniculus

<400> SEQUENCE: 73

Gln Glu Gln Leu Val Glu Ser Gly Gly Gly Leu Val Gln Pro Glu Gly
1               5                   10                  15

Ser Leu Thr Leu Thr Cys Thr Ala Ser Gly Phe Ser Phe Ser Ser Ile
            20                  25                  30

Tyr Tyr Met Cys Trp Val Arg Gln Ala Pro Gly Lys Gly Leu Glu Trp
        35                  40                  45

Ile Gly Cys Ile Tyr Thr Gly Asn Ser Asp Phe Thr Tyr Tyr Ala Asn
    50                  55                  60

Trp Ala Lys Gly Arg Leu Ser Ile Ser Arg Ser Thr Ser Leu Ser Thr
65                  70                  75                  80

Val Thr Leu Gln Met Thr Ser Leu Thr Ala Ala Asp Thr Ala Thr Tyr
                85                  90                  95

Phe Cys Ala Arg Phe Arg Asp Asp Tyr Ala Ser Leu Lys Leu Trp Gly
            100                 105                 110

Pro Gly Thr Leu Val Thr Val Ser Ser
        115                 120

<210> SEQ ID NO 74
<211> LENGTH: 118
<212> TYPE: PRT
<213> ORGANISM: Oryctolagus cuniculus

<400> SEQUENCE: 74

Gln Glu His Leu Met Glu Ser Gly Gly Gly Leu Val Gln Pro Glu Gly
1               5                   10                  15

Ser Leu Thr Leu Ser Cys Thr Ala Ser Gly Phe Ser Phe Ser Ser Thr
            20                  25                  30

Tyr Trp Ile Cys Trp Val Arg Gln Ala Pro Gly Lys Gly Leu Glu Trp
        35                  40                  45

Ile Gly Cys Ile Asn Thr Gly Ser Gly Ser Thr Tyr Tyr Ala Asn
    50                  55                  60

Trp Val Lys Gly Arg Phe Thr Ile Ser Lys Thr Ser Thr Thr Val
65              70                  75                  80

Thr Leu Gln Met Thr Ser Leu Thr Ala Ala Asp Thr Ala Thr Tyr Phe
            85                  90                  95

Cys Ala Arg Gly Asp Asp Ser Tyr Tyr Glu Leu Trp Gly Gln Gly Thr
            100                 105                 110

Leu Val Thr Val Ser Ser
            115

<210> SEQ ID NO 75
<211> LENGTH: 126
<212> TYPE: PRT
<213> ORGANISM: Oryctolagus cuniculus

<400> SEQUENCE: 75

Gln Gln Leu Glu Gln Ser Gly Gly Gly Ala Glu Gly Gly Leu Val Lys
1               5                   10                  15

Pro Gly Gly Ser Leu Glu Leu Cys Cys Lys Ala Ser Gly Phe Ser Gln
            20                  25                  30

Ser Asn Asn Tyr Trp Met His Trp Val Arg Gln Ala Pro Gly Lys Gly
        35                  40                  45

Leu Glu Trp Ile Gly Cys Ile Tyr Ala Gly Ser Ser Asp Ser Thr Tyr
    50                  55                  60

Tyr Ala Ser Trp Val Asn Gly Arg Phe Thr Leu Ser Arg Asp Ile Asp
65              70                  75                  80

Gln Ser Ile Gly Cys Leu Gln Leu Asn Ser Leu Thr Ala Ala Asp Thr
            85                  90                  95

Ala Ile Tyr Tyr Cys Ala Arg Ala Ile Ala Asp Phe Ser Ser Gly Trp
            100                 105                 110

Gly Asp Leu Trp Gly Gln Gly Thr Leu Val Thr Val Ser Ser
            115                 120                 125

<210> SEQ ID NO 76
<211> LENGTH: 111
<212> TYPE: PRT
<213> ORGANISM: Oryctolagus cuniculus

<400> SEQUENCE: 76

Gln Ser Leu Glu Glu Ser Gly Gly Gly Leu Val Thr Pro Gly Ala Ser
1               5                   10                  15

Leu Thr Leu Thr Cys Thr Ala Ser Gly Phe Thr Leu Ser Ser Asp Tyr
            20                  25                  30

Trp Ile Cys Trp Val Arg Gln Ala Pro Gly Lys Gly Leu Glu Trp Ile
        35                  40                  45

Ala Cys Ile Tyr Ala Gly Ser Ser Val Thr Tyr Tyr Ala Arg Trp Ala
    50                  55                  60

```
Lys Gly Arg Phe Thr Ile Ser Lys Thr Ser Thr Thr Val Thr Leu
 65                  70                  75                  80

Gln Met Thr Ser Leu Thr Ala Ala Asp Thr Ala Thr Tyr Phe Cys Ala
                 85                  90                  95

Arg Gly Gly Leu Trp Gly Pro Gly Thr Leu Val Thr Val Ser Ser
            100                 105                 110
```

<210> SEQ ID NO 77
<211> LENGTH: 118
<212> TYPE: PRT
<213> ORGANISM: Oryctolagus cuniculus

<400> SEQUENCE: 77

```
Gln Ser Leu Glu Glu Ser Gly Gly Arg Leu Val Thr Pro Gly Thr Pro
  1               5                  10                  15

Leu Thr Leu Thr Cys Thr Val Ser Gly Phe Ser Leu Ser Arg Cys Ala
                 20                  25                  30

Met Ile Trp Val Arg Gln Ala Pro Gly Lys Gly Leu Glu Trp Ile Gly
             35                  40                  45

Phe Ile Gly Arg Gly Gly Ser Thr Trp Tyr Ala Ser Trp Val Asn Gly
         50                  55                  60

Arg Phe Thr Ile Ser Lys Thr Ser Ser Thr Val Asp Leu Lys Ile
 65                  70                  75                  80

Thr Ser Pro Thr Thr Glu Asp Thr Ala Thr Tyr Phe Cys Ala Arg Asp
                 85                  90                  95

Gly Asp Tyr Ser Asp Tyr Tyr Thr Phe Asp Leu Trp Gly Gln Gly Thr
            100                 105                 110

Leu Val Thr Val Ser Ser
        115
```

<210> SEQ ID NO 78
<211> LENGTH: 110
<212> TYPE: PRT
<213> ORGANISM: Oryctolagus cuniculus

<400> SEQUENCE: 78

```
Ala Phe Glu Met Thr Gln Thr Pro Ser Ser Val Ser Glu Pro Val Gly
  1               5                  10                  15

Gly Thr Val Thr Ile Lys Cys Gln Ala Ser Gln Ser Ile Tyr Ile Tyr
                 20                  25                  30

Leu Ser Trp Tyr Gln Gln Lys Pro Gly Gln Arg Pro Lys Leu Leu Ile
             35                  40                  45

Tyr Asp Ala Ser Lys Leu Ala Ser Gly Val Pro Ser Arg Phe Ser Gly
         50                  55                  60

Ser Gly Ser Gly Thr Glu Phe Thr Leu Thr Ile Ser Gly Val Gln Ser
 65                  70                  75                  80

Asp Asp Ala Ala Thr Tyr Tyr Cys Gln Gln Gly Ala Thr Thr Tyr Asn
                 85                  90                  95

Val Asp Asn Val Phe Gly Gly Gly Thr Glu Val Val Val Lys
            100                 105                 110
```

<210> SEQ ID NO 79
<211> LENGTH: 110
<212> TYPE: PRT
<213> ORGANISM: Oryctolagus cuniculus

<400> SEQUENCE: 79

```
Ala Leu Val Met Thr Gln Thr Pro Ala Ser Val Glu Ala Ala Val Gly
```

```
                1               5                   10                  15
            Gly Thr Val Thr Ile Lys Cys Gln Ala Ser Gln Thr Ile Ser Ile Asn
                            20                  25                  30

Leu Ala Trp Tyr Gln Gln Lys Pro Gly Gln Arg Pro Lys Leu Leu Ile
                            35                  40                  45

Tyr Tyr Ala Ser Thr Leu Ala Ser Gly Val Pro Ser Arg Phe Ser Gly
                            50                  55                  60

Ser Gly Ser Gly Thr Glu Phe Thr Leu Thr Ile Ser Gly Val Gln Ser
            65                  70                  75                  80

Asp Asp Ala Ala Thr Tyr Tyr Cys Gln Gln Gly Tyr Thr Glu Asp Asn
                            85                  90                  95

Ile Asp Asn Thr Phe Gly Gly Gly Thr Glu Val Val Val Lys
                            100                 105                 110

<210> SEQ ID NO 80
<211> LENGTH: 111
<212> TYPE: PRT
<213> ORGANISM: Oryctolagus cuniculus

<400> SEQUENCE: 80

Ala Leu Val Met Thr Gln Thr Pro Ser Ser Val Ser Ala Ala Val Gly
            1               5                   10                  15

Gly Thr Val Thr Ile Asn Cys Gln Ala Ser Glu Asn Ile Tyr Ser Ser
                            20                  25                  30

Leu Ala Trp Tyr Gln Gln Lys Pro Gly Gln Pro Pro Lys Leu Leu Ile
                            35                  40                  45

Tyr Asp Ala Ser Asp Leu Ala Ser Gly Val Pro Ser Arg Phe Lys Gly
                            50                  55                  60

Ser Gly Ser Gly Lys Glu Phe Thr Leu Thr Ile Ser Asp Leu Glu Ser
            65                  70                  75                  80

Asp Asp Ala Ala Thr Tyr Tyr Cys Gln Gln Gly Tyr Tyr Ser Gly Gly
                            85                  90                  95

Thr Asp Asn Asp Val Phe Gly Gly Gly Thr Glu Val Val Val Lys
                            100                 105                 110

<210> SEQ ID NO 81
<211> LENGTH: 108
<212> TYPE: PRT
<213> ORGANISM: Oryctolagus cuniculus

<400> SEQUENCE: 81

Asp Val Val Met Thr Gln Thr Pro Ala Ser Val Ser Glu Pro Val Gly
            1               5                   10                  15

Gly Thr Val Thr Ile Lys Cys Gln Ala Ser Gln Ser Ile Tyr Ser Phe
                            20                  25                  30

Leu Ser Trp Tyr Gln Gln Lys Pro Gly Gln Pro Pro Lys Leu Leu Ile
                            35                  40                  45

Tyr Ala Ala Ser Asp Leu Glu Ser Gly Val Pro Ser Arg Phe Ser Gly
                            50                  55                  60

Ser Gly Tyr Gly Thr Glu Phe Thr Leu Thr Ile Ser Asp Leu Glu Ser
            65                  70                  75                  80

Ala Asp Ala Ala Thr Tyr Tyr Cys Gln Cys Asn Tyr Ile Ile Asp Tyr
                            85                  90                  95

Gly Ala Phe Gly Gly Gly Thr Glu Val Val Val Lys
                            100                 105
```

<210> SEQ ID NO 82
<211> LENGTH: 110
<212> TYPE: PRT
<213> ORGANISM: Oryctolagus cuniculus

<400> SEQUENCE: 82

Ala Leu Val Met Thr Gln Thr Pro Ser Pro Val Ser Ala Ala Val Gly
1               5                   10                  15

Gly Thr Val Thr Ile Asn Cys Gln Ala Ser Glu Asp Ile Tyr Ser Asn
            20                  25                  30

Leu Ala Trp Phe Gln Gln Lys Pro Gly Gln Pro Pro Lys Leu Leu Ile
        35                  40                  45

Tyr Arg Ala Ser Thr Leu Ala Ser Gly Val Pro Ser Arg Phe Lys Gly
    50                  55                  60

Ser Gly Ser Gly Thr Glu Phe Thr Leu Thr Ile Ser Gly Leu Gln Ser
65                  70                  75                  80

Asp Asp Ala Ala Thr Tyr Tyr Cys Leu Gly Val Tyr Thr Tyr Pro Ser
                85                  90                  95

Ala Asp Asn Ala Phe Gly Gly Gly Thr Glu Val Val Val Arg
            100                 105                 110

<210> SEQ ID NO 83
<211> LENGTH: 111
<212> TYPE: PRT
<213> ORGANISM: Oryctolagus cuniculus

<400> SEQUENCE: 83

Ala Leu Val Met Thr Gln Thr Pro Ala Ser Val Ser Glu Pro Val Gly
1               5                   10                  15

Gly Thr Val Thr Ile Lys Cys Gln Ala Ser Glu Asn Ile Gly Asn Gly
            20                  25                  30

Leu Ala Trp Tyr Gln Gln Lys Pro Gly Gln Pro Pro Asn Leu Leu Ile
        35                  40                  45

Tyr Gly Ala Ser Thr Leu Ala Ser Gly Val Pro Ser Arg Phe Ser Gly
    50                  55                  60

Ser Gly Tyr Gly Thr Glu Phe Thr Leu Thr Val Ser Asp Leu Glu Ser
65                  70                  75                  80

Gly Asp Ala Ala Thr Tyr Tyr Cys Gln Cys Thr Tyr Trp Asn Pro Asp
                85                  90                  95

Tyr Ile Gly Gly Ala Phe Gly Gly Gly Thr Glu Val Val Val Thr
            100                 105                 110

<210> SEQ ID NO 84
<211> LENGTH: 110
<212> TYPE: PRT
<213> ORGANISM: Oryctolagus cuniculus

<400> SEQUENCE: 84

Ala Ile Glu Met Thr Gln Ser Pro Pro Ser Leu Ser Ala Ser Val Gly
1               5                   10                  15

Glu Thr Val Arg Ile Arg Cys Leu Ala Ser Glu Asp Ile Tyr Ser Gly
            20                  25                  30

Ile Ser Trp Tyr Gln Gln Lys Pro Gly Lys Pro Pro Thr Leu Leu Ile
        35                  40                  45

Tyr Ala Ala Ser Asn Leu Glu Ser Gly Val Pro Pro Arg Phe Ser Gly
    50                  55                  60

Ser Gly Ser Gly Thr Asp Tyr Thr Leu Thr Ile Gly Gly Val Gln Ala
65                  70                  75                  80

```
Glu Asp Ala Ala Thr Tyr Tyr Cys Leu Gly Gly Tyr Ser Tyr Ser Asn
                85                  90                  95

Thr Gly Pro Thr Phe Gly Ala Gly Thr Lys Val Glu Ile Lys
            100                 105                 110

<210> SEQ ID NO 85
<211> LENGTH: 110
<212> TYPE: PRT
<213> ORGANISM: Oryctolagus cuniculus

<400> SEQUENCE: 85

Ala Ile Glu Met Thr Gln Thr Pro Phe Ser Val Ser Ala Ala Val Gly
1               5                   10                  15

Gly Thr Val Thr Ile Asn Cys Gln Ala Ser Glu Ser Ile Tyr Ser Asn
            20                  25                  30

Leu Ala Trp Tyr Gln Gln Ile Leu Gly Gln Pro Pro Lys Leu Leu Ile
        35                  40                  45

Tyr Ala Ala Ser Leu Leu Ala Ser Gly Val Pro Ser Arg Phe Lys Gly
    50                  55                  60

Ser Gly Ser Gly Thr Glu Tyr Thr Leu Thr Ile Ser Gly Val Gln Ser
65                  70                  75                  80

Ala Asp Ala Ala Thr Tyr Tyr Cys Gln Ser Ala Ser Tyr Ser Thr Gly
                85                  90                  95

Pro Asp Trp Thr Phe Gly Gly Gly Thr Glu Val Val Val Glu
            100                 105                 110

<210> SEQ ID NO 86
<211> LENGTH: 110
<212> TYPE: PRT
<213> ORGANISM: Oryctolagus cuniculus

<400> SEQUENCE: 86

Ala Phe Glu Met Thr Gln Thr Pro Ser Ser Val Ser Glu Pro Val Gly
1               5                   10                  15

Gly Thr Val Thr Ile Lys Cys Gln Ala Ser Gln Ser Ile Tyr Asn Tyr
            20                  25                  30

Leu Ser Trp Tyr Gln Gln Lys Pro Gly Gln Arg Pro Lys Leu Leu Ile
        35                  40                  45

Tyr Arg Ala Ser Thr Leu Ala Ser Gly Val Pro Ser Arg Phe Lys Gly
    50                  55                  60

Ser Gly Ser Gly Thr Glu Phe Thr Leu Thr Ile Ser Gly Val Glu Ser
65                  70                  75                  80

Ala Asp Ala Ala Thr Tyr Tyr Cys Gln Gln Gly Ala Thr Ser Tyr Asp
                85                  90                  95

Ile Glu Asn Pro Phe Gly Gly Gly Thr Glu Val Val Val Lys
            100                 105                 110

<210> SEQ ID NO 87
<211> LENGTH: 110
<212> TYPE: PRT
<213> ORGANISM: Oryctolagus cuniculus

<400> SEQUENCE: 87

Ala Phe Glu Met Thr Gln Thr Pro Ser Ser Val Ser Glu Pro Val Gly
1               5                   10                  15

Gly Thr Val Thr Ile Lys Cys Gln Ala Ser Gln Ser Ile Tyr Asn Tyr
            20                  25                  30
```

Leu Ser Trp Tyr Gln Gln Lys Pro Gly Gln Pro Pro Lys Leu Leu Ile
            35                  40                  45

Tyr Asp Ala Ser Glu Leu Ala Ser Gly Val Pro Ser Arg Phe Lys Gly
        50                  55                  60

Ser Gly Ser Gly Thr Glu Phe Thr Leu Thr Ile Ser Gly Val Gln Ser
65                  70                  75                  80

Asp Asp Ala Ala Thr Tyr Tyr Cys Gln Gln Gly Ala Thr Thr Tyr Asn
                85                  90                  95

Ile Glu Asn Val Phe Gly Gly Gly Thr Glu Val Val Val Lys
            100                 105                 110

<210> SEQ ID NO 88
<211> LENGTH: 111
<212> TYPE: PRT
<213> ORGANISM: Oryctolagus cuniculus

<400> SEQUENCE: 88

Ala Gln Ala Leu Thr Gln Thr Pro Ser Ser Val Ser Ala Ala Val Gly
1               5                   10                  15

Gly Thr Val Thr Ile Asn Cys Gln Ser Ser Gln Ser Val Tyr Ser Asp
            20                  25                  30

Tyr Leu Ala Trp Tyr Gln Gln Lys Pro Gly Gln Pro Pro Lys Leu Leu
        35                  40                  45

Ile Tyr Gln Ala Ser Lys Leu Ala Thr Gly Val Pro Ser Arg Phe Lys
    50                  55                  60

Gly Ser Gly Ser Gly Thr Gln Phe Thr Leu Thr Ile Ser Gly Val Gln
65                  70                  75                  80

Ser Asp Asp Ala Ala Thr Tyr Tyr Cys Gln Ala Thr Tyr Tyr Gly Ser
                85                  90                  95

Gly Trp Tyr Arg Ala Phe Gly Gly Gly Thr Glu Leu Val Val Lys
            100                 105                 110

<210> SEQ ID NO 89
<211> LENGTH: 111
<212> TYPE: PRT
<213> ORGANISM: Oryctolagus cuniculus

<400> SEQUENCE: 89

Ala Leu Val Met Thr Gln Thr Pro Ser Pro Val Ser Ala Ala Val Gly
1               5                   10                  15

Gly Thr Val Thr Ile Asn Cys Gln Ala Ser Glu Asp Ile Tyr Ser Asn
            20                  25                  30

Leu Ala Trp Phe Gln Gln Lys Pro Gly Gln Pro Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Glu Phe Thr Leu Thr Ile Ser Ala Leu Gln Ser
65                  70                  75                  80

Asp Asp Ala Ala Thr Tyr Tyr Cys Leu Gly Val Arg Thr Tyr Phe Asn
                85                  90                  95

Thr Leu Asn Asn Ser Phe Gly Gly Gly Thr Glu Val Val Val Lys
            100                 105                 110

<210> SEQ ID NO 90
<211> LENGTH: 111
<212> TYPE: PRT
<213> ORGANISM: Oryctolagus cuniculus

```
<400> SEQUENCE: 90

Ala Gln Ala Leu Thr Gln Thr Pro Ser Ser Val Ser Ala Ala Val Gly
1               5                   10                  15

Gly Thr Val Thr Ile Asn Cys Gln Ser Ser Gln Ser Val Tyr Ser Asp
            20                  25                  30

Tyr Leu Ala Trp Tyr Gln Gln Lys Pro Gly Gln Ser Pro Lys Leu Leu
        35                  40                  45

Ile Tyr Lys Ala Ser Lys Leu Ala Ser Gly Val Pro Ser Arg Phe Lys
50                  55                  60

Gly Ser Gly Ser Gly Thr Glu Phe Thr Leu Thr Ile Ser Gly Val Gln
65                  70                  75                  80

Ser Asp Asp Ala Ala Thr Tyr Tyr Cys Gln Ala Thr Tyr Tyr Ser Val
                85                  90                  95

Gly Trp Tyr Arg Ala Phe Gly Gly Gly Thr Glu Val Val Val Lys
            100                 105                 110

<210> SEQ ID NO 91
<211> LENGTH: 111
<212> TYPE: PRT
<213> ORGANISM: Oryctolagus cuniculus

<400> SEQUENCE: 91

Ala Leu Val Leu Thr Gln Thr Pro Ser Pro Val Ser Ala Ala Val Gly
1               5                   10                  15

Gly Thr Val Thr Ile Asn Cys Gln Ala Ser Glu Asp Ile Tyr Ser Asn
            20                  25                  30

Leu Ala Trp Phe Gln Gln Lys Pro Gly Gln Pro Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Glu Phe Thr Leu Thr Ile Ser Gly Leu Gln Ser
65                  70                  75                  80

Asp Asp Ala Ala Thr Tyr Tyr Cys Leu Gly Val Tyr Thr Tyr Leu Ser
                85                  90                  95

Asp Leu Phe Phe Val Phe Gly Gly Gly Thr Glu Val Val Val Lys
            100                 105                 110

<210> SEQ ID NO 92
<211> LENGTH: 110
<212> TYPE: PRT
<213> ORGANISM: Oryctolagus cuniculus

<400> SEQUENCE: 92

Ala Leu Val Met Thr Gln Thr Pro Ser Pro Val Ser Ala Ala Val Gly
1               5                   10                  15

Gly Thr Val Thr Ile Asn Cys Gln Ala Ser Glu Asp Ile Tyr Ser Asn
            20                  25                  30

Leu Ala Trp Phe Gln Gln Lys Pro Gly Gln Pro Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Glu Phe Thr Leu Thr Ile Ser Gly Leu Gln Ser
65                  70                  75                  80

Asp Asp Ala Ala Thr Tyr Tyr Cys Leu Gly Val Tyr Thr Tyr Ser Thr
                85                  90                  95

Asp Ile His Ala Phe Gly Gly Gly Thr Glu Val Val Val Lys
```

<210> SEQ ID NO 93
<211> LENGTH: 109
<212> TYPE: PRT
<213> ORGANISM: Oryctolagus cuniculus

<400> SEQUENCE: 93

Asp Val Val Met Thr Gln Thr Pro Ala Ser Val Ser Glu Pro Val Gly
1               5                   10                  15

Gly Thr Val Thr Ile Asn Cys Gln Ala Ser Glu Ser Ile Ser Asp Tyr
            20                  25                  30

Leu Ser Trp Tyr Gln Gln Lys Pro Gly Gln Pro Pro Lys Leu Leu Ile
        35                  40                  45

Tyr Arg Ala Ser Thr Leu Glu Ser Gly Val Ser Ser Arg Phe Lys Gly
    50                  55                  60

Ser Gly Ser Gly Thr Gln Phe Thr Leu Thr Ile Ser Asp Leu Glu Ser
65                  70                  75                  80

Ala Asp Ala Ala Thr Tyr Tyr Cys Gln Ser Asn Tyr Tyr Asp Ser Arg
                85                  90                  95

Gly Asn Ala Phe Gly Gly Gly Thr Glu Val Val Val Lys
            100                 105

<210> SEQ ID NO 94
<211> LENGTH: 110
<212> TYPE: PRT
<213> ORGANISM: Oryctolagus cuniculus

<400> SEQUENCE: 94

Ala Gln Val Leu Thr Gln Thr Ala Ser Ser Val Ser Ala Thr Val Gly
1               5                   10                  15

Gly Thr Val Thr Ile Ser Cys Gln Ser Ser Gln Ser Val Tyr Asn Asn
            20                  25                  30

Asn Tyr Leu Ser Trp Tyr Gln Gln Lys Pro Gly Gln Pro Pro Lys Leu
        35                  40                  45

Leu Ile Tyr Lys Ala Ser Thr Leu Ala Ser Gly Val Pro Leu Arg Phe
    50                  55                  60

Ser Gly Ser Gly Ser Gly Thr Gln Phe Thr Leu Thr Ile Ser Gly Val
65                  70                  75                  80

Gln Ser Asp Asp Ala Ala Thr Tyr Tyr Cys Ala Gly Tyr Glu Thr
                85                  90                  95

Thr Asp Val Gly Phe Gly Gly Gly Thr Glu Val Val Val Lys
            100                 105                 110

<210> SEQ ID NO 95
<211> LENGTH: 113
<212> TYPE: PRT
<213> ORGANISM: Oryctolagus cuniculus

<400> SEQUENCE: 95

Ala Gln Val Leu Thr Gln Thr Pro Ser Pro Val Ser Ala Ala Val Gly
1               5                   10                  15

Gly Thr Val Thr Ile Ser Cys Gln Ala Ser Gln Ser Val Tyr Asn Ser
            20                  25                  30

Asn His Leu Ser Trp Tyr Gln Gln Lys Pro Gly Gln Pro Pro Arg Leu
        35                  40                  45

Leu Ile Tyr Ser Ala Ser Thr Leu Ala Ser Gly Val Pro Ser Arg Phe
    50                  55                  60

-continued

Lys Gly Ser Gly Ser Gly Thr Gln Phe Thr Leu Thr Ile Ser Gly Val
65                  70                  75                  80

Gln Ser Asp Asp Ala Ala Thr Tyr Tyr Cys Gln Gly Glu Phe Ser Cys
                85                  90                  95

Val Ser Ala Asp Cys Ile Ala Phe Gly Gly Gly Thr Glu Val Val Val
            100                 105                 110

Lys

<210> SEQ ID NO 96
<211> LENGTH: 110
<212> TYPE: PRT
<213> ORGANISM: Oryctolagus cuniculus

<400> SEQUENCE: 96

Ala Ile Glu Met Thr Gln Thr Pro Ser Ser Val Ser Ala Ala Val Gly
1               5                   10                  15

Gly Thr Val Thr Ile Asn Cys Gln Ala Ser Gln Asn Ile Tyr Ser Asn
                20                  25                  30

Leu Ala Trp Tyr Gln Gln Lys Pro Gly Gln Arg Pro Lys Leu Leu Ile
            35                  40                  45

Tyr Ala Ala Ser Leu Leu Ala Ser Gly Val Pro Ser Arg Phe Lys Gly
        50                  55                  60

Asn Gly Ser Gly Thr Glu Tyr Thr Leu Thr Ile Ser Asp Leu Glu Ser
65                  70                  75                  80

Ala Asp Ala Ala Thr Tyr Tyr Cys Gln Gly Ala Val Tyr Ser Gly Asn
                85                  90                  95

Thr Glu Trp Ala Phe Gly Gly Gly Thr Glu Val Val Val Lys
            100                 105                 110

<210> SEQ ID NO 97
<211> LENGTH: 113
<212> TYPE: PRT
<213> ORGANISM: Oryctolagus cuniculus

<400> SEQUENCE: 97

Ala Leu Met Met Thr Gln Thr Pro Ser Pro Val Ser Ala Ala Val Gly
1               5                   10                  15

Gly Thr Val Thr Ile Asn Cys Gln Ala Ser Glu Asp Ile Tyr Ser Asn
                20                  25                  30

Leu Ala Trp Tyr Gln Gln Lys Pro Gly Gln Pro Pro Lys Leu Leu Ile
            35                  40                  45

Tyr Ser Ala Ser Thr Leu Ala Ser Gly Val Pro Ser Arg Phe Ser Gly
        50                  55                  60

Ser Gly Ser Gly Thr Glu Phe Thr Leu Thr Ile Ser Gly Val Gln Ser
65                  70                  75                  80

Asp Asp Ala Ala Thr Tyr Tyr Cys Leu Gly Val Cys Thr Asp Ile Ser
                85                  90                  95

Val Asp Asp Val Tyr Asn Ser Phe Gly Gly Gly Thr Glu Val Val Val
            100                 105                 110

Lys

<210> SEQ ID NO 98
<211> LENGTH: 114
<212> TYPE: PRT
<213> ORGANISM: Oryctolagus cuniculus

<400> SEQUENCE: 98

```
Ala Leu Val Met Thr Gln Thr Pro Ser Pro Val Ser Ala Ala Val Gly
1               5                   10                  15

Gly Thr Val Thr Ile Asn Cys Gln Ala Ser Glu Asp Ile Tyr Ser Asn
                20                  25                  30

Leu Ala Trp Phe Gln Gln Lys Pro Gly Gln Pro Pro Lys Leu Leu Ile
            35                  40                  45

Tyr Gln Ala Ser Thr Leu Ala Ser Gly Val Pro Ser Arg Phe Ser Gly
    50                  55                  60

Ser Gly Ser Gly Thr Glu Phe Thr Leu Thr Ile Ser Gly Leu Gln Ser
65                  70                  75                  80

Asp Asp Ala Ala Ala Tyr Tyr Cys Leu Gly Val Cys Thr Tyr Ile Gly
                85                  90                  95

Ala Asp Asn Thr Leu Tyr Asn Thr Phe Gly Gly Gly Thr Glu Val Val
                100                 105                 110

Val Lys

<210> SEQ ID NO 99
<211> LENGTH: 110
<212> TYPE: PRT
<213> ORGANISM: Oryctolagus cuniculus

<400> SEQUENCE: 99

Ala Leu Val Met Thr Gln Thr Pro Ser Pro Val Ser Ala Ala Val Gly
1               5                   10                  15

Gly Thr Val Thr Ile Asn Cys Gln Ala Ser Glu Asp Ile Tyr Ser Asn
                20                  25                  30

Leu Ala Trp Phe Gln Gln Lys Pro Gly Gln Pro Pro Lys Leu Leu Ile
            35                  40                  45

Tyr Asp Ala Ser Thr Leu Ala Ser Gly Val Pro Ser Arg Phe Ser Gly
    50                  55                  60

Ser Gly Ser Gly Thr Glu Phe Thr Leu Thr Ile Ser Gly Leu Gln Ser
65                  70                  75                  80

Asp Asp Ala Ala Thr Tyr Tyr Cys Leu Gly Val Tyr Thr His Ile Ser
                85                  90                  95

Ala Asp Asn Ala Phe Gly Gly Gly Thr Glu Val Val Val Lys
                100                 105                 110

<210> SEQ ID NO 100
<211> LENGTH: 110
<212> TYPE: PRT
<213> ORGANISM: Oryctolagus cuniculus

<400> SEQUENCE: 100

Ala Phe Glu Met Thr Gln Thr Pro Ser Ser Val Ser Glu Pro Val Gly
1               5                   10                  15

Gly Thr Val Thr Ile Lys Cys Gln Ala Ser Gln Ser Ile His Asn Tyr
                20                  25                  30

Leu Ser Trp Tyr Gln Gln Lys Pro Gly Gln Arg Pro Lys Leu Leu Ile
            35                  40                  45

Tyr Arg Ala Ser Thr Leu Ala Ser Gly Val Pro Ser Arg Phe Lys Gly
    50                  55                  60

Ser Gly Ser Gly Thr Glu Phe Thr Leu Thr Ile Ser Gly Val Glu Ser
65                  70                  75                  80

Ala Asp Ala Ala Thr Tyr Tyr Cys Gln Gln Gly Ala Thr Ser Tyr Asp
                85                  90                  95
```

```
Ile Asp Asn Ala Phe Gly Gly Gly Thr Glu Val Val Val Lys
            100                 105                 110
```

<210> SEQ ID NO 101
<211> LENGTH: 110
<212> TYPE: PRT
<213> ORGANISM: Oryctolagus cuniculus

<400> SEQUENCE: 101

```
Ala Phe Glu Met Thr Gln Thr Pro Ala Ser Val Glu Ala Val Gly
1               5                   10                  15

Gly Thr Val Thr Ile Asn Cys Gln Ala Ser Gln Ser Ile Gly Ser Trp
            20                  25                  30

Leu Ser Trp Tyr Gln Gln Lys Val Gly Gln Arg Pro Lys Leu Leu Ile
            35                  40                  45

Ser Arg Ala Ser Thr Leu Ala Ser Gly Val Pro Ser Arg Phe Lys Gly
        50                  55                  60

Ser Gly Ser Gly Thr Glu Tyr Thr Leu Thr Ile Ser Gly Val Gln Ser
65                  70                  75                  80

Asp Asp Ala Ala Thr Phe Tyr Cys Gln Gln Gly Ala Thr Thr Tyr Asp
                85                  90                  95

Val Asp Asn Val Phe Gly Gly Gly Thr Glu Val Val Val Arg
            100                 105                 110
```

<210> SEQ ID NO 102
<211> LENGTH: 110
<212> TYPE: PRT
<213> ORGANISM: Oryctolagus cuniculus

<400> SEQUENCE: 102

```
Ala Tyr Asp Met Thr Gln Thr Pro Ala Ser Val Glu Ala Val Gly
1               5                   10                  15

Gly Thr Val Asn Ile Lys Cys Gln Ala Ser Gln Ser Ile Ser Asn Trp
            20                  25                  30

Leu Ala Trp Tyr Gln Gln Lys Pro Gly Gln Arg Pro Lys Leu Leu Ile
            35                  40                  45

Tyr Arg Ala Ser Thr Leu Ala Ser Gly Val Ser Ser Arg Phe Lys Gly
        50                  55                  60

Ser Gly Ser Gly Thr Gln Phe Thr Leu Thr Ile Ser Gly Val Glu Ser
65                  70                  75                  80

Ala Asp Ala Ala Thr Tyr Tyr Cys Gln Gln Gly Ala Ser Thr Thr Asp
                85                  90                  95

Val Asp Asn Val Phe Gly Gly Gly Thr Glu Val Val Val Lys
            100                 105                 110
```

<210> SEQ ID NO 103
<211> LENGTH: 108
<212> TYPE: PRT
<213> ORGANISM: Oryctolagus cuniculus

<400> SEQUENCE: 103

```
Asp Ile Val Met Thr Gln Thr Pro Ala Ser Val Glu Ala Val Gly
1               5                   10                  15

Gly Thr Val Thr Ile Lys Cys Gln Ala Ser Gln Ser Ile Gly Tyr Tyr
            20                  25                  30

Leu Ala Trp Tyr Gln Gln Lys Pro Gly Gln Pro Pro Lys Leu Leu Ile
            35                  40                  45

Ser Arg Ala Ser Thr Leu Ala Ser Gly Val Pro Ser Arg Phe Lys Gly
```

```
                50                  55                  60
Ser Gly Ser Gly Thr Gln Phe Thr Leu Thr Ile Ser Asp Leu Glu Ser
 65                  70                  75                  80

Ala Asp Val Ala Thr Tyr Tyr Cys Gln Ser Tyr Tyr Asn Ser Asp Ser
                 85                  90                  95

Asp Ala Phe Gly Gly Gly Thr Glu Val Val Val Lys
            100                 105

<210> SEQ ID NO 104
<211> LENGTH: 111
<212> TYPE: PRT
<213> ORGANISM: Oryctolagus cuniculus

<400> SEQUENCE: 104

Ala Gln Ala Leu Thr Gln Thr Pro Ser Pro Val Ser Ala Ala Val Gly
 1               5                  10                  15

Gly Thr Val Thr Ile Asn Cys Gln Ser Ser Gln Ser Val Tyr Ser Asp
                20                  25                  30

Tyr Leu Gly Trp Tyr Gln Gln Lys Pro Gly Gln Pro Pro Lys Leu Leu
             35                  40                  45

Ile Tyr Trp Ala Ser Lys Leu Glu Thr Gly Val Pro Ser Arg Phe Lys
 50                  55                  60

Gly Ser Gly Ser Gly Thr Gln Phe Thr Leu Thr Ile Ser Gly Val Gln
 65                  70                  75                  80

Ser Asp Asp Ala Ala Thr Tyr Tyr Cys Gln Ala Thr Tyr Tyr Gly Ser
                 85                  90                  95

Gly Trp Tyr Arg Ala Phe Gly Gly Gly Thr Glu Val Val Val Lys
            100                 105                 110

<210> SEQ ID NO 105
<211> LENGTH: 113
<212> TYPE: PRT
<213> ORGANISM: Oryctolagus cuniculus

<400> SEQUENCE: 105

Ala Leu Val Met Thr Gln Thr Pro Ser Pro Val Ser Ala Ala Val Gly
 1               5                  10                  15

Gly Thr Val Thr Ile Ser Cys Gln Ala Ser Glu Asp Ile Tyr Ser Asn
                20                  25                  30

Leu Ala Trp Tyr Gln Gln Lys Arg Gly Gln Pro Pro Lys Leu Leu Ile
             35                  40                  45

Tyr Tyr Ala Ser Thr Leu Ala Ser Gly Val Pro Ser Arg Phe Ser Gly
 50                  55                  60

Ser Gly Ser Gly Thr Glu Phe Thr Leu Thr Ile Ser Gly Leu Gln Ser
 65                  70                  75                  80

Asp Asp Ala Ala Thr Tyr Tyr Cys Leu Gly Val Cys Thr Tyr Ile Asn
                 85                  90                  95

Ala Asn Gly Trp Asp Asn Ala Phe Gly Gly Gly Thr Glu Val Val Val
            100                 105                 110

Lys

<210> SEQ ID NO 106
<211> LENGTH: 110
<212> TYPE: PRT
<213> ORGANISM: Oryctolagus cuniculus

<400> SEQUENCE: 106
```

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Tyr Ile Tyr
            20                  25                  30

Leu Ala Trp Tyr Gln Gln Lys Pro Gly Gln Arg Pro Lys Gln Leu Ile
            35                  40                  45

Tyr Asp Ala Ser Lys Leu Ala Ser Gly Val Pro Ser Arg Phe Ser Gly
    50                  55                  60

Ser Gly Ser Gly Thr Glu Phe Thr Leu Thr Ile Ser Gly Val Glu Ser
65                  70                  75                  80

Ala Asp Ala Ala Thr Tyr Tyr Cys Gln Gln Gly Ala Thr Ile Trp Asn
                85                  90                  95

Val Asp Asn Pro Phe Gly Gly Gly Thr Glu Val Val Val Lys
            100                 105                 110

<210> SEQ ID NO 107
<211> LENGTH: 110
<212> TYPE: PRT
<213> ORGANISM: Oryctolagus cuniculus

<400> SEQUENCE: 107

Ala Tyr Asp Met Thr Gln Thr Pro Ala Ser Val Glu Ala Ala Val Gly
1               5                   10                  15

Gly Thr Val Asn Ile Lys Cys Gln Ala Ser Gln Ser Ile Ser Asn Trp
            20                  25                  30

Leu Ala Trp Tyr Gln Gln Lys Pro Gly Gln Pro Pro Lys Leu Leu Ile
            35                  40                  45

Tyr Arg Ala Ser Thr Leu Ala Ser Gly Val Ser Ser Arg Phe Lys Gly
    50                  55                  60

Ser Gly Ser Gly Thr Gln Phe Thr Leu Thr Ile Ser Gly Val Glu Ser
65                  70                  75                  80

Ala Asp Ala Ala Thr Tyr Tyr Cys Gln Gln Gly Ala Ser Thr Thr Asp
                85                  90                  95

Val Asp Asn Val Phe Gly Gly Gly Thr Glu Val Val Val Lys
            100                 105                 110

<210> SEQ ID NO 108
<211> LENGTH: 110
<212> TYPE: PRT
<213> ORGANISM: Oryctolagus cuniculus

<400> SEQUENCE: 108

Asp Ile Val Met Thr Gln Thr Pro Ser Pro Val Ser Gly Ala Val Gly
1               5                   10                  15

Gly Thr Val Thr Ile Lys Cys Gln Ala Ser Glu Asp Ile Tyr Ser Asn
            20                  25                  30

Leu Ala Trp Tyr Gln Gln Lys Pro Gly Gln Pro Pro Lys Leu Leu Ile
            35                  40                  45

Tyr Tyr Val Ser Thr Leu Glu Ser Gly Val Pro Ser Arg Phe Lys Gly
    50                  55                  60

Ser Arg Ser Gly Thr Asp Tyr Thr Leu Thr Ile Ser Asp Leu Glu Ser
65                  70                  75                  80

Ala Asp Ala Ala Thr Tyr Tyr Cys Gln Cys Thr Glu Gly Gly Ser Gly
                85                  90                  95

Ser Asp Tyr Thr Phe Gly Gly Gly Thr Glu Val Val Val Lys
            100                 105                 110

<210> SEQ ID NO 109
<211> LENGTH: 114
<212> TYPE: PRT
<213> ORGANISM: Oryctolagus cuniculus

<400> SEQUENCE: 109

Ala Leu Val Met Thr Gln Thr Pro Ser Pro Val Ser Ala Ala Val Gly
1               5                   10                  15

Gly Thr Val Thr Ile Asn Cys Gln Ala Ser Glu Asp Ile Tyr Ser Asn
            20                  25                  30

Leu Ala Trp Phe Gln Gln Lys Pro Gly Gln Pro Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Glu Phe Thr Leu Thr Ile Ser Gly Val Gln Ser
65                  70                  75                  80

Asp Asp Ala Ala Thr Tyr Tyr Cys Leu Gly Ile Tyr Thr Tyr Ile Ser
                85                  90                  95

Ala Asp Gly Ser Leu Tyr Asn Ala Phe Gly Gly Thr Glu Val Val
            100                 105                 110

Val Lys

<210> SEQ ID NO 110
<211> LENGTH: 114
<212> TYPE: PRT
<213> ORGANISM: Oryctolagus cuniculus

<400> SEQUENCE: 110

Ala Leu Val Met Thr Gln Thr Pro Ser Pro Val Ser Ala Ala Val Gly
1               5                   10                  15

Gly Thr Val Thr Ile Asn Cys Gln Ala Ser Glu Asp Ile Tyr Ser Asn
            20                  25                  30

Leu Ala Trp Phe Gln Gln Lys Pro Gly Gln Pro Pro Lys Leu Leu Ile
        35                  40                  45

Tyr Gln Ala Ser Lys Leu Ala Ser Gly Val Pro Ser Arg Phe Ser Gly
    50                  55                  60

Ser Gly Ser Gly Thr Glu Phe Thr Leu Thr Ile Ser Gly Leu Gln Ser
65                  70                  75                  80

Asp Asp Val Ala Thr Tyr Tyr Cys Leu Gly Val Gly Thr Tyr Ile Ser
                85                  90                  95

Gly Asp Gly Ser Leu Asp Asn Ala Phe Gly Gly Thr Glu Val Val
            100                 105                 110

Val Lys

<210> SEQ ID NO 111
<211> LENGTH: 110
<212> TYPE: PRT
<213> ORGANISM: Oryctolagus cuniculus

<400> SEQUENCE: 111

Ala Tyr Asp Met Thr Gln Thr Pro Ala Ser Val Glu Ala Ala Val Gly
1               5                   10                  15

Gly Thr Val Thr Ile Lys Cys Gln Ala Ser Gln Ser Ile Ser Asn Trp
            20                  25                  30

Leu Ala Trp Tyr Gln Gln Lys Pro Gly Gln Arg Pro Lys Leu Leu Ile
        35                  40                  45

```
Tyr Arg Ala Ser Thr Leu Ala Ser Gly Val Ser Ser Arg Phe Lys Gly
 50                  55                  60
Ser Gly Ser Gly Thr Gln Phe Thr Leu Thr Ile Ser Gly Val Glu Ser
 65                  70                  75                  80
Ala Asp Ala Ala Thr Tyr Tyr Cys Gln Gln Gly Ala Ser Thr Thr Asp
                 85                  90                  95
Val Asp Asn Val Phe Gly Gly Gly Thr Glu Val Val Val Lys
            100                 105                 110
```

<210> SEQ ID NO 112
<211> LENGTH: 111
<212> TYPE: PRT
<213> ORGANISM: Oryctolagus cuniculus

<400> SEQUENCE: 112

```
Asp Val Val Met Thr Gln Thr Pro Ala Ser Val Glu Ala Ala Val Gly
 1               5                   10                  15
Gly Thr Val Thr Ile Lys Cys Gln Ala Ser Gln Asn Ile Tyr Ser Asn
             20                  25                  30
Cys Ala Trp Tyr Gln Gln Lys Leu Gly Gln Arg Pro Lys Leu Leu Ile
         35                  40                  45
Tyr Tyr Val Ser Thr Leu Glu Ser Gly Val Pro Ser Arg Phe Glu Gly
 50                  55                  60
Ser Gly Tyr Gly Thr Glu Phe Thr Leu Thr Ile Ser Asp Leu Gln Ser
 65                  70                  75                  80
Ala Asp Ala Ala Thr Tyr Tyr Cys Gln Tyr Tyr Tyr Asp Ser Ser Ser
                 85                  90                  95
Ser Thr Ser Trp Ala Phe Gly Gly Gly Thr Glu Val Val Val Lys
            100                 105                 110
```

<210> SEQ ID NO 113
<211> LENGTH: 112
<212> TYPE: PRT
<213> ORGANISM: Oryctolagus cuniculus

<400> SEQUENCE: 113

```
Asp Ile Val Met Thr Gln Thr Pro Ala Ser Val Glu Ala Ala Val Gly
 1               5                   10                  15
Gly Thr Ile Thr Ile Asn Cys Gln Ala Ser Glu Asn Ile Tyr Ser Ser
             20                  25                  30
Leu Ala Trp Tyr Gln Gln Lys Pro Gly Gln Pro Pro Lys Leu Leu Ile
         35                  40                  45
Tyr Asp Ala Ser Thr Leu Ala Ser Gly Val Ser Ser Arg Phe Lys Gly
 50                  55                  60
Ser Gly Ser Gly Thr Gln Phe Thr Leu Thr Ile Ser Gly Val Gln Ser
 65                  70                  75                  80
Asp Asp Ala Ala Thr Tyr Tyr Cys Gln Ser Tyr Tyr Cys Ser Val Ser
                 85                  90                  95
Ser Ser Cys Gly Tyr Gly Phe Gly Gly Gly Thr Glu Val Val Val Lys
            100                 105                 110
```

<210> SEQ ID NO 114
<211> LENGTH: 115
<212> TYPE: PRT
<213> ORGANISM: Oryctolagus cuniculus

<400> SEQUENCE: 114

```
Ala Leu Val Met Thr Gln Thr Pro Ser Pro Val Ser Ala Ala Val Gly
```

-continued

```
                1               5                  10                 15
Gly Thr Val Thr Ile Asn Cys Gln Ala Ser Glu Asp Ile Tyr Ser Asn
                20                  25                 30

Leu Ala Trp Phe Gln Gln Lys Pro Gly Gln Pro Lys Leu Leu Ile
            35                  40                 45

Tyr Asp Ala Ser Thr Leu Ala Ser Gly Val Pro Ser Arg Phe Ser Gly
        50                  55                 60

Ser Gly Ser Gly Thr Glu Phe Thr Leu Thr Ile Ser Gly Leu Gln Ser
65                  70                 75                  80

Asp Asp Ala Ala Thr Tyr Tyr Cys Leu Gly Val Tyr Thr Tyr Ile Ser
                85                  90                 95

Ala Asp Gly Thr Leu Val Tyr Asn Ala Phe Gly Gly Gly Thr Glu Val
                100                 105                110

Val Val Arg
        115

<210> SEQ ID NO 115
<211> LENGTH: 113
<212> TYPE: PRT
<213> ORGANISM: Oryctolagus cuniculus

<400> SEQUENCE: 115

Ala Leu Val Met Thr Gln Thr Pro Ser Pro Val Ser Ala Ala Val Gly
1               5                  10                 15

Gly Thr Val Thr Ile Asn Cys Gln Ala Ser Glu Asp Ile Tyr Ser Asn
                20                  25                 30

Leu Ala Trp Phe Gln Gln Lys Pro Gly Gln Pro Pro Lys Leu Leu Ile
            35                  40                 45

Tyr Gly Ala Ser Thr Leu Ala Ser Gly Val Pro Ser Arg Phe Ser Gly
        50                  55                 60

Ser Gly Ser Gly Thr Glu Phe Thr Leu Thr Ile Ser Gly Val Gln Ser
65                  70                 75                  80

Asp Asp Ala Ala Thr Tyr Tyr Cys Leu Gly Val Cys Thr Asp Ile Ser
                85                  90                 95

Thr Asp Asp Leu Tyr Asn Ala Phe Gly Gly Gly Thr Glu Leu Val Val
                100                 105                110

Lys

<210> SEQ ID NO 116
<211> LENGTH: 111
<212> TYPE: PRT
<213> ORGANISM: Oryctolagus cuniculus

<400> SEQUENCE: 116

Ala Gln Ala Leu Thr Gln Thr Pro Ser Ser Val Ser Ala Ala Val Gly
1               5                  10                 15

Gly Thr Val Thr Ile Asn Cys Gln Ser Ser Gln Ser Val Tyr Ser Asp
                20                  25                 30

Tyr Leu Val Trp Tyr Gln Gln Lys Pro Gly Gln Pro Pro Lys Leu Leu
            35                  40                 45

Ile Tyr Gln Ala Ser Lys Leu Ala Ser Gly Val Pro Ser Arg Phe Lys
        50                  55                 60

Gly Ser Gly Ser Gly Thr Gln Phe Thr Leu Thr Ile Ser Gly Val Gln
65                  70                 75                  80

Ser Asp Asp Ala Ala Thr Tyr Tyr Cys Gln Ala Thr Tyr Ser Ser Thr
                85                  90                 95
```

```
Gly Trp Tyr Arg Ala Phe Gly Gly Thr Glu Val Val Lys
            100                 105                 110
```

<210> SEQ ID NO 117
<211> LENGTH: 112
<212> TYPE: PRT
<213> ORGANISM: Oryctolagus cuniculus

<400> SEQUENCE: 117

```
Asp Ile Val Met Thr Gln Thr Pro Ala Ser Val Ser Ala Pro Val Gly
1               5                   10                  15

Gly Thr Val Thr Ile Asn Cys Gln Ala Ser Glu Ser Ile Tyr Ser Asp
            20                  25                  30

Leu Ala Trp Tyr Gln Gln Lys Pro Gly Gln Pro Pro Lys Leu Leu Ile
        35                  40                  45

Ser Phe Val Ala Thr Leu Glu Ser Gly Val Pro Ser Arg Phe Lys Gly
    50                  55                  60

Ser Gly Ser Gly Thr Glu Phe Thr Leu Thr Ile Ser Asp Leu Glu Ser
65                  70                  75                  80

Ala Asp Ala Ala Thr Tyr Tyr Cys Gln Cys Thr Tyr Gly Gly Ser Gly
                85                  90                  95

Ser Gly Asn Gly Ala Ala Phe Gly Gly Thr Glu Val Val Lys
            100                 105                 110
```

<210> SEQ ID NO 118
<211> LENGTH: 111
<212> TYPE: PRT
<213> ORGANISM: Oryctolagus cuniculus

<400> SEQUENCE: 118

```
Ala Leu Val Met Thr Gln Thr Pro Ser Pro Val Ser Ala Ala Val Gly
1               5                   10                  15

Gly Thr Val Thr Ile Asn Cys Gln Ala Ser Glu Asp Ile Tyr Ser Asn
            20                  25                  30

Leu Ala Trp Tyr Gln Gln Lys Pro Gly Gln Pro Pro Lys Leu Leu Met
        35                  40                  45

Tyr Gly Val Ser Thr Leu Ala Ser Gly Val Pro Ser Arg Phe Ser Asp
    50                  55                  60

Ser Gly Ser Gly Thr Glu Phe Thr Leu Thr Ile Ser Gly Leu Gln Ser
65                  70                  75                  80

Asp Asp Ala Ala Thr Tyr Tyr Cys Leu Gly Val Tyr Thr Tyr Ile Ser
                85                  90                  95

Asp Val Tyr Tyr Thr Phe Gly Gly Thr Glu Val Val Lys
            100                 105                 110
```

<210> SEQ ID NO 119
<211> LENGTH: 109
<212> TYPE: PRT
<213> ORGANISM: Oryctolagus cuniculus

<400> SEQUENCE: 119

```
Asp Val Val Met Thr Gln Thr Pro Ala Ser Val Glu Ala Ala Val Gly
1               5                   10                  15

Gly Thr Val Thr Ile Lys Cys Gln Ala Ser Gln Ser Ile Ser Ser Tyr
            20                  25                  30

Cys Ser Trp Tyr Gln Gln Lys Pro Gly Gln Pro Pro Lys Leu Leu Ile
        35                  40                  45
```

Tyr Arg Ala Ser Thr Leu Glu Ser Gly Val Pro Ser Arg Phe Lys Gly
            50                  55                  60

Ser Gly Ser Gly Thr Glu Phe Thr Leu Thr Ile Ser Asp Leu Glu Ser
 65                  70                  75                  80

Ala Asp Ala Ala Thr Tyr Tyr Cys Gln Ser Ser Tyr Tyr Asp Leu Leu
                 85                  90                  95

Gly Asn Gly Phe Gly Gly Gly Thr Glu Val Val Val Lys
                100                 105

<210> SEQ ID NO 120
<211> LENGTH: 113
<212> TYPE: PRT
<213> ORGANISM: Oryctolagus cuniculus

<400> SEQUENCE: 120

Ala Leu Val Met Thr Gln Thr Pro Ser Pro Val Ser Ala Ala Val Gly
 1               5                  10                  15

Gly Thr Val Thr Ile Asn Cys Gln Ala Ser Glu Asp Ile Tyr Ser Asn
                 20                  25                  30

Leu Ala Trp Phe Gln Gln Lys Pro Gly Gln Pro Pro Lys Leu Leu Ile
            35                  40                  45

Tyr Asp Ala Ser Thr Leu Ala Ser Gly Val Pro Ser Arg Phe Ser Gly
            50                  55                  60

Ser Gly Ser Gly Thr Glu Phe Thr Leu Thr Ile Ser Gly Leu Gln Ser
 65                  70                  75                  80

Asp Asp Ala Ala Thr Tyr Tyr Cys Leu Gly Val Tyr Thr Tyr Ile Ser
                 85                  90                  95

Pro Asp Gly Thr Asp Asn Ala Phe Gly Gly Gly Thr Glu Val Val Val
                100                 105                 110

Lys

<210> SEQ ID NO 121
<211> LENGTH: 111
<212> TYPE: PRT
<213> ORGANISM: Oryctolagus cuniculus

<400> SEQUENCE: 121

Ala Leu Val Met Thr Gln Thr Pro Ser Pro Val Ser Ala Ala Val Gly
 1               5                  10                  15

Gly Thr Val Thr Ile Asn Cys Gln Ala Ser Gln Asn Ile Ala Ser Ala
                 20                  25                  30

Tyr Leu Ser Trp Tyr Gln Gln Lys Pro Gly Gln Pro Pro Lys Leu Leu
            35                  40                  45

Ile Tyr Ala Ala Ser Thr Leu Thr Asp Gly Val Pro Ser Arg Phe Lys
            50                  55                  60

Gly Ser Gly Ser Val Thr Glu Phe Thr Leu Thr Ile Ser Gly Val Gln
 65                  70                  75                  80

Ser Asp Asp Ala Ala Thr Tyr Tyr Cys Ala Gly Tyr Lys Ser Tyr Thr
                 85                  90                  95

Asp Asp Glu Phe Ala Phe Gly Gly Gly Thr Glu Val Val Val Lys
                100                 105                 110

<210> SEQ ID NO 122
<211> LENGTH: 110
<212> TYPE: PRT
<213> ORGANISM: Oryctolagus cuniculus

<400> SEQUENCE: 122

```
Ala Tyr Asp Met Thr Gln Thr Pro Ala Ser Val Glu Val Ala Val Gly
1               5                   10                  15

Gly Thr Val Thr Ile Lys Cys Gln Ala Ser Glu Ser Ile Ser Thr Trp
            20                  25                  30

Leu Ala Trp Tyr Gln Gln Lys Pro Gly Gln Pro Pro Asn Leu Leu Ile
        35                  40                  45

Tyr Arg Ala Ser Thr Leu Ala Ser Gly Val Pro Ser Arg Phe Tyr Gly
    50                  55                  60

Ser Gly Tyr Gly Thr Glu Phe Thr Leu Thr Ile Ser Gly Val Glu Ser
65                  70                  75                  80

Ala Asp Ala Ala Thr Tyr Tyr Cys Gln Gln Gly Tyr Thr Val Asn Asn
                85                  90                  95

Ile Asp Asn Val Phe Gly Gly Gly Thr Glu Val Val Val Lys
                100                 105                 110
```

<210> SEQ ID NO 123
<211> LENGTH: 110
<212> TYPE: PRT
<213> ORGANISM: Oryctolagus cuniculus

<400> SEQUENCE: 123

```
Asp Ile Val Met Thr Gln Thr Pro Ala Ser Val Glu Ala Ala Val Gly
1               5                   10                  15

Gly Thr Val Thr Ile Arg Cys Gln Ala Ser Gln Ser Ile Ser Ser Tyr
            20                  25                  30

Leu Ala Trp Tyr Gln Arg Lys Pro Gly Gln Pro Pro Lys Val Leu Ile
        35                  40                  45

Tyr Lys Ala Ser Thr Leu Ala Ser Gly Val Ser Ser Arg Phe Lys Gly
    50                  55                  60

Ser Gly Ser Gly Thr Glu Tyr Thr Leu Thr Ile Ser Asp Leu Glu Ser
65                  70                  75                  80

Ala Asp Ala Ala Thr Tyr Tyr Cys Gln Gln Gly Tyr Ala Ser Ser Gly
                85                  90                  95

Val Asp Asn Val Phe Gly Gly Gly Thr Glu Val Val Val Lys
                100                 105                 110
```

<210> SEQ ID NO 124
<211> LENGTH: 113
<212> TYPE: PRT
<213> ORGANISM: Oryctolagus cuniculus

<400> SEQUENCE: 124

```
Asp Ile Val Met Thr Gln Thr Pro Ala Ser Val Ser Glu Pro Val Gly
1               5                   10                  15

Gly Thr Val Thr Ile Arg Cys Gln Ala Ser Gln Ser Ile Ser Ser Trp
            20                  25                  30

Leu Ser Trp Tyr Gln Gln Lys Pro Gly Gln Pro Pro Lys Leu Leu Ile
        35                  40                  45

Tyr Gln Ala Ser Ala Leu Ala Ser Gly Val Ser Ser Arg Phe Ile Gly
    50                  55                  60

Ser Gly Tyr Gly Thr Glu Phe Thr Leu Thr Ile Ser Gly Val Gln Ser
65                  70                  75                  80

Glu Asp Ala Ala Thr Tyr Tyr Cys Gln Cys Thr Tyr Gly Ile Gly Ser
                85                  90                  95

Asn Ser Asp Tyr Gly Val Ala Phe Gly Gly Gly Thr Glu Val Val Val
                100                 105                 110
```

<210> SEQ ID NO 125
<211> LENGTH: 113
<212> TYPE: PRT
<213> ORGANISM: Oryctolagus cuniculus

<400> SEQUENCE: 125

Asp Ile Val Met Thr Gln Thr Pro Ala Ser Val Ser Glu Pro Val Gly
1               5                   10                  15

Gly Thr Val Thr Ile Lys Cys Gln Ala Ser Gln Ser Ile Thr Thr Trp
            20                  25                  30

Leu Ala Trp Tyr Gln Gln Lys Pro Gly Gln Pro Pro Lys Leu Leu Ile
        35                  40                  45

Tyr Gln Ala Ser Ala Leu Ala Ser Gly Val Ser Ser Arg Phe Ile Gly
    50                  55                  60

Ser Gly Tyr Gly Thr Glu Phe Thr Leu Thr Ile Ser Gly Val Gln Ser
65                  70                  75                  80

Glu Asp Ala Ala Thr Tyr Tyr Cys Gln Cys Thr Tyr Gly Ile Gly Ser
                85                  90                  95

Gly Ser Ser Tyr Gly Val Ala Phe Gly Gly Gly Thr Glu Val Val Val
            100                 105                 110

Lys

<210> SEQ ID NO 126
<211> LENGTH: 113
<212> TYPE: PRT
<213> ORGANISM: Oryctolagus cuniculus

<400> SEQUENCE: 126

Asp Val Val Met Thr Gln Thr Pro Ala Ser Val Glu Ala Ala Val Gly
1               5                   10                  15

Gly Thr Val Thr Ile Met Cys Gln Ala Ser Glu Thr Ile Tyr Ser Gly
            20                  25                  30

Leu Ala Trp Tyr Gln Gln Lys Pro Gly Gln Pro Pro Lys Leu Leu Ile
        35                  40                  45

Tyr Tyr Thr Ser Ser Leu Ala Ser Gly Val Pro Ser Arg Phe Lys Gly
    50                  55                  60

Ser Gly Ser Gly Thr Glu Phe Thr Leu Thr Ile Ser Asp Leu Glu Ser
65                  70                  75                  80

Ala Asp Ala Ala Thr Tyr Tyr Cys Gln Thr Tyr Tyr Asp Ser Glu Gly
                85                  90                  95

Arg Ser Tyr Gly Tyr Asn Ser Phe Gly Gly Gly Thr Glu Val Val Val
            100                 105                 110

Lys

<210> SEQ ID NO 127
<211> LENGTH: 112
<212> TYPE: PRT
<213> ORGANISM: Oryctolagus cuniculus

<400> SEQUENCE: 127

Asp Ile Val Met Thr Gln Thr Pro Ser Ser Val Glu Ala Ala Val Gly
1               5                   10                  15

Gly Thr Val Thr Ile Lys Cys Gln Ala Ser Gln Ser Ile Asn Ser Arg
            20                  25                  30

-continued

```
Leu Ala Trp Tyr Gln Gln Lys Pro Gly Gln Pro Pro Lys Leu Leu Ile
             35                  40                  45
Tyr Ser Ala Ser Thr Leu Ala Ser Gly Val Ser Arg Phe Lys Gly
 50                  55                  60
Ser Gly Ser Gly Thr Glu Phe Thr Leu Thr Ile Ser Asp Leu Glu Ser
 65                  70                  75                  80
Ala Asp Gly Ala Thr Tyr Tyr Cys Leu Ser His Tyr Leu Thr Ser Ser
                 85                  90                  95
Ser Ser Tyr Gly Asp Ala Phe Gly Gly Gly Thr Glu Val Val Val Lys
                100                 105                 110
```

<210> SEQ ID NO 128
<211> LENGTH: 111
<212> TYPE: PRT
<213> ORGANISM: Oryctolagus cuniculus

<400> SEQUENCE: 128

```
Ala Gln Val Leu Thr Gln Thr Pro Ser Ser Val Ser Ala Ala Val Gly
 1               5                  10                  15
Gly Thr Val Thr Ile Asn Cys Gln Ser Ser Pro Ser Val Tyr Asn Asn
                 20                  25                  30
Tyr Leu Ser Trp Tyr Gln Gln Lys Pro Gly Gln Pro Pro Lys Leu Leu
             35                  40                  45
Ile Tyr Gly Ala Ser Ser Leu Ala Ser Gly Val Pro Ser Arg Phe Lys
 50                  55                  60
Gly Ser Gly Ser Gly Thr Gln Phe Thr Leu Thr Ile Ser Asp Leu Glu
 65                  70                  75                  80
Ser Asp Asp Ala Ala Thr Tyr Tyr Cys Gln Gly Tyr Asn Ser Tyr
                 85                  90                  95
Ser Asp Thr Phe Ala Phe Gly Gly Gly Thr Glu Val Leu Val Lys
                100                 105                 110
```

<210> SEQ ID NO 129
<211> LENGTH: 113
<212> TYPE: PRT
<213> ORGANISM: Oryctolagus cuniculus

<400> SEQUENCE: 129

```
Ala Leu Val Met Thr Gln Thr Pro Ser Pro Val Ser Ala Ala Val Gly
 1               5                  10                  15
Gly Thr Val Thr Ile Asn Cys Gln Ala Ser Glu Asp Ile Tyr Ser Asn
                 20                  25                  30
Leu Ala Trp Phe Gln Gln Lys Pro Gly Gln Pro Pro Lys Leu Leu Ile
             35                  40                  45
Tyr Gly Ala Ser Thr Leu Ala Ser Gly Val Pro Ser Arg Phe Ser Gly
 50                  55                  60
Ser Gly Ser Gly Thr Glu Phe Thr Leu Thr Ile Ser Gly Val Gln Ser
 65                  70                  75                  80
Asp Asp Ala Ala Thr Tyr Tyr Cys Leu Gly Val Cys Thr Asp Ile Ser
                 85                  90                  95
Ala Asp Asp Leu Tyr Asn Thr Phe Gly Gly Gly Thr Glu Val Val Val
                100                 105                 110
Lys
```

<210> SEQ ID NO 130
<211> LENGTH: 110
<212> TYPE: PRT

```
<213> ORGANISM: Oryctolagus cuniculus

<400> SEQUENCE: 130

Ala Ile Asp Met Thr Gln Thr Pro Ser Pro Ala Ser Ala Gly Val Gly
1               5                   10                  15

Asp Thr Val Thr Ile Asn Cys Gln Ala Ser Glu Asn Ile Tyr Asn Phe
            20                  25                  30

Leu Ala Trp Tyr Gln Gln Lys Pro Gly His Ser Pro Lys Leu Leu Ile
        35                  40                  45

Tyr Val Ala Ser Lys Leu Ala Ser Gly Val Pro Ser Arg Phe Lys Gly
    50                  55                  60

Ser Gly Ser Gly Thr Gln Phe Thr Leu Thr Ile Ser Asp Val Gln Ser
65                  70                  75                  80

Asp Asp Ala Ala Thr Tyr Tyr Cys Gln Gln Thr Tyr Arg Tyr Asn Asp
                85                  90                  95

Gly Asp Thr Ala Phe Gly Gly Gly Thr Glu Val Val Val Lys
            100                 105                 110

<210> SEQ ID NO 131
<211> LENGTH: 111
<212> TYPE: PRT
<213> ORGANISM: Oryctolagus cuniculus

<400> SEQUENCE: 131

Ala Ala Val Leu Thr Gln Thr Pro Ser Pro Val Ser Ala Ala Val Gly
1               5                   10                  15

Gly Thr Val Thr Ile Ser Cys Gln Ala Ser Gln Ser Val Tyr Lys Asn
            20                  25                  30

Asn Arg Leu Ala Trp Tyr Gln Gln Lys Pro Gly Gln Pro Pro Lys Leu
        35                  40                  45

Leu Ile Tyr Leu Ala Ser Thr Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Ser Asp Asp Ala Ala Thr Tyr Tyr Cys Ala Gly Gly Tyr Ser Thr
                85                  90                  95

Ile Ser Glu Asn Ala Phe Gly Gly Gly Thr Glu Val Val Val Lys
            100                 105                 110

<210> SEQ ID NO 132
<211> LENGTH: 110
<212> TYPE: PRT
<213> ORGANISM: Oryctolagus cuniculus

<400> SEQUENCE: 132

Asp Ile Val Met Thr Gln Thr Pro Ser Ser Val Glu Ala Ala Val Gly
1               5                   10                  15

Gly Thr Val Thr Ile Lys Cys Gln Ala Ser Gln Ser Ile Asn Ser Arg
            20                  25                  30

Leu Ala Trp Tyr Gln Gln Lys Pro Gly Gln Pro Pro Lys Leu Leu Ile
        35                  40                  45

Tyr Asp Ala Ser Thr Leu Ala Ser Gly Val Ser Ser Arg Phe Ser Gly
    50                  55                  60

Ser Gly Thr Glu Phe Thr Leu Thr Ile Ser Asp Leu Glu Ser Ala Asp
65                  70                  75                  80

Gly Ala Thr Tyr Tyr Cys Leu Ser His Tyr Leu Thr Ser Ser Ser Ser
                85                  90                  95
```

Tyr Gly Asn Ala Phe Gly Gly Gly Thr Glu Val Val Val Lys
            100                 105                 110

<210> SEQ ID NO 133
<211> LENGTH: 110
<212> TYPE: PRT
<213> ORGANISM: Oryctolagus cuniculus

<400> SEQUENCE: 133

Asp Val Val Met Thr Gln Thr Pro Ala Ser Val Ser Glu Pro Val Gly
1               5                   10                  15

Gly Thr Val Thr Ile Lys Cys Gln Ala Ser Gln Asn Ile Gly Ser Asn
            20                  25                  30

Leu Ala Trp Tyr Gln Gln Arg Ser Gly Gln Pro Pro Lys Leu Leu Ile
        35                  40                  45

Tyr Gly Ala Ser Thr Leu Ala Ser Gly Val Pro Ser Arg Phe Ser Gly
    50                  55                  60

Ser Gly Ser Gly Thr Glu Phe Thr Leu Thr Ile Ser Gly Val Gln Ser
65                  70                  75                  80

Ala Asp Ala Ala Thr Tyr Phe Cys Gln Cys Ser Gly Tyr Asp Ile Thr
                85                  90                  95

Gly Val Phe Pro Phe Gly Gly Gly Ser Glu Val Val Val Lys
            100                 105                 110

<210> SEQ ID NO 134
<211> LENGTH: 110
<212> TYPE: PRT
<213> ORGANISM: Oryctolagus cuniculus

<400> SEQUENCE: 134

Asp Val Val Met Thr Gln Thr Pro Ala Ser Val Ser Glu Arg Val Gly
1               5                   10                  15

Gly Thr Val Thr Ile Lys Cys Gln Ala Ser Gln Ser Ile Gly Ser Asn
            20                  25                  30

Leu Ala Trp Tyr Gln Gln Lys Pro Gly Gln Pro Pro Lys Leu Leu Ile
        35                  40                  45

Tyr Gly Ala Ser Asn Leu Glu Ser Gly Val Pro Ser Arg Phe Ser Gly
    50                  55                  60

Ser Gly Ser Gly Thr Glu Phe Thr Leu Ser Ile Ser Gly Val Gln Ser
65                  70                  75                  80

Ala Asp Ala Ala Thr Tyr Tyr Cys Gln Cys Ser Gly Tyr Asp Thr Thr
                85                  90                  95

Gly Val Phe Pro Phe Gly Gly Gly Ser Glu Val Val Val Lys
            100                 105                 110

<210> SEQ ID NO 135
<211> LENGTH: 110
<212> TYPE: PRT
<213> ORGANISM: Oryctolagus cuniculus

<400> SEQUENCE: 135

Asp Val Val Met Thr Gln Thr Pro Ala Ser Val Ser Glu Pro Val Gly
1               5                   10                  15

Gly Thr Val Thr Ile Lys Cys Gln Ala Ser Gln Asn Ile Gly Ser Asn
            20                  25                  30

Leu Ala Trp Tyr Gln Gln Lys Pro Gly Gln Pro Pro Lys Leu Leu Ile
        35                  40                  45

Tyr Gly Ala Ser Thr Leu Ala Ser Gly Val Pro Ser Arg Phe Ser Gly
        50                  55                  60

Ser Gly Ser Gly Thr Glu Phe Thr Leu Thr Ile Ser Gly Val Gln Ser
65                  70                  75                  80

Ala Asp Ala Thr Thr Tyr Tyr Cys Gln Cys Ser Gly Tyr Asp Thr Thr
                85                  90                  95

Gly Val Phe Pro Phe Gly Gly Gly Ser Glu Val Val Val Arg
                100                 105                 110

<210> SEQ ID NO 136
<211> LENGTH: 110
<212> TYPE: PRT
<213> ORGANISM: Oryctolagus cuniculus

<400> SEQUENCE: 136

Ala Tyr Asp Met Thr Gln Thr Pro Ala Ser Val Glu Ala Ala Val Gly
1               5                   10                  15

Gly Thr Val Thr Ile Lys Cys Gln Ala Ser Gln Ser Ile Ser Ser Tyr
                20                  25                  30

Leu Ser Trp Tyr Gln Gln Lys Pro Gly Gln Pro Pro Lys Leu Leu Ile
            35                  40                  45

Tyr Gly Ala Ser Thr Leu Ala Ser Gly Val Pro Ser Arg Phe Lys Gly
        50                  55                  60

Ser Gly Ser Gly Thr Glu Tyr Thr Leu Thr Ile Ser Gly Val Glu Ser
65                  70                  75                  80

Asp Asp Ala Ala Thr Tyr Tyr Cys Gln Gln Gly Tyr Ser Tyr Asn Asn
                85                  90                  95

Val Asp Asn Thr Phe Gly Gly Gly Thr Glu Val Val Val Lys
                100                 105                 110

<210> SEQ ID NO 137
<211> LENGTH: 112
<212> TYPE: PRT
<213> ORGANISM: Oryctolagus cuniculus

<400> SEQUENCE: 137

Gln Ala Val Val Thr Gln Thr Pro Ser Pro Val Ser Ala Ala Val Gly
1               5                   10                  15

Gly Thr Val Ile Ile Ser Cys Gln Ser Ser Gln Ser Val Asp Gly Asn
                20                  25                  30

Asn Leu Leu Ser Trp Tyr Gln Gln Lys Pro Gly Gln Pro Pro Lys Leu
            35                  40                  45

Leu Ile Tyr Asp Ala Ser Asn Leu Ala Ser Gly Val Pro Ser Arg Phe
        50                  55                  60

Ser Gly Ser Gly Ser Gly Thr Gln Phe Thr Leu Thr Ile Ser Gly Val
65                  70                  75                  80

Gln Ser Asp Asp Ala Ala Thr Tyr Tyr Cys Gln Gly Ser Tyr Tyr Ser
                85                  90                  95

Ser Ser Trp Tyr Asn Val Phe Gly Gly Gly Thr Glu Val Val Val Lys
                100                 105                 110

<210> SEQ ID NO 138
<211> LENGTH: 111
<212> TYPE: PRT
<213> ORGANISM: Oryctolagus cuniculus

<400> SEQUENCE: 138

Ala Gln Ala Leu Thr Gln Thr Pro Ser Ser Val Ser Ala Ala Val Gly

```
1               5                  10                 15
Gly Thr Val Thr Ile Asn Cys Gln Ser Ser Gln Ser Val Tyr Ser Asp
                20                 25                 30

Tyr Leu Ala Trp Tyr Gln Gln Lys Pro Gly Gln Pro Pro Lys Leu Leu
                35                 40                 45

Ile Tyr Trp Ala Ser Lys Leu Ala Ser Gly Val Pro Ser Arg Phe Lys
                50                 55                 60

Gly Ser Gly Ser Gly Thr Gln Phe Thr Leu Thr Ile Ser Gly Val Gln
65                  70                 75                 80

Ser Asp Asp Ala Ala Thr Tyr Tyr Cys Gln Ala Thr Tyr Asn Gly Arg
                85                 90                 95

Gly Trp Tyr Arg Ala Phe Gly Glu Gly Thr Glu Val Val Val Lys
                100                105                110

<210> SEQ ID NO 139
<211> LENGTH: 110
<212> TYPE: PRT
<213> ORGANISM: Oryctolagus cuniculus

<400> SEQUENCE: 139

Ala Leu Val Met Thr Gln Thr Pro Ser Pro Val Ser Ala Ala Val Gly
1               5                  10                 15

Gly Thr Val Thr Ile Asn Cys Gln Ala Ser Glu Asp Ile Tyr Ser Asn
                20                 25                 30

Leu Ala Trp Phe Gln Gln Lys Pro Gly Gln Pro Pro Lys Leu Leu Ile
                35                 40                 45

Tyr Asp Ala Ser Thr Leu Ala Ser Gly Val Pro Ser Arg Phe Ser Gly
                50                 55                 60

Ser Gly Ser Gly Thr Glu Phe Thr Leu Thr Ile Ser Gly Leu Gln Ser
65                  70                 75                 80

Asp Asp Ala Ala Thr Tyr Tyr Cys Leu Gly Val Tyr Thr His Ile Ser
                85                 90                 95

Ala Asp Asn Ala Phe Gly Gly Gly Thr Glu Val Val Val Lys
                100                105                110

<210> SEQ ID NO 140
<211> LENGTH: 111
<212> TYPE: PRT
<213> ORGANISM: Oryctolagus cuniculus

<400> SEQUENCE: 140

Ala Tyr Asp Met Thr Gln Thr Pro Ala Ser Val Glu Ala Ala Val Gly
1               5                  10                 15

Gly Thr Val Thr Ile Lys Cys Gln Ala Ser Gln Ser Ile Ser Ser Trp
                20                 25                 30

Leu Ser Trp Tyr Gln Gln Lys Pro Gly Gln Pro Pro Lys Gln Leu Ile
                35                 40                 45

Tyr Arg Ala Ser Thr Leu Ala Ser Gly Val Ser Arg Phe Lys Gly
                50                 55                 60

Ser Gly Ser Gly Thr Asp Tyr Thr Leu Thr Ile Ser Gly Val Gln Ser
65                  70                 75                 80

Asp Asp Ala Ala Thr Tyr Tyr Cys Gln Gln Gly Tyr Ile Thr Ser Ser
                85                 90                 95

Asn Ile Lys Asn Val Phe Gly Gly Gly Thr Glu Val Val Val Lys
                100                105                110
```

```
<210> SEQ ID NO 141
<211> LENGTH: 110
<212> TYPE: PRT
<213> ORGANISM: Oryctolagus cuniculus

<400> SEQUENCE: 141

Asp Val Val Met Thr Gln Thr Pro Ala Ser Val Ser Gly Pro Val Gly
1               5                   10                  15

Gly Thr Val Thr Ile Asn Cys Gln Ala Ser Glu Ser Ile Ser Asn Tyr
            20                  25                  30

Leu Ser Trp Tyr Gln Gln Lys Ser Gly Gln Pro Pro Lys Leu Leu Ile
        35                  40                  45

Tyr Leu Ala Ser Thr Leu Ala Ser Gly Val Pro Ser Arg Phe Lys Gly
    50                  55                  60

Ser Gly Ser Gly Thr Glu Phe Thr Leu Thr Ile Ser Asp Leu Glu Ser
65                  70                  75                  80

Ala Asp Ala Ala Thr Tyr Tyr Cys Gln Asn Trp Trp Val Ile Glu His
                85                  90                  95

Asn Gly Ala Ala Phe Gly Gly Gly Thr Glu Val Val Val Lys
            100                 105                 110

<210> SEQ ID NO 142
<211> LENGTH: 110
<212> TYPE: PRT
<213> ORGANISM: Oryctolagus cuniculus

<400> SEQUENCE: 142

Ala Phe Glu Met Thr Gln Thr Pro Ser Ser Val Ser Glu Pro Val Gly
1               5                   10                  15

Gly Thr Val Thr Ile Lys Cys Gln Ala Ser Gln Asn Ile Tyr Ile Tyr
            20                  25                  30

Leu Ser Trp Tyr Gln Gln Lys Pro Gly Gln Pro Pro Lys Leu Leu Ile
        35                  40                  45

Tyr Asp Ala Ser Thr Leu Ala Ser Gly Val Ser Arg Phe Ser Gly
    50                  55                  60

Ser Gly Ser Gly Thr Glu Phe Thr Leu Thr Ile Ser Gly Val Gln Ser
65                  70                  75                  80

Glu Asp Ala Ala Ile Tyr Tyr Cys Gln Gln Gly Ala Thr Thr Tyr Asp
                85                  90                  95

Val Asp Asn Val Phe Gly Gly Gly Thr Glu Val Val Val Lys
            100                 105                 110

<210> SEQ ID NO 143
<211> LENGTH: 114
<212> TYPE: PRT
<213> ORGANISM: Oryctolagus cuniculus

<400> SEQUENCE: 143

Asp Ile Val Met Thr Gln Thr Pro Ala Ser Val Glu Ala Ala Val Gly
1               5                   10                  15

Gly Thr Val Thr Ile Lys Cys Gln Ala Ser Glu Ser Ile Ser Ala Asn
            20                  25                  30

Tyr Trp Ser Trp Tyr Gln Gln Lys Pro Gly Gln Pro Pro Lys Leu Leu
        35                  40                  45

Ile Tyr Gly Ala Ser Thr Leu Ala Ser Gly Val Pro Ser Arg Phe Lys
    50                  55                  60

Gly Ser Gly Ser Gly Pro Gln Phe Thr Leu Thr Ile Ser Asp Leu Glu
65                  70                  75                  80
```

```
Ser Ala Asp Ala Ala Thr Tyr Phe Cys Gln Ser Trp Tyr Ser Gly
                85                  90                  95

Ser Gly Ser Tyr His Ser Trp Ala Phe Gly Gly Gly Thr Glu Val Val
            100                 105                 110

Leu Lys

<210> SEQ ID NO 144
<211> LENGTH: 110
<212> TYPE: PRT
<213> ORGANISM: Oryctolagus cuniculus

<400> SEQUENCE: 144

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Tyr Ile Tyr
            20                  25                  30

Leu Ala Trp Tyr Gln Gln Lys Pro Gly Gln Arg Pro Lys Gln Leu Ile
        35                  40                  45

Tyr Asp Ala Ser Lys Leu Ala Ser Gly Val Pro Ser Arg Phe Ser Gly
    50                  55                  60

Ser Gly Ser Gly Thr Glu Phe Thr Leu Thr Ile Ser Gly Val Glu Ser
65                  70                  75                  80

Ala Asp Ala Ala Thr Tyr Tyr Cys Gln Gln Gly Ala Thr Ile Trp Asn
                85                  90                  95

Val Asp Asn Pro Phe Gly Gly Gly Thr Glu Val Val Val Lys
            100                 105                 110

<210> SEQ ID NO 145
<211> LENGTH: 111
<212> TYPE: PRT
<213> ORGANISM: Oryctolagus cuniculus

<400> SEQUENCE: 145

Ala Ala Val Leu Thr Gln Thr Pro Ser Pro Val Ser Ala Ala Val Gly
1               5                   10                  15

Gly Thr Val Ser Ile Ser Cys Gln Ser Ser Gln Ser Val Tyr Gly Asn
            20                  25                  30

Asn Glu Leu Ser Trp Phe Gln Gln Lys Pro Gly Gln Pro Pro Lys Leu
        35                  40                  45

Leu Ile Tyr Gly Ala Ser Ile Leu Ala Ser Gly Val Pro Ser Arg Phe
    50                  55                  60

Ser Gly Ser Gly Ser Gly Thr Glu Phe Thr Leu Thr Ile Ser Asp Val
65                  70                  75                  80

Gln Ser Asp Asp Ala Ala Thr Tyr Tyr Cys Ala Gly Gly Tyr Ser Ser
                85                  90                  95

Thr Ser Asp Asn Ala Phe Gly Gly Gly Thr Glu Val Val Val Lys
            100                 105                 110

<210> SEQ ID NO 146
<211> LENGTH: 111
<212> TYPE: PRT
<213> ORGANISM: Oryctolagus cuniculus

<400> SEQUENCE: 146

Asp Val Val Met Thr Gln Thr Pro Ala Ser Val Ser Glu Pro Val Gly
1               5                   10                  15

Gly Thr Val Thr Ile Lys Cys Gln Ala Ser Glu Asp Ile Ser Ser Tyr
```

```
                    20                  25                  30

Leu Ala Trp Tyr Gln Gln Lys Pro Gly Gln Pro Pro Lys Leu Leu Ile
                35                  40                  45

Tyr Asp Ala Ser Asp Leu Ala Ser Gly Val Pro Ser Arg Phe Ser Gly
            50                  55                  60

Gly Gly Tyr Gly Thr Glu Phe Ser Leu Thr Ile Ser Asp Leu Glu Ser
65                  70                  75                  80

Ala Asp Ala Ala Thr Tyr Tyr Cys Gln Cys Ala Asp Tyr Ala Thr Thr
                85                  90                  95

Tyr Gly Leu Gly Ala Phe Gly Gly Thr Glu Val Val Val Lys
                100                 105                 110

<210> SEQ ID NO 147
<211> LENGTH: 111
<212> TYPE: PRT
<213> ORGANISM: Oryctolagus cuniculus

<400> SEQUENCE: 147

Ala Gln Ala Leu Thr Gln Thr Pro Ser Ser Val Ser Ala Ala Val Gly
1               5                   10                  15

Gly Thr Val Thr Ile Asn Cys Gln Ser Ser Gln Ser Val Tyr Ser Asp
                20                  25                  30

Tyr Leu Ala Trp Tyr Gln Gln Lys Pro Gly Gln Pro Pro Lys Leu Leu
                35                  40                  45

Ile Ser Gln Ala Ser Lys Leu Ala Ser Gly Val Pro Ser Arg Phe Lys
            50                  55                  60

Gly Ser Gly Ser Gly Thr Gln Phe Thr Leu Thr Ile Ser Asp Leu Glu
65                  70                  75                  80

Ser Asp Asp Ala Ala Thr Tyr Tyr Cys Gln Ala Thr Tyr Ser Ser Ser
                85                  90                  95

Gly Trp Tyr Arg Ala Phe Gly Gly Thr Glu Val Val Val Lys
                100                 105                 110

<210> SEQ ID NO 148
<211> LENGTH: 110
<212> TYPE: PRT
<213> ORGANISM: Oryctolagus cuniculus

<400> SEQUENCE: 148

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Asp Tyr Tyr
                20                  25                  30

Leu Ala Trp Tyr Gln Gln Lys Pro Gly Gln Pro Pro Lys Leu Leu Ile
                35                  40                  45

Tyr Arg Ala Ser Thr Leu Ala Ser Gly Val Ser Ser Arg Phe Lys Gly
            50                  55                  60

Ser Gly Ser Gly Thr Asp Tyr Thr Leu Thr Ile Ser Gly Val Glu Ser
65                  70                  75                  80

Ala Asp Ala Ala Thr Tyr Tyr Cys Gln Gln Gly Tyr Ser Gly Asn Asn
                85                  90                  95

Val Asp Asn Thr Phe Gly Gly Gly Thr Glu Val Val Val Lys
                100                 105                 110

<210> SEQ ID NO 149
<211> LENGTH: 112
<212> TYPE: PRT
```

-continued

<213> ORGANISM: Oryctolagus cuniculus

<400> SEQUENCE: 149

```
Ala Gln Val Leu Thr Gln Thr Ala Ser Pro Val Ser Ala Ala Val Gly
1               5                   10                  15
Gly Thr Val Thr Ile Asn Cys Gln Ser Ser Gln Ser Val Asn Gly Asn
            20                  25                  30
Asn Tyr Leu Ala Trp Tyr Gln Gln Lys Pro Gly Gln Pro Pro Lys Leu
        35                  40                  45
Leu Ile Trp Leu Ala Ser Ser Leu Ala Ser Gly Val Pro Ser Arg Phe
    50                  55                  60
Lys Gly Ser Gly Ser Gly Thr Gln Phe Ala Leu Thr Ile Ser Asp Leu
65                  70                  75                  80
Glu Ser Asp Asp Ala Ala Thr Tyr Tyr Cys Ala Gly Ala Tyr Ser Thr
                85                  90                  95
Ser Gly Glu Glu Asn Ala Phe Gly Gly Gly Thr Glu Val Val Val Lys
            100                 105                 110
```

<210> SEQ ID NO 150
<211> LENGTH: 110
<212> TYPE: PRT
<213> ORGANISM: Oryctolagus cuniculus

<400> SEQUENCE: 150

```
Asp Val Val Met Thr Gln Thr Pro Ala Ser Val Ser Glu Pro Val Gly
1               5                   10                  15
Gly Thr Val Thr Ile Lys Cys Gln Ala Ser Gln Ser Ile Ser Ser Tyr
            20                  25                  30
Leu Ser Trp Tyr Gln Gln Lys Pro Gly Gln Pro Pro Lys Leu Leu Ile
        35                  40                  45
Tyr Gly Ala Ser Asn Leu Ala Ser Gly Val Pro Ser Arg Phe Lys Gly
    50                  55                  60
Ser Gly Ser Gly Thr Glu Phe Thr Leu Thr Ile Ser Asp Leu Glu Ser
65                  70                  75                  80
Ala Asp Ala Ala Thr Tyr Tyr Cys Gln Cys Thr Tyr Tyr Asp Asn Asn
                85                  90                  95
Tyr Gly Gly Ala Phe Gly Gly Gly Thr Glu Val Val Val Lys
            100                 105                 110
```

<210> SEQ ID NO 151
<211> LENGTH: 110
<212> TYPE: PRT
<213> ORGANISM: Oryctolagus cuniculus

<400> SEQUENCE: 151

```
Asp Thr Val Leu Thr Gln Thr Pro Ser Ser Val Ser Ala Ala Val Gly
1               5                   10                  15
Asp Thr Val Thr Ile Lys Cys Gln Ala Ser Gln Asn Ile Tyr Ser Gly
            20                  25                  30
Leu Ala Trp Tyr Gln Gln Lys Pro Gly Gln Pro Pro Lys Leu Leu Ile
        35                  40                  45
Tyr Tyr Ala Ser Thr Leu Ala Ser Gly Val Pro Ser Arg Phe Lys Gly
    50                  55                  60
Ser Gly Ser Gly Thr Glu Phe Thr Leu Thr Ile Ser Asp Leu Glu Ser
65                  70                  75                  80
Ala Asp Ala Ala Thr Tyr Tyr Cys Gln Thr Tyr Tyr Gly Val Tyr Val
                85                  90                  95
```

```
Tyr Gly Ile Ile Phe Gly Gly Gly Thr Glu Val Val Val Lys
            100                 105                 110

<210> SEQ ID NO 152
<211> LENGTH: 111
<212> TYPE: PRT
<213> ORGANISM: Oryctolagus cuniculus

<400> SEQUENCE: 152

Ala Leu Val Met Thr Gln Thr Pro Ser Pro Val Ser Ala Ala Val Gly
1               5                   10                  15

Gly Thr Val Thr Ile Asn Cys Gln Ala Ser Glu Asp Ile Tyr Ser Asn
            20                  25                  30

Leu Ala Trp Phe Gln Gln Lys Pro Gly Gln Pro Pro Lys Leu Leu Ile
        35                  40                  45

Tyr Gly Ala Ser Thr Leu Ala Ser Gly Val Pro Ser Arg Phe Ser Gly
    50                  55                  60

Ser Gly Ser Gly Thr Glu Phe Thr Leu Thr Ile Ser Gly Leu Gln Ser
65                  70                  75                  80

Asp Asp Ala Ala Thr Tyr Tyr Cys Leu Gly Val Cys Thr Asp Ile Ser
                85                  90                  95

Ala Val Tyr Asn Val Phe Gly Gly Gly Thr Glu Val Val Val Lys
            100                 105                 110

<210> SEQ ID NO 153
<211> LENGTH: 113
<212> TYPE: PRT
<213> ORGANISM: Oryctolagus cuniculus

<400> SEQUENCE: 153

Ala Gln Val Leu Thr Gln Thr Pro Ser Ser Met Ser Ala Ala Val Gly
1               5                   10                  15

Gly Thr Val Thr Ile Asn Cys Gln Ala Ser Gln Ser Val Tyr Lys Asn
            20                  25                  30

Asn Tyr Leu Ser Trp Tyr Gln Gln Lys Pro Gly Gln Pro Pro Lys Arg
        35                  40                  45

Leu Met Tyr Ser Ala Ser Thr Leu Asp Ser Gly Val Pro Leu Arg Phe
    50                  55                  60

Ser Gly Ser Gly Ser Gly Thr Gln Phe Thr Leu Thr Ile Ser Asp Val
65                  70                  75                  80

Gln Ser Glu Asp Ala Ala Thr Tyr Tyr Cys Gln Gly Asn Tyr Asp Cys
                85                  90                  95

Ser Ser Ala Asp Cys Ile Ala Phe Gly Gly Gly Thr Glu Val Val Val
            100                 105                 110

Lys

<210> SEQ ID NO 154
<211> LENGTH: 110
<212> TYPE: PRT
<213> ORGANISM: Oryctolagus cuniculus

<400> SEQUENCE: 154

Asp Val Val Met Thr Gln Thr Pro Ala Ser Val Ser Glu Pro Val Gly
1               5                   10                  15

Gly Thr Val Thr Ile Lys Cys Gln Ala Ser Gln Asn Ile Gly Ser Asn
            20                  25                  30

Leu Ala Trp Tyr Gln Gln Lys Pro Gly Gln Pro Pro Lys Leu Leu Ile
```

```
                35                  40                  45
Tyr Gly Ala Ser Thr Leu Ala Ser Gly Val Pro Ser Arg Phe Ser Gly
         50                  55                  60

Ser Gly Ser Gly Thr Glu Phe Thr Leu Thr Ile Ser Gly Val Gln Ser
 65                  70                  75                  80

Ala Asp Ala Ala Thr Tyr Tyr Cys Gln Cys Ser Gly Tyr Asp Thr Thr
                 85                  90                  95

Gly Val Phe Pro Phe Gly Gly Gly Ser Glu Val Val Val Lys
            100                 105                 110
```

<210> SEQ ID NO 155
<211> LENGTH: 5
<212> TYPE: PRT
<213> ORGANISM: Oryctolagus cuniculus

<400> SEQUENCE: 155

```
Ser Tyr Ala Met Gly
 1               5
```

<210> SEQ ID NO 156
<211> LENGTH: 6
<212> TYPE: PRT
<213> ORGANISM: Oryctolagus cuniculus

<400> SEQUENCE: 156

```
Phe Gly Tyr Tyr Met Cys
 1               5
```

<210> SEQ ID NO 157
<211> LENGTH: 6
<212> TYPE: PRT
<213> ORGANISM: Oryctolagus cuniculus

<400> SEQUENCE: 157

```
Ser Tyr Tyr Tyr Met Cys
 1               5
```

<210> SEQ ID NO 158
<211> LENGTH: 5
<212> TYPE: PRT
<213> ORGANISM: Oryctolagus cuniculus

<400> SEQUENCE: 158

```
Ser Tyr Asp Met Ser
 1               5
```

<210> SEQ ID NO 159
<211> LENGTH: 6
<212> TYPE: PRT
<213> ORGANISM: Oryctolagus cuniculus

<400> SEQUENCE: 159

```
Ser Ser Tyr Trp Ile Cys
 1               5
```

<210> SEQ ID NO 160
<211> LENGTH: 5
<212> TYPE: PRT
<213> ORGANISM: Oryctolagus cuniculus

<400> SEQUENCE: 160

```
Asn Tyr Ala Met Gly
 1               5
```

<210> SEQ ID NO 161
<211> LENGTH: 5
<212> TYPE: PRT
<213> ORGANISM: Oryctolagus cuniculus

<400> SEQUENCE: 161

Ser Tyr Tyr Met Ser
1               5

<210> SEQ ID NO 162
<211> LENGTH: 6
<212> TYPE: PRT
<213> ORGANISM: Oryctolagus cuniculus

<400> SEQUENCE: 162

Ser Ser His Tyr Met Cys
1               5

<210> SEQ ID NO 163
<211> LENGTH: 5
<212> TYPE: PRT
<213> ORGANISM: Oryctolagus cuniculus

<400> SEQUENCE: 163

Asn Tyr Ala Met Ser
1               5

<210> SEQ ID NO 164
<211> LENGTH: 5
<212> TYPE: PRT
<213> ORGANISM: Oryctolagus cuniculus

<400> SEQUENCE: 164

Asn Tyr Ala Met Ser
1               5

<210> SEQ ID NO 165
<211> LENGTH: 5
<212> TYPE: PRT
<213> ORGANISM: Oryctolagus cuniculus

<400> SEQUENCE: 165

Ile Tyr Ala Met Gly
1               5

<210> SEQ ID NO 166
<211> LENGTH: 6
<212> TYPE: PRT
<213> ORGANISM: Oryctolagus cuniculus

<400> SEQUENCE: 166

Thr Asn Tyr Trp Ile Cys
1               5

<210> SEQ ID NO 167
<211> LENGTH: 5
<212> TYPE: PRT
<213> ORGANISM: Oryctolagus cuniculus

<400> SEQUENCE: 167

Ile Tyr Ala Met Gly
1               5

```
<210> SEQ ID NO 168
<211> LENGTH: 6
<212> TYPE: PRT
<213> ORGANISM: Oryctolagus cuniculus

<400> SEQUENCE: 168

Ser Asp Ala Trp Ile Cys
1               5

<210> SEQ ID NO 169
<211> LENGTH: 6
<212> TYPE: PRT
<213> ORGANISM: Oryctolagus cuniculus

<400> SEQUENCE: 169

Ser Ser Tyr Tyr Met Cys
1               5

<210> SEQ ID NO 170
<211> LENGTH: 5
<212> TYPE: PRT
<213> ORGANISM: Oryctolagus cuniculus

<400> SEQUENCE: 170

Asn Tyr His Ile Ser
1               5

<210> SEQ ID NO 171
<211> LENGTH: 5
<212> TYPE: PRT
<213> ORGANISM: Oryctolagus cuniculus

<400> SEQUENCE: 171

Ser Asn Gly Ile Asn
1               5

<210> SEQ ID NO 172
<211> LENGTH: 6
<212> TYPE: PRT
<213> ORGANISM: Oryctolagus cuniculus

<400> SEQUENCE: 172

Ser Ser Asp Phe Met Cys
1               5

<210> SEQ ID NO 173
<211> LENGTH: 6
<212> TYPE: PRT
<213> ORGANISM: Oryctolagus cuniculus

<400> SEQUENCE: 173

Ser Thr Tyr Tyr Met Cys
1               5

<210> SEQ ID NO 174
<211> LENGTH: 6
<212> TYPE: PRT
<213> ORGANISM: Oryctolagus cuniculus

<400> SEQUENCE: 174

Ser Asn Tyr Trp Met Cys
1               5

<210> SEQ ID NO 175
<211> LENGTH: 6
```

```
<212> TYPE: PRT
<213> ORGANISM: Oryctolagus cuniculus

<400> SEQUENCE: 175

Ser Ser Tyr Trp Ile Cys
1               5

<210> SEQ ID NO 176
<211> LENGTH: 6
<212> TYPE: PRT
<213> ORGANISM: Oryctolagus cuniculus

<400> SEQUENCE: 176

Thr Ser Tyr Trp Arg Cys
1               5

<210> SEQ ID NO 177
<211> LENGTH: 5
<212> TYPE: PRT
<213> ORGANISM: Oryctolagus cuniculus

<400> SEQUENCE: 177

Asn Tyr Ala Met Ser
1               5

<210> SEQ ID NO 178
<211> LENGTH: 5
<212> TYPE: PRT
<213> ORGANISM: Oryctolagus cuniculus

<400> SEQUENCE: 178

Ser Asp Ala Val Gly
1               5

<210> SEQ ID NO 179
<211> LENGTH: 5
<212> TYPE: PRT
<213> ORGANISM: Oryctolagus cuniculus

<400> SEQUENCE: 179

Ser Tyr Tyr Met Ser
1               5

<210> SEQ ID NO 180
<211> LENGTH: 6
<212> TYPE: PRT
<213> ORGANISM: Oryctolagus cuniculus

<400> SEQUENCE: 180

Ser Asn Tyr Tyr Met Cys
1               5

<210> SEQ ID NO 181
<211> LENGTH: 5
<212> TYPE: PRT
<213> ORGANISM: Oryctolagus cuniculus

<400> SEQUENCE: 181

Val Tyr Ala Met Gly
1               5

<210> SEQ ID NO 182
<211> LENGTH: 6
<212> TYPE: PRT
<213> ORGANISM: Oryctolagus cuniculus
```

```
<400> SEQUENCE: 182

Ser Ala Tyr Trp Ile Cys
1               5

<210> SEQ ID NO 183
<211> LENGTH: 5
<212> TYPE: PRT
<213> ORGANISM: Oryctolagus cuniculus

<400> SEQUENCE: 183

Ser Tyr Tyr Met Ser
1               5

<210> SEQ ID NO 184
<211> LENGTH: 5
<212> TYPE: PRT
<213> ORGANISM: Oryctolagus cuniculus

<400> SEQUENCE: 184

Ser Tyr Tyr Met Ser
1               5

<210> SEQ ID NO 185
<211> LENGTH: 5
<212> TYPE: PRT
<213> ORGANISM: Oryctolagus cuniculus

<400> SEQUENCE: 185

Ser Tyr Ala Met Gly
1               5

<210> SEQ ID NO 186
<211> LENGTH: 6
<212> TYPE: PRT
<213> ORGANISM: Oryctolagus cuniculus

<400> SEQUENCE: 186

Asn Ser Tyr Trp Ile Cys
1               5

<210> SEQ ID NO 187
<211> LENGTH: 6
<212> TYPE: PRT
<213> ORGANISM: Oryctolagus cuniculus

<400> SEQUENCE: 187

Ser Ser Tyr Trp Ile Cys
1               5

<210> SEQ ID NO 188
<211> LENGTH: 5
<212> TYPE: PRT
<213> ORGANISM: Oryctolagus cuniculus

<400> SEQUENCE: 188

Ser Tyr Tyr Met Ser
1               5

<210> SEQ ID NO 189
<211> LENGTH: 6
<212> TYPE: PRT
<213> ORGANISM: Oryctolagus cuniculus

<400> SEQUENCE: 189
```

```
Ser Tyr Tyr Val Ile Cys
1               5

<210> SEQ ID NO 190
<211> LENGTH: 5
<212> TYPE: PRT
<213> ORGANISM: Oryctolagus cuniculus

<400> SEQUENCE: 190

Gly Tyr Ala Met Ser
1               5

<210> SEQ ID NO 191
<211> LENGTH: 6
<212> TYPE: PRT
<213> ORGANISM: Oryctolagus cuniculus

<400> SEQUENCE: 191

Ser Ser Tyr Trp Ile Cys
1               5

<210> SEQ ID NO 192
<211> LENGTH: 6
<212> TYPE: PRT
<213> ORGANISM: Oryctolagus cuniculus

<400> SEQUENCE: 192

Ser Asn Tyr Trp Ile Cys
1               5

<210> SEQ ID NO 193
<211> LENGTH: 5
<212> TYPE: PRT
<213> ORGANISM: Oryctolagus cuniculus

<400> SEQUENCE: 193

Val Tyr Ala Met Gly
1               5

<210> SEQ ID NO 194
<211> LENGTH: 5
<212> TYPE: PRT
<213> ORGANISM: Oryctolagus cuniculus

<400> SEQUENCE: 194

Ser Tyr Ala Met Gly
1               5

<210> SEQ ID NO 195
<211> LENGTH: 6
<212> TYPE: PRT
<213> ORGANISM: Oryctolagus cuniculus

<400> SEQUENCE: 195

Ser Ser Tyr Trp Ile Cys
1               5

<210> SEQ ID NO 196
<211> LENGTH: 5
<212> TYPE: PRT
<213> ORGANISM: Oryctolagus cuniculus

<400> SEQUENCE: 196

Thr Tyr Tyr Met Ser
```

```
1               5
```

<210> SEQ ID NO 197
<211> LENGTH: 6
<212> TYPE: PRT
<213> ORGANISM: Oryctolagus cuniculus

<400> SEQUENCE: 197

```
Ser Asn Tyr Trp Met Cys
1               5
```

<210> SEQ ID NO 198
<211> LENGTH: 6
<212> TYPE: PRT
<213> ORGANISM: Oryctolagus cuniculus

<400> SEQUENCE: 198

```
Ser Ala Tyr Trp Met Cys
1               5
```

<210> SEQ ID NO 199
<211> LENGTH: 6
<212> TYPE: PRT
<213> ORGANISM: Oryctolagus cuniculus

<400> SEQUENCE: 199

```
Ala Ser Tyr Trp Ile Cys
1               5
```

<210> SEQ ID NO 200
<211> LENGTH: 6
<212> TYPE: PRT
<213> ORGANISM: Oryctolagus cuniculus

<400> SEQUENCE: 200

```
Ser Gly Tyr Tyr Met Cys
1               5
```

<210> SEQ ID NO 201
<211> LENGTH: 5
<212> TYPE: PRT
<213> ORGANISM: Oryctolagus cuniculus

<400> SEQUENCE: 201

```
Ile Tyr Gly Met Gly
1               5
```

<210> SEQ ID NO 202
<211> LENGTH: 5
<212> TYPE: PRT
<213> ORGANISM: Oryctolagus cuniculus

<400> SEQUENCE: 202

```
Val Tyr Asn Met Gly
1               5
```

<210> SEQ ID NO 203
<211> LENGTH: 5
<212> TYPE: PRT
<213> ORGANISM: Oryctolagus cuniculus

<400> SEQUENCE: 203

```
Asp Tyr Tyr Met Gly
1               5
```

```
<210> SEQ ID NO 204
<211> LENGTH: 5
<212> TYPE: PRT
<213> ORGANISM: Oryctolagus cuniculus

<400> SEQUENCE: 204

Ser Gly Gly Met Ser
1               5

<210> SEQ ID NO 205
<211> LENGTH: 6
<212> TYPE: PRT
<213> ORGANISM: Oryctolagus cuniculus

<400> SEQUENCE: 205

Tyr Thr Tyr Val Met Cys
1               5

<210> SEQ ID NO 206
<211> LENGTH: 6
<212> TYPE: PRT
<213> ORGANISM: Oryctolagus cuniculus

<400> SEQUENCE: 206

Ser Asn Tyr Trp Ile Cys
1               5

<210> SEQ ID NO 207
<211> LENGTH: 6
<212> TYPE: PRT
<213> ORGANISM: Oryctolagus cuniculus

<400> SEQUENCE: 207

Gly Asn Tyr Tyr Met Cys
1               5

<210> SEQ ID NO 208
<211> LENGTH: 5
<212> TYPE: PRT
<213> ORGANISM: Oryctolagus cuniculus

<400> SEQUENCE: 208

Asp Tyr Asp Ile Tyr
1               5

<210> SEQ ID NO 209
<211> LENGTH: 5
<212> TYPE: PRT
<213> ORGANISM: Oryctolagus cuniculus

<400> SEQUENCE: 209

Ser Gly Gly Met Thr
1               5

<210> SEQ ID NO 210
<211> LENGTH: 5
<212> TYPE: PRT
<213> ORGANISM: Oryctolagus cuniculus

<400> SEQUENCE: 210

Ser Tyr Gly Met Ile
1               5

<210> SEQ ID NO 211
```

```
<211> LENGTH: 5
<212> TYPE: PRT
<213> ORGANISM: Oryctolagus cuniculus

<400> SEQUENCE: 211

Arg Cys Ala Met Ile
1               5

<210> SEQ ID NO 212
<211> LENGTH: 5
<212> TYPE: PRT
<213> ORGANISM: Oryctolagus cuniculus

<400> SEQUENCE: 212

Ser Cys Ala Met Ile
1               5

<210> SEQ ID NO 213
<211> LENGTH: 5
<212> TYPE: PRT
<213> ORGANISM: Oryctolagus cuniculus

<400> SEQUENCE: 213

Ser Tyr Ala Met Gly
1               5

<210> SEQ ID NO 214
<211> LENGTH: 5
<212> TYPE: PRT
<213> ORGANISM: Oryctolagus cuniculus

<400> SEQUENCE: 214

Ser Tyr Trp Met Ser
1               5

<210> SEQ ID NO 215
<211> LENGTH: 5
<212> TYPE: PRT
<213> ORGANISM: Oryctolagus cuniculus

<400> SEQUENCE: 215

Ile Tyr Ala Met Gly
1               5

<210> SEQ ID NO 216
<211> LENGTH: 6
<212> TYPE: PRT
<213> ORGANISM: Oryctolagus cuniculus

<400> SEQUENCE: 216

Thr Ser Tyr Trp Arg Cys
1               5

<210> SEQ ID NO 217
<211> LENGTH: 5
<212> TYPE: PRT
<213> ORGANISM: Oryctolagus cuniculus

<400> SEQUENCE: 217

Ser Tyr Asp Met Ser
1               5

<210> SEQ ID NO 218
<211> LENGTH: 6
<212> TYPE: PRT
```

<213> ORGANISM: Oryctolagus cuniculus

<400> SEQUENCE: 218

Ser Ser Tyr Trp Ile Cys
1               5

<210> SEQ ID NO 219
<211> LENGTH: 5
<212> TYPE: PRT
<213> ORGANISM: Oryctolagus cuniculus

<400> SEQUENCE: 219

Thr Tyr Thr Met Ser
1               5

<210> SEQ ID NO 220
<211> LENGTH: 6
<212> TYPE: PRT
<213> ORGANISM: Oryctolagus cuniculus

<400> SEQUENCE: 220

Ser Gly Tyr Asp Met Cys
1               5

<210> SEQ ID NO 221
<211> LENGTH: 5
<212> TYPE: PRT
<213> ORGANISM: Oryctolagus cuniculus

<400> SEQUENCE: 221

Ser Tyr His Met Ser
1               5

<210> SEQ ID NO 222
<211> LENGTH: 5
<212> TYPE: PRT
<213> ORGANISM: Oryctolagus cuniculus

<400> SEQUENCE: 222

Ser Tyr Ala Met Ser
1               5

<210> SEQ ID NO 223
<211> LENGTH: 5
<212> TYPE: PRT
<213> ORGANISM: Oryctolagus cuniculus

<400> SEQUENCE: 223

Val Tyr Ala Met Ser
1               5

<210> SEQ ID NO 224
<211> LENGTH: 5
<212> TYPE: PRT
<213> ORGANISM: Oryctolagus cuniculus

<400> SEQUENCE: 224

Val Tyr Ala Met Gly
1               5

<210> SEQ ID NO 225
<211> LENGTH: 5
<212> TYPE: PRT
<213> ORGANISM: Oryctolagus cuniculus

```
<400> SEQUENCE: 225

Ser Tyr His Met Gln
1               5

<210> SEQ ID NO 226
<211> LENGTH: 5
<212> TYPE: PRT
<213> ORGANISM: Oryctolagus cuniculus

<400> SEQUENCE: 226

Asp Tyr Ala Met Ile
1               5

<210> SEQ ID NO 227
<211> LENGTH: 6
<212> TYPE: PRT
<213> ORGANISM: Oryctolagus cuniculus

<400> SEQUENCE: 227

Ser Ile Tyr Tyr Met Cys
1               5

<210> SEQ ID NO 228
<211> LENGTH: 6
<212> TYPE: PRT
<213> ORGANISM: Oryctolagus cuniculus

<400> SEQUENCE: 228

Ser Thr Tyr Trp Ile Cys
1               5

<210> SEQ ID NO 229
<211> LENGTH: 6
<212> TYPE: PRT
<213> ORGANISM: Oryctolagus cuniculus

<400> SEQUENCE: 229

Asn Asn Tyr Trp Met His
1               5

<210> SEQ ID NO 230
<211> LENGTH: 6
<212> TYPE: PRT
<213> ORGANISM: Oryctolagus cuniculus

<400> SEQUENCE: 230

Ser Asp Tyr Trp Ile Cys
1               5

<210> SEQ ID NO 231
<211> LENGTH: 5
<212> TYPE: PRT
<213> ORGANISM: Oryctolagus cuniculus

<400> SEQUENCE: 231

Arg Cys Ala Met Ile
1               5

<210> SEQ ID NO 232
<211> LENGTH: 16
<212> TYPE: PRT
<213> ORGANISM: Oryctolagus cuniculus

<400> SEQUENCE: 232
```

-continued

Val Ile Thr Ser Ser Ala Thr Thr Tyr Tyr Ala Ser Trp Ala Lys Gly
1               5                   10                  15

<210> SEQ ID NO 233
<211> LENGTH: 17
<212> TYPE: PRT
<213> ORGANISM: Oryctolagus cuniculus

<400> SEQUENCE: 233

Cys Ile Tyr Gly Asp Ser Ser Asp Thr Leu Tyr Ala Asn Trp Ala Lys
1               5                   10                  15

Gly

<210> SEQ ID NO 234
<211> LENGTH: 18
<212> TYPE: PRT
<213> ORGANISM: Oryctolagus cuniculus

<400> SEQUENCE: 234

Cys Ile Phe Ile Gly Tyr Gly Asp Val Thr Trp Tyr Ala Ser Trp Ala
1               5                   10                  15

Lys Gly

<210> SEQ ID NO 235
<211> LENGTH: 16
<212> TYPE: PRT
<213> ORGANISM: Oryctolagus cuniculus

<400> SEQUENCE: 235

Thr Ile Tyr Ile Gly Gly Thr Thr Ala Tyr Ala Ser Trp Pro Lys Gly
1               5                   10                  15

<210> SEQ ID NO 236
<211> LENGTH: 18
<212> TYPE: PRT
<213> ORGANISM: Oryctolagus cuniculus

<400> SEQUENCE: 236

Cys Ile Tyr Thr Gly Ser Ser Gly Ile Thr Tyr Tyr Ala Ser Trp Val
1               5                   10                  15

Asn Gly

<210> SEQ ID NO 237
<211> LENGTH: 16
<212> TYPE: PRT
<213> ORGANISM: Oryctolagus cuniculus

<400> SEQUENCE: 237

Val Ile Ser Ser Asp Gly Phe Phe Tyr Asp Ala Ser Trp Ala Lys Gly
1               5                   10                  15

<210> SEQ ID NO 238
<211> LENGTH: 16
<212> TYPE: PRT
<213> ORGANISM: Oryctolagus cuniculus

<400> SEQUENCE: 238

Ile Ile Ser Gly Ser Ala Ser Thr Tyr Tyr Ala Thr Trp Ala Lys Gly
1               5                   10                  15

<210> SEQ ID NO 239
<211> LENGTH: 18
<212> TYPE: PRT

<213> ORGANISM: Oryctolagus cuniculus

<400> SEQUENCE: 239

Cys Ile Tyr Ala Gly Ser Ser Gly Asn Thr Tyr Ala Asn Trp Ala
1               5                   10                  15
Lys Gly

<210> SEQ ID NO 240
<211> LENGTH: 16
<212> TYPE: PRT
<213> ORGANISM: Oryctolagus cuniculus

<400> SEQUENCE: 240

Ser Val Ile Ser Gly Gly Ser Thr Tyr Tyr Ala Thr Trp Ala Arg Gly
1               5                   10                  15

<210> SEQ ID NO 241
<211> LENGTH: 16
<212> TYPE: PRT
<213> ORGANISM: Oryctolagus cuniculus

<400> SEQUENCE: 241

Ile Ile Asp Ser Gly Gly Ser Ala Tyr Tyr Ala Thr Trp Ala Arg Gly
1               5                   10                  15

<210> SEQ ID NO 242
<211> LENGTH: 17
<212> TYPE: PRT
<213> ORGANISM: Oryctolagus cuniculus

<400> SEQUENCE: 242

Asp Ile Tyr Ala Gly Ser Gly Ser Thr Trp Tyr Ala Ser Trp Ala Lys
1               5                   10                  15
Gly

<210> SEQ ID NO 243
<211> LENGTH: 18
<212> TYPE: PRT
<213> ORGANISM: Oryctolagus cuniculus

<400> SEQUENCE: 243

Cys Ile Tyr Ala Asn Ser Val Gly Ser Thr Tyr Tyr Ala Ser Trp Val
1               5                   10                  15
Asn Gly

<210> SEQ ID NO 244
<211> LENGTH: 17
<212> TYPE: PRT
<213> ORGANISM: Oryctolagus cuniculus

<400> SEQUENCE: 244

Asp Ile Tyr Pro Gly Ser Asp Ser Thr Trp Tyr Ala Ser Trp Ala Lys
1               5                   10                  15
Gly

<210> SEQ ID NO 245
<211> LENGTH: 18
<212> TYPE: PRT
<213> ORGANISM: Oryctolagus cuniculus

<400> SEQUENCE: 245

Cys Ile Tyr Ala Gly Ser Ala Ser Asn Thr Tyr Tyr Ala Thr Trp Val

Asn Gly

<210> SEQ ID NO 246
<211> LENGTH: 18
<212> TYPE: PRT
<213> ORGANISM: Oryctolagus cuniculus

<400> SEQUENCE: 246

Cys Ile Tyr Ala Gly Ser Ser Gly Val Thr Tyr Tyr Ala Ser Trp Ala
1               5                   10                  15

Lys Gly

<210> SEQ ID NO 247
<211> LENGTH: 17
<212> TYPE: PRT
<213> ORGANISM: Oryctolagus cuniculus

<400> SEQUENCE: 247

Tyr Ile Tyr Ala Gly Arg Asp Phe Thr Tyr Tyr Ala Asn Trp Ala Glu
1               5                   10                  15

Gly

<210> SEQ ID NO 248
<211> LENGTH: 16
<212> TYPE: PRT
<213> ORGANISM: Oryctolagus cuniculus

<400> SEQUENCE: 248

Tyr Ile Gly Ala Gly Asp Ile Thr Tyr Cys Ala Ser Trp Ala Lys Gly
1               5                   10                  15

<210> SEQ ID NO 249
<211> LENGTH: 18
<212> TYPE: PRT
<213> ORGANISM: Oryctolagus cuniculus

<400> SEQUENCE: 249

Cys Ile Tyr Ala Gly Ser Ser Val Ser Ile Tyr Tyr Ala Thr Trp Ala
1               5                   10                  15

Lys Gly

<210> SEQ ID NO 250
<211> LENGTH: 18
<212> TYPE: PRT
<213> ORGANISM: Oryctolagus cuniculus

<400> SEQUENCE: 250

Cys Ile Tyr Ala Gly Ser Ser Gly Ser Thr Tyr Tyr Ala Ser Trp Ala
1               5                   10                  15

Lys Gly

<210> SEQ ID NO 251
<211> LENGTH: 18
<212> TYPE: PRT
<213> ORGANISM: Oryctolagus cuniculus

<400> SEQUENCE: 251

Cys Ile Tyr Thr Gly Gly Ser Gly Val Thr Tyr Tyr Ala Ser Trp Ala
1               5                   10                  15

Lys Gly

<210> SEQ ID NO 252
<211> LENGTH: 18
<212> TYPE: PRT
<213> ORGANISM: Oryctolagus cuniculus

<400> SEQUENCE: 252

Cys Ile Tyr Ala Gly Ser Ser Gly Ile Thr Tyr Tyr Ala Ser Trp Val
1               5                   10                  15

Ser Gly

<210> SEQ ID NO 253
<211> LENGTH: 18
<212> TYPE: PRT
<213> ORGANISM: Oryctolagus cuniculus

<400> SEQUENCE: 253

Cys Ile Tyr Ala Gly Ser Ser Asp Ala Thr Tyr Tyr Ala Asn Trp Val
1               5                   10                  15

Asn Gly

<210> SEQ ID NO 254
<211> LENGTH: 16
<212> TYPE: PRT
<213> ORGANISM: Oryctolagus cuniculus

<400> SEQUENCE: 254

Ser Val Ile Ser Gly Gly Ser Thr Tyr Tyr Ala Thr Trp Ala Lys Gly
1               5                   10                  15

<210> SEQ ID NO 255
<211> LENGTH: 16
<212> TYPE: PRT
<213> ORGANISM: Oryctolagus cuniculus

<400> SEQUENCE: 255

Ile Ile Val Ser Ser Gly Glu Thr Phe Tyr Ala Ser Trp Ala Arg Gly
1               5                   10                  15

<210> SEQ ID NO 256
<211> LENGTH: 17
<212> TYPE: PRT
<213> ORGANISM: Oryctolagus cuniculus

<400> SEQUENCE: 256

Tyr Ile Tyr Ala Ala Gly Pro Ile Thr Tyr Tyr Ala Thr Trp Ala Lys
1               5                   10                  15

Gly

<210> SEQ ID NO 257
<211> LENGTH: 17
<212> TYPE: PRT
<213> ORGANISM: Oryctolagus cuniculus

<400> SEQUENCE: 257

Cys Ile Tyr Thr Asn Ser Gly Asn Thr Trp Ser Ala Ser Trp Ala Lys
1               5                   10                  15

Gly

<210> SEQ ID NO 258
<211> LENGTH: 17
<212> TYPE: PRT

<210> SEQ ID NO 258
<211> LENGTH: 16
<212> TYPE: PRT
<213> ORGANISM: Oryctolagus cuniculus

<400> SEQUENCE: 258

Asp Ile Tyr Ile Ala Ser Asp Gly Thr Trp Tyr Ala Asn Trp Ala Lys
1               5                   10                  15
Gly

<210> SEQ ID NO 259
<211> LENGTH: 18
<212> TYPE: PRT
<213> ORGANISM: Oryctolagus cuniculus

<400> SEQUENCE: 259

Cys Ile Tyr Ala Asp Ser Ser Ile Thr Tyr Tyr Ala Ser Trp Val
1               5                   10                  15
Asn Gly

<210> SEQ ID NO 260
<211> LENGTH: 16
<212> TYPE: PRT
<213> ORGANISM: Oryctolagus cuniculus

<400> SEQUENCE: 260

Gly Ile Ala Thr Asp Gly Asn Thr Tyr Tyr Ala Asn Trp Ala Lys Gly
1               5                   10                  15

<210> SEQ ID NO 261
<211> LENGTH: 17
<212> TYPE: PRT
<213> ORGANISM: Oryctolagus cuniculus

<400> SEQUENCE: 261

Tyr Ile Tyr Ala Ala Gly Pro Ile Thr Tyr Tyr Ala Thr Trp Ala Lys
1               5                   10                  15
Gly

<210> SEQ ID NO 262
<211> LENGTH: 16
<212> TYPE: PRT
<213> ORGANISM: Oryctolagus cuniculus

<400> SEQUENCE: 262

Ile Ile Asn Ser Tyr Gly Ser Ile Tyr Tyr Ala Ser Trp Ala Lys Gly
1               5                   10                  15

<210> SEQ ID NO 263
<211> LENGTH: 18
<212> TYPE: PRT
<213> ORGANISM: Oryctolagus cuniculus

<400> SEQUENCE: 263

Cys Ile Tyr Val Gly Ser Ser Gly Ser Thr Tyr Tyr Ala Ser Trp Val
1               5                   10                  15
Asn Gly

<210> SEQ ID NO 264
<211> LENGTH: 18
<212> TYPE: PRT
<213> ORGANISM: Oryctolagus cuniculus

<400> SEQUENCE: 264

Cys Ile Tyr Val Gly Ser Ser Gly Ser Thr Tyr Tyr Ala Ser Trp Val

```
1               5                   10                  15

Ser Gly

<210> SEQ ID NO 265
<211> LENGTH: 17
<212> TYPE: PRT
<213> ORGANISM: Oryctolagus cuniculus

<400> SEQUENCE: 265

Tyr Ile Tyr Ala Ala Gly Pro Ile Thr Tyr Tyr Ala Thr Trp Ala Lys
1               5                   10                  15

Gly

<210> SEQ ID NO 266
<211> LENGTH: 17
<212> TYPE: PRT
<213> ORGANISM: Oryctolagus cuniculus

<400> SEQUENCE: 266

Cys Ile Gly Thr Gly Asp Gly Leu Thr Tyr Tyr Ala Ser Trp Ala Lys
1               5                   10                  15

Gly

<210> SEQ ID NO 267
<211> LENGTH: 17
<212> TYPE: PRT
<213> ORGANISM: Oryctolagus cuniculus

<400> SEQUENCE: 267

Ile Ile Tyr Ala Gly Ser Gly Gly Thr Tyr Tyr Ala Ser Trp Val Lys
1               5                   10                  15

Gly

<210> SEQ ID NO 268
<211> LENGTH: 18
<212> TYPE: PRT
<213> ORGANISM: Oryctolagus cuniculus

<400> SEQUENCE: 268

Cys Ile Tyr Thr Gly Ser Ser Gly Asn Thr Tyr Tyr Ala Ser Trp Val
1               5                   10                  15

Asn Gly

<210> SEQ ID NO 269
<211> LENGTH: 17
<212> TYPE: PRT
<213> ORGANISM: Oryctolagus cuniculus

<400> SEQUENCE: 269

Cys Ile Tyr Thr Ser Thr Gly Asn Thr Trp Tyr Ala Ser Trp Ala Lys
1               5                   10                  15

Gly

<210> SEQ ID NO 270
<211> LENGTH: 17
<212> TYPE: PRT
<213> ORGANISM: Oryctolagus cuniculus

<400> SEQUENCE: 270

Asp Ile Tyr Thr Gly Ser Gly Ser Thr Trp Tyr Ala Ser Trp Ala Lys
1               5                   10                  15
```

Gly

<210> SEQ ID NO 271
<211> LENGTH: 16
<212> TYPE: PRT
<213> ORGANISM: Oryctolagus cuniculus

<400> SEQUENCE: 271

Ile Ile Ser Asn Ser Gly Thr Thr Tyr Tyr Ala Ser Trp Ala Lys Gly
1               5                   10                  15

<210> SEQ ID NO 272
<211> LENGTH: 18
<212> TYPE: PRT
<213> ORGANISM: Oryctolagus cuniculus

<400> SEQUENCE: 272

Cys Ile Tyr Ala Gly Ser Ser Gly Ser Thr Tyr Tyr Ala Asn Trp Val
1               5                   10                  15

Asn Gly

<210> SEQ ID NO 273
<211> LENGTH: 16
<212> TYPE: PRT
<213> ORGANISM: Oryctolagus cuniculus

<400> SEQUENCE: 273

Tyr Met His Val Gly Gly Phe Pro Val Tyr Ala Ser Trp Ala Lys Gly
1               5                   10                  15

<210> SEQ ID NO 274
<211> LENGTH: 18
<212> TYPE: PRT
<213> ORGANISM: Oryctolagus cuniculus

<400> SEQUENCE: 274

Cys Ile Tyr Ala Gly Ser Ser Asp Ser Thr Tyr Tyr Ala Ser Trp Val
1               5                   10                  15

Asn Gly

<210> SEQ ID NO 275
<211> LENGTH: 18
<212> TYPE: PRT
<213> ORGANISM: Oryctolagus cuniculus

<400> SEQUENCE: 275

Cys Ile Tyr Ala Gly Ser Ser Gly Ser Thr Tyr Tyr Ala Ser Trp Ala
1               5                   10                  15

Lys Gly

<210> SEQ ID NO 276
<211> LENGTH: 17
<212> TYPE: PRT
<213> ORGANISM: Oryctolagus cuniculus

<400> SEQUENCE: 276

Cys Ile Tyr Ile Gly Gly Gly Gly Arg Tyr Tyr Ala Ser Trp Ala Lys
1               5                   10                  15

Gly

<210> SEQ ID NO 277

```
<211> LENGTH: 17
<212> TYPE: PRT
<213> ORGANISM: Oryctolagus cuniculus

<400> SEQUENCE: 277

Cys Ile Gly Met Gly Ser Gly Lys Thr Tyr Tyr Ala Ser Trp Ala Lys
1               5                   10                  15

Gly

<210> SEQ ID NO 278
<211> LENGTH: 16
<212> TYPE: PRT
<213> ORGANISM: Oryctolagus cuniculus

<400> SEQUENCE: 278

Ser Ile Ser Ser Gly Gly Ser Thr Tyr Tyr Ala Thr Trp Ala Lys Gly
1               5                   10                  15

<210> SEQ ID NO 279
<211> LENGTH: 16
<212> TYPE: PRT
<213> ORGANISM: Oryctolagus cuniculus

<400> SEQUENCE: 279

Ile Ile Ser Ser Ser Gly Thr Thr Tyr Tyr Ala Ser Trp Ala Lys Gly
1               5                   10                  15

<210> SEQ ID NO 280
<211> LENGTH: 16
<212> TYPE: PRT
<213> ORGANISM: Oryctolagus cuniculus

<400> SEQUENCE: 280

Thr Ile Asp Gly Gly Gly Ser Thr Tyr Tyr Ala Ser Trp Ala Lys Gly
1               5                   10                  15

<210> SEQ ID NO 281
<211> LENGTH: 17
<212> TYPE: PRT
<213> ORGANISM: Oryctolagus cuniculus

<400> SEQUENCE: 281

Tyr Ile Asn Thr Gly Ser Gly Ser Thr Tyr Tyr Ala Ser Trp Val Asn
1               5                   10                  15

Gly

<210> SEQ ID NO 282
<211> LENGTH: 18
<212> TYPE: PRT
<213> ORGANISM: Oryctolagus cuniculus

<400> SEQUENCE: 282

Cys Ile Tyr Thr Gly Arg Ser Gly Gly Leu Tyr Tyr Ala Asn Trp Ala
1               5                   10                  15

Lys Gly

<210> SEQ ID NO 283
<211> LENGTH: 17
<212> TYPE: PRT
<213> ORGANISM: Oryctolagus cuniculus

<400> SEQUENCE: 283

Cys Ile Tyr Thr Ser Thr Asp Thr Thr Tyr Tyr Pro Asn Trp Ala Lys
```

-continued

```
<210> SEQ ID NO 284
<211> LENGTH: 18
<212> TYPE: PRT
<213> ORGANISM: Oryctolagus cuniculus

<400> SEQUENCE: 284

Cys Ile Val Val Gly Ser Gly Gly Asn Thr Tyr Tyr Ala Gly Trp Ala
1               5                   10                  15

Lys Arg

<210> SEQ ID NO 285
<211> LENGTH: 16
<212> TYPE: PRT
<213> ORGANISM: Oryctolagus cuniculus

<400> SEQUENCE: 285

Val Ile Asp Ile Glu Asn Ser Val Tyr Tyr Pro Thr Trp Ala Lys Gly
1               5                   10                  15

<210> SEQ ID NO 286
<211> LENGTH: 17
<212> TYPE: PRT
<213> ORGANISM: Oryctolagus cuniculus

<400> SEQUENCE: 286

Tyr Ile Asn Thr Gly Ser Gly Arg Thr Tyr Tyr Ala Ser Trp Ala Lys
1               5                   10                  15

Gly

<210> SEQ ID NO 287
<211> LENGTH: 16
<212> TYPE: PRT
<213> ORGANISM: Oryctolagus cuniculus

<400> SEQUENCE: 287

Phe Ile Gly Arg Gly Gly Ala Thr Trp Tyr Ala Ser Trp Val Lys Gly
1               5                   10                  15

<210> SEQ ID NO 288
<211> LENGTH: 16
<212> TYPE: PRT
<213> ORGANISM: Oryctolagus cuniculus

<400> SEQUENCE: 288

Phe Ile Gly Arg Gly Gly Ser Thr Trp Tyr Ala Ser Trp Val Asn Gly
1               5                   10                  15

<210> SEQ ID NO 289
<211> LENGTH: 16
<212> TYPE: PRT
<213> ORGANISM: Oryctolagus cuniculus

<400> SEQUENCE: 289

Phe Ile Gly Arg Gly Gly Ser Thr Trp Tyr Ala Ser Trp Val Asn Gly
1               5                   10                  15

<210> SEQ ID NO 290
<211> LENGTH: 16
<212> TYPE: PRT
<213> ORGANISM: Oryctolagus cuniculus
```

<400> SEQUENCE: 290

Ile Ile Ser Ser Ser Gly Arg Thr Tyr Tyr Ala Asn Trp Ala Lys Gly
1               5                   10                  15

<210> SEQ ID NO 291
<211> LENGTH: 16
<212> TYPE: PRT
<213> ORGANISM: Oryctolagus cuniculus

<400> SEQUENCE: 291

Met Ile Tyr Gly Ser Gly Tyr Thr Tyr Tyr Ala Ser Trp Ala Lys Gly
1               5                   10                  15

<210> SEQ ID NO 292
<211> LENGTH: 17
<212> TYPE: PRT
<213> ORGANISM: Oryctolagus cuniculus

<400> SEQUENCE: 292

Asp Ile Tyr Ala Gly Ser Gly Ser Thr Trp Tyr Ala Ser Trp Val Lys
1               5                   10                  15

Gly

<210> SEQ ID NO 293
<211> LENGTH: 18
<212> TYPE: PRT
<213> ORGANISM: Oryctolagus cuniculus

<400> SEQUENCE: 293

Cys Ile Tyr Ala Gly Ser Gly Asp Val Thr Tyr Tyr Ala Asn Trp Val
1               5                   10                  15

Asn Gly

<210> SEQ ID NO 294
<211> LENGTH: 16
<212> TYPE: PRT
<213> ORGANISM: Oryctolagus cuniculus

<400> SEQUENCE: 294

Thr Ile Tyr Val Ser Gly Arg Val Tyr Tyr Ala Thr Trp Ala Lys Gly
1               5                   10                  15

<210> SEQ ID NO 295
<211> LENGTH: 17
<212> TYPE: PRT
<213> ORGANISM: Oryctolagus cuniculus

<400> SEQUENCE: 295

Cys Ile Tyr Thr Gly Ser Gly Gly Thr Tyr Tyr Ala Ser Trp Glu Lys
1               5                   10                  15

Gly

<210> SEQ ID NO 296
<211> LENGTH: 16
<212> TYPE: PRT
<213> ORGANISM: Oryctolagus cuniculus

<400> SEQUENCE: 296

Ile Ile Leu Ser Ser Gly Ser Thr Tyr Tyr Ala Thr Trp Ala Lys Gly
1               5                   10                  15

-continued

```
<210> SEQ ID NO 297
<211> LENGTH: 17
<212> TYPE: PRT
<213> ORGANISM: Oryctolagus cuniculus

<400> SEQUENCE: 297

Cys Ile Tyr Thr Gly Ser Gly Ser Thr Tyr Tyr Ala Asn Trp Ala Lys
1               5                   10                  15

Gly

<210> SEQ ID NO 298
<211> LENGTH: 16
<212> TYPE: PRT
<213> ORGANISM: Oryctolagus cuniculus

<400> SEQUENCE: 298

Gly Ile Ala Thr Asp Gly Asn Thr Tyr Tyr Ala Asn Trp Ala Lys Gly
1               5                   10                  15

<210> SEQ ID NO 299
<211> LENGTH: 16
<212> TYPE: PRT
<213> ORGANISM: Oryctolagus cuniculus

<400> SEQUENCE: 299

Val Ile Gly Ser Ser Gly Asn Leu Tyr Tyr Ala Ser Trp Ala Lys Gly
1               5                   10                  15

<210> SEQ ID NO 300
<211> LENGTH: 16
<212> TYPE: PRT
<213> ORGANISM: Oryctolagus cuniculus

<400> SEQUENCE: 300

Ile Ser Val Ser Asn Ile Arg Thr Trp Tyr Ala Thr Trp Ala Lys Gly
1               5                   10                  15

<210> SEQ ID NO 301
<211> LENGTH: 17
<212> TYPE: PRT
<213> ORGANISM: Oryctolagus cuniculus

<400> SEQUENCE: 301

Asp Ile Tyr Ala Gly Ser Val Asn Thr Trp Tyr Ala Thr Trp Ala Lys
1               5                   10                  15

Gly

<210> SEQ ID NO 302
<211> LENGTH: 16
<212> TYPE: PRT
<213> ORGANISM: Oryctolagus cuniculus

<400> SEQUENCE: 302

Tyr Ile Asn Ser Leu Gly Gly Ser Tyr Tyr Ala Ser Trp Ala Lys Gly
1               5                   10                  15

<210> SEQ ID NO 303
<211> LENGTH: 16
<212> TYPE: PRT
<213> ORGANISM: Oryctolagus cuniculus

<400> SEQUENCE: 303

Phe Ile Glu Pro Gly Gly Arg Ala Tyr Cys Ala Ser Trp Ala Lys Gly
1               5                   10                  15
```

<210> SEQ ID NO 304
<211> LENGTH: 18
<212> TYPE: PRT
<213> ORGANISM: Oryctolagus cuniculus

<400> SEQUENCE: 304

Cys Ile Tyr Thr Gly Asn Ser Asp Phe Thr Tyr Tyr Ala Asn Trp Ala
1               5                   10                  15

Lys Gly

<210> SEQ ID NO 305
<211> LENGTH: 18
<212> TYPE: PRT
<213> ORGANISM: Oryctolagus cuniculus

<400> SEQUENCE: 305

Cys Ile Asn Thr Gly Ser Gly Gly Ser Thr Tyr Tyr Ala Asn Trp Val
1               5                   10                  15

Lys Gly

<210> SEQ ID NO 306
<211> LENGTH: 18
<212> TYPE: PRT
<213> ORGANISM: Oryctolagus cuniculus

<400> SEQUENCE: 306

Cys Ile Tyr Ala Gly Ser Ser Asp Ser Thr Tyr Tyr Ala Ser Trp Val
1               5                   10                  15

Asn Gly

<210> SEQ ID NO 307
<211> LENGTH: 17
<212> TYPE: PRT
<213> ORGANISM: Oryctolagus cuniculus

<400> SEQUENCE: 307

Cys Ile Tyr Ala Gly Ser Ser Val Thr Tyr Tyr Ala Arg Trp Ala Lys
1               5                   10                  15

Gly

<210> SEQ ID NO 308
<211> LENGTH: 16
<212> TYPE: PRT
<213> ORGANISM: Oryctolagus cuniculus

<400> SEQUENCE: 308

Phe Ile Gly Arg Gly Gly Ser Thr Trp Tyr Ala Ser Trp Val Asn Gly
1               5                   10                  15

<210> SEQ ID NO 309
<211> LENGTH: 15
<212> TYPE: PRT
<213> ORGANISM: Oryctolagus cuniculus

<400> SEQUENCE: 309

Gly Gly Pro Gly Tyr Ser Thr Asn Thr His Tyr Ala Phe Asp Pro
1               5                   10                  15

<210> SEQ ID NO 310
<211> LENGTH: 9
<212> TYPE: PRT

```
<213> ORGANISM: Oryctolagus cuniculus

<400> SEQUENCE: 310

Tyr Pro Gly Gly Ser Tyr Tyr Asn Leu
1               5

<210> SEQ ID NO 311
<211> LENGTH: 11
<212> TYPE: PRT
<213> ORGANISM: Oryctolagus cuniculus

<400> SEQUENCE: 311

Ala Leu Gly Ser Ser Gly Tyr Arg Val Asn Leu
1               5                   10

<210> SEQ ID NO 312
<211> LENGTH: 12
<212> TYPE: PRT
<213> ORGANISM: Oryctolagus cuniculus

<400> SEQUENCE: 312

Leu Gln Gly Ala Asn Tyr Tyr Asn Ser Leu Ala Leu
1               5                   10

<210> SEQ ID NO 313
<211> LENGTH: 9
<212> TYPE: PRT
<213> ORGANISM: Oryctolagus cuniculus

<400> SEQUENCE: 313

Asp Gly Pro Ser Thr Leu Phe Asn Phe
1               5

<210> SEQ ID NO 314
<211> LENGTH: 11
<212> TYPE: PRT
<213> ORGANISM: Oryctolagus cuniculus

<400> SEQUENCE: 314

Asp Arg Gly Thr Ser Thr Gly Ser Leu Asp Leu
1               5                   10

<210> SEQ ID NO 315
<211> LENGTH: 17
<212> TYPE: PRT
<213> ORGANISM: Oryctolagus cuniculus

<400> SEQUENCE: 315

Thr His Tyr Ala Ala Val Ala Gly Tyr Gly Tyr Ala Ser Arg Leu Asp
1               5                   10                  15

Leu

<210> SEQ ID NO 316
<211> LENGTH: 11
<212> TYPE: PRT
<213> ORGANISM: Oryctolagus cuniculus

<400> SEQUENCE: 316

Val Asp Ala Ser Ser Ser Gly Ser Trp Asp Leu
1               5                   10

<210> SEQ ID NO 317
<211> LENGTH: 14
<212> TYPE: PRT
```

<213> ORGANISM: Oryctolagus cuniculus

<400> SEQUENCE: 317

Gly Cys Pro Gly Tyr Asn Gly Asp Lys Tyr Thr Phe Asp Leu
1               5                   10

<210> SEQ ID NO 318
<211> LENGTH: 15
<212> TYPE: PRT
<213> ORGANISM: Oryctolagus cuniculus

<400> SEQUENCE: 318

Gly Gly Pro Ala Tyr Ser Thr Asn Thr His Tyr Thr Leu Asp Leu
1               5                   10                  15

<210> SEQ ID NO 319
<211> LENGTH: 13
<212> TYPE: PRT
<213> ORGANISM: Oryctolagus cuniculus

<400> SEQUENCE: 319

Glu Ile Asp Ala Gly Tyr Val Gly Tyr Gly Phe Asn Leu
1               5                   10

<210> SEQ ID NO 320
<211> LENGTH: 12
<212> TYPE: PRT
<213> ORGANISM: Oryctolagus cuniculus

<400> SEQUENCE: 320

Val Asp Pro Gly Tyr Ser Phe Asp Ala Phe Asp Pro
1               5                   10

<210> SEQ ID NO 321
<211> LENGTH: 13
<212> TYPE: PRT
<213> ORGANISM: Oryctolagus cuniculus

<400> SEQUENCE: 321

Glu Ile Asp Ala Gly Tyr Val Gly Tyr Gly Phe Asp Leu
1               5                   10

<210> SEQ ID NO 322
<211> LENGTH: 15
<212> TYPE: PRT
<213> ORGANISM: Oryctolagus cuniculus

<400> SEQUENCE: 322

Asp Arg Gly Tyr Asp Asp Tyr Gly Asp Ile Thr Arg Leu Asp Leu
1               5                   10                  15

<210> SEQ ID NO 323
<211> LENGTH: 9
<212> TYPE: PRT
<213> ORGANISM: Oryctolagus cuniculus

<400> SEQUENCE: 323

Glu Thr Asp Gly Asn Tyr Phe Asn Leu
1               5

<210> SEQ ID NO 324
<211> LENGTH: 11
<212> TYPE: PRT
<213> ORGANISM: Oryctolagus cuniculus

<400> SEQUENCE: 324

Asp Gly Gly Ser Pro Asn Trp Thr Leu Asp Leu
1               5                   10

<210> SEQ ID NO 325
<211> LENGTH: 8
<212> TYPE: PRT
<213> ORGANISM: Oryctolagus cuniculus

<400> SEQUENCE: 325

Trp Gly Pro Gly Ala Leu Asp Leu
1               5

<210> SEQ ID NO 326
<211> LENGTH: 11
<212> TYPE: PRT
<213> ORGANISM: Oryctolagus cuniculus

<400> SEQUENCE: 326

Ser Thr Gly Ser Val Gly Arg Gly Phe Asn Leu
1               5                   10

<210> SEQ ID NO 327
<211> LENGTH: 11
<212> TYPE: PRT
<213> ORGANISM: Oryctolagus cuniculus

<400> SEQUENCE: 327

Val Asp Gly Ser Ser Ser Gly Ser Trp Asp Leu
1               5                   10

<210> SEQ ID NO 328
<211> LENGTH: 10
<212> TYPE: PRT
<213> ORGANISM: Oryctolagus cuniculus

<400> SEQUENCE: 328

Asp Leu Val Val Val Thr Ser Phe Asn Leu
1               5                   10

<210> SEQ ID NO 329
<211> LENGTH: 11
<212> TYPE: PRT
<213> ORGANISM: Oryctolagus cuniculus

<400> SEQUENCE: 329

Asp Ile Tyr Ala Ser Thr Ser Gly Tyr Asp Leu
1               5                   10

<210> SEQ ID NO 330
<211> LENGTH: 9
<212> TYPE: PRT
<213> ORGANISM: Oryctolagus cuniculus

<400> SEQUENCE: 330

Gly Val Gly Phe Gly Tyr Phe Asn Leu
1               5

<210> SEQ ID NO 331
<211> LENGTH: 14
<212> TYPE: PRT
<213> ORGANISM: Oryctolagus cuniculus

<400> SEQUENCE: 331

Gly Cys Pro Gly Tyr Asn Gly Asp Lys Tyr Ala Leu Asp Leu
1               5                   10

<210> SEQ ID NO 332
<211> LENGTH: 15
<212> TYPE: PRT
<213> ORGANISM: Oryctolagus cuniculus

<400> SEQUENCE: 332

Gly Gly Pro Gly Tyr Ser Phe Asp Thr Glu Tyr Ala Phe Asp Pro
1               5                   10                  15

<210> SEQ ID NO 333
<211> LENGTH: 15
<212> TYPE: PRT
<213> ORGANISM: Oryctolagus cuniculus

<400> SEQUENCE: 333

Asp Gly Ser Gly Ser Gly Thr Tyr Gly Tyr Asn Gly Met Asp Leu
1               5                   10                  15

<210> SEQ ID NO 334
<211> LENGTH: 10
<212> TYPE: PRT
<213> ORGANISM: Oryctolagus cuniculus

<400> SEQUENCE: 334

Asp Leu Asn Tyr Pro Asp Thr Ser Asn Leu
1               5                   10

<210> SEQ ID NO 335
<211> LENGTH: 13
<212> TYPE: PRT
<213> ORGANISM: Oryctolagus cuniculus

<400> SEQUENCE: 335

Glu Ile Asp Ala Gly Tyr Val Gly Tyr Gly Phe Asn Leu
1               5                   10

<210> SEQ ID NO 336
<211> LENGTH: 11
<212> TYPE: PRT
<213> ORGANISM: Oryctolagus cuniculus

<400> SEQUENCE: 336

Asp Tyr Gly Gly Ser Gly Tyr Asn Phe Asn Leu
1               5                   10

<210> SEQ ID NO 337
<211> LENGTH: 15
<212> TYPE: PRT
<213> ORGANISM: Oryctolagus cuniculus

<400> SEQUENCE: 337

Gly Gly Pro Ala Tyr Ser Arg Gly Thr His Tyr Ala Met Asp Leu
1               5                   10                  15

<210> SEQ ID NO 338
<211> LENGTH: 15
<212> TYPE: PRT
<213> ORGANISM: Oryctolagus cuniculus

<400> SEQUENCE: 338

Asp Gly Ser Gly Ser Gly Thr Tyr Gly Tyr Asn Gly Met Asp Leu
1               5                   10                  15

<210> SEQ ID NO 339
<211> LENGTH: 12
<212> TYPE: PRT
<213> ORGANISM: Oryctolagus cuniculus

<400> SEQUENCE: 339

Ser Ala Tyr Ser Asn Asn Gly Asp Arg Leu His Leu
1               5                   10

<210> SEQ ID NO 340
<211> LENGTH: 13
<212> TYPE: PRT
<213> ORGANISM: Oryctolagus cuniculus

<400> SEQUENCE: 340

Asp Gly Ala Thr Ser Thr Ser Gly His Leu Phe Glu Leu
1               5                   10

<210> SEQ ID NO 341
<211> LENGTH: 11
<212> TYPE: PRT
<213> ORGANISM: Oryctolagus cuniculus

<400> SEQUENCE: 341

Asp Ile Tyr Gly Ser Thr Asn Gly Tyr Asp Leu
1               5                   10

<210> SEQ ID NO 342
<211> LENGTH: 15
<212> TYPE: PRT
<213> ORGANISM: Oryctolagus cuniculus

<400> SEQUENCE: 342

Asp Gly Ser Gly Ser Gly Thr Tyr Gly Tyr Asn Gly Met Asp Leu
1               5                   10                  15

<210> SEQ ID NO 343
<211> LENGTH: 12
<212> TYPE: PRT
<213> ORGANISM: Oryctolagus cuniculus

<400> SEQUENCE: 343

Asp Arg Tyr Ala Thr Val Ser Gly Ile Leu Asn Leu
1               5                   10

<210> SEQ ID NO 344
<211> LENGTH: 11
<212> TYPE: PRT
<213> ORGANISM: Oryctolagus cuniculus

<400> SEQUENCE: 344

Ala Val Pro Asp Asp Ser Ala Gly Lys Lys Leu
1               5                   10

<210> SEQ ID NO 345
<211> LENGTH: 10
<212> TYPE: PRT
<213> ORGANISM: Oryctolagus cuniculus

<400> SEQUENCE: 345

Asp Ala Asn Ser His Tyr Met Met Asn Leu
1               5                   10

```
<210> SEQ ID NO 346
<211> LENGTH: 10
<212> TYPE: PRT
<213> ORGANISM: Oryctolagus cuniculus

<400> SEQUENCE: 346

Asp Leu Leu Val Val Thr Ser Phe Asn Leu
1               5                   10

<210> SEQ ID NO 347
<211> LENGTH: 13
<212> TYPE: PRT
<213> ORGANISM: Oryctolagus cuniculus

<400> SEQUENCE: 347

Glu Ile Asp Ala Gly Tyr Val Gly Tyr Gly Phe Asn Leu
1               5                   10

<210> SEQ ID NO 348
<211> LENGTH: 12
<212> TYPE: PRT
<213> ORGANISM: Oryctolagus cuniculus

<400> SEQUENCE: 348

Asp Arg Tyr Ala Asn Thr His Gly Ile Phe Ser Leu
1               5                   10

<210> SEQ ID NO 349
<211> LENGTH: 12
<212> TYPE: PRT
<213> ORGANISM: Oryctolagus cuniculus

<400> SEQUENCE: 349

Ser Ile Val Asp Phe Ser Ser Gly Trp Gly Asp Leu
1               5                   10

<210> SEQ ID NO 350
<211> LENGTH: 11
<212> TYPE: PRT
<213> ORGANISM: Oryctolagus cuniculus

<400> SEQUENCE: 350

Asp Phe Gly Pro Pro Asn Trp Thr Leu Asp Leu
1               5                   10

<210> SEQ ID NO 351
<211> LENGTH: 11
<212> TYPE: PRT
<213> ORGANISM: Oryctolagus cuniculus

<400> SEQUENCE: 351

Pro Gly Tyr Gly Gly Tyr Gly Tyr Tyr Gly Leu
1               5                   10

<210> SEQ ID NO 352
<211> LENGTH: 9
<212> TYPE: PRT
<213> ORGANISM: Oryctolagus cuniculus

<400> SEQUENCE: 352

His Ala Ala Trp Phe Glu Leu Asp Leu
1               5

<210> SEQ ID NO 353
<211> LENGTH: 13
```

```
<212> TYPE: PRT
<213> ORGANISM: Oryctolagus cuniculus

<400> SEQUENCE: 353

Asp Pro Val Thr Ser Gly Ser Asp Tyr Val Tyr Asp Leu
1               5                   10

<210> SEQ ID NO 354
<211> LENGTH: 11
<212> TYPE: PRT
<213> ORGANISM: Oryctolagus cuniculus

<400> SEQUENCE: 354

Lys Asp Gly Ser Gly Asn Glu His Tyr Asn Leu
1               5                   10

<210> SEQ ID NO 355
<211> LENGTH: 15
<212> TYPE: PRT
<213> ORGANISM: Oryctolagus cuniculus

<400> SEQUENCE: 355

Ser Asp Gly Tyr Thr Asn Gly Asp Tyr Asp Thr Tyr Phe Asn Leu
1               5                   10                  15

<210> SEQ ID NO 356
<211> LENGTH: 15
<212> TYPE: PRT
<213> ORGANISM: Oryctolagus cuniculus

<400> SEQUENCE: 356

Ala Asp Gly Tyr Thr Glu Gly Asp Tyr Ala Thr Tyr Phe Asn Leu
1               5                   10                  15

<210> SEQ ID NO 357
<211> LENGTH: 13
<212> TYPE: PRT
<213> ORGANISM: Oryctolagus cuniculus

<400> SEQUENCE: 357

Asn Tyr Tyr Ala Gly Leu Ser Asp Val Phe Phe Gly Trp
1               5                   10

<210> SEQ ID NO 358
<211> LENGTH: 6
<212> TYPE: PRT
<213> ORGANISM: Oryctolagus cuniculus

<400> SEQUENCE: 358

Gly Leu Pro Ser Asp Leu
1               5

<210> SEQ ID NO 359
<211> LENGTH: 10
<212> TYPE: PRT
<213> ORGANISM: Oryctolagus cuniculus

<400> SEQUENCE: 359

Tyr Ile Gly Ala Trp Gly Pro Trp Ser Leu
1               5                   10

<210> SEQ ID NO 360
<211> LENGTH: 10
<212> TYPE: PRT
<213> ORGANISM: Oryctolagus cuniculus
```

```
<400> SEQUENCE: 360

Asp Leu Leu Val Val Thr Ser Phe Asn Leu
1               5                   10

<210> SEQ ID NO 361
<211> LENGTH: 14
<212> TYPE: PRT
<213> ORGANISM: Oryctolagus cuniculus

<400> SEQUENCE: 361

Gly Ser Tyr Asp Asp Tyr Gly Asp Tyr Trp Tyr Phe Thr Leu
1               5                   10

<210> SEQ ID NO 362
<211> LENGTH: 9
<212> TYPE: PRT
<213> ORGANISM: Oryctolagus cuniculus

<400> SEQUENCE: 362

Gly Asp Tyr Ile Met Thr Leu Asp Leu
1               5

<210> SEQ ID NO 363
<211> LENGTH: 6
<212> TYPE: PRT
<213> ORGANISM: Oryctolagus cuniculus

<400> SEQUENCE: 363

Gly Leu Pro Ser Asp Leu
1               5

<210> SEQ ID NO 364
<211> LENGTH: 12
<212> TYPE: PRT
<213> ORGANISM: Oryctolagus cuniculus

<400> SEQUENCE: 364

Asp Gly Asp Ser Ser Asp Tyr Tyr Ala Phe Asn Leu
1               5                   10

<210> SEQ ID NO 365
<211> LENGTH: 12
<212> TYPE: PRT
<213> ORGANISM: Oryctolagus cuniculus

<400> SEQUENCE: 365

Asp Gly Asp Tyr Ser Asp Tyr Tyr Thr Phe Asp Leu
1               5                   10

<210> SEQ ID NO 366
<211> LENGTH: 12
<212> TYPE: PRT
<213> ORGANISM: Oryctolagus cuniculus

<400> SEQUENCE: 366

Asp Gly Asp Phe Ser Asp Tyr Tyr Thr Phe Asn Leu
1               5                   10

<210> SEQ ID NO 367
<211> LENGTH: 14
<212> TYPE: PRT
<213> ORGANISM: Oryctolagus cuniculus

<400> SEQUENCE: 367
```

```
Leu Ile Thr Val Asp Tyr Tyr Ile Tyr Asp Tyr Phe Asn Leu
1               5                   10

<210> SEQ ID NO 368
<211> LENGTH: 7
<212> TYPE: PRT
<213> ORGANISM: Oryctolagus cuniculus

<400> SEQUENCE: 368

Asp Pro Gln Tyr Phe Ile Leu
1               5

<210> SEQ ID NO 369
<211> LENGTH: 13
<212> TYPE: PRT
<213> ORGANISM: Oryctolagus cuniculus

<400> SEQUENCE: 369

Glu Ile Asp Ala Gly Tyr Val Gly Tyr Gly Phe Asn Leu
1               5                   10

<210> SEQ ID NO 370
<211> LENGTH: 9
<212> TYPE: PRT
<213> ORGANISM: Oryctolagus cuniculus

<400> SEQUENCE: 370

Gly Val Gly Phe Gly Tyr Phe Asn Leu
1               5

<210> SEQ ID NO 371
<211> LENGTH: 7
<212> TYPE: PRT
<213> ORGANISM: Oryctolagus cuniculus

<400> SEQUENCE: 371

Gly Ser Ile Asp Tyr Asp Pro
1               5

<210> SEQ ID NO 372
<211> LENGTH: 8
<212> TYPE: PRT
<213> ORGANISM: Oryctolagus cuniculus

<400> SEQUENCE: 372

Asp Pro Gly Tyr Ser Ser Trp Leu
1               5

<210> SEQ ID NO 373
<211> LENGTH: 15
<212> TYPE: PRT
<213> ORGANISM: Oryctolagus cuniculus

<400> SEQUENCE: 373

Gly Gly Pro Gly Tyr Ser Ile Asp Thr Lys Tyr Ala Phe Asp Pro
1               5                   10                  15

<210> SEQ ID NO 374
<211> LENGTH: 10
<212> TYPE: PRT
<213> ORGANISM: Oryctolagus cuniculus

<400> SEQUENCE: 374

Asn Ser Asn Asp Trp Met Tyr Phe Asn Leu
```

<210> SEQ ID NO 375
<211> LENGTH: 15
<212> TYPE: PRT
<213> ORGANISM: Oryctolagus cuniculus

<400> SEQUENCE: 375

Gly Gly Pro Ala Tyr Ser Arg Gly Thr His Tyr Ala Met Asp Leu
1               5                   10                  15

<210> SEQ ID NO 376
<211> LENGTH: 12
<212> TYPE: PRT
<213> ORGANISM: Oryctolagus cuniculus

<400> SEQUENCE: 376

Tyr Thr Ile Asp Ser Gly Ile Tyr Thr Tyr Asp Leu
1               5                   10

<210> SEQ ID NO 377
<211> LENGTH: 12
<212> TYPE: PRT
<213> ORGANISM: Oryctolagus cuniculus

<400> SEQUENCE: 377

His Val Ser Arg Ser Gly Asn Tyr Gly Leu Asp Leu
1               5                   10

<210> SEQ ID NO 378
<211> LENGTH: 13
<212> TYPE: PRT
<213> ORGANISM: Oryctolagus cuniculus

<400> SEQUENCE: 378

Glu Ile Asp Ala Gly Tyr Val Gly Tyr Gly Phe Asn Leu
1               5                   10

<210> SEQ ID NO 379
<211> LENGTH: 7
<212> TYPE: PRT
<213> ORGANISM: Oryctolagus cuniculus

<400> SEQUENCE: 379

Asp Phe Ala Gly Ser Asp Leu
1               5

<210> SEQ ID NO 380
<211> LENGTH: 14
<212> TYPE: PRT
<213> ORGANISM: Oryctolagus cuniculus

<400> SEQUENCE: 380

Ser Tyr Val Phe Tyr Ser Thr Tyr Pro Tyr Ala Ser Asp Leu
1               5                   10

<210> SEQ ID NO 381
<211> LENGTH: 10
<212> TYPE: PRT
<213> ORGANISM: Oryctolagus cuniculus

<400> SEQUENCE: 381

Phe Arg Asp Asp Tyr Ala Ser Leu Lys Leu
1               5                   10

<210> SEQ ID NO 382
<211> LENGTH: 8
<212> TYPE: PRT
<213> ORGANISM: Oryctolagus cuniculus

<400> SEQUENCE: 382

Gly Asp Asp Ser Tyr Tyr Glu Leu
1               5

<210> SEQ ID NO 383
<211> LENGTH: 12
<212> TYPE: PRT
<213> ORGANISM: Oryctolagus cuniculus

<400> SEQUENCE: 383

Ala Ile Ala Asp Phe Ser Ser Gly Trp Gly Asp Leu
1               5                   10

<210> SEQ ID NO 384
<211> LENGTH: 3
<212> TYPE: PRT
<213> ORGANISM: Oryctolagus cuniculus

<400> SEQUENCE: 384

Gly Gly Leu
1

<210> SEQ ID NO 385
<211> LENGTH: 12
<212> TYPE: PRT
<213> ORGANISM: Oryctolagus cuniculus

<400> SEQUENCE: 385

Asp Gly Asp Tyr Ser Asp Tyr Tyr Thr Phe Asp Leu
1               5                   10

<210> SEQ ID NO 386
<211> LENGTH: 11
<212> TYPE: PRT
<213> ORGANISM: Oryctolagus cuniculus

<400> SEQUENCE: 386

Gln Ala Ser Gln Ser Ile Tyr Ile Tyr Leu Ser
1               5                   10

<210> SEQ ID NO 387
<211> LENGTH: 11
<212> TYPE: PRT
<213> ORGANISM: Oryctolagus cuniculus

<400> SEQUENCE: 387

Gln Ala Ser Gln Thr Ile Ser Ile Asn Leu Ala
1               5                   10

<210> SEQ ID NO 388
<211> LENGTH: 11
<212> TYPE: PRT
<213> ORGANISM: Oryctolagus cuniculus

<400> SEQUENCE: 388

Gln Ala Ser Glu Asn Ile Tyr Ser Ser Leu Ala
1               5                   10

<210> SEQ ID NO 389

```
<211> LENGTH: 11
<212> TYPE: PRT
<213> ORGANISM: Oryctolagus cuniculus

<400> SEQUENCE: 389

Gln Ala Ser Gln Ser Ile Tyr Ser Phe Leu Ser
1               5                   10

<210> SEQ ID NO 390
<211> LENGTH: 11
<212> TYPE: PRT
<213> ORGANISM: Oryctolagus cuniculus

<400> SEQUENCE: 390

Gln Ala Ser Glu Asp Ile Tyr Ser Asn Leu Ala
1               5                   10

<210> SEQ ID NO 391
<211> LENGTH: 11
<212> TYPE: PRT
<213> ORGANISM: Oryctolagus cuniculus

<400> SEQUENCE: 391

Gln Ala Ser Glu Asn Ile Gly Asn Gly Leu Ala
1               5                   10

<210> SEQ ID NO 392
<211> LENGTH: 11
<212> TYPE: PRT
<213> ORGANISM: Oryctolagus cuniculus

<400> SEQUENCE: 392

Leu Ala Ser Glu Asp Ile Tyr Ser Gly Ile Ser
1               5                   10

<210> SEQ ID NO 393
<211> LENGTH: 11
<212> TYPE: PRT
<213> ORGANISM: Oryctolagus cuniculus

<400> SEQUENCE: 393

Gln Ala Ser Glu Ser Ile Tyr Ser Asn Leu Ala
1               5                   10

<210> SEQ ID NO 394
<211> LENGTH: 11
<212> TYPE: PRT
<213> ORGANISM: Oryctolagus cuniculus

<400> SEQUENCE: 394

Gln Ala Ser Gln Ser Ile Tyr Asn Tyr Leu Ser
1               5                   10

<210> SEQ ID NO 395
<211> LENGTH: 11
<212> TYPE: PRT
<213> ORGANISM: Oryctolagus cuniculus

<400> SEQUENCE: 395

Gln Ala Ser Gln Ser Ile Tyr Asn Tyr Leu Ser
1               5                   10

<210> SEQ ID NO 396
<211> LENGTH: 12
<212> TYPE: PRT
```

```
<213> ORGANISM: Oryctolagus cuniculus

<400> SEQUENCE: 396

Gln Ser Ser Gln Ser Val Tyr Ser Asp Tyr Leu Ala
1               5                   10

<210> SEQ ID NO 397
<211> LENGTH: 11
<212> TYPE: PRT
<213> ORGANISM: Oryctolagus cuniculus

<400> SEQUENCE: 397

Gln Ala Ser Glu Asp Ile Tyr Ser Asn Leu Ala
1               5                   10

<210> SEQ ID NO 398
<211> LENGTH: 12
<212> TYPE: PRT
<213> ORGANISM: Oryctolagus cuniculus

<400> SEQUENCE: 398

Gln Ser Ser Gln Ser Val Tyr Ser Asp Tyr Leu Ala
1               5                   10

<210> SEQ ID NO 399
<211> LENGTH: 11
<212> TYPE: PRT
<213> ORGANISM: Oryctolagus cuniculus

<400> SEQUENCE: 399

Gln Ala Ser Glu Asp Ile Tyr Ser Asn Leu Ala
1               5                   10

<210> SEQ ID NO 400
<211> LENGTH: 11
<212> TYPE: PRT
<213> ORGANISM: Oryctolagus cuniculus

<400> SEQUENCE: 400

Gln Ala Ser Glu Asp Ile Tyr Ser Asn Leu Ala
1               5                   10

<210> SEQ ID NO 401
<211> LENGTH: 11
<212> TYPE: PRT
<213> ORGANISM: Oryctolagus cuniculus

<400> SEQUENCE: 401

Gln Ala Ser Glu Ser Ile Ser Asp Tyr Leu Ser
1               5                   10

<210> SEQ ID NO 402
<211> LENGTH: 13
<212> TYPE: PRT
<213> ORGANISM: Oryctolagus cuniculus

<400> SEQUENCE: 402

Gln Ser Ser Gln Ser Val Tyr Asn Asn Asn Tyr Leu Ser
1               5                   10

<210> SEQ ID NO 403
<211> LENGTH: 13
<212> TYPE: PRT
<213> ORGANISM: Oryctolagus cuniculus
```

<400> SEQUENCE: 403

Gln Ala Ser Gln Ser Val Tyr Asn Ser Asn His Leu Ser
1               5                   10

<210> SEQ ID NO 404
<211> LENGTH: 11
<212> TYPE: PRT
<213> ORGANISM: Oryctolagus cuniculus

<400> SEQUENCE: 404

Gln Ala Ser Gln Asn Ile Tyr Ser Asn Leu Ala
1               5                   10

<210> SEQ ID NO 405
<211> LENGTH: 11
<212> TYPE: PRT
<213> ORGANISM: Oryctolagus cuniculus

<400> SEQUENCE: 405

Gln Ala Ser Glu Asp Ile Tyr Ser Asn Leu Ala
1               5                   10

<210> SEQ ID NO 406
<211> LENGTH: 11
<212> TYPE: PRT
<213> ORGANISM: Oryctolagus cuniculus

<400> SEQUENCE: 406

Gln Ala Ser Glu Asp Ile Tyr Ser Asn Leu Ala
1               5                   10

<210> SEQ ID NO 407
<211> LENGTH: 11
<212> TYPE: PRT
<213> ORGANISM: Oryctolagus cuniculus

<400> SEQUENCE: 407

Gln Ala Ser Glu Asp Ile Tyr Ser Asn Leu Ala
1               5                   10

<210> SEQ ID NO 408
<211> LENGTH: 11
<212> TYPE: PRT
<213> ORGANISM: Oryctolagus cuniculus

<400> SEQUENCE: 408

Gln Ala Ser Gln Ser Ile His Asn Tyr Leu Ser
1               5                   10

<210> SEQ ID NO 409
<211> LENGTH: 11
<212> TYPE: PRT
<213> ORGANISM: Oryctolagus cuniculus

<400> SEQUENCE: 409

Gln Ala Ser Gln Ser Ile Gly Ser Trp Leu Ser
1               5                   10

<210> SEQ ID NO 410
<211> LENGTH: 11
<212> TYPE: PRT
<213> ORGANISM: Oryctolagus cuniculus

<400> SEQUENCE: 410

Gln Ala Ser Gln Ser Ile Ser Asn Trp Leu Ala
1               5                   10

<210> SEQ ID NO 411
<211> LENGTH: 11
<212> TYPE: PRT
<213> ORGANISM: Oryctolagus cuniculus

<400> SEQUENCE: 411

Gln Ala Ser Gln Ser Ile Gly Tyr Tyr Leu Ala
1               5                   10

<210> SEQ ID NO 412
<211> LENGTH: 12
<212> TYPE: PRT
<213> ORGANISM: Oryctolagus cuniculus

<400> SEQUENCE: 412

Gln Ser Ser Gln Ser Val Tyr Ser Asp Tyr Leu Gly
1               5                   10

<210> SEQ ID NO 413
<211> LENGTH: 11
<212> TYPE: PRT
<213> ORGANISM: Oryctolagus cuniculus

<400> SEQUENCE: 413

Gln Ala Ser Glu Asp Ile Tyr Ser Asn Leu Ala
1               5                   10

<210> SEQ ID NO 414
<211> LENGTH: 11
<212> TYPE: PRT
<213> ORGANISM: Oryctolagus cuniculus

<400> SEQUENCE: 414

Gln Ala Ser Gln Ser Ile Tyr Ile Tyr Leu Ala
1               5                   10

<210> SEQ ID NO 415
<211> LENGTH: 11
<212> TYPE: PRT
<213> ORGANISM: Oryctolagus cuniculus

<400> SEQUENCE: 415

Gln Ala Ser Gln Ser Ile Ser Asn Trp Leu Ala
1               5                   10

<210> SEQ ID NO 416
<211> LENGTH: 11
<212> TYPE: PRT
<213> ORGANISM: Oryctolagus cuniculus

<400> SEQUENCE: 416

Gln Ala Ser Glu Asp Ile Tyr Ser Asn Leu Ala
1               5                   10

<210> SEQ ID NO 417
<211> LENGTH: 11
<212> TYPE: PRT
<213> ORGANISM: Oryctolagus cuniculus

<400> SEQUENCE: 417

Gln Ala Ser Glu Asp Ile Tyr Ser Asn Leu Ala
1               5                   10

<210> SEQ ID NO 418
<211> LENGTH: 11
<212> TYPE: PRT
<213> ORGANISM: Oryctolagus cuniculus

<400> SEQUENCE: 418

Gln Ala Ser Glu Asp Ile Tyr Ser Asn Leu Ala
1               5                   10

<210> SEQ ID NO 419
<211> LENGTH: 11
<212> TYPE: PRT
<213> ORGANISM: Oryctolagus cuniculus

<400> SEQUENCE: 419

Gln Ala Ser Gln Ser Ile Ser Asn Trp Leu Ala
1               5                   10

<210> SEQ ID NO 420
<211> LENGTH: 11
<212> TYPE: PRT
<213> ORGANISM: Oryctolagus cuniculus

<400> SEQUENCE: 420

Gln Ala Ser Gln Asn Ile Tyr Ser Asn Cys Ala
1               5                   10

<210> SEQ ID NO 421
<211> LENGTH: 11
<212> TYPE: PRT
<213> ORGANISM: Oryctolagus cuniculus

<400> SEQUENCE: 421

Gln Ala Ser Glu Asn Ile Tyr Ser Ser Leu Ala
1               5                   10

<210> SEQ ID NO 422
<211> LENGTH: 11
<212> TYPE: PRT
<213> ORGANISM: Oryctolagus cuniculus

<400> SEQUENCE: 422

Gln Ala Ser Glu Asp Ile Tyr Ser Asn Leu Ala
1               5                   10

<210> SEQ ID NO 423
<211> LENGTH: 11
<212> TYPE: PRT
<213> ORGANISM: Oryctolagus cuniculus

<400> SEQUENCE: 423

Gln Ala Ser Glu Asp Ile Tyr Ser Asn Leu Ala
1               5                   10

<210> SEQ ID NO 424
<211> LENGTH: 12
<212> TYPE: PRT
<213> ORGANISM: Oryctolagus cuniculus

<400> SEQUENCE: 424

Gln Ser Ser Gln Ser Val Tyr Ser Asp Tyr Leu Val
1               5                   10

```
<210> SEQ ID NO 425
<211> LENGTH: 11
<212> TYPE: PRT
<213> ORGANISM: Oryctolagus cuniculus

<400> SEQUENCE: 425

Gln Ala Ser Glu Ser Ile Tyr Ser Asp Leu Ala
1               5                   10

<210> SEQ ID NO 426
<211> LENGTH: 11
<212> TYPE: PRT
<213> ORGANISM: Oryctolagus cuniculus

<400> SEQUENCE: 426

Gln Ala Ser Glu Asp Ile Tyr Ser Asn Leu Ala
1               5                   10

<210> SEQ ID NO 427
<211> LENGTH: 11
<212> TYPE: PRT
<213> ORGANISM: Oryctolagus cuniculus

<400> SEQUENCE: 427

Gln Ala Ser Gln Ser Ile Ser Ser Tyr Cys Ser
1               5                   10

<210> SEQ ID NO 428
<211> LENGTH: 11
<212> TYPE: PRT
<213> ORGANISM: Oryctolagus cuniculus

<400> SEQUENCE: 428

Gln Ala Ser Glu Asp Ile Tyr Ser Asn Leu Ala
1               5                   10

<210> SEQ ID NO 429
<211> LENGTH: 12
<212> TYPE: PRT
<213> ORGANISM: Oryctolagus cuniculus

<400> SEQUENCE: 429

Gln Ala Ser Gln Asn Ile Ala Ser Ala Tyr Leu Ser
1               5                   10

<210> SEQ ID NO 430
<211> LENGTH: 11
<212> TYPE: PRT
<213> ORGANISM: Oryctolagus cuniculus

<400> SEQUENCE: 430

Gln Ala Ser Glu Ser Ile Ser Thr Trp Leu Ala
1               5                   10

<210> SEQ ID NO 431
<211> LENGTH: 11
<212> TYPE: PRT
<213> ORGANISM: Oryctolagus cuniculus

<400> SEQUENCE: 431

Gln Ala Ser Gln Ser Ile Ser Ser Tyr Leu Ala
1               5                   10

<210> SEQ ID NO 432
<211> LENGTH: 11
```

```
<212> TYPE: PRT
<213> ORGANISM: Oryctolagus cuniculus

<400> SEQUENCE: 432

Gln Ala Ser Gln Ser Ile Ser Ser Trp Leu Ser
1               5                   10

<210> SEQ ID NO 433
<211> LENGTH: 11
<212> TYPE: PRT
<213> ORGANISM: Oryctolagus cuniculus

<400> SEQUENCE: 433

Gln Ala Ser Gln Ser Ile Thr Thr Trp Leu Ala
1               5                   10

<210> SEQ ID NO 434
<211> LENGTH: 11
<212> TYPE: PRT
<213> ORGANISM: Oryctolagus cuniculus

<400> SEQUENCE: 434

Gln Ala Ser Glu Thr Ile Tyr Ser Gly Leu Ala
1               5                   10

<210> SEQ ID NO 435
<211> LENGTH: 11
<212> TYPE: PRT
<213> ORGANISM: Oryctolagus cuniculus

<400> SEQUENCE: 435

Gln Ala Ser Gln Ser Ile Asn Ser Arg Leu Ala
1               5                   10

<210> SEQ ID NO 436
<211> LENGTH: 12
<212> TYPE: PRT
<213> ORGANISM: Oryctolagus cuniculus

<400> SEQUENCE: 436

Gln Ser Ser Pro Ser Val Tyr Asn Asn Tyr Leu Ser
1               5                   10

<210> SEQ ID NO 437
<211> LENGTH: 11
<212> TYPE: PRT
<213> ORGANISM: Oryctolagus cuniculus

<400> SEQUENCE: 437

Gln Ala Ser Glu Asp Ile Tyr Ser Asn Leu Ala
1               5                   10

<210> SEQ ID NO 438
<211> LENGTH: 11
<212> TYPE: PRT
<213> ORGANISM: Oryctolagus cuniculus

<400> SEQUENCE: 438

Gln Ala Ser Glu Asn Ile Tyr Asn Phe Leu Ala
1               5                   10

<210> SEQ ID NO 439
<211> LENGTH: 13
<212> TYPE: PRT
<213> ORGANISM: Oryctolagus cuniculus
```

<400> SEQUENCE: 439

Gln Ala Ser Gln Ser Val Tyr Lys Asn Asn Arg Leu Ala
1               5                   10

<210> SEQ ID NO 440
<211> LENGTH: 11
<212> TYPE: PRT
<213> ORGANISM: Oryctolagus cuniculus

<400> SEQUENCE: 440

Gln Ala Ser Gln Ser Ile Asn Ser Arg Leu Ala
1               5                   10

<210> SEQ ID NO 441
<211> LENGTH: 11
<212> TYPE: PRT
<213> ORGANISM: Oryctolagus cuniculus

<400> SEQUENCE: 441

Gln Ala Ser Gln Asn Ile Gly Ser Asn Leu Ala
1               5                   10

<210> SEQ ID NO 442
<211> LENGTH: 11
<212> TYPE: PRT
<213> ORGANISM: Oryctolagus cuniculus

<400> SEQUENCE: 442

Gln Ala Ser Gln Ser Ile Gly Ser Asn Leu Ala
1               5                   10

<210> SEQ ID NO 443
<211> LENGTH: 11
<212> TYPE: PRT
<213> ORGANISM: Oryctolagus cuniculus

<400> SEQUENCE: 443

Gln Ala Ser Gln Asn Ile Gly Ser Asn Leu Ala
1               5                   10

<210> SEQ ID NO 444
<211> LENGTH: 11
<212> TYPE: PRT
<213> ORGANISM: Oryctolagus cuniculus

<400> SEQUENCE: 444

Gln Ala Ser Gln Ser Ile Ser Ser Tyr Leu Ser
1               5                   10

<210> SEQ ID NO 445
<211> LENGTH: 13
<212> TYPE: PRT
<213> ORGANISM: Oryctolagus cuniculus

<400> SEQUENCE: 445

Gln Ser Ser Gln Ser Val Asp Gly Asn Asn Leu Leu Ser
1               5                   10

<210> SEQ ID NO 446
<211> LENGTH: 12
<212> TYPE: PRT
<213> ORGANISM: Oryctolagus cuniculus

<400> SEQUENCE: 446

Gln Ser Ser Gln Ser Val Tyr Ser Asp Tyr Leu Ala
1               5                   10

<210> SEQ ID NO 447
<211> LENGTH: 11
<212> TYPE: PRT
<213> ORGANISM: Oryctolagus cuniculus

<400> SEQUENCE: 447

Gln Ala Ser Glu Asp Ile Tyr Ser Asn Leu Ala
1               5                   10

<210> SEQ ID NO 448
<211> LENGTH: 11
<212> TYPE: PRT
<213> ORGANISM: Oryctolagus cuniculus

<400> SEQUENCE: 448

Gln Ala Ser Gln Ser Ile Ser Ser Trp Leu Ser
1               5                   10

<210> SEQ ID NO 449
<211> LENGTH: 11
<212> TYPE: PRT
<213> ORGANISM: Oryctolagus cuniculus

<400> SEQUENCE: 449

Gln Ala Ser Glu Ser Ile Ser Asn Tyr Leu Ser
1               5                   10

<210> SEQ ID NO 450
<211> LENGTH: 11
<212> TYPE: PRT
<213> ORGANISM: Oryctolagus cuniculus

<400> SEQUENCE: 450

Gln Ala Ser Gln Asn Ile Tyr Ile Tyr Leu Ser
1               5                   10

<210> SEQ ID NO 451
<211> LENGTH: 12
<212> TYPE: PRT
<213> ORGANISM: Oryctolagus cuniculus

<400> SEQUENCE: 451

Gln Ala Ser Glu Ser Ile Ser Ala Asn Tyr Trp Ser
1               5                   10

<210> SEQ ID NO 452
<211> LENGTH: 11
<212> TYPE: PRT
<213> ORGANISM: Oryctolagus cuniculus

<400> SEQUENCE: 452

Gln Ala Ser Gln Ser Ile Tyr Ile Tyr Leu Ala
1               5                   10

<210> SEQ ID NO 453
<211> LENGTH: 13
<212> TYPE: PRT
<213> ORGANISM: Oryctolagus cuniculus

<400> SEQUENCE: 453

Gln Ser Ser Gln Ser Val Tyr Gly Asn Asn Glu Leu Ser

```
1               5                   10
```

<210> SEQ ID NO 454
<211> LENGTH: 11
<212> TYPE: PRT
<213> ORGANISM: Oryctolagus cuniculus

<400> SEQUENCE: 454

```
Gln Ala Ser Glu Asp Ile Ser Ser Tyr Leu Ala
1               5                   10
```

<210> SEQ ID NO 455
<211> LENGTH: 12
<212> TYPE: PRT
<213> ORGANISM: Oryctolagus cuniculus

<400> SEQUENCE: 455

```
Gln Ser Ser Gln Ser Val Tyr Ser Asp Tyr Leu Ala
1               5                   10
```

<210> SEQ ID NO 456
<211> LENGTH: 11
<212> TYPE: PRT
<213> ORGANISM: Oryctolagus cuniculus

<400> SEQUENCE: 456

```
Gln Ala Ser Gln Ser Ile Asp Tyr Tyr Leu Ala
1               5                   10
```

<210> SEQ ID NO 457
<211> LENGTH: 13
<212> TYPE: PRT
<213> ORGANISM: Oryctolagus cuniculus

<400> SEQUENCE: 457

```
Gln Ser Ser Gln Ser Val Asn Gly Asn Asn Tyr Leu Ala
1               5                   10
```

<210> SEQ ID NO 458
<211> LENGTH: 11
<212> TYPE: PRT
<213> ORGANISM: Oryctolagus cuniculus

<400> SEQUENCE: 458

```
Gln Ala Ser Gln Ser Ile Ser Ser Tyr Leu Ser
1               5                   10
```

<210> SEQ ID NO 459
<211> LENGTH: 11
<212> TYPE: PRT
<213> ORGANISM: Oryctolagus cuniculus

<400> SEQUENCE: 459

```
Gln Ala Ser Gln Asn Ile Tyr Ser Gly Leu Ala
1               5                   10
```

<210> SEQ ID NO 460
<211> LENGTH: 11
<212> TYPE: PRT
<213> ORGANISM: Oryctolagus cuniculus

<400> SEQUENCE: 460

```
Gln Ala Ser Glu Asp Ile Tyr Ser Asn Leu Ala
1               5                   10
```

```
<210> SEQ ID NO 461
<211> LENGTH: 13
<212> TYPE: PRT
<213> ORGANISM: Oryctolagus cuniculus

<400> SEQUENCE: 461

Gln Ala Ser Gln Ser Val Tyr Lys Asn Asn Tyr Leu Ser
1               5                   10

<210> SEQ ID NO 462
<211> LENGTH: 11
<212> TYPE: PRT
<213> ORGANISM: Oryctolagus cuniculus

<400> SEQUENCE: 462

Gln Ala Ser Gln Asn Ile Gly Ser Asn Leu Ala
1               5                   10

<210> SEQ ID NO 463
<211> LENGTH: 7
<212> TYPE: PRT
<213> ORGANISM: Oryctolagus cuniculus

<400> SEQUENCE: 463

Asp Ala Ser Lys Leu Ala Ser
1               5

<210> SEQ ID NO 464
<211> LENGTH: 7
<212> TYPE: PRT
<213> ORGANISM: Oryctolagus cuniculus

<400> SEQUENCE: 464

Tyr Ala Ser Thr Leu Ala Ser
1               5

<210> SEQ ID NO 465
<211> LENGTH: 7
<212> TYPE: PRT
<213> ORGANISM: Oryctolagus cuniculus

<400> SEQUENCE: 465

Asp Ala Ser Asp Leu Ala Ser
1               5

<210> SEQ ID NO 466
<211> LENGTH: 7
<212> TYPE: PRT
<213> ORGANISM: Oryctolagus cuniculus

<400> SEQUENCE: 466

Ala Ala Ser Asp Leu Glu Ser
1               5

<210> SEQ ID NO 467
<211> LENGTH: 7
<212> TYPE: PRT
<213> ORGANISM: Oryctolagus cuniculus

<400> SEQUENCE: 467

Arg Ala Ser Thr Leu Ala Ser
1               5

<210> SEQ ID NO 468
```

```
<211> LENGTH: 7
<212> TYPE: PRT
<213> ORGANISM: Oryctolagus cuniculus

<400> SEQUENCE: 468

Gly Ala Ser Thr Leu Ala Ser
1               5

<210> SEQ ID NO 469
<211> LENGTH: 7
<212> TYPE: PRT
<213> ORGANISM: Oryctolagus cuniculus

<400> SEQUENCE: 469

Ala Ala Ser Asn Leu Glu Ser
1               5

<210> SEQ ID NO 470
<211> LENGTH: 7
<212> TYPE: PRT
<213> ORGANISM: Oryctolagus cuniculus

<400> SEQUENCE: 470

Ala Ala Ser Leu Leu Ala Ser
1               5

<210> SEQ ID NO 471
<211> LENGTH: 7
<212> TYPE: PRT
<213> ORGANISM: Oryctolagus cuniculus

<400> SEQUENCE: 471

Arg Ala Ser Thr Leu Ala Ser
1               5

<210> SEQ ID NO 472
<211> LENGTH: 7
<212> TYPE: PRT
<213> ORGANISM: Oryctolagus cuniculus

<400> SEQUENCE: 472

Asp Ala Ser Glu Leu Ala Ser
1               5

<210> SEQ ID NO 473
<211> LENGTH: 7
<212> TYPE: PRT
<213> ORGANISM: Oryctolagus cuniculus

<400> SEQUENCE: 473

Gln Ala Ser Lys Leu Ala Thr
1               5

<210> SEQ ID NO 474
<211> LENGTH: 7
<212> TYPE: PRT
<213> ORGANISM: Oryctolagus cuniculus

<400> SEQUENCE: 474

Arg Ala Ser Thr Leu Ala Ser
1               5

<210> SEQ ID NO 475
<211> LENGTH: 7
<212> TYPE: PRT
```

```
<213> ORGANISM: Oryctolagus cuniculus

<400> SEQUENCE: 475

Lys Ala Ser Lys Leu Ala Ser
1               5

<210> SEQ ID NO 476
<211> LENGTH: 7
<212> TYPE: PRT
<213> ORGANISM: Oryctolagus cuniculus

<400> SEQUENCE: 476

Arg Ala Ser Thr Leu Ala Ser
1               5

<210> SEQ ID NO 477
<211> LENGTH: 7
<212> TYPE: PRT
<213> ORGANISM: Oryctolagus cuniculus

<400> SEQUENCE: 477

Arg Ala Ser Thr Leu Ala Ser
1               5

<210> SEQ ID NO 478
<211> LENGTH: 7
<212> TYPE: PRT
<213> ORGANISM: Oryctolagus cuniculus

<400> SEQUENCE: 478

Arg Ala Ser Thr Leu Glu Ser
1               5

<210> SEQ ID NO 479
<211> LENGTH: 7
<212> TYPE: PRT
<213> ORGANISM: Oryctolagus cuniculus

<400> SEQUENCE: 479

Lys Ala Ser Thr Leu Ala Ser
1               5

<210> SEQ ID NO 480
<211> LENGTH: 7
<212> TYPE: PRT
<213> ORGANISM: Oryctolagus cuniculus

<400> SEQUENCE: 480

Ser Ala Ser Thr Leu Ala Ser
1               5

<210> SEQ ID NO 481
<211> LENGTH: 7
<212> TYPE: PRT
<213> ORGANISM: Oryctolagus cuniculus

<400> SEQUENCE: 481

Ala Ala Ser Leu Leu Ala Ser
1               5

<210> SEQ ID NO 482
<211> LENGTH: 7
<212> TYPE: PRT
<213> ORGANISM: Oryctolagus cuniculus
```

```
<400> SEQUENCE: 482

Ser Ala Ser Thr Leu Ala Ser
1               5

<210> SEQ ID NO 483
<211> LENGTH: 7
<212> TYPE: PRT
<213> ORGANISM: Oryctolagus cuniculus

<400> SEQUENCE: 483

Gln Ala Ser Thr Leu Ala Ser
1               5

<210> SEQ ID NO 484
<211> LENGTH: 7
<212> TYPE: PRT
<213> ORGANISM: Oryctolagus cuniculus

<400> SEQUENCE: 484

Asp Ala Ser Thr Leu Ala Ser
1               5

<210> SEQ ID NO 485
<211> LENGTH: 7
<212> TYPE: PRT
<213> ORGANISM: Oryctolagus cuniculus

<400> SEQUENCE: 485

Arg Ala Ser Thr Leu Ala Ser
1               5

<210> SEQ ID NO 486
<211> LENGTH: 7
<212> TYPE: PRT
<213> ORGANISM: Oryctolagus cuniculus

<400> SEQUENCE: 486

Arg Ala Ser Thr Leu Ala Ser
1               5

<210> SEQ ID NO 487
<211> LENGTH: 7
<212> TYPE: PRT
<213> ORGANISM: Oryctolagus cuniculus

<400> SEQUENCE: 487

Arg Ala Ser Thr Leu Ala Ser
1               5

<210> SEQ ID NO 488
<211> LENGTH: 7
<212> TYPE: PRT
<213> ORGANISM: Oryctolagus cuniculus

<400> SEQUENCE: 488

Arg Ala Ser Thr Leu Ala Ser
1               5

<210> SEQ ID NO 489
<211> LENGTH: 7
<212> TYPE: PRT
<213> ORGANISM: Oryctolagus cuniculus

<400> SEQUENCE: 489
```

Trp Ala Ser Lys Leu Glu Thr
1               5

<210> SEQ ID NO 490
<211> LENGTH: 7
<212> TYPE: PRT
<213> ORGANISM: Oryctolagus cuniculus

<400> SEQUENCE: 490

Tyr Ala Ser Thr Leu Ala Ser
1               5

<210> SEQ ID NO 491
<211> LENGTH: 7
<212> TYPE: PRT
<213> ORGANISM: Oryctolagus cuniculus

<400> SEQUENCE: 491

Asp Ala Ser Lys Leu Ala Ser
1               5

<210> SEQ ID NO 492
<211> LENGTH: 7
<212> TYPE: PRT
<213> ORGANISM: Oryctolagus cuniculus

<400> SEQUENCE: 492

Arg Ala Ser Thr Leu Ala Ser
1               5

<210> SEQ ID NO 493
<211> LENGTH: 7
<212> TYPE: PRT
<213> ORGANISM: Oryctolagus cuniculus

<400> SEQUENCE: 493

Tyr Val Ser Thr Leu Glu Ser
1               5

<210> SEQ ID NO 494
<211> LENGTH: 7
<212> TYPE: PRT
<213> ORGANISM: Oryctolagus cuniculus

<400> SEQUENCE: 494

Arg Ala Ser Thr Leu Ala Ser
1               5

<210> SEQ ID NO 495
<211> LENGTH: 7
<212> TYPE: PRT
<213> ORGANISM: Oryctolagus cuniculus

<400> SEQUENCE: 495

Gln Ala Ser Lys Leu Ala Ser
1               5

<210> SEQ ID NO 496
<211> LENGTH: 7
<212> TYPE: PRT
<213> ORGANISM: Oryctolagus cuniculus

<400> SEQUENCE: 496

Arg Ala Ser Thr Leu Ala Ser
1               5

```
<210> SEQ ID NO 497
<211> LENGTH: 7
<212> TYPE: PRT
<213> ORGANISM: Oryctolagus cuniculus

<400> SEQUENCE: 497

Tyr Val Ser Thr Leu Glu Ser
1               5

<210> SEQ ID NO 498
<211> LENGTH: 7
<212> TYPE: PRT
<213> ORGANISM: Oryctolagus cuniculus

<400> SEQUENCE: 498

Asp Ala Ser Thr Leu Ala Ser
1               5

<210> SEQ ID NO 499
<211> LENGTH: 7
<212> TYPE: PRT
<213> ORGANISM: Oryctolagus cuniculus

<400> SEQUENCE: 499

Asp Ala Ser Thr Leu Ala Ser
1               5

<210> SEQ ID NO 500
<211> LENGTH: 7
<212> TYPE: PRT
<213> ORGANISM: Oryctolagus cuniculus

<400> SEQUENCE: 500

Gly Ala Ser Thr Leu Ala Ser
1               5

<210> SEQ ID NO 501
<211> LENGTH: 7
<212> TYPE: PRT
<213> ORGANISM: Oryctolagus cuniculus

<400> SEQUENCE: 501

Gln Ala Ser Lys Leu Ala Ser
1               5

<210> SEQ ID NO 502
<211> LENGTH: 7
<212> TYPE: PRT
<213> ORGANISM: Oryctolagus cuniculus

<400> SEQUENCE: 502

Phe Val Ala Thr Leu Glu Ser
1               5

<210> SEQ ID NO 503
<211> LENGTH: 7
<212> TYPE: PRT
<213> ORGANISM: Oryctolagus cuniculus

<400> SEQUENCE: 503

Gly Val Ser Thr Leu Ala Ser
1               5
```

```
<210> SEQ ID NO 504
<211> LENGTH: 7
<212> TYPE: PRT
<213> ORGANISM: Oryctolagus cuniculus

<400> SEQUENCE: 504

Arg Ala Ser Thr Leu Glu Ser
1               5

<210> SEQ ID NO 505
<211> LENGTH: 7
<212> TYPE: PRT
<213> ORGANISM: Oryctolagus cuniculus

<400> SEQUENCE: 505

Asp Ala Ser Thr Leu Ala Ser
1               5

<210> SEQ ID NO 506
<211> LENGTH: 7
<212> TYPE: PRT
<213> ORGANISM: Oryctolagus cuniculus

<400> SEQUENCE: 506

Ala Ala Ser Thr Leu Thr Asp
1               5

<210> SEQ ID NO 507
<211> LENGTH: 7
<212> TYPE: PRT
<213> ORGANISM: Oryctolagus cuniculus

<400> SEQUENCE: 507

Arg Ala Ser Thr Leu Ala Ser
1               5

<210> SEQ ID NO 508
<211> LENGTH: 7
<212> TYPE: PRT
<213> ORGANISM: Oryctolagus cuniculus

<400> SEQUENCE: 508

Lys Ala Ser Thr Leu Ala Ser
1               5

<210> SEQ ID NO 509
<211> LENGTH: 7
<212> TYPE: PRT
<213> ORGANISM: Oryctolagus cuniculus

<400> SEQUENCE: 509

Gln Ala Ser Ala Leu Ala Ser
1               5

<210> SEQ ID NO 510
<211> LENGTH: 7
<212> TYPE: PRT
<213> ORGANISM: Oryctolagus cuniculus

<400> SEQUENCE: 510

Gln Ala Ser Ala Leu Ala Ser
1               5

<210> SEQ ID NO 511
<211> LENGTH: 7
```

```
<212> TYPE: PRT
<213> ORGANISM: Oryctolagus cuniculus

<400> SEQUENCE: 511

Tyr Thr Ser Ser Leu Ala Ser
1               5

<210> SEQ ID NO 512
<211> LENGTH: 7
<212> TYPE: PRT
<213> ORGANISM: Oryctolagus cuniculus

<400> SEQUENCE: 512

Ser Ala Ser Thr Leu Ala Ser
1               5

<210> SEQ ID NO 513
<211> LENGTH: 7
<212> TYPE: PRT
<213> ORGANISM: Oryctolagus cuniculus

<400> SEQUENCE: 513

Gly Ala Ser Ser Leu Ala Ser
1               5

<210> SEQ ID NO 514
<211> LENGTH: 7
<212> TYPE: PRT
<213> ORGANISM: Oryctolagus cuniculus

<400> SEQUENCE: 514

Gly Ala Ser Thr Leu Ala Ser
1               5

<210> SEQ ID NO 515
<211> LENGTH: 7
<212> TYPE: PRT
<213> ORGANISM: Oryctolagus cuniculus

<400> SEQUENCE: 515

Val Ala Ser Lys Leu Ala Ser
1               5

<210> SEQ ID NO 516
<211> LENGTH: 7
<212> TYPE: PRT
<213> ORGANISM: Oryctolagus cuniculus

<400> SEQUENCE: 516

Leu Ala Ser Thr Leu Ala Ser
1               5

<210> SEQ ID NO 517
<211> LENGTH: 7
<212> TYPE: PRT
<213> ORGANISM: Oryctolagus cuniculus

<400> SEQUENCE: 517

Asp Ala Ser Thr Leu Ala Ser
1               5

<210> SEQ ID NO 518
<211> LENGTH: 7
<212> TYPE: PRT
<213> ORGANISM: Oryctolagus cuniculus
```

<400> SEQUENCE: 518

Gly Ala Ser Thr Leu Ala Ser
1               5

<210> SEQ ID NO 519
<211> LENGTH: 7
<212> TYPE: PRT
<213> ORGANISM: Oryctolagus cuniculus

<400> SEQUENCE: 519

Gly Ala Ser Asn Leu Glu Ser
1               5

<210> SEQ ID NO 520
<211> LENGTH: 7
<212> TYPE: PRT
<213> ORGANISM: Oryctolagus cuniculus

<400> SEQUENCE: 520

Gly Ala Ser Thr Leu Ala Ser
1               5

<210> SEQ ID NO 521
<211> LENGTH: 7
<212> TYPE: PRT
<213> ORGANISM: Oryctolagus cuniculus

<400> SEQUENCE: 521

Gly Ala Ser Thr Leu Ala Ser
1               5

<210> SEQ ID NO 522
<211> LENGTH: 7
<212> TYPE: PRT
<213> ORGANISM: Oryctolagus cuniculus

<400> SEQUENCE: 522

Asp Ala Ser Asn Leu Ala Ser
1               5

<210> SEQ ID NO 523
<211> LENGTH: 7
<212> TYPE: PRT
<213> ORGANISM: Oryctolagus cuniculus

<400> SEQUENCE: 523

Trp Ala Ser Lys Leu Ala Ser
1               5

<210> SEQ ID NO 524
<211> LENGTH: 7
<212> TYPE: PRT
<213> ORGANISM: Oryctolagus cuniculus

<400> SEQUENCE: 524

Asp Ala Ser Thr Leu Ala Ser
1               5

<210> SEQ ID NO 525
<211> LENGTH: 7
<212> TYPE: PRT
<213> ORGANISM: Oryctolagus cuniculus

<400> SEQUENCE: 525

```
Arg Ala Ser Thr Leu Ala Ser
1               5

<210> SEQ ID NO 526
<211> LENGTH: 7
<212> TYPE: PRT
<213> ORGANISM: Oryctolagus cuniculus

<400> SEQUENCE: 526

Leu Ala Ser Thr Leu Ala Ser
1               5

<210> SEQ ID NO 527
<211> LENGTH: 7
<212> TYPE: PRT
<213> ORGANISM: Oryctolagus cuniculus

<400> SEQUENCE: 527

Asp Ala Ser Thr Leu Ala Ser
1               5

<210> SEQ ID NO 528
<211> LENGTH: 7
<212> TYPE: PRT
<213> ORGANISM: Oryctolagus cuniculus

<400> SEQUENCE: 528

Gly Ala Ser Thr Leu Ala Ser
1               5

<210> SEQ ID NO 529
<211> LENGTH: 7
<212> TYPE: PRT
<213> ORGANISM: Oryctolagus cuniculus

<400> SEQUENCE: 529

Asp Ala Ser Lys Leu Ala Ser
1               5

<210> SEQ ID NO 530
<211> LENGTH: 7
<212> TYPE: PRT
<213> ORGANISM: Oryctolagus cuniculus

<400> SEQUENCE: 530

Gly Ala Ser Ile Leu Ala Ser
1               5

<210> SEQ ID NO 531
<211> LENGTH: 7
<212> TYPE: PRT
<213> ORGANISM: Oryctolagus cuniculus

<400> SEQUENCE: 531

Asp Ala Ser Asp Leu Ala Ser
1               5

<210> SEQ ID NO 532
<211> LENGTH: 7
<212> TYPE: PRT
<213> ORGANISM: Oryctolagus cuniculus

<400> SEQUENCE: 532

Gln Ala Ser Lys Leu Ala Ser
```

1               5

<210> SEQ ID NO 533
<211> LENGTH: 7
<212> TYPE: PRT
<213> ORGANISM: Oryctolagus cuniculus

<400> SEQUENCE: 533

Arg Ala Ser Thr Leu Ala Ser
1               5

<210> SEQ ID NO 534
<211> LENGTH: 7
<212> TYPE: PRT
<213> ORGANISM: Oryctolagus cuniculus

<400> SEQUENCE: 534

Leu Ala Ser Ser Leu Ala Ser
1               5

<210> SEQ ID NO 535
<211> LENGTH: 7
<212> TYPE: PRT
<213> ORGANISM: Oryctolagus cuniculus

<400> SEQUENCE: 535

Gly Ala Ser Asn Leu Ala Ser
1               5

<210> SEQ ID NO 536
<211> LENGTH: 7
<212> TYPE: PRT
<213> ORGANISM: Oryctolagus cuniculus

<400> SEQUENCE: 536

Tyr Ala Ser Thr Leu Ala Ser
1               5

<210> SEQ ID NO 537
<211> LENGTH: 7
<212> TYPE: PRT
<213> ORGANISM: Oryctolagus cuniculus

<400> SEQUENCE: 537

Gly Ala Ser Thr Leu Ala Ser
1               5

<210> SEQ ID NO 538
<211> LENGTH: 7
<212> TYPE: PRT
<213> ORGANISM: Oryctolagus cuniculus

<400> SEQUENCE: 538

Ser Ala Ser Thr Leu Asp Ser
1               5

<210> SEQ ID NO 539
<211> LENGTH: 7
<212> TYPE: PRT
<213> ORGANISM: Oryctolagus cuniculus

<400> SEQUENCE: 539

Gly Ala Ser Thr Leu Ala Ser
1               5

```
<210> SEQ ID NO 540
<211> LENGTH: 12
<212> TYPE: PRT
<213> ORGANISM: Oryctolagus cuniculus

<400> SEQUENCE: 540

Gln Gln Gly Ala Thr Thr Tyr Asn Val Asp Asn Val
1               5                   10

<210> SEQ ID NO 541
<211> LENGTH: 12
<212> TYPE: PRT
<213> ORGANISM: Oryctolagus cuniculus

<400> SEQUENCE: 541

Gln Gln Gly Tyr Thr Glu Asp Asn Ile Asp Asn Thr
1               5                   10

<210> SEQ ID NO 542
<211> LENGTH: 13
<212> TYPE: PRT
<213> ORGANISM: Oryctolagus cuniculus

<400> SEQUENCE: 542

Gln Gln Gly Tyr Tyr Ser Gly Gly Thr Asp Asn Asp Val
1               5                   10

<210> SEQ ID NO 543
<211> LENGTH: 10
<212> TYPE: PRT
<213> ORGANISM: Oryctolagus cuniculus

<400> SEQUENCE: 543

Gln Cys Asn Tyr Ile Ile Asp Tyr Gly Ala
1               5                   10

<210> SEQ ID NO 544
<211> LENGTH: 12
<212> TYPE: PRT
<213> ORGANISM: Oryctolagus cuniculus

<400> SEQUENCE: 544

Leu Gly Val Tyr Thr Tyr Pro Ser Ala Asp Asn Ala
1               5                   10

<210> SEQ ID NO 545
<211> LENGTH: 13
<212> TYPE: PRT
<213> ORGANISM: Oryctolagus cuniculus

<400> SEQUENCE: 545

Gln Cys Thr Tyr Trp Asn Pro Asp Tyr Ile Gly Gly Ala
1               5                   10

<210> SEQ ID NO 546
<211> LENGTH: 12
<212> TYPE: PRT
<213> ORGANISM: Oryctolagus cuniculus

<400> SEQUENCE: 546

Leu Gly Gly Tyr Ser Tyr Ser Asn Thr Gly Pro Thr
1               5                   10

<210> SEQ ID NO 547
```

```
<210> SEQ ID NO 547
<211> LENGTH: 12
<212> TYPE: PRT
<213> ORGANISM: Oryctolagus cuniculus

<400> SEQUENCE: 547

Gln Ser Ala Ser Tyr Ser Thr Gly Pro Asp Trp Thr
1               5                   10

<210> SEQ ID NO 548
<211> LENGTH: 12
<212> TYPE: PRT
<213> ORGANISM: Oryctolagus cuniculus

<400> SEQUENCE: 548

Gln Gln Gly Ala Thr Ser Tyr Asp Ile Glu Asn Pro
1               5                   10

<210> SEQ ID NO 549
<211> LENGTH: 12
<212> TYPE: PRT
<213> ORGANISM: Oryctolagus cuniculus

<400> SEQUENCE: 549

Gln Gln Gly Ala Thr Thr Tyr Asn Ile Glu Asn Val
1               5                   10

<210> SEQ ID NO 550
<211> LENGTH: 12
<212> TYPE: PRT
<213> ORGANISM: Oryctolagus cuniculus

<400> SEQUENCE: 550

Gln Ala Thr Tyr Tyr Gly Ser Gly Trp Tyr Arg Ala
1               5                   10

<210> SEQ ID NO 551
<211> LENGTH: 13
<212> TYPE: PRT
<213> ORGANISM: Oryctolagus cuniculus

<400> SEQUENCE: 551

Leu Gly Val Arg Thr Tyr Phe Asn Thr Leu Asn Asn Ser
1               5                   10

<210> SEQ ID NO 552
<211> LENGTH: 12
<212> TYPE: PRT
<213> ORGANISM: Oryctolagus cuniculus

<400> SEQUENCE: 552

Gln Ala Thr Tyr Tyr Ser Val Gly Trp Tyr Arg Ala
1               5                   10

<210> SEQ ID NO 553
<211> LENGTH: 13
<212> TYPE: PRT
<213> ORGANISM: Oryctolagus cuniculus

<400> SEQUENCE: 553

Leu Gly Val Tyr Thr Tyr Leu Ser Asp Leu Phe Phe Val
1               5                   10

<210> SEQ ID NO 554
<211> LENGTH: 12
<212> TYPE: PRT
```

```
<213> ORGANISM: Oryctolagus cuniculus

<400> SEQUENCE: 554

Leu Gly Val Tyr Thr Tyr Ser Thr Asp Ile His Ala
1               5                   10

<210> SEQ ID NO 555
<211> LENGTH: 11
<212> TYPE: PRT
<213> ORGANISM: Oryctolagus cuniculus

<400> SEQUENCE: 555

Gln Ser Asn Tyr Tyr Asp Ser Arg Gly Asn Ala
1               5                   10

<210> SEQ ID NO 556
<211> LENGTH: 10
<212> TYPE: PRT
<213> ORGANISM: Oryctolagus cuniculus

<400> SEQUENCE: 556

Ala Gly Phe Tyr Glu Thr Thr Asp Val Gly
1               5                   10

<210> SEQ ID NO 557
<211> LENGTH: 13
<212> TYPE: PRT
<213> ORGANISM: Oryctolagus cuniculus

<400> SEQUENCE: 557

Gln Gly Glu Phe Ser Cys Val Ser Ala Asp Cys Ile Ala
1               5                   10

<210> SEQ ID NO 558
<211> LENGTH: 12
<212> TYPE: PRT
<213> ORGANISM: Oryctolagus cuniculus

<400> SEQUENCE: 558

Gln Gly Ala Val Tyr Ser Gly Asn Thr Glu Trp Ala
1               5                   10

<210> SEQ ID NO 559
<211> LENGTH: 15
<212> TYPE: PRT
<213> ORGANISM: Oryctolagus cuniculus

<400> SEQUENCE: 559

Leu Gly Val Cys Thr Asp Ile Ser Val Asp Asp Val Tyr Asn Ser
1               5                   10                  15

<210> SEQ ID NO 560
<211> LENGTH: 16
<212> TYPE: PRT
<213> ORGANISM: Oryctolagus cuniculus

<400> SEQUENCE: 560

Leu Gly Val Cys Thr Tyr Ile Gly Ala Asp Asn Thr Leu Tyr Asn Thr
1               5                   10                  15

<210> SEQ ID NO 561
<211> LENGTH: 12
<212> TYPE: PRT
<213> ORGANISM: Oryctolagus cuniculus
```

```
<400> SEQUENCE: 561

Leu Gly Val Tyr Thr His Ile Ser Ala Asp Asn Ala
1               5                   10

<210> SEQ ID NO 562
<211> LENGTH: 12
<212> TYPE: PRT
<213> ORGANISM: Oryctolagus cuniculus

<400> SEQUENCE: 562

Gln Gln Gly Ala Thr Ser Tyr Asp Ile Asp Asn Ala
1               5                   10

<210> SEQ ID NO 563
<211> LENGTH: 12
<212> TYPE: PRT
<213> ORGANISM: Oryctolagus cuniculus

<400> SEQUENCE: 563

Gln Gln Gly Ala Thr Thr Tyr Asp Val Asp Asn Val
1               5                   10

<210> SEQ ID NO 564
<211> LENGTH: 12
<212> TYPE: PRT
<213> ORGANISM: Oryctolagus cuniculus

<400> SEQUENCE: 564

Gln Gln Gly Ala Ser Thr Thr Asp Val Asp Asn Val
1               5                   10

<210> SEQ ID NO 565
<211> LENGTH: 10
<212> TYPE: PRT
<213> ORGANISM: Oryctolagus cuniculus

<400> SEQUENCE: 565

Gln Ser Tyr Tyr Asn Ser Asp Ser Asp Ala
1               5                   10

<210> SEQ ID NO 566
<211> LENGTH: 12
<212> TYPE: PRT
<213> ORGANISM: Oryctolagus cuniculus

<400> SEQUENCE: 566

Gln Ala Thr Tyr Tyr Gly Ser Gly Trp Tyr Arg Ala
1               5                   10

<210> SEQ ID NO 567
<211> LENGTH: 15
<212> TYPE: PRT
<213> ORGANISM: Oryctolagus cuniculus

<400> SEQUENCE: 567

Leu Gly Val Cys Thr Tyr Ile Asn Ala Asn Gly Trp Asp Asn Ala
1               5                   10                  15

<210> SEQ ID NO 568
<211> LENGTH: 12
<212> TYPE: PRT
<213> ORGANISM: Oryctolagus cuniculus

<400> SEQUENCE: 568
```

```
Gln Gln Gly Ala Thr Ile Trp Asn Val Asp Asn Pro
1               5                   10
```

<210> SEQ ID NO 569
<211> LENGTH: 12
<212> TYPE: PRT
<213> ORGANISM: Oryctolagus cuniculus

<400> SEQUENCE: 569

```
Gln Gln Gly Ala Ser Thr Thr Asp Val Asp Asn Val
1               5                   10
```

<210> SEQ ID NO 570
<211> LENGTH: 12
<212> TYPE: PRT
<213> ORGANISM: Oryctolagus cuniculus

<400> SEQUENCE: 570

```
Gln Cys Thr Glu Gly Gly Ser Gly Ser Asp Tyr Thr
1               5                   10
```

<210> SEQ ID NO 571
<211> LENGTH: 16
<212> TYPE: PRT
<213> ORGANISM: Oryctolagus cuniculus

<400> SEQUENCE: 571

```
Leu Gly Ile Tyr Thr Tyr Ile Ser Ala Asp Gly Ser Leu Tyr Asn Ala
1               5                   10                  15
```

<210> SEQ ID NO 572
<211> LENGTH: 16
<212> TYPE: PRT
<213> ORGANISM: Oryctolagus cuniculus

<400> SEQUENCE: 572

```
Leu Gly Val Gly Thr Tyr Ile Ser Gly Asp Gly Ser Leu Asp Asn Ala
1               5                   10                  15
```

<210> SEQ ID NO 573
<211> LENGTH: 12
<212> TYPE: PRT
<213> ORGANISM: Oryctolagus cuniculus

<400> SEQUENCE: 573

```
Gln Gln Gly Ala Ser Thr Thr Asp Val Asp Asn Val
1               5                   10
```

<210> SEQ ID NO 574
<211> LENGTH: 13
<212> TYPE: PRT
<213> ORGANISM: Oryctolagus cuniculus

<400> SEQUENCE: 574

```
Gln Tyr Thr Tyr Asp Ser Ser Ser Thr Ser Trp Ala
1               5                   10
```

<210> SEQ ID NO 575
<211> LENGTH: 14
<212> TYPE: PRT
<213> ORGANISM: Oryctolagus cuniculus

<400> SEQUENCE: 575

```
Gln Ser Tyr Tyr Cys Ser Val Ser Ser Cys Gly Tyr Gly
1               5                   10
```

<210> SEQ ID NO 576
<211> LENGTH: 17
<212> TYPE: PRT
<213> ORGANISM: Oryctolagus cuniculus

<400> SEQUENCE: 576

Leu Gly Val Tyr Thr Tyr Ile Ser Ala Asp Gly Thr Leu Val Tyr Asn
1               5                   10                  15
Ala

<210> SEQ ID NO 577
<211> LENGTH: 15
<212> TYPE: PRT
<213> ORGANISM: Oryctolagus cuniculus

<400> SEQUENCE: 577

Leu Gly Val Cys Thr Asp Ile Ser Thr Asp Asp Leu Tyr Asn Ala
1               5                   10                  15

<210> SEQ ID NO 578
<211> LENGTH: 12
<212> TYPE: PRT
<213> ORGANISM: Oryctolagus cuniculus

<400> SEQUENCE: 578

Gln Ala Thr Tyr Ser Ser Thr Gly Trp Tyr Arg Ala
1               5                   10

<210> SEQ ID NO 579
<211> LENGTH: 14
<212> TYPE: PRT
<213> ORGANISM: Oryctolagus cuniculus

<400> SEQUENCE: 579

Gln Cys Thr Tyr Gly Gly Ser Gly Ser Gly Asn Gly Ala Ala
1               5                   10

<210> SEQ ID NO 580
<211> LENGTH: 13
<212> TYPE: PRT
<213> ORGANISM: Oryctolagus cuniculus

<400> SEQUENCE: 580

Leu Gly Val Tyr Thr Tyr Ile Ser Asp Val Tyr Tyr Thr
1               5                   10

<210> SEQ ID NO 581
<211> LENGTH: 11
<212> TYPE: PRT
<213> ORGANISM: Oryctolagus cuniculus

<400> SEQUENCE: 581

Gln Ser Ser Tyr Tyr Asp Leu Leu Gly Asn Gly
1               5                   10

<210> SEQ ID NO 582
<211> LENGTH: 15
<212> TYPE: PRT
<213> ORGANISM: Oryctolagus cuniculus

<400> SEQUENCE: 582

Leu Gly Val Tyr Thr Tyr Ile Ser Pro Asp Gly Thr Asp Asn Ala
1               5                   10                  15

<210> SEQ ID NO 583
<211> LENGTH: 12
<212> TYPE: PRT
<213> ORGANISM: Oryctolagus cuniculus

<400> SEQUENCE: 583

Ala Gly Tyr Lys Ser Tyr Thr Asp Asp Glu Phe Ala
1               5                   10

<210> SEQ ID NO 584
<211> LENGTH: 12
<212> TYPE: PRT
<213> ORGANISM: Oryctolagus cuniculus

<400> SEQUENCE: 584

Gln Gln Gly Tyr Thr Val Asn Asn Ile Asp Asn Val
1               5                   10

<210> SEQ ID NO 585
<211> LENGTH: 12
<212> TYPE: PRT
<213> ORGANISM: Oryctolagus cuniculus

<400> SEQUENCE: 585

Gln Gln Gly Tyr Ala Ser Ser Gly Val Asp Asn Val
1               5                   10

<210> SEQ ID NO 586
<211> LENGTH: 15
<212> TYPE: PRT
<213> ORGANISM: Oryctolagus cuniculus

<400> SEQUENCE: 586

Gln Cys Thr Tyr Gly Ile Gly Ser Asn Ser Asp Tyr Gly Val Ala
1               5                   10                  15

<210> SEQ ID NO 587
<211> LENGTH: 15
<212> TYPE: PRT
<213> ORGANISM: Oryctolagus cuniculus

<400> SEQUENCE: 587

Gln Cys Thr Tyr Gly Ile Gly Ser Gly Ser Tyr Gly Val Ala
1               5                   10                  15

<210> SEQ ID NO 588
<211> LENGTH: 15
<212> TYPE: PRT
<213> ORGANISM: Oryctolagus cuniculus

<400> SEQUENCE: 588

Gln Thr Tyr Tyr Asp Ser Glu Gly Arg Ser Tyr Gly Tyr Asn Ser
1               5                   10                  15

<210> SEQ ID NO 589
<211> LENGTH: 14
<212> TYPE: PRT
<213> ORGANISM: Oryctolagus cuniculus

<400> SEQUENCE: 589

Leu Ser His Tyr Leu Thr Ser Ser Ser Tyr Gly Asp Ala
1               5                   10

<210> SEQ ID NO 590
<211> LENGTH: 12
<212> TYPE: PRT
<213> ORGANISM: Oryctolagus cuniculus

<400> SEQUENCE: 590

Gln Gly Gly Tyr Asn Ser Tyr Ser Asp Thr Phe Ala
1               5                   10

<210> SEQ ID NO 591
<211> LENGTH: 15
<212> TYPE: PRT
<213> ORGANISM: Oryctolagus cuniculus

<400> SEQUENCE: 591

Leu Gly Val Cys Thr Asp Ile Ser Ala Asp Asp Leu Tyr Asn Thr
1               5                   10                  15

<210> SEQ ID NO 592
<211> LENGTH: 12
<212> TYPE: PRT
<213> ORGANISM: Oryctolagus cuniculus

<400> SEQUENCE: 592

Gln Gln Thr Tyr Arg Tyr Asn Asp Gly Asp Thr Ala
1               5                   10

<210> SEQ ID NO 593
<211> LENGTH: 11
<212> TYPE: PRT
<213> ORGANISM: Oryctolagus cuniculus

<400> SEQUENCE: 593

Ala Gly Gly Tyr Ser Thr Ile Ser Glu Asn Ala
1               5                   10

<210> SEQ ID NO 594
<211> LENGTH: 14
<212> TYPE: PRT
<213> ORGANISM: Oryctolagus cuniculus

<400> SEQUENCE: 594

Leu Ser His Tyr Leu Thr Ser Ser Ser Ser Tyr Gly Asn Ala
1               5                   10

<210> SEQ ID NO 595
<211> LENGTH: 12
<212> TYPE: PRT
<213> ORGANISM: Oryctolagus cuniculus

<400> SEQUENCE: 595

Gln Cys Ser Gly Tyr Asp Ile Thr Gly Val Phe Pro
1               5                   10

<210> SEQ ID NO 596
<211> LENGTH: 12
<212> TYPE: PRT
<213> ORGANISM: Oryctolagus cuniculus

<400> SEQUENCE: 596

Gln Cys Ser Gly Tyr Asp Thr Thr Gly Val Phe Pro
1               5                   10

<210> SEQ ID NO 597
<211> LENGTH: 12

```
<212> TYPE: PRT
<213> ORGANISM: Oryctolagus cuniculus

<400> SEQUENCE: 597

Gln Cys Ser Gly Tyr Asp Thr Thr Gly Val Phe Pro
1               5                   10

<210> SEQ ID NO 598
<211> LENGTH: 12
<212> TYPE: PRT
<213> ORGANISM: Oryctolagus cuniculus

<400> SEQUENCE: 598

Gln Gln Gly Tyr Ser Tyr Asn Asn Val Asp Asn Thr
1               5                   10

<210> SEQ ID NO 599
<211> LENGTH: 12
<212> TYPE: PRT
<213> ORGANISM: Oryctolagus cuniculus

<400> SEQUENCE: 599

Gln Gly Ser Tyr Tyr Ser Ser Ser Trp Tyr Asn Val
1               5                   10

<210> SEQ ID NO 600
<211> LENGTH: 12
<212> TYPE: PRT
<213> ORGANISM: Oryctolagus cuniculus

<400> SEQUENCE: 600

Gln Ala Thr Tyr Asn Gly Arg Gly Trp Tyr Arg Ala
1               5                   10

<210> SEQ ID NO 601
<211> LENGTH: 12
<212> TYPE: PRT
<213> ORGANISM: Oryctolagus cuniculus

<400> SEQUENCE: 601

Leu Gly Val Tyr Thr His Ile Ser Ala Asp Asn Ala
1               5                   10

<210> SEQ ID NO 602
<211> LENGTH: 13
<212> TYPE: PRT
<213> ORGANISM: Oryctolagus cuniculus

<400> SEQUENCE: 602

Gln Gln Gly Tyr Ile Thr Ser Ser Asn Ile Lys Asn Val
1               5                   10

<210> SEQ ID NO 603
<211> LENGTH: 12
<212> TYPE: PRT
<213> ORGANISM: Oryctolagus cuniculus

<400> SEQUENCE: 603

Gln Asn Trp Trp Val Ile Glu His Asn Gly Ala Ala
1               5                   10

<210> SEQ ID NO 604
<211> LENGTH: 12
<212> TYPE: PRT
<213> ORGANISM: Oryctolagus cuniculus
```

-continued

<400> SEQUENCE: 604

Gln Gln Gly Ala Thr Thr Tyr Asp Val Asp Asn Val
1               5                   10

<210> SEQ ID NO 605
<211> LENGTH: 15
<212> TYPE: PRT
<213> ORGANISM: Oryctolagus cuniculus

<400> SEQUENCE: 605

Gln Ser Trp Tyr Tyr Ser Gly Ser Gly Ser Tyr His Ser Trp Ala
1               5                   10                  15

<210> SEQ ID NO 606
<211> LENGTH: 12
<212> TYPE: PRT
<213> ORGANISM: Oryctolagus cuniculus

<400> SEQUENCE: 606

Gln Gln Gly Ala Thr Ile Trp Asn Val Asp Asn Pro
1               5                   10

<210> SEQ ID NO 607
<211> LENGTH: 11
<212> TYPE: PRT
<213> ORGANISM: Oryctolagus cuniculus

<400> SEQUENCE: 607

Ala Gly Gly Tyr Ser Ser Thr Ser Asp Asn Ala
1               5                   10

<210> SEQ ID NO 608
<211> LENGTH: 13
<212> TYPE: PRT
<213> ORGANISM: Oryctolagus cuniculus

<400> SEQUENCE: 608

Gln Cys Ala Asp Tyr Ala Thr Thr Tyr Gly Leu Gly Ala
1               5                   10

<210> SEQ ID NO 609
<211> LENGTH: 12
<212> TYPE: PRT
<213> ORGANISM: Oryctolagus cuniculus

<400> SEQUENCE: 609

Gln Ala Thr Tyr Ser Ser Ser Gly Trp Tyr Arg Ala
1               5                   10

<210> SEQ ID NO 610
<211> LENGTH: 12
<212> TYPE: PRT
<213> ORGANISM: Oryctolagus cuniculus

<400> SEQUENCE: 610

Gln Gln Gly Tyr Ser Gly Asn Asn Val Asp Asn Thr
1               5                   10

<210> SEQ ID NO 611
<211> LENGTH: 12
<212> TYPE: PRT
<213> ORGANISM: Oryctolagus cuniculus

<400> SEQUENCE: 611

```
Ala Gly Ala Tyr Ser Thr Ser Gly Glu Glu Asn Ala
1               5                   10

<210> SEQ ID NO 612
<211> LENGTH: 12
<212> TYPE: PRT
<213> ORGANISM: Oryctolagus cuniculus

<400> SEQUENCE: 612

Gln Cys Thr Tyr Tyr Asp Asn Asn Tyr Gly Gly Ala
1               5                   10

<210> SEQ ID NO 613
<211> LENGTH: 12
<212> TYPE: PRT
<213> ORGANISM: Oryctolagus cuniculus

<400> SEQUENCE: 613

Gln Thr Tyr Tyr Gly Val Tyr Val Tyr Gly Ile Ile
1               5                   10

<210> SEQ ID NO 614
<211> LENGTH: 13
<212> TYPE: PRT
<213> ORGANISM: Oryctolagus cuniculus

<400> SEQUENCE: 614

Leu Gly Val Cys Thr Asp Ile Ser Ala Val Tyr Asn Val
1               5                   10

<210> SEQ ID NO 615
<211> LENGTH: 13
<212> TYPE: PRT
<213> ORGANISM: Oryctolagus cuniculus

<400> SEQUENCE: 615

Gln Gly Asn Tyr Asp Cys Ser Ser Ala Asp Cys Ile Ala
1               5                   10

<210> SEQ ID NO 616
<211> LENGTH: 12
<212> TYPE: PRT
<213> ORGANISM: Oryctolagus cuniculus

<400> SEQUENCE: 616

Gln Cys Ser Gly Tyr Asp Thr Thr Gly Val Phe Pro
1               5                   10
```